(12) United States Patent
Boga et al.

(10) Patent No.: US 8,999,966 B2
(45) Date of Patent: Apr. 7, 2015

(54) COMPOUNDS THAT ARE ERK INHIBITORS

(75) Inventors: Sobhana Babu Boga, Scotch Plains, NJ (US); Joseph M. Kelly, Parlin, NJ (US); Hugh Y. Zhu, Warren, NJ (US); Abdul-Basit Alhassan, Scotch Plains, NJ (US); Xin Yao, Westfield, NJ (US); Xiaolei Gao, Bridgewater, NJ (US); James J-S Wang, Westfield, NJ (US); Jagdish A. Desai, Monroe Township, NJ (US); Subrahmanyam Gudipati, Edison, NJ (US); Sie-Mun Lo, Springfield, VA (US); Liang Zhu, Waltham, MA (US); Alan B. Cooper, West Caldwell, NJ (US); Yongqi Deng, Newton, MA (US); Gerald W. Shipps, Jr., Stoneham, MA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 13/881,050

(22) PCT Filed: Oct. 24, 2011

(86) PCT No.: PCT/US2011/057414
§ 371 (c)(1),
(2), (4) Date: Apr. 23, 2013

(87) PCT Pub. No.: WO2012/058127
PCT Pub. Date: May 3, 2012

(65) Prior Publication Data
US 2013/0237518 A1    Sep. 12, 2013

Related U.S. Application Data

(60) Provisional application No. 61/408,092, filed on Oct. 29, 2010.

(51) Int. Cl.
| | | |
|---|---|---|
| A61K 31/397 | (2006.01) |
| A61K 31/5377 | (2006.01) |
| A61K 31/506 | (2006.01) |
| A61K 31/4545 | (2006.01) |
| A61K 31/454 | (2006.01) |
| A61K 31/4523 | (2006.01) |
| A61K 31/4427 | (2006.01) |
| A61K 31/4439 | (2006.01) |
| A61K 31/444 | (2006.01) |
| C07D 413/14 | (2006.01) |
| C07D 401/14 | (2006.01) |
| C07D 403/14 | (2006.01) |
| C07D 221/00 | (2006.01) |
| C07D 221/02 | (2006.01) |
| C07D 211/80 | (2006.01) |
| C07D 405/14 | (2006.01) |
| C07D 409/14 | (2006.01) |
| C07D 417/14 | (2006.01) |
| C07D 471/04 | (2006.01) |
| A61K 45/06 | (2006.01) |

(52) U.S. Cl.
CPC ............ *C07D 401/14* (2013.01); *C07D 405/14* (2013.01); *C07D 409/14* (2013.01); *C07D 413/14* (2013.01); *C07D 417/14* (2013.01); *C07D 471/04* (2013.01); *A61K 31/444* (2013.01); *A61K 31/454* (2013.01); *A61K 31/4545* (2013.01); *A61K 31/5377* (2013.01); *A61K 45/06* (2013.01)

(58) Field of Classification Search
USPC ......... 514/210.18, 233.8, 256, 300, 303, 318, 514/321, 333; 544/124, 333; 546/112, 113, 546/119, 121, 194, 199
See application file for complete search history.

(56) References Cited

U.S. PATENT DOCUMENTS

| | | | |
|---|---|---|---|
| 8,252,811 B2 * | 8/2012 | Xie et al. .................... 514/299 |
| 2005/0009876 A1 | 1/2005 | Bhagwat et al. |
| 2009/0118284 A1 | 5/2009 | Cooper et al. |

OTHER PUBLICATIONS

Ohori et al., Identification of a selective ERK inhibitor and structural determination of the inhibitor-ERK2 complex. Biochemical and Biophysical Research Communications, 2005, vol. 336, Issue 1, pp. 357-363; p. 359, col. 2, para 2 to p. 362, col. 2, para 1; p. 361, Fig 3.
International Search Report and the Written Opinion, PCT/US11/57414, date of mailing Feb. 27, 2013—8 pages.

\* cited by examiner

*Primary Examiner* — Samantha Shterengarts
(74) *Attorney, Agent, or Firm* — Richard S. Parr; Laura M. Ginkel

(57) ABSTRACT

Disclosed are the ERK inhibitors of formula (1): and the pharmaceutically acceptable salts thereof, wherein: A is a five membered monocyclic heteroaryl ring; and B is a monocyclic heterocycloalkyl ring, or a monocyclic heterocycloalkenyl ring, or a bridged monocyclic heterocycloalkyl ring, or a fused (monocyclic heterocycloalkyl ring) cyclopropyl ring. Also disclosed are methods of treating cancer using the compounds of formula (1).

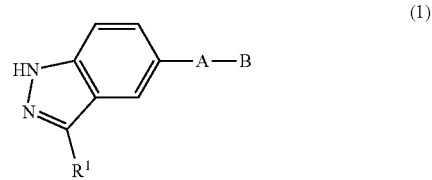

(1)

6 Claims, No Drawings

US 8,999,966 B2

COMPOUNDS THAT ARE ERK INHIBITORS

REFERENCE TO RELATED APPLICATION

This application claims the benefit of U.S. Provisional Application Ser. No. 61/408,092 filed Oct. 29, 2010.

BACKGROUND

The processes involved in tumor growth, progression, and metastasis are mediated by signaling pathways that are activated in cancer cells. The ERK pathway plays a central role in regulating mammalian cell growth by relaying extracellular signals from ligand-bound cell surface tyrosine kinase receptors such as erbB family, PDGF, FGF, and VEGF receptor tyrosine kinase. Activation of the ERK pathway is via a cascade of phosphorylation events that begins with activation of Ras. Activation of Ras leads to the recruitment and activation of Raf, a serine-threonine kinase. Activated Raf then phosphorylates and activates MEK1/2, which then phosphorylates and activates ERK1/2. When activated, ERK1/2 phosphorylates several downstream targets involved in a multitude of cellular events including cytoskeletal changes and transcriptional activation. The ERK/MAPK pathway is one of the most important for cell proliferation, and it is believed that the ERK/MAPK pathway is frequently activated in many tumors. Ras genes, which are upstream of ERK1/2, are mutated in several cancers including colorectal, melanoma, breast and pancreatic tumors. The high Ras activity is accompanied by elevated ERK activity in many human tumors. In addition, mutations of BRAF, a serine-threonine kinase of the Raf family, are associated with increased kinase activity. Mutations in BRAF have been identified in melanomas (60%), thyroid cancers (greater than 40%) and colorectal cancers. These observations indicate that the ERK1/2 signalling pathway is an attractive pathway for anticancer therapies in a broad spectrum of human tumours.

Therefore, a welcome contribution to the art would be small-molecules (i.e., compounds) that inhibit ERK activity (i.e., ERK1 and ERK2 activity), which small-molecules would be useful for treating a broad spectrum of cancers, such as, for example, melanoma, pancreatic cancer, thyroid cancer, colorectal cancer, lung cancer, breast cancer, and ovarian cancer. Such a contribution is provided by this invention.

SUMMARY OF THE INVENTION

This invention provides compounds that inhibit the activity of ERK1 and/or the activity of ERK2. The compounds of this invention also inhibit the phosphorylation of ERK1 and ERK2.

Thus, this invention provides compounds that are ERK inhibitors (i.e., ERK1 inhibitors and/or ERK2 inhibitors), said compounds being of the formula (1):

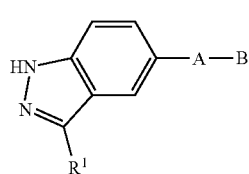

(1)

or the pharmaceutically acceptable salts, esters, solvates, and prodrugs thereof, wherein: (1) A is a five membered monocyclic heteroaryl ring; (2) B is a monocyclic heterocycloalkyl ring, a monocyclic heterocycloalkenyl ring, a bridged monocyclic heterocycloalkyl ring, or a fused heterocyloalkylcyclopropyl ring (i.e., a monocyclic ring heterocycloalkyl ring fused to a cyclopropyl ring); and (3) $R^1$ is an aryl ring, a monocyclic heteroaryl ring, a fused heteroarylaryl ring (i.e., monocyclic heteroaryl ring fused to an aryl ring), a fused heteroarylheteroaryl ring (i.e., a monocyclic heteroaryl ring fused to a monocyclic heteroaryl ring), or a fused arylheterocycloalkyl ring (i.e., an aryl ring fused to a monocyclic heterocycloalkyl ring).

This invention provides: (1) compounds of formula (1); (2) compounds of formula (1) in pure or isolated form; (3) pharmaceutically acceptable salts of the compounds of formula (1); (4) solvates of the compounds of formula (1); (5) compounds of formula (1) wherein from one to all of the hydrogens are deuterium; (6) compounds of formula (1) wherein at least one H is deuterium; (7) compounds of formula (1) wherein 1 to 5H are deuterium; (8) compounds of formula (1) wherein 1 to 2H are deuterium; and (9) compounds of formula (1) wherein one H is deuterium.

This invention also provides compounds of formulas (200) to (384).

This invention also provides a pharmaceutical composition comprising an effective amount of at least one (e.g., 1) compound of formula (1) and a pharmaceutically acceptable carrier. This invention also provides a pharmaceutical composition comprising an effective amount of at least one (e.g., 1) compound of formula (1) and an effective amount of at least one (e.g., 1) other pharmaceutically active ingredient (such as, for example, a chemotherapeutic agent), and a pharmaceutically acceptable carrier.

This invention also provides a method of inhibiting ERK (i.e., inhibiting the activity of ERK1 and/or ERK2) in a patient in need of such treatment comprising administering to said patient an effective amount of at least one (e.g., 1) compound of formula (1). In one example ERK 1 is inhibited, in another example ERK 2 is inhibited, and in another example ERK 1 and 2 are inhibited.

This invention also provides a method for treating cancer in a patient in need of such treatment, said method comprising administering to said patient an effective amount of at least one (e.g., 1) compound of formula (1). This invention also provides a method for treating cancer in a patient in need of such treatment, said method comprising administering to said patient an effective amount of at least one (e.g., 1) compound of formula (1), in combination with an effective amount of at least one chemotherapeutic agent. The methods of this invention include the administration of a pharmaceutical composition comprising at least one (e.g., 1) compound of this invention and a pharmaceutically acceptable carrier. This invention also provides any of the above methods of treating cancer wherein the cancer is colo-rectal. This invention also provides any of the above methods of treating cancer wherein the cancer is melanoma.

The methods of treating cancers described herein can optionally include the administration of an effective amount of radiation (i.e., the methods of treating cancers described herein optionally include the administration of radiation therapy).

DETAILED DESCRIPTION OF THE INVENTION

All patents, publications and pending patent applications identified herein are hereby incorporated by reference.

As described herein, unless otherwise indicated, the use of a drug or compound in a specified period is per treatment cycle. For example, once a day means once per day of each day of the treatment cycle, and once a week means one time per week during the treatment cycle.

The following abbreviations have the following meanings unless defined otherwise: t-BuOH is tert-butyl alcohol; DBU is 1,8-diazabicyclo[5.4.0]undec-7-ene; DCM is dichloromethane; DIPEA is diisopropylethylamine; DMAP is 4-dimethylaminopyridine; DMF is dimethylformamide; DMSO is dimethyl sulfoxide; Dppf is 1,1'-bis(diphenylphosphino)-ferrocene; Et is ethyl; EtOAc is ethyl acetate; EtOH is ethanol; HATU is N,N,N',N'-tetramethyl-O-(7-azabenzotriazol-1-yl)uranium hexafluorophosphate; HPLC is high pressure liquid chromatography; LCMS is liquid chromatography mass spectrometry; LDA is lithium diisopropylamide; Me is methyl; MeOH is methanol; SM is starting material; TBAF is tetrabutylammonium fluoride; TIPS-acetylene is triisopropylsilyl acetylene; Tr is triphenyl methane; TFA is trifluoroacetic acid; THF is tetrahydrofuran; and TLC is thin layer chromatography.

As used herein, unless otherwise specified, the terms below have the meaning indicated.

The term "composition" is intended to encompass a product comprising the specified ingredients in the specified amounts, as well as any product which results, directly or indirectly, from combination of the specified ingredients in the specified amounts.

The term "anti-cancer agent" means a drug (medicament or pharmaceutically active ingredient) for treating cancer.

The term "antineoplastic agent" means a drug (medicament or pharmaceutically active ingredient) for treating cancer (i.e., a chemotherapeutic agent).

The term "at least one", as used in reference to the number of compounds of this invention, or the number of chemotherapeutic agents, means one or more than one. In one example "at least one" means 1-4, and in another example 1-3, and in another example 1-2, and in another example 1. The meaning of 'at least one" for the compounds is independent of the meaning for the chemotherapeutic agents.

The term "chemotherapeutic agent" means a drug (medicament or pharmaceutically active ingredient) for treating cancer (i.e., and antineoplastic agent);

The term "compound" with reference to the antineoplastic agents, includes the agents that are antibodies.

The term "concurrently" means (1) simultaneously in time (e.g., at the same time); or (2) at different times during the course of a common treatment schedule.

The term "consecutively" means one following the other.

The term "different" as used in the phrase "different antineoplastic agents" means that the agents are not the same compound or structure; preferably, "different" as used in the phrase "different antineoplastic agents" means not from the same class of antineoplastic agents; for example, one antineoplastic agent is a taxane, and another antineoplastic agent is a platinum coordinator compound.

The term "effective amount" means a "therapeutically effective amount". The term "therapeutically effective amount" means that amount of active compound or pharmaceutical agent that elicits the biological or medicinal response in a tissue, system, animal or human that is being sought by a researcher, veterinarian, medical doctor or other clinician. Thus, for example, in the methods of treating cancer described herein "effective amount" (or "therapeutically effective amount") means, the amount of the compound (or drug), or radiation, that results in: (a) the reduction, alleviation or disappearance of one or more symptoms caused by the cancer, (b) the reduction of tumor size, (c) the elimination of the tumor, and/or (d) long-term disease stabilization (growth arrest) of the tumor. Also, for example, an effective amount, or a therapeutically effective amount of the ERK inhibitor (i.e., a compound of this invention) is that amount which results in the reduction in ERK (ERK1 and/or ERK2) activity and phosphorylation. The reduction in ERK activity may be determined by the analysis of pharmacodynamic markers such as phosphorylated RSK1,2 and phosphorylated ERK1, 2, using techniques well known in the art.

The term "treating cancer" or "treatment of cancer" refers to administration to a mammal afflicted with a cancerous condition and refers to an effect that alleviates the cancerous condition by killing the cancerous cells, and also refers to an effect that results in the inhibition of growth and/or metastasis of the cancer.

The term "one or more" has the same meaning as "at least one".

The term "patient" means an animal, such as a mammal (e.g., a human being, and preferably a human being).

The term sequentially-represents (1) administration of one component of the method ((a) compound of the invention, or (b) chemotherapeutic agent, signal transduction inhibitor and/or radiation therapy) followed by administration of the other component or components. After administration of one component, the next component can be administered substantially immediately after the first component, or the next component can be administered after an effective time period after the first component. The effective time period is the amount of time given for realization of maximum benefit from the administration of the first component.

The term "solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like; "hydrate" is a solvate wherein the solvent molecule is $H_2O$.

The term "fused" as in, for example, "fused heteroarylaryl" means a monocyclic heteroaryl ring fused to an aryl ring (i.e., both rings having two atoms in common).

The term "monocyclic", as used to describe a ring, means the ring is a single ring (i.e., the ring is not a fused ring). Thus, for example, a "monocyclic heteroaryl ring" means a single heteroaryl ring. A bridged monocyclic ring means a monocyclic ring wherein two atoms in the ring are connected by a bridge. Thus, for example, a "bridged monocyclic heterocycloalkyl ring" means a monocyclic heterocycloalkyl ring wherein two atoms in the ring are connected by a bridge.

The term "administration" and variants thereof (e.g., "administering" a compound) in reference to a compound of the invention means introducing the compound or a prodrug of the compound into the system of the animal in need of treatment. When a compound of the invention or prodrug thereof is provided in combination with one or more other active agents (e.g., a cytotoxic agent, etc.), "administration" and its variants are each understood to include concurrent and sequential introduction of the compound or prodrug thereof and other agents.

As used herein, unless otherwise specified, the terms below have the meanings indicated, and unless otherwise specified, the definitions of each term (i.e., moiety or substituent) apply when that term is used individually or as a component of another term (e.g., the definition of aryl is the same for aryl and for the aryl portion of arylheterocycloalkyl, and the like).

The term "alkoxy" means an alkyl-O— group (i.e., the bond to the parent moiety is through the ether oxygen) in which the alkyl group is as defined below. Non-limiting examples of suitable alkoxy groups include methoxy, ethoxy, n-propoxy, isopropoxy, n-butoxy and heptoxy.

The term "alkyl" (including the alkyl portions of other moieties, such as alkoxy) means an aliphatic hydrocarbon group (chain) that can be straight or branched wherein said group comprises about 1 to about 20 carbon atoms in the chain. In one example said alkyl group comprises about 1 to about 12 carbon atoms in the chain, in another example about 1 to about 6 carbon atoms in the chain; in another example 1 to about 4 carbon atoms in the chain; and in another example 1 to about 2 carbon atoms in the chain. Branched alkyl means that one or more lower alkyl groups, such as methyl, ethyl or propyl, are attached to a linear alkyl chain. "Lower alkyl" means a group comprising about 1 to about 6 carbon atoms in the chain, and said chain can be straight or branched.

The term "alkylene" (including the alkylene portions of other moieties, such as -alkylene-aryl) means a chain comprising at least one —(CH$_2$)— group. Examples of alkylene chains include, but are not limited to: —(CH$_2$)$_{1-6}$—, —(CH$_2$)$_{1-4}$—, —(CH$_2$)$_{1-2}$— and —(CH$_2$)—.

The term "amino" means an —NH$_2$ group.

The term "aryl" (sometimes abbreviated "ar") (including the aryl portion of fused heteroarylaryl and fused arylheterocycloalkyl) means an aromatic monocyclic or multicyclic ring system comprising about 6 to about 14 carbon atoms, preferably about 6 to about 10 carbon atoms. Non-limiting examples of suitable aryl groups include phenyl and naphthyl.

The term "cycloalkyl" means a non-aromatic mono- or multicyclic ring system comprising about 3 to about 7 carbon atoms, preferably about 3 to about 6 carbon atoms. Non-limiting examples of suitable monocyclic cycloalkyls include cyclopropyl, cyclopentyl, cyclohexyl, cycloheptyl and the like. Non-limiting examples of suitable multicyclic cycloalkyls include 1-decalin, norbornyl, adamantyl and the like.

The term "halo" means fluoro, chloro, bromo, or iodo groups. Preferred halos are fluoro, chloro or bromo, and more preferred are fluoro and chloro.

The term "halogen" means fluorine, chlorine, bromine, or iodine. Preferred halogens are fluorine, chlorine and bromine.

The term "heteroaryl" means an aromatic monocyclic or multicyclic ring system comprising about 5 to about 14 ring atoms, preferably about 5 to about 10 ring atoms, in which one or more of the ring atoms is an element other than carbon, for example nitrogen, oxygen or sulfur, alone or in combination. Preferred heteroaryls comprise about 5 to about 6 ring atoms. The prefix aza, oxa or thia before the heteroaryl root name means that at least a nitrogen, oxygen or sulfur atom, respectively, is present as a ring atom. A nitrogen atom of a heteroaryl can be optionally oxidized to the corresponding N-oxide. Non-limiting examples of suitable heteroaryls include pyridyl, pyrazinyl, furanyl, thienyl, pyrimidinyl, isoxazolyl, isothiazolyl, oxazolyl, thiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl, furopyridine

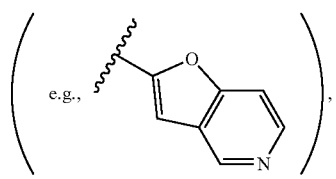

e.g., and the like.

The term "fused heteroarylaryl" means a monocyclic heteroaryl ring fused to an aryl ring (i.e., the heteroaryl ring and the aryl ring have two atoms in common).

The term "fused heteroarylheteroarylaryl" means a monocyclic heteroaryl ring fused to a monocyclic heteroaryl ring (i.e., the two heteoaryl rings have two atoms in common).

The term "fused arylheterocycloalkyl" means a monocyclic aryl ring fused to a monocyclic heterocycloalkyl ring (i.e., the aryl and heterocycloalkyl rings have two atoms in common).

The term "heterocycloalkenyl" (or "heterocyclenyl") means a non-aromatic monocyclic or multicyclic ring system comprising about 3 to about 10 ring atoms, preferably about 5 to about 10 ring atoms, in which one or more of the atoms in the ring system is an element other than carbon (for example one or more heteroatoms independently selected from the group consisting of nitrogen, oxygen and sulfur atom), and which contains at least one carbon-carbon double bond or carbon-nitrogen double bond; there are no adjacent oxygen and/or sulfur atoms present in the ring system. Preferred heterocyclenyl rings contain about 5 to about 6 ring atoms. The prefix aza, oxa or thia before the heterocyclenyl root name means that at least a nitrogen, oxygen or sulfur atom, respectively, is present as a ring atom. The nitrogen or sulfur atom of the heterocyclenyl can be optionally oxidized to the corresponding N-oxide, S-oxide or S,S-dioxide. Non-limiting examples of suitable monocyclic azaheterocyclenyl groups include 1,2,3,4-tetrahydropyridine, 1,2-dihydropyridyl, 1,4-dihydropyridyl, 1,2,3,6-tetrahydropyridine, 1,4,5,6-tetrahydropyrimidine, 2-pyrrolinyl, 3-pyrrolinyl, 2-imidazolinyl, 2-pyrazolinyl, and the like. Non-limiting examples of suitable oxaheterocyclenyl groups include 3,4-dihydro-2H-pyran, dihydrofuranyl, fluorodihydrofuranyl, and the like. A non-limiting example of a suitable multicyclic oxaheterocyclenyl group is 7-oxabicyclo[2.2.1]heptenyl; non-limiting examples of suitable monocyclic thiaheterocyclenyl rings include dihydrothiophenyl, dihydrothiopyranyl, and the like.

The term "heterocycloalkyl" (or "heterocyclyl") means a non-aromatic saturated monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur, alone or in combination. There are no adjacent oxygen and/or sulfur atoms present in the ring system. Preferred heterocyclyls contain about 5 to about 6 ring atoms. The prefix aza, oxa or thia before the heterocyclyl root name means that at least a nitrogen, oxygen or sulfur atom respectively is present as a ring atom. The nitrogen or sulfur atom of the heterocyclyl can be optionally oxidized to the corresponding N-oxide, S-oxide or S,S-dioxide. Non-limiting examples of suitable monocyclic heterocyclyl rings include piperidyl, pyrrolidinyl, piperazinyl, morpholinyl, thiomorpholinyl, thiazolidinyl, 1,3-dioxolanyl, 1,4-dioxanyl, tetrahydrofuranyl, tetrahydrothiophenyl, tetrahydrothiopyranyl, and the like.

The term "bridged heterocycloalkyl" (or "bridged heterocyclyl") means a heterocycloalkyl group as defined above having an alkylene chain (generally a 1 or 2 carbon alkylene chain, not counting the atoms in the ring to which the alkylene chain is bound to) bridging two carbon atoms in the ring.

Any carbon or heteroatom with unsatisfied valences in the text, schemes, examples, structural formulae, and any tables herein is assumed to have the hydrogen atom or atoms to satisfy the valences. And any one or more of these hydrogen atoms can be deuterium.

Those skilled the art will appreciate that formulas showing a bond that does not have a substituent at the end of the bond represents a methyl group. Thus, for example,

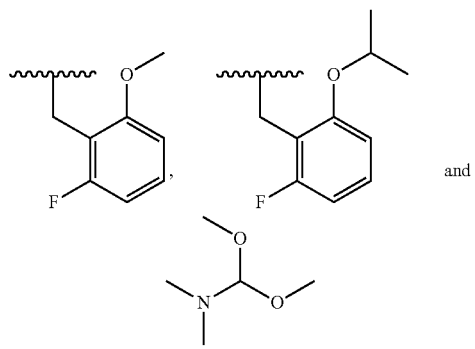

represent the same moieties as:

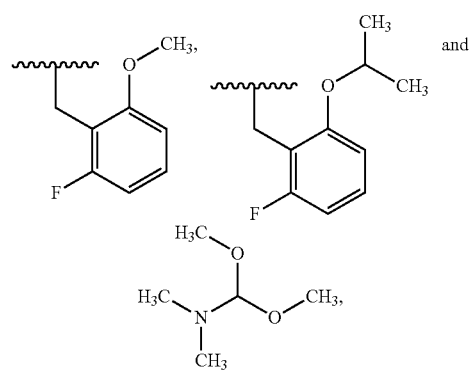

respectively.

One or more compounds of the invention may also exist as, or be optionally converted to, a solvate. Preparation of solvates is generally known. Thus, for example, M. Caira et al, *J. Pharmaceutical Sci.*, 93(3), 601-611 (2004) describe the preparation of the solvates of the antifungal fluconazole in ethyl acetate as well as from water. Similar preparations of solvates, hemisolvate, hydrates and the like are described by E. C. van Tonder et al, *AAPS PharmSciTech.*, 5(1), article 12 (2004); and A. L. Bingham et al, *Chem. Commun.*, 603-604 (2001). A typical, non-limiting, process involves dissolving the inventive compound in desired amounts of the desired solvent (organic or water or mixtures thereof) at a higher than ambient temperature, and cooling the solution at a rate sufficient to form crystals which are then isolated by standard methods. Analytical techniques such as, for example I. R. spectroscopy, show the presence of the solvent (or water) in the crystals as a solvate (or hydrate).

The term "pharmaceutical composition" is also intended to encompass both the bulk composition and individual dosage units comprised of more than one (e.g., two) pharmaceutically active agents such as, for example, a compound of the present invention and an additional agent selected from the lists of the additional agents described herein, along with any pharmaceutically inactive excipients. The bulk composition and each individual dosage unit can contain fixed amounts of the afore-said "more than one pharmaceutically active agents". The bulk composition is material that has not yet been formed into individual dosage units. An illustrative dosage unit is an oral dosage unit such as tablets, capsules, pills and the like. Similarly, the herein-described methods of treating a patient by administering a pharmaceutical composition of the present invention is also intended to encompass the administration of the afore-said bulk composition and individual dosage units.

The compounds of the present invention may have asymmetric centers, chiral axes, and chiral planes (as described in: E. L. Eliel and S. H. Wilen, Stereochemistry of Carbon Compounds, John Wiley & Sons, New York, 1994, pages 1119-1190), and occur as racemates, racemic mixtures, and as individual diastereomers, with all possible isomers and mixtures thereof, including optical isomers, being included in the present invention. In addition, the compounds disclosed herein may exist as tautomers and both tautomeric forms are intended to be encompassed by the scope of the invention, even though only one tautomeric structure is depicted. Also, for example, all keto-enol and imine-enamine forms of the compounds are included in the invention.

Tautomeric forms such as, for example, the moieties:

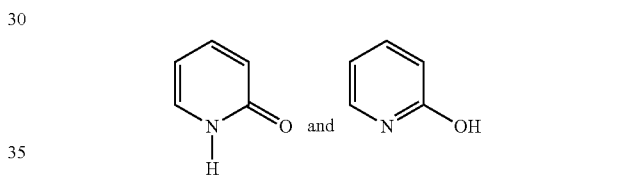

are considered equivalent in certain embodiments of this invention.

Thus, all stereoisomers (for example, geometric isomers, optical isomers and the like) of the present compounds (including those of the salts, solvates and prodrugs of the compounds as well as the salts and solvates of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention. Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the *IUPAC* 1974 Recommendations. The use of the terms "salt", "solvate" "prodrug" and the like, is intended to equally apply to the salt, solvate and prodrug of enantiomers, stereoisomers, rotamers, tautomers, racemates or prodrugs of the inventive compounds.

Diasteromeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Also, some of the compounds of Formula (1) may be atropisomers and are considered as part of this invention. Enantiomers can also be separated by use of chiral HPLC column.

When any variable (e.g. $R^3$, etc.) occurs more than one time in any constituent, its definition on each occurrence is independent at every other occurrence. Also, combinations of substituents and variables are permissible only if such combinations result in stable compounds. Lines drawn into the ring systems from substituents indicate that the indicated bond may be attached to any of the substitutable ring atoms. If the ring system is bicyclic, it is intended that the bond be attached to any of the suitable atoms on either ring of the bicyclic moiety.

It is understood that substituents and substitution patterns on the compounds of the instant invention can be selected by one of ordinary skill in the art to provide compounds that are chemically stable and that can be readily synthesized by techniques known in the art, as well as those methods set forth below, from readily available starting materials. If a substituent is itself substituted with more than one group, it is understood that these multiple groups may be on the same carbon or on different carbons, so long as a stable structure results. Also, "optionally substituted" means optional substitution with the specified groups, radicals or moieties.

It is understood that one or more silicon (Si) atoms can be incorporated into the compounds of the instant invention in place of one or more carbon atoms by one of ordinary skill in the art to provide compounds that are chemically stable and that can be readily synthesized by techniques known in the art from readily available starting materials. Carbon and silicon differ in their covalent radius leading to differences in bond distance and the steric arrangement when comparing analogous C-element and Si-element bonds. These differences lead to subtle changes in the size and shape of silicon-containing compounds when compared to carbon. One of ordinary skill in the art would understand that size and shape differences can lead to subtle or dramatic changes in potency, solubility, lack of off target activity, packaging properties, and so on. (Diass, J. O. et al. Organometallics (2006) 5:1188-1198; Showell, G. A. et al. Bioorganic & Medicinal Chemistry Letters (2006) 16:2555-2558).

Prodrugs of the compounds of the invention are also contemplated herein. The term "prodrug", as employed herein, denotes a compound that is a drug precursor which, upon administration to a subject, undergoes chemical conversion by metabolic or chemical processes to yield a compound of formula (1) or a salt and/or solvate thereof. A discussion of prodrugs is provided in T. Higuchi and V. Stella, *Pro-drugs as Novel Delivery Systems* (1987) 14 of the A.C.S. Symposium Series, and in *Bioreversible Carriers in Drug Design*, (1987) Edward B. Roche, ed., American Pharmaceutical Association and Pergamon Press, both of which are incorporated herein by reference thereto.

This invention also includes the compounds of this invention in isolated and purified form.

Polymorphic forms of the compounds of formula (1), and of the salts, solvates and prodrugs of the compounds of formula (1), are intended to be included in the present invention.

The pharmaceutically acceptable salts of the instant compounds can be synthesized from the compounds of this invention which contain a basic or acidic moiety by conventional chemical methods. Generally, the salts of the basic compounds are prepared either by ion exchange chromatography or by reacting the free base with stoichiometric amounts or with an excess of the desired salt-forming inorganic or organic acid in a suitable solvent or various combinations of solvents. Similarly, the salts of the acidic compounds are formed by reactions with the appropriate inorganic or organic base.

Thus, pharmaceutically acceptable salts of the compounds of this invention include the conventional non-toxic salts of the compounds of this invention as formed by reacting a basic instant compound with an inorganic or organic acid. For example, conventional non-toxic salts include those derived from inorganic acids such as hydrochloric, hydrobromic, sulfuric, sulfamic, phosphoric, nitric and the like, as well as salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxy-benzoic, fumaric, toluenesulfonic, methanesulfonic, ethane disulfonic, oxalic, isethionic, trifluoroacetic (TFA) and the like.

When the compound of the present invention is acidic, suitable "pharmaceutically acceptable salts" refers to salts prepared form pharmaceutically acceptable non-toxic bases including inorganic bases and organic bases. Salts derived from inorganic bases include aluminum, ammonium, calcium, copper, ferric, ferrous, lithium, magnesium, manganic salts, manganous, potassium, sodium, zinc and the like. Particularly preferred are the ammonium, calcium, magnesium, potassium and sodium salts. Salts derived from pharmaceutically acceptable organic non-toxic bases include salts of primary, secondary and tertiary amines, substituted amines including naturally occurring substituted amines, cyclic amines and basic ion exchange resins, such as arginine, betaine caffeine, choline, N,N'-dibenzylethylenediamine, diethylamin, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine tripropylamine, tromethamine and the like.

The preparation of the pharmaceutically acceptable salts described above and other typical pharmaceutically acceptable salts is more fully described by Berg et al., "Pharmaceutical Salts," *J. Pharm. Sci.*, 1977:66:1-19.

It will also be noted that the compounds of the present invention are potentially internal salts or zwitterions, since under physiological conditions a deprotonated acidic moiety in the compound, such as a carboxyl group, may be anionic, and this electronic charge might then be balanced off internally against the cationic charge of a protonated or alkylated basic moiety, such as a quaternary nitrogen atom.

All such acid and base salts are intended to be pharmaceutically acceptable salts within the scope of the invention and all acid and base salts are considered equivalent to the free fauns of the corresponding compounds for purposes of the invention.

In hetero-atom containing ring systems of this invention, there are no hydroxyl groups on carbon atoms adjacent to a N, O or S, and there are no N or S groups on carbon adjacent to another heteroatom. Thus, for example, in the ring:

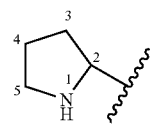

there is no —OH attached directly to carbons marked 2 and 5.

The term "purified", "in purified form" or "in isolated and purified form" for a compound refers to the physical state of said compound after being isolated from a synthetic process or natural source or combination thereof. Thus, the term "purified", "in purified form" or "in isolated and purified form" for a compound refers to the physical state of said compound after being obtained from a purification process or processes described herein or well known to the skilled artisan, in sufficient purity to be characterizable by standard analytical techniques described herein or well known to the skilled artisan.

When a functional group in a compound is termed "protected", this means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in organic Synthesis* (1991), Wiley, New York.

The present invention also embraces isotopically-labelled compounds of the present invention which are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, fluorine, chlorine, and iodine, such as $^2$H, $^3$H, $^{11}$C, $^{13}$C, $^{14}$C, $^{15}$N, $^{18}$O, $^{17}$O, $^{31}$P, $^{32}$P, $^{35}$S, $^{18}$F, $^{36}$Cl, and $^{123}$I, respectively.

Certain isotopically-labelled compounds of formula (1) (e.g., those labeled with $^3$H and $^{14}$C) are useful in compound and/or substrate tissue distribution assays. Tritiated (i.e., $^3$H) and carbon-14 (i.e., $^{14}$C) isotopes are particularly preferred for their ease of preparation and detectability. Certain isotopically-labelled compounds of Formula (1) can be useful for medical imaging purposes. E.g., those labeled with positron-emitting isotopes like $^{11}$C or $^{18}$F can be useful for application in Positron Emission Tomography (PET) and those labeled with gamma ray emitting isotopes like $^{123}$I can be useful for application in Single photon emission computed tomography (SPECT). Further, substitution with heavier isotopes such as deuterium (i.e., $^2$H) may afford certain therapeutic advantages resulting from greater metabolic stability (e.g., increased in vivo half-life or reduced dosage requirements) and hence may be preferred in some circumstances. Isotopically labeled compounds of Formula (I), in particular those containing isotopes with longer half lives (T½>1 day), can generally be prepared by following procedures analogous to those disclosed in the Schemes and/or in the Examples herein below, by substituting an appropriate isotopically labeled reagent for a non-isotopically labeled reagent.

This invention provides compounds of formula (1):

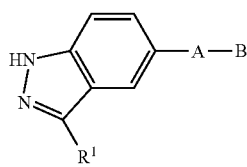

(1)

or a pharmaceutically acceptable salt thereof, wherein:
$R^1$ is selected from the group consisting of: (1) aryl, (2) monocyclic heteroaryl rings, (3) fused heteroarylaryl rings, (4) fused heteroarylheteroaryl rings, and (5) fused arylheterocycloalkyl rings; and said $R^1$ groups are optionally substituted with 1 to 3 substituents independently selected from the group consisting of: (a) —$CF_3$, (b) alkyl, (c) alkyl substituted with hydroxy, (d) cycloalkyl, alkoxy, (e) —$SO_2N(R^6)_2$, (f) =O, (g) —$N(R^8)_2$, (h) halo, (i) —$SO_2R^{10}$, (j) —$SOR^{10}$, (k) alkyl substituted with halo, (l) —$SR^{12}$, (m) —OH, and (n) —$N(R^{14})C(O)R^{16}$;

A is a five membered monocyclic heteroaryl ring comprising 1 to 4 heteroatoms independently selected from the group consisting of: N, O and S, and the remaining non-heteroatoms are carbon; and said A ring is optionally substituted with 1 to 3 substituents independently selected from the group consisting of: (a) alkyl, (b) aryl and (c) —O-alkyl;

B is a ring selected from the group consisting of: (1) monocyclic heterocycloalkyl rings, (2) monocyclic heterocycloalkenyl rings, (3) bridged monocyclic heterocycloalkyl rings, and (4) fused (monocyclic heterocycloalkyl)cyclopropyl rings; and said B ring comprises 1 to 4 heteroatoms wherein one heteroatom is —$NR^4$—, and when there is more than one heteroatom, the remaining heteroatoms are independently selected from the group consisting of: —$NR^5$—, O and S, SO, and $SO_2$, and the remaining non-heteroatoms in the ring are carbon; and said B rings are optionally substituted with 1 to 3 (in one example 3, in another example 2, and in another example one, and in another example none) $R^3$ substitutents independently selected from the group consisting of: (a) alkyl, (b) aryl, (c) —C(O)—($C_1$-$C_6$)alkyl, (d) —$SR^{18}$, (e) —C(O)—($C_3$-$C_6$)cycloalkyl, (f) —$N(R^{18})_2$, (g) —NH—C(O)—$R^{18}$, (h) —NH—S(O)$_2R^{18}$, (i) —C(O)—$N(R^{20})_2$ and (j) =O;

$R^4$ is selected from the group consisting of: (1) —($C_1$-$C_2$)alkylene-aryl, (2) —C(O)-aryl, (3) —($C_1$-$C_2$)alkylene-heteroaryl, (4) —($C_1$-$C_2$)alkylene-(fused heteroarylaryl), (5) —($C_1$-$C_2$)alkylene-C(O)-heterocycloalkyl, (6) fused (aryl-cycloalkyl), (7) —($C_1$-$C_2$)alkylene-cycloalkyl, (8) —($C_1$-$C_2$)alkylene-(bridgedheterocycloalkyl), (9) —C(O)—($C_1$-$C_2$)alkylene-aryl, and (10) —C(O)—($C_1$-$C_2$)alkylene-aryl; and wherein said $R^4$ groups are optionally substituted with 1 to 5 substituents independently selected from the group consisting of: (a) alkyl, (b) alkoxy, (c) halo, (d) —O-alkylene-O-alkyl, (e) —O-alkylene-CN, (f) —O-(halo substituted alkyl), (g) —$NH_2$, (h) —O—($C_3$-$C_6$)cycloalkyl, (i) —S-alkyl, (j) —$N(R^{22})_2$, (k) —C(O)—($C_1$-$C_4$)alkyl, (l) —C(O)—$N(R^{18})_2$, (m) cycloalkyl, (n) —$CF_3$, (O)—$CF_2$, and (p) —CF; and wherein said fused heteroarylaryl moiety of (4) is a fused monocyclic heteroaryl ring fused to an aryl ring, said heterocycloalkyl moiety of (5) is a monocyclic ring, said fused (arylcycloalkyl) in (6) is a monocyclic aryl ring fused to a monocyclic cycloalkyl ring, and said heterocycloalkyl moiety of (8) (not including the bridge) is a monocyclic ring; and provided that when $R^4$ is substituted, and when the alkylene group of said $R^4$ group (1), (3), (4), (5), (7), or (8) is substituted, then the alkylene carbon bound to the nitrogen of the B ring for said $R^4$ groups (1), (3), (4), (5), (7), and (8) is not substituted with a heteroatom (i.e. said alkylene carbon atom bound to said nitrogen of said B ring is not substituted with O, halo (e.g., Cl, Br and F), or N);

each $R^5$ is independently selected from the group consisting of: (1) H, (2) ($C_1$-$C_4$)alkyl, (3) —C(O)—($C_1$-$C_4$)alkyl, and (4) —C(O)—$N(R^{18})_2$;

each $R^6$ is independently selected from the group consisting of: (1) alkyl, (2) cycloalkyl, (3) —$CF_3$, (4) —$CF_2$, and (5) —CF;

each $R^8$ is independently selected from the group consisting of: (1) H, (2) alkyl, and (3) cycloalkyl;

each $R^{10}$ is independently selected from the group consisting of: (1) alkyl, (2) cycloalkyl, and (3) —N($R^{18}$)$_2$;

each $R^{12}$ is independently selected from the group consisting of: (1) alkyl, and (2) cycloalkyl;

each $R^{14}$ is independently selected from the group consisting of: (1) H, (2) alkyl, and (3) cycloalkyl;

each $R^{16}$ is independently selected from the group consisting of: (1) alkyl, and (2) cycloalkyl;

each $R^{18}$ is independently selected from the group consisting of: (1) H, (2) ($C_1$-$C_4$)alkyl, and (3) ($C_3$-$C_6$)cycloalkyl;

each $R^{20}$ is independently selected from the group consisting of: (1) H, and (2) ($C_1$-$C_4$) alkyl; and (3) wherein each $R^{20}$ can be taken together, along with the nitrogen to which they are bonded, to form a heterocycloalkyl ring, wherein said heterocycloalkyl ring is optionally substituted with 1-2 independently selected halo atoms; and each $R^{22}$ is independently selected from the group consisting of: alkyl.

Examples of the A ring substituent (a) alkyl include but are not limited to methyl and ethyl. Examples of the A ring substituent (b) aryl include but are not limited to phenyl. Examples of the A ring substituent (c) —O-alkyl include but are not limited to —O—($C_1$-$C_4$)alkyl and —O—($C_2$-$C_2$ alkyl), and in one example —OCH$_3$, and in another example —OC$_2$H$_5$.

Examples of the B ring monocyclic heterocycloalkyl rings include but are not limited to 6 to 8 membered monocyclic heterocycloalkyl rings. Examples of the B ring monocyclic heterocycloalkenyl rings include but are not limited to 6-8 membered monocyclic heterocycloalkenyl rings comprising 1 double bond. Examples of the B ring bridged monocyclic heterocycloalkyl rings include but are not limited to 6 membered monocyclic heterocycloalkyl rings (excluding the bridge atoms) comprising a one or two carbon bridge. Examples of the B ring fused (monocyclic heterocycloalkyl) cyclopropyl rings include but are not limited to fused (6 to 8 membered monocyclic heterocycloalkyl)cyclopropyl rings.

In one embodiment said B ring is substituted with 3 of the optional substituents defined in formula (1). In another embodiment said B ring is substituted with 2 of the optional substituents defined in formula (1). In another embodiment said B ring is substituted with 1 of the optional substituents defined in formula (1). In another embodiment said B ring is not substituted with any of the optional substituents defined in formula (1).

Examples of the B ring substituent (a) alkyl include but are not limited to $C_1$ to $C_6$ alkyl, $C_1$ to $C_4$ alkyl, and $C_1$ to $C_2$ alkyl, and in one example —CH$_3$. Examples of the B ring substituent (b) aryl include but are not limited to $C_6$ to $C_{10}$ aryl and in one example phenyl. Examples of the B ring substituent (c) —C(O)—($C_1$-$C_6$)alkyl include but are not limited to —C(O)—($C_1$-$C_4$)alkyl and —C(O)—($C_1$-$C_2$)alkyl. Examples of the B ring substituent (i) —C(O)—N($R^{20}$)$_2$ include but are not limited to:

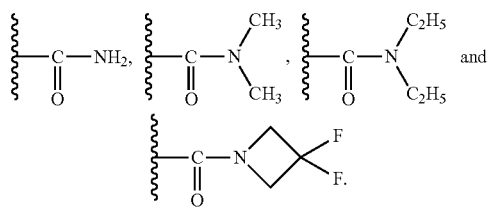

Examples of the $R^4$ substituent (a) alkyl include but are not limited to ($C_1$-$C_6$)alkyl, and in one example ($C_1$-$C_4$)alkyl, and in another example ($C_1$-$C_2$)alkyl, and in another example —CH$_3$, and in another example ethyl. Examples of the $R^4$ substituent (b) alkoxy include but are not limited to $C_1$-$C_4$ alkoxy, and in one example $C_1$-$C_2$ alkoxy, and in another example —OCH$_3$, and in another example —OCH(CH$_3$)$_2$. Examples of the $R^4$ substituent (c) halo include but are not limited to F, Cl, and Br, and in one example F, and in another example Cl. Examples of the $R^4$ substituent (d) —O-alkylene-O-alkyl include but are not limited to —O—(CH$_2$)$_2$—O—CH$_3$, and —O—(CH$_2$)$_3$—O—CH$_3$). Examples of the $R^4$ substituent (e) —O-alkylene-CN include but are not limited to —O—CH$_2$—CN. Examples of the $R^4$ substituent (f) —O-(halo substituted alkyl) include but are not limited to —OCF$_3$. Examples of the $R^4$ substituent (i) —S-alkyl include but are not limited to —S—($C_1$-$C_4$)alkyl, and in one example —S—($C_1$-$C_2$)alkyl. Examples of the $R^4$ substituent (k) —C(O)—($C_1$-$C_4$)alkyl include but are not limited to —C(O)—($C_1$-$C_2$) alkyl). Examples of the $R^4$ substituent (m) cycloalkyl include but are not limited to ($C_3$-$C_6$)cycloalkyl, and in one example cyclopropyl, and in another example cyclobutyl, and in another example cyclopentyl, and in another example cyclohexyl.

In one embodiment $R^4$ is not substituted. In another embodiment $R^4$ is substituted. In another embodiment $R^4$ is substituted but said substitution is not on the alkylene moiety of said $R^4$ groups (1), (3), (4), (5), (7), and (8). In another embodiment the alkylene group in said $R^4$ groups (1), (3), (4), (5), (7), and (8) is $C_1$ alkylene. In another embodiment the alkylene group in said $R^4$ groups (1), (3), (4), (5), (7), and (8) is —CH$_2$—.

Examples of said $R^5$ ($C_1$-$C_4$)alkyl include but are not limited to ($C_1$-$C_2$)alkyl). Examples of said $R^5$—C(O)—($C_1$-$C_4$) alkyl include but are not limited to —C(O)—($C_1$-$C_2$)alkyl.

Examples of said $R^6$ alkyl include but are not limited to ($C_1$-$C_4$)alkyl, and in one example ($C_1$-$C_2$)alkyl, and in another example —CH$_3$. Examples of said $R^6$ cycloalkyl include but are not limited to ($C_3$-$C_6$)cycloalkyl.

Examples of said $R^8$ alkyl include but are not limited to ($C_1$-$C_4$)alkyl, and in one example ($C_1$-$C_2$)alkyl. Examples of said cycloalkyl include but are not limited to ($C_3$-$C_6$)cycloalkyl.

Examples of said $R^{10}$ alkyl include but are not limited to ($C_1$-$C_4$)alkyl, and in one example ($C_1$-$C_2$)alkyl, and in another example —CH(CH$_3$)$_2$. Examples of said $R^{10}$ cycloalkyl include but are not limited to ($C_3$-$C_6$)cycloalkyl.

Examples of said $R^{12}$ alkyl include but are not limited to ($C_1$-$C_4$)alkyl, and in one example ($C_1$-$C_2$)alkyl, and in another example —CH(CH$_3$)$_2$). Examples of said $R^{12}$ cycloalkyl include but are not limited to ($C_3$-$C_6$)cycloalkyl.

Examples of said $R^{14}$ alkyl include but are not limited to ($C_1$-$C_4$)alkyl, and in one example ($C_1$-$C_2$)alkyl. Examples of said $R^{14}$ cycloalkyl include but are not limited to ($C_3$-$C_6$) cycloalkyl.

Examples of said $R^{16}$ alkyl include but are not limited to ($C_1$-$C_4$)alkyl, and in one example ($C_1$-$C_2$)alkyl. Examples of said $R^{16}$ cycloalkyl include but are not limited to ($C_3$-$C_6$) cycloalkyl.

Examples of said $R^{18}$ ($C_1$-$C_4$)alkyl include but are not limited to ($C_1$-$C_2$)alkyl, and in one example methyl, and in another example ethyl. Examples of said $R^{18}$ ($C_3$-$C_6$)cycloalkyl include but are not limited to cyclopropyl, cyclobutyl, cyclopentyl, and cyclohexyl. Thus, in one embodiment said cycloalkyl is cyclopropyl, in another embodiment cyclobutyl, in another embodiment cyclopentyl and in another embodiment cyclohexyl.

Examples of said $R^{20}$ ($C_1$-$C_4$) alkyl include but are not limited to ($C_1$-$C_2$)alkyl, and in one example methyl, and in another example ethyl. Examples of the heterocycloalkyl ring formed (when each of said $R^{20}$ groups are taken together with the nitrogen to which they are bonded) include but are not limited to 4 membered heterocycloalkyl rings. In one example the optional halo atoms on the heterocycloalkyl ring are F. In one example said heterocycloalkyl ring is substituted with 2 F atoms, and in another example said heterocycloalkyl ring is a 4 membered heterocycloalkyl ring substituted with two F atoms.

Examples of said $R^{22}$ alkyl include but are not limited to $C_1-C_4$)alkyl, and in one example ($C_1-C_2$)alkyl, and in another example methyl, and in another example ethyl.

In one embodiment of the invention said A ring is selected from the group consisting of: triazolyl, oxadiazolyl, thiadiazolyl, tetrazolyl, pyrazolyl, imidazolyl, and imidazolidinyl, and said A ring is optionally substituted as described above for formula (1).

Thus, in another embodiment of this invention said A ring is selected from the group consisting of:

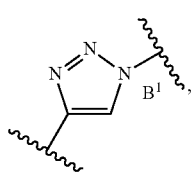 (2)

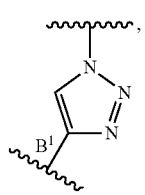 (3)

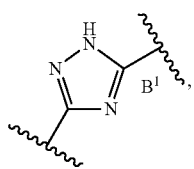 (4)

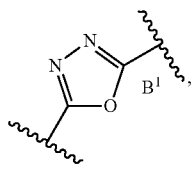 (5)

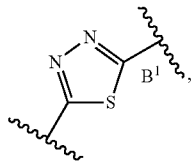 (6)

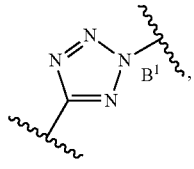 (7)

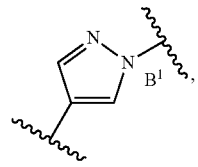 (8)

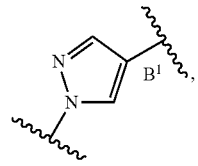 (9)

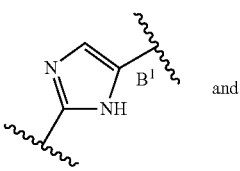 (10) and

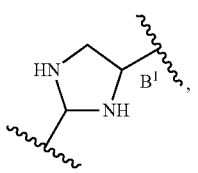 (11)

wherein $B^1$ indicates the bond to the B ring, and wherein said A ring is optionally substituted as described above for formula (1).

In another embodiment said A ring is selected from the group consisting of formulas (2) to (11) above, and said A rings are unsubstituted.

In another embodiment of this invention said A ring is selected from the group consisting of:

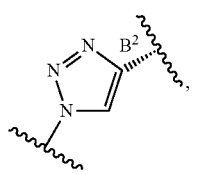 (12)

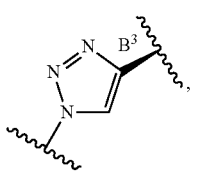 (13)

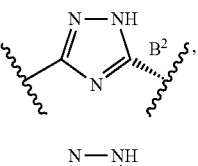 (14)

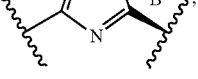 (15)

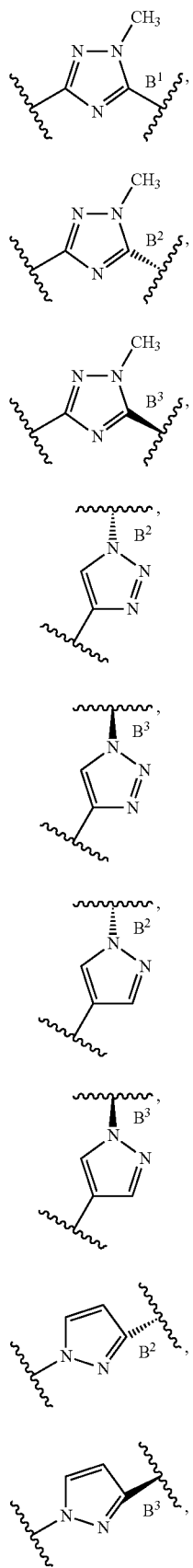

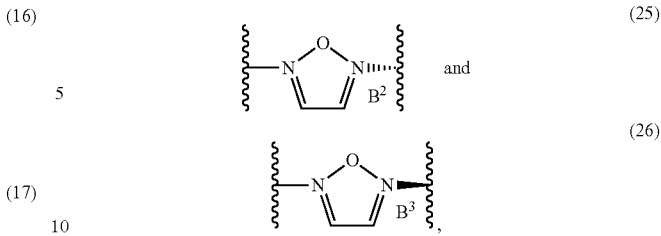

wherein $B^1$, $B^2$, and $B^3$ indicate the bond to the B ring.

In one embodiment said A ring is (2). In another embodiment said A ring is (3). In another embodiment said A ring is (4). In another embodiment said A ring is (5). In another embodiment said A ring is (6). In another embodiment said A ring is (7). In another embodiment said A ring is (8). In another embodiment said A ring is (9). In another embodiment said A ring is (10). In another embodiment said A ring is (11). In another embodiment said A ring is (12). In another embodiment said A ring is (13). In another embodiment said A ring is (14). In another embodiment said A ring is (15). In another embodiment said A ring is (16). In another embodiment said A ring is (17). In another embodiment said A ring is (18). In another embodiment said A ring is (19). In another embodiment said A ring is (20). In another embodiment said A ring is (21). In another embodiment said A ring is (22). In another embodiment said A ring is (23). In another embodiment said A ring is (24). In another embodiment said A ring is (25). In another embodiment said A ring is (26).

In one embodiment ring B is a 6 to 8 membered heterocycloalkyl ring comprising 1 to 4 heteroatoms as described above for formula (1). In another embodiment ring B is a 6 membered heterocycloalkyl ring comprising —$NR^4$— and one other heteroatom. In another embodiment ring B is a 6 membered heterocycloalkyl ring comprising one heteroatom and said heteroatom is —$NR^4$—. In another embodiment ring B is a 6 membered heterocycloalkyl ring comprising —$NR^4$— and one other heteroatom, and said other heteroatom is —O—. The heterocycloalkyl rings described in this paragraph are optionally substituted as described above for formula (1).

In one embodiment ring B is a 6 to 8 membered heterocycloalkenyl comprising one double bond, and 1 to 4 heteroatoms as described above for formula (1). In another embodiment said heterocycloalkenyl ring is a 6 membered ring comprising one double bond, —$NR^4$— and one other heteroatom. In another embodiment said heterocycloalkenyl ring is a 6 membered ring which comprises one double bond, and one heteroatom and said heteroatom is —$NR^4$—. The heterocycloalkenyl rings described in this paragraph are optionally substituted as described above for formula (1).

In another embodiment ring B is a bridged heterocycloalkyl ring. In another embodiment ring B is a 6 membered (excluding the atoms forming the bridge) bridged heterocycloalkyl ring wherein said bridge comprises one or two carbons (excluding the atoms that are ring members). In one embodiment there are two carbons in the bridge. In another embodiment there is one carbon in the bridge. In another embodiment the bridged heterocycloalkyl ring comprises a one carbon bridge, as described in this paragraph, and one heteroatom and said heteroatom is —$NR^4$—.

In another embodiment ring B is a fused heterocycloalkylcyclopropyl ring wherein said heterocycloalkyl moiety comprises 6 to 8 ring members. In another embodiment ring B is a fused heterocycloalkylcyclopropyl ring wherein said heterocycloalkyl moiety comprises 6 ring members. In another embodiment ring B is a fused heterocycloalkylcyclopropyl ring wherein said heterocycloalkyl moiety comprises 6 ring members and one heteroatom and said heteroatom is —NR⁴—.

In one embodiment said B ring is selected from the group consisting of

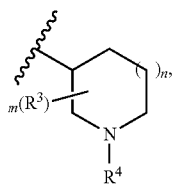
(27)

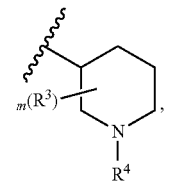
(28)

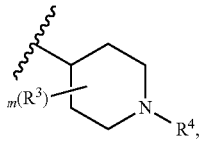
(29)

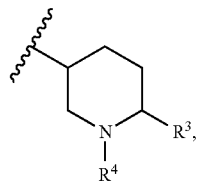
(30)

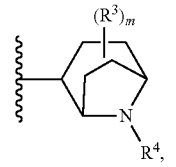
(31)

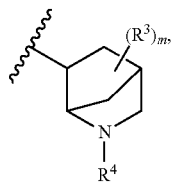
(32)

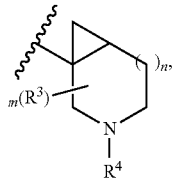
(33)

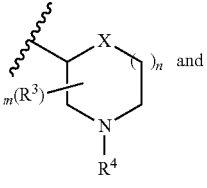 and
(34)

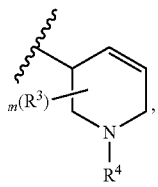
(34.1)

wherein $R^3$ is defined above for formula (1), m is 0 to 3 (and in one embodiment m is 3, and in another embodiment m is 2, and in another embodiment m is 1, and in another embodiment m is 0 (i.e., there is no $R^3$ substituent)), and n is 1 to 3 (and in one embodiment n is 3, and in another embodiment n is 2, and in another embodiment n is 1), and X is selected from the group consisting of —$NR^5$—, O, S, SO, $SO_2$ and C (in one embodiment X is —$NR^5$— (e.g., X is —NH—), in another embodiment X is O, in another embodiment X is S, in another embodiment X is SO, in another embodiment X is $SO_2$ and in another embodiment X is C).

In one embodiment said B ring is (27) (and in one example n is 1, in another example n is 2 and in another example n is 3). In another embodiment said B ring is (28). In another embodiment said B ring is (29). In another embodiment said B ring is (30). In another embodiment said B ring is (31). In another embodiment said B ring is (32). In another embodiment said B ring is (33) (and in one example n is 1, in another example n is 2 and in another example n is 3). In another embodiment said B ring is (34) (and in one example n is 1, in another example n is 2 and in another example n is 3). In another embodiment said B ring is (34.1).

In one embodiment said B ring is (27), n is 1 and m is 0. In another embodiment said B ring is (27) n is 1 and m is 1. In another embodiment said B ring is (27) n is 1 and m is 2. In another embodiment said B ring is (27) n is 1 and m is 3. In another embodiment said 13 ring is (27) n is 2 and m is 0. In another embodiment said B ring is (27) n is 2 and m is 1. In another embodiment said B ring is (27) n is 2 and m is 2. In another embodiment said B ring is (27) n is 2 and m is 3. In another embodiment said B ring is (27) n is 3 and m is 0. In another embodiment said B ring is (27) n is 3 and m is 1. In another embodiment said B ring is (27) n is 3 and m is 2. In another embodiment said B ring is (27) n is 3 and m is 3.

In one embodiment said B ring is (33), n is 1 and m is O. In another embodiment said B ring is (33) n is 1 and m is 1. In another embodiment said B ring is (33) n is 1 and m is 2. In another embodiment said B ring is (33) n is 1 and m is 3. In another embodiment said B ring is (33) n is 2 and m is 0. In another embodiment said B ring is (33) n is 2 and m is 1. In another embodiment said B ring is (33) n is 2 and m is 2. In another embodiment said B ring is (33) n is 2 and m is 3. In another embodiment said B ring is (33) n is 3 and m is 0. In another embodiment said B ring is (33) n is 3 and m is 1. In another embodiment said B ring is (33) n is 3 and m is 2. In another embodiment said B ring is (33) n is 3 and m is 3.

In one embodiment said B ring is (34), n is 1 and m is O. In another embodiment said B ring is (34) n is 1 and m is 1. In another embodiment said B ring is (34) n is 1 and m is 2. In another embodiment said B ring is (34) n is 1 and m is 3. In another embodiment said B ring is (34) n is 2 and m is O. In another embodiment said B ring is (34) n is 2 and m is 1. In another embodiment said B ring is (34) n is 2 and m is 2. In another embodiment said B ring is (34) n is 2 and m is 3. In another embodiment said B ring is (34) n is 3 and m is 0. In another embodiment said B ring is (34) n is 3 and m is 1. In another embodiment said B ring is (34) n is 3 and m is 2. In another embodiment said B ring is (34) n is 3 and m is 3. In another embodiment said B ring is any one of the rings (34), as described in this paragraph, wherein X is O. In another embodiment said B ring is any one of the rings (34), as described in this paragraph, wherein X is —NR$^5$—. In another embodiment said B ring is any one of the rings (34), as described in this paragraph, wherein X is S. In another embodiment said B ring is any one of the rings (34), as described in this paragraph, wherein X is SO. In another embodiment said B ring is any one of the rings (34), as described in this paragraph, wherein X is SO$_2$. In another embodiment said B ring is any one of the rings (34), as described in this paragraph, wherein X is C.

In another embodiment, for any one of B rings (28), (29), (30), (31), (32) and (34.1) m is 0. In another embodiment, for any one of B rings (28), (29), (30), (31), (32) and (34.1) m is 1. In another embodiment, for any one of B rings (28), (29), (30), (31), (32) and (34.1) m is 2. In another embodiment, for any one of B rings (28), (29), (30), (31), (32) and (34.1) m is 3.

In another embodiment said B ring is selected from the group consisting of:

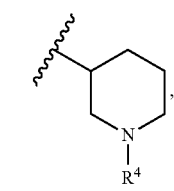
(35)

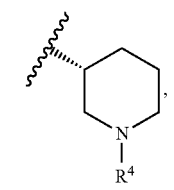
(35.1)

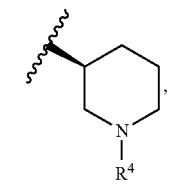
(35.2)

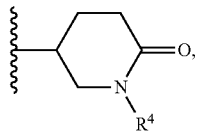
(36)

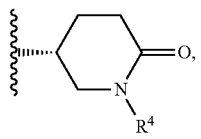
(37)

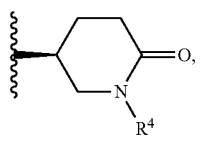
(38)

-continued

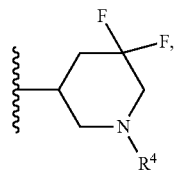
(39)

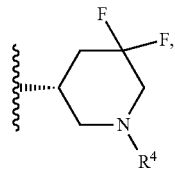
(40)

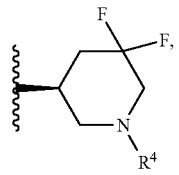
(41)

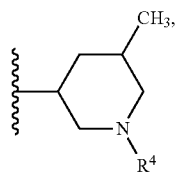
(42)

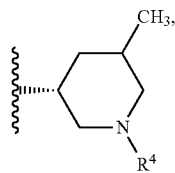
(43)

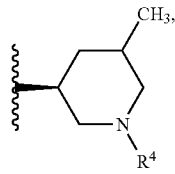
(44)

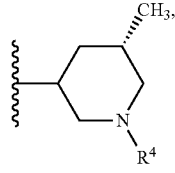
(45)

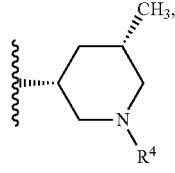
(46)

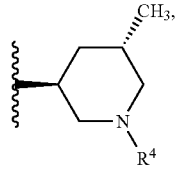
(47)

(48) 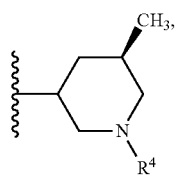

(49) 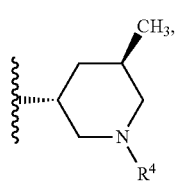

(50) 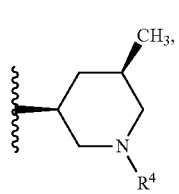

(51) 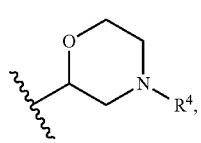

(52) 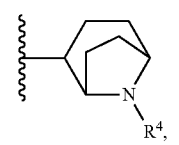

(53) 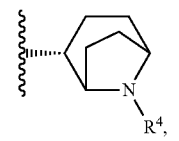

(54) 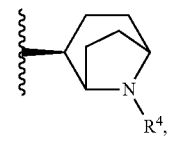

(54.1) 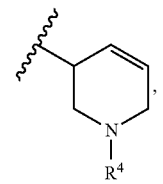

(54.2) 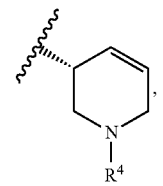

(54.3) 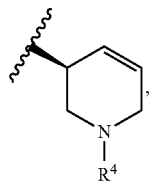

(54.4) 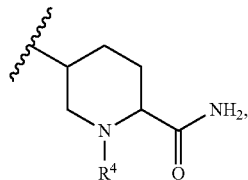

(54.5) 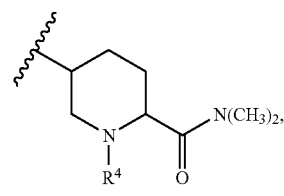

(54.6) 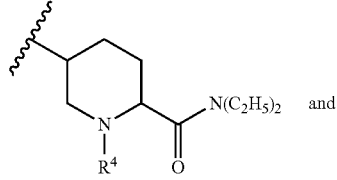

(54.7) 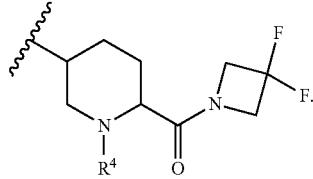

In one embodiment said B ring is (35). In another embodiment B is (35.1). In another embodiment B is (35.2). In another embodiment B is (36). In another embodiment B is (37). In another embodiment B is (38). In another embodiment B is (39). In another embodiment B is (40). In another embodiment B is (41). In another embodiment B is (42). In another embodiment B is (43). In another embodiment B is (44). In another embodiment B is (45). In another embodiment B is (46). In another embodiment B is (47). In another embodiment B is (48). In another embodiment B is (49). In another embodiment B is (50). In another embodiment B is (51). In another embodiment B is (52). In another embodiment B is (53). In another embodiment B is (54). In another embodiment B is (54.1). In another embodiment B is (54.2). In another embodiment B is (54.3). In another embodiment B is (54.4). In another embodiment B is (54.5). In another embodiment B is (54.6). In another embodiment B is (54.7).

Examples of the -alkylene-aryl (e.g., —($C_1$ to $C_2$)alkylene-aryl) $R^4$ groups include, but are not limited to -alkylene-phenyl (e.g., —($C_1$ to $C_2$)alkylene-phenyl), —$CH_2$-aryl, —$CH_2$-phenyl, —$(CH_2)_2$-aryl, and —$(CH_2)_2$-phenyl. In other examples of the $R^4$-alkylene-aryl group, one or more H atoms on said alkylene moiety are replaced with deuterium. Thus, examples of $R^4$ also include —CHD-aryl, —CHD-phenyl, —$CD_2$-aryl and —$CD_2$-phenyl, wherein D represents deuterium.

Examples of the substituted -alkylene-aryl $R^4$ group include, for example, the above defined and exemplified -alkylene-aryl $R^4$ groups substituted with 1 to 5 substituents independently selected from the group consisting of: (1) alkoxy, such as, for example, $C_1$ to $C_4$ alkoxy, $C_1$ to $C_3$ alkoxy, $C_1$ to $C_2$ alkoxy, and in one example —$OCH_3$, and in another example —$OCH(CH_3)_2$), (2) halo (e.g., F, Cl, and Br, and in one example F and in another example Cl), (3) —O-alkylene-O-alkyl, such as, for example, —O—($C_1$ to $C_4$)alkylene-O—($C_1$ to $C_4$)alkyl, —O—($C_1$ to $C_2$)alkylene-O—($C_1$ to $C_2$)alkyl, and —O—($C_1$ to $C_4$)alkylene-O—($C_1$)alkyl, and in one example, —O—$(CH_2)_2$—O—$CH_3$, and in another example —O—$(CH_2)_3$—O—$CH_3$), (4) —O-alkylene-CN, such as, for example —O—($C_1$ to $C_4$)alkylene-CN and —O—($C_1$ to $C_2$)alkylene-CN, and in one example, —O—$CH_2$—CN), (5) alkyl, such as, for example, $C_1$ to $C_4$ alkyl, $C_1$ to $C_2$ alkyl, and in one example, —$CH_3$, (6) —O-(halo substituted alkyl), such as, for example, —O-(halo substituted ($C_1$ to $C_4$)alkyl, —O-(halo substituted ($C_1$ to $C_2$)alkyl and —O-(halo substituted methyl, and in one example, —$OCF_3$, and (7) —$NH_2$.

Examples of the —C(O)-aryl $R^4$ group include, —C(O)-phenyl.

Examples of the substituted —C(O)-aryl include substituted —C(O)-phenyl, wherein the aryl (e.g., the phenyl moiety) is substituted with 1-5 substituents independently selected from the group consisting of: halo, —($C_1$-$C_4$)alkoxy and —O—($C_3$ to $C_6$)cycloalkyl.

Examples of the -alkylene-heteroaryl $R^4$ group include, for example, —($C_1$ to $C_4$)alkylene-(5 or 6 membered) heteroaryl and —($C_1$ to $C_2$)alkylene-(5 or 6 membered) heteroaryl, such as, for example, —$CH_2$-(5 or 6 membered) heteroaryl, and in one example —$CH_2$-thienyl, and in another example —$CH_2$-triazolyl, and in another example —$CH_2$-pyrimidinyl.

Examples of the substituted -alkylene-heteroaryl $R^4$ group include, for example, the -alkylene-heteroaryl groups defined and exemplified above substituted with 1-5 substituents independently selected from the group consisting of: (1) alkyl, such as, for example, $C_1$ to $C_4$ alkyl, $C_1$ to $C_2$ alkyl, and in one example, —$CH_3$ and (2) alkoxy, such as, for example, $C_1$ to $C_4$ alkoxy, $C_1$ to $C_3$ alkoxy, $C_1$ to $C_2$ alkoxy, and in one example —$OCH_3$. Thus, in one example the heteroaryl moiety is methylpyridyl and in another example the heteroaryl moiety is methoxypyridyl.

Examples of the -alkylene-(fused heteroarylaryl) $R^4$ group include, for example, —($C_1$ to $C_4$)alkylene-(fused (5 or 6 membered)heteroaryl (6 membered)aryl) and —($C_1$ to $C_2$)alkylene-(fused (5 or 6 membered)heteroaryl (6 membered)aryl), such as, for example —$CH_2$— (fused (5 or 6 membered)heteroaryl (6 membered)aryl), such as, for example, —$CH_2$-benzothienyl, —$CH_2$-benzopyrazolyl, —$CH_2$-quinoxalinyl, and —$CH_2$-benzofuranyl.

Examples of the substituted -alkylene-(fused heteroarylaryl) $R^4$ groups include the -alkylene-(fused heteroarylaryl) groups as defined and exemplified substituted with 1 to 3 substitutents independently selected from the group consisting of: alkyl (such as, for example, $C_1$ to $C_4$ alkyl and $C_1$ to $C_2$ alkyl, and in one example, —$CH_3$), halo (e.g., Br, Cl and F), alkoxy (in one example, $C_1$-$C_4$ alkoxy, and in another example $C_1$-$C_2$ alkoxy), —S-alkyl (and in one example —S—($C_1$-$C_4$)alkyl, and in another example —S—($C_1$-$C_2$) alkyl), and —$N(R^{22})_2$. In one example the substituted -alkylene-(fused heteroarylaryl) $R^4$ group is N-methylbenzopyrazolyl.

Examples of the -alkylene-C(O)-heterocycloalkyl $R^4$ group include, for example, —($C_1$ to $C_4$)alkylene-C(O)-(5 or 6 membered)heterocycloalkyl and —($C_1$ to $C_2$)alkylene-C(O)-(5 or 6 membered)heterocycloalkyl, such as, for example, —$CH_2$—C(O)-(5 or 6 membered)-heterocycloalkyl, and in one example, —$CH_2$—C(O)-piperidyl.

Examples of the substituted -alkylene-C(O)-heterocycloalkyl include the -alkylene-C(O)-heterocycloalkyl defined and exemplified above substituted with 1 to 3 substituents independently selected from the group consisting of: alkyl (and in one example ($C_1$-$C_6$)alkyl, and in another example ($C_1$-$C_4$)alkyl, and in another example ($C_1$-$C_2$)alkyl—C(O)—($C_1$-$C_4$)alkyl (and in one example —C(O)—($C_1$-$C_4$)alkyl, and in another example —C(O)—($C_1$-$C_4$)alkyl), —C(O)—N($R^{18}$)$_2$, cycloalkyl (e.g., ($C_3$-$C_6$)cycloalkyl), —$CF_3$, —$CF_2$, and —CF. In one example the substituted -alkylene-C(O)-heterocycloalkyl group is a substituted —$CH_2$—C(O)-piperidyl.

Examples of the fused (arylcycloalkyl) $R^4$ group include, for example, fused ($C_6$ aryl $C_3$ to $C_6$ cycloalkyl) and fused ($C_6$ aryl $C_5$ to $C_6$ cycloalkyl), such as, for example, fused phenyl ($C_5$ to $C_6$)cycloalkyl, and in one example this $R^4$ group is benzocyclopentyl.

Examples of the substituted fused (arylcycloalkyl) $R^4$ group include the fused (arylcycloalkyl) described and exemplified above substituted with 1-3 substituents independently selected from the group consisting of: halo, alkoxy (in one example, $C_1$-$C_4$ alkoxy, and in another example $C_1$-$C_2$ alkoxy), ($C_1$-$C_4$)alkyl (and in one example ($C_1$-$C_4$)alkyl, and in another example ($C_1$-$C_2$)alkyl, and in another example methyl, and in another example ethyl), —C(O)—($C_1$-$C_4$) alkyl (and in one example —C(O)—($C_1$-$C_4$)alkyl, and in another example —C(O)—($C_1$-$C_4$)alkyl), and —C(O)—N($R^{18}$)$_2$, and ($C_3$-$C_6$)cycloalkyl (and in one example cyclopropyl, and in another example cyclobutyl, and in another example cyclopentyl, and in another example cyclohexyl).

Examples of the -alkylene-cycloalkyl $R^4$ group include, for example, —($C_1$ to $C_4$)alkylene(C5 to C6)cycloalkyl and —($C_1$ to $C_2$)alkylene(C5 to C6)cycloalkyl, such as, for example, —$CH_2$—(C5 to C6)cycloalkyl, and in one example, —$CH_2$-cyclohexyl.

Examples of the substituted -alkylene-cycloalkyl $R^4$ group include the -alkylene-cycloalkyl groups defined and exemplified above substituted with 1 to 3 substituents independently selected from the group consisting of: halo, alkoxy (in one example, $C_1$-$C_4$ alkoxy, and in another example $C_1$-$C_2$ alkoxy), ($C_1$-$C_4$)alkyl (and in one example ($C_1$-$C_4$)alkyl, and in another example ($C_1$-$C_2$)alkyl, and in another example methyl, and in another example ethyl), —C(O)—($C_1$-$C_4$) alkyl (and in one example —C(O)—($C_1$-$C_4$)alkyl, and in another example —C(O)—($C_1$-$C_4$)alkyl), and —C(O)—N($R^{18}$)$_2$, and ($C_3$-$C_6$)cycloalkyl (and in one example cyclopropyl, and in another example cyclobutyl, and in another example cyclopentyl, and in another example cyclohexyl).

In one embodiment the $R^4$ groups are selected from the group consisting of:

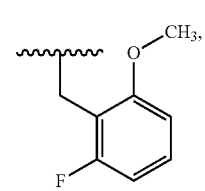

(55)

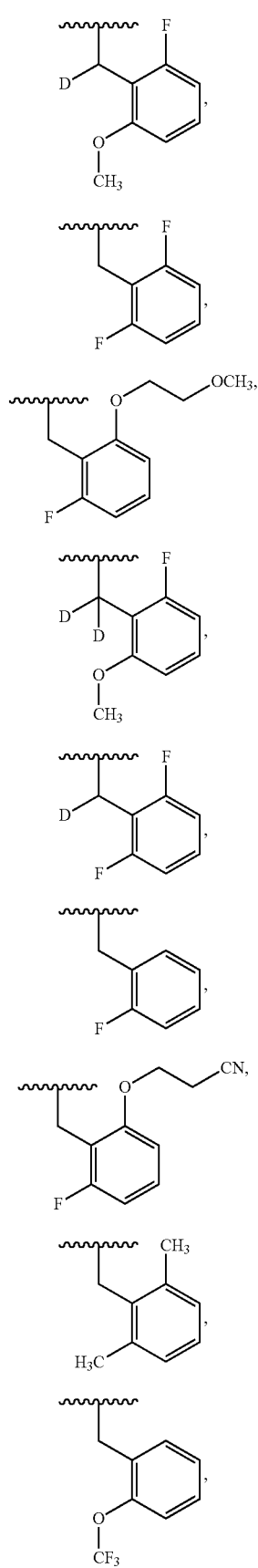
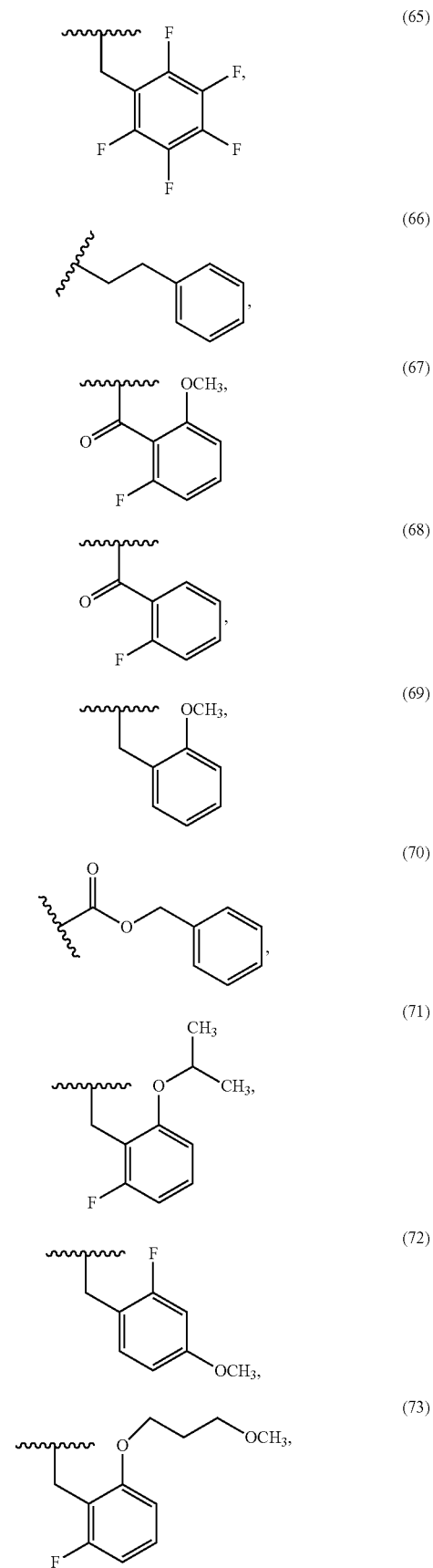

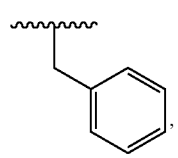 (74)
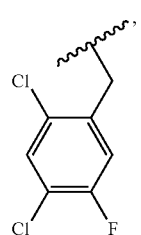 (75)
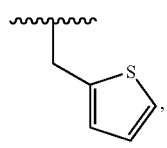 (76)
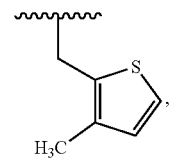 (77)
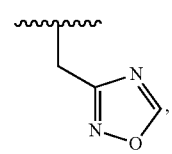 (78)
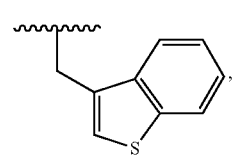 (79)
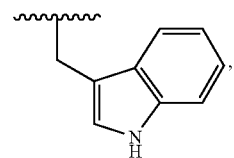 (80)
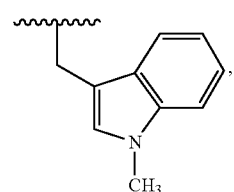 (81)
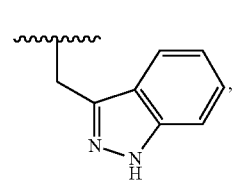 (82)
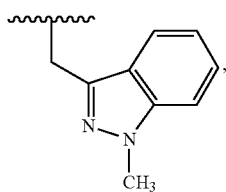 (83)
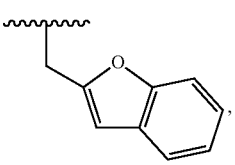 (84)
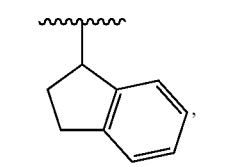 (85)
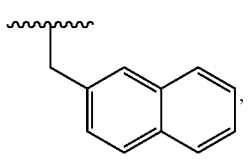 (86)
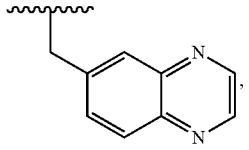 (87)
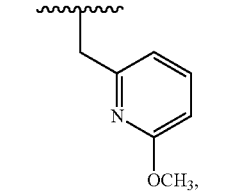 (88)
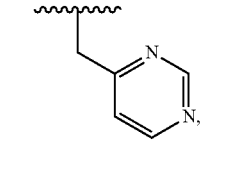 (89)
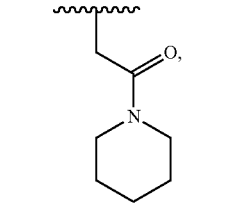 (90)
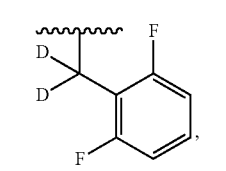 (91)

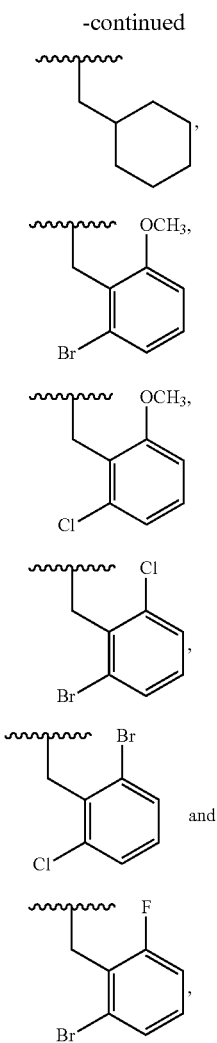

wherein D represents deuterium.

In one embodiment R⁴ is (55). In another embodiment R⁴ is (56). In another embodiment R⁴ is (57). In another embodiment R⁴ is (58). In another embodiment R⁴ is (59). In another embodiment R⁴ is (60). In another embodiment R⁴ is (61). In another embodiment R⁴ is (62). In another embodiment R⁴ is (63). In another embodiment R⁴ is (64). In another embodiment R⁴ is (65). In another embodiment R⁴ is (66). In another embodiment R⁴ is (67). In another embodiment R⁴ is (68). In another embodiment R⁴ is (69). In another embodiment R⁴ is (70). In another embodiment R⁴ is (71). In another embodiment R⁴ is (72). In another embodiment R⁴ is (73). In another embodiment R⁴ is (74). In another embodiment R⁴ is (75). In another embodiment R⁴ is (76). In another embodiment R⁴ is (77). In another embodiment R⁴ is (78). In another embodiment R⁴ is (79). In another embodiment R⁴ is (80). In another embodiment R⁴ is (81). In another embodiment R⁴ is (82). In another embodiment R⁴ is (83). In another embodiment R⁴ is (84). In another embodiment R⁴ is (85). In another embodiment R⁴ is (86). In another embodiment R⁴ is (87). In another embodiment R⁴ is (88). In another embodiment R⁴ is (89). In another embodiment R⁴ is (90). In another embodiment R⁴ is (91). In another embodiment R⁴ is (92). In another embodiment R⁴ is (90). In another embodiment R⁴ is (91). In another embodiment R⁴ is (92.1). In another embodiment R⁴ is (90). In another embodiment R⁴ is (91). In another embodiment R⁴ is (92.2). In another embodiment R⁴ is (90). In another embodiment R⁴ is (91). In another embodiment R⁴ is (92.3). In another embodiment R⁴ is (90). In another embodiment R⁴ is (91). In another embodiment R⁴ is (92.4). In another embodiment R⁴ is (90). In another embodiment R⁴ is (91). In another embodiment R⁴ is (92.5).

Examples of the R¹ aryl groups include, but are not limited to: $C_6$ to $C_{10}$ aryl. The aryl groups can be optionally substituted as described above in the definition of R¹. Examples of the R¹ aryl groups include but are not limited to: phenyl, N,N-dimethylbenzenesulfonamide, $(CH(CH_3)_2O)$-phenyl, fluorophenyl, isopropylsulfonylphenyl, trifluoromethylphenyl, $(C(CH_3)_2S)$phenyl, and N-(2-hydroxyphenyl)acetamide.

Examples of the R¹ monocyclic heteroaryl groups include, but are not limited to: 5 or 6 membered heteroaryl rings comprising 1 to 4 heteroatoms selected from the group consisting of N, O and S. The remaining ring atoms are carbon. The heteroaryl rings can be optionally substituted as defined above in the definition of R¹. Examples of R¹ heteroaryl groups include, but are not limited to: pyridyl, pyrimidinyl, isoxazolyl, pyrazolyl, methanolpyridyl, cyclopropylpyrimidinyl, methylpyridin-one, methylpyridyl, trifluoromethylpyridyl (e.g., o-$CF_3$pyridyl), methoxypyrimidinyl, aminopyridyl, cyclopropylpyridyl, $(C(CH_3)_2OH)$-pyridyl, difluoropyridyl, dimethylisoxazolyl, chloropyridyl, ethylpyrazolyl and methylpyrazolyl.

The R¹ fused heteroarylaryl rings comprise a monocyclic heteroaryl ring fused to an aryl ring. Examples of the R¹ fused heteroarylaryl rings include, but are not limited to a 5 or 6 membered heteroaryl ring fused to a $C_6$ to $C_{10}$ aryl ring (such as, for example phenyl). The heteroaryl moiety comprises 1 to 4 heteroatoms independently selected from the group consisting of: N, O and S, and the remaining non-heteroatoms are carbon. The fused heteroarylaryl rings can be optionally substituted as described above in the definition of R¹. Examples of the fused heteroarylaryl rings include, but are not limited to: indazolyl, methylindazolyl, benzothiazolyl, methylbenzothiazolyl, benzofuranyl, benzimidazolyl and indolyl.

The R¹ fused heteroarylheteroaryl rings comprise a monocyclic heteroaryl ring fused to a monocyclic heteroaryl ring. Examples of the R¹ fused heteroarylheteroaryl rings include, but are not limited to: a 5 or 6 membered heteroaryl ring fused to a 5 or 6 membered heteroaryl ring. Each heteroaryl moiety independently comprises 1 to 4 heteroatoms independently selected from the group consisting of: N, O and S, and the remaining non-heteroatoms are carbon. The fused heteroarylheteroaryl rings can be optionally substituted as described above in the definition of R¹. Examples of the heteroarylheteroaryl fused rings include, but are not limited to: imidazopyridinyl, indazolyl, methylindazolyl, pyrrolopyridyl and triazolopyridyl.

The R¹ fused arylheterocycloalkyl rings comprise an aryl ring fused to a monocyclic heterocycloalkyl ring. Examples of the R¹ fused arylheterocycloalkyl rings include, but are not limited to: a $C_6$ to $C_{10}$ aryl ring (e.g., phenyl) fused to a 5 or 6 membered heterocycloalkyl ring. The heterocycloalkyl ring comprises 1 to 3 heteroatoms independently selected from the group consisting of: N, O, S, SO and $SO_2$. The remaining atoms in the heterocycloalkyl ring are carbon. The fused arylheterocycloalkyl rings can be optionally substituted as described above in the definition of R¹. Examples of the fused arylheteocycloalkyl rings include, but are not limited to: dihydrobenzofuranyl, benzodioxolyl and dimethyldihydrobenzofuranyl.

Examples of the R¹ group include, but are not limited to:
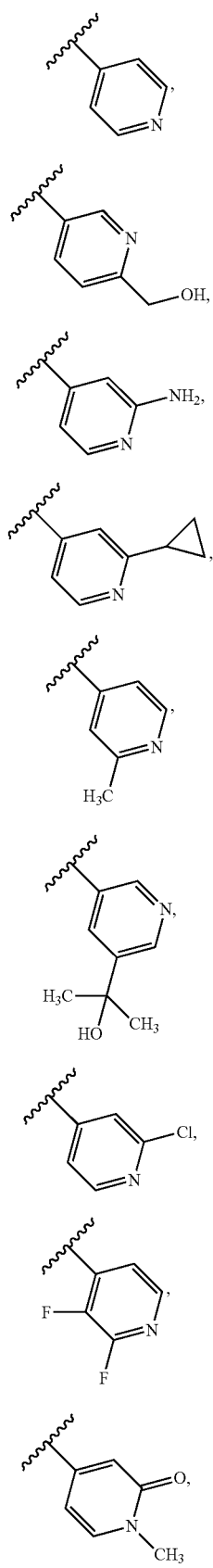
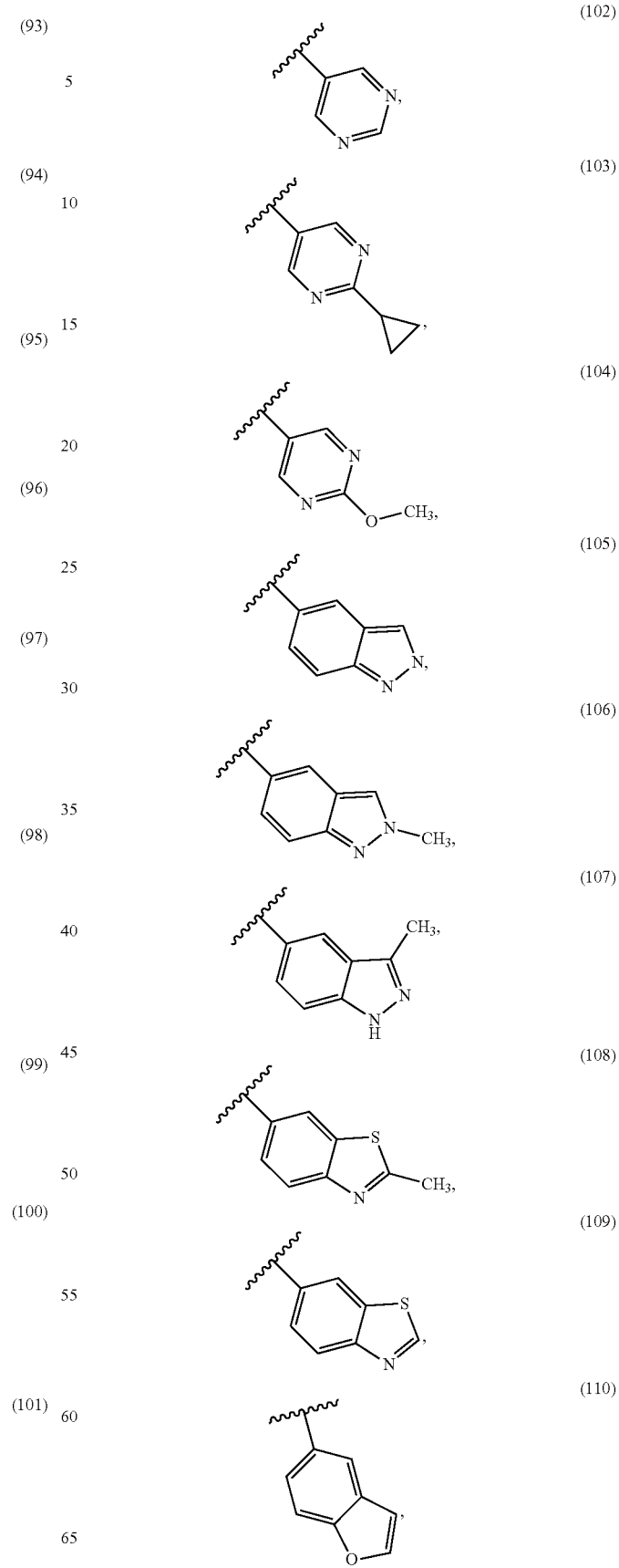

-continued
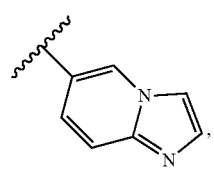 (111)
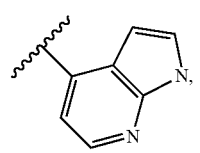 (112)
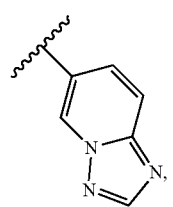 (113)
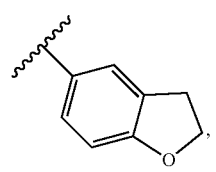 (114)
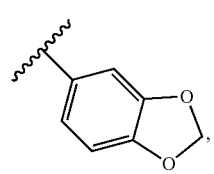 (115)
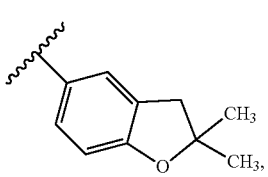 (116)
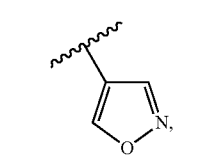 (117)
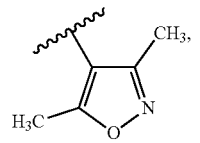 (118)
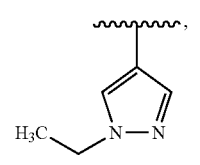 (119)
-continued
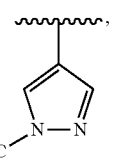 (120)
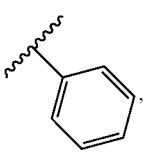 (121)
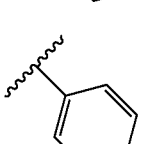 (122)
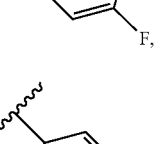 (123)
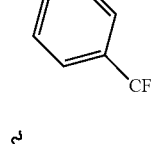 (124)
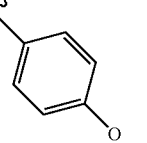 (125)
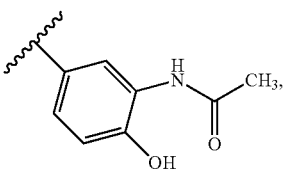 (126)
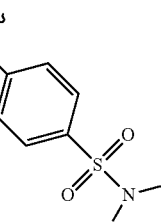 (127)

(128)
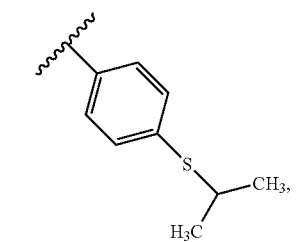

(129)
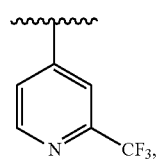

(130)
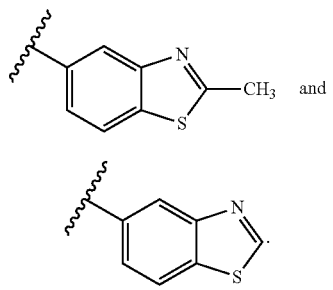
and (131)

In one embodiment $R^1$ is (92). In another embodiment $R^1$ is (93). In another embodiment $R^1$ is (94). In another embodiment $R^1$ is (95). In another embodiment $R^1$ is (96). In another embodiment $R^1$ is (97). In another embodiment $R^1$ is (98). In another embodiment $R^1$ is (99). In another embodiment $R^1$ is (100). In another embodiment $R^1$ is (101). In another embodiment $R^1$ is (102). In another embodiment $R^1$ is (103). In another embodiment $R^1$ is (104). In another embodiment $R^1$ is (105). In another embodiment is (106). In another embodiment $R^1$ is (107). In another embodiment is (108). In another embodiment $R^1$ is (109). In another embodiment $R^1$ is (110). In another embodiment $R^1$ is (111). In another embodiment $R^1$ is (112). In another embodiment $R^1$ is (113). In another embodiment $R^1$ is (114). In another embodiment $R^1$ is (115). In another embodiment $R^1$ is (116). In another embodiment $R^1$ is (117). In another embodiment $R^1$ is (118). In another embodiment $R^1$ is (119). In another embodiment $R^1$ is (120). In another embodiment $R^1$ is (121). In another embodiment $R^1$ is (122). In another embodiment $R^1$ is (123). In another embodiment $R^1$ is (124). In another embodiment $R^1$ is (125). In another embodiment $R^1$ is (126). In another embodiment $R^1$ is (127). In another embodiment $R^1$ is (128). In another embodiment $R^1$ is (129). In another embodiment $R^1$ is (130). In another embodiment $R^1$ is (131).

One embodiment of this invention is directed to compounds of formula (1) wherein: said A ring is selected from the group consisting of: rings of formulas (2) to (11); said B ring is selected from the group consisting of: rings of formulas (27) to (34.1); and said $R^4$ group is selected from the group consisting of: alkyl (e.g., methyl) and moieties of formulas (55) to (92.5).

Another embodiment of this invention is directed to compounds of formula (1) wherein: said A ring is selected from the group consisting of rings of formulas (2) to (11); said B ring is selected from the group consisting of: rings of formulas (27) to (34.1); said $R^4$ group is selected from the group consisting of: alkyl (e.g., methyl) and moieties of formulas (55) to (92.5); and said $R^1$ group is selected from the group consisting of formulas: (93) to (131).

Another embodiment of this invention is directed to compounds of formula (1) wherein: said A ring is selected from the group consisting of: rings of formulas (12) to (26); said B ring is selected from the group consisting of: rings of formulas (35) to (54.3); and said $R^4$ group is selected from the group consisting of: alkyl (e.g., methyl) and moieties of formulas (55) to (92.5).

Another embodiment of this invention is directed to compounds of formula (1) wherein: said A ring is selected from the group consisting of: rings of formulas (12) to (26); said B ring is selected from the group consisting of: rings of formulas (35) to (54.3); said $R^4$ group is selected from the group consisting of: alkyl (e.g., methyl) and moieties of formulas (55) to (92.5); and said $R^1$ group is selected from the group consisting of formulas: (93) to (131).

In one embodiment of this invention (I) said A ring is a triazolyl, and (II) said B ring is selected from the group consisting of piperidinyl and morpholinyl, wherein said B ring is optionally substituted as described above in the definition of B in formula (1), and (III) said $R^4$ group is selected from the group consisting of —$CH_2$-phenyl, substituted —$CH_2$-phenyl, substituted —$CD_2$-phenyl, substituted —CHD-phenyl and —$CH_2$-cycloalkyl (e.g., —$CH_2$-cyclohexyl), wherein the substitutents on said substituted —$CH_2$-phenyl are as described in the definition of $R^4$ for formula (1) and any embodiments thereto, and (IV) said $R^1$ groups are selected from the group consisting of: pyridyl, substituted pyridyl, triazololpyridinyl, indazolyl, substituted indazolyl and imidazolylpyridyl, wherein said substitutents for said substituted $R^1$ groups are as defined for $R^1$ in formula (1) and any embodiments thereto.

In one embodiment of this invention: (I) said A ring is the ring of formula (3), and (II) said B ring is selected from the group consisting of: rings of the formulas (34), (51), (27), (35) and (12), and (III) said $R^4$ group is selected from the group consisting of: groups of the formulas (55), (56), (57), (58), (59), (60), (61) and (92), and (IV) said $R^1$ group is selected from the group consisting of: groups of the formulas (93), (97), (106), (111) and (113).

In another embodiment of this invention: (I) said A ring is triazolyl, and (II) said B ring is piperidinyl, and (III) said $R^4$ group is selected from the group consisting of: —$CH_2$-phenyl, —$CH_2$-indolyl, —$CH_2$-naphthyl, and —$CH_2$-indazolyl, and said $R^4$ groups are optionally substituted as described in the definition of $R^4$ in formula (1) and any embodiments thereto, and (IV) said $R^1$ group is pyridyl, wherein said pyridyl is optionally substituted as described in the definition of $R^1$ in formula (1) and any embodiments thereto.

In another embodiment of this invention: (I) said A ring is a ring of formula (2) or (19), and (II) said B ring is a ring of formula (27) or (35.1), and (III) said $R^4$ group is selected from the group consisting of groups of the formula (55), (57), (61), (81), (83) and (86), and (IV) said $R^1$ group is a group of the formula (93) or (97).

In another embodiment of this invention: (I) said A ring is triazolyl, and (II) said B ring is piperidinyl, and (III) said $R^4$ group is selected from the group consisting of —$CH_2$-phenyl and —$CH_2$-thienyl, said $R^4$ groups optionally substituted as described in the definition of $R^4$ in formula (1) and any embodiments thereto, and (IV) said $R^1$ group is pyridyl, optionally substituted as described in the definition of $R^1$ in formula (1) and any embodiments thereto.

In another embodiment of this invention: (I) said A ring is a ring of formula (4) or (14), and (II) said B ring is a ring of formula (27) or (35.1), and (III) said R⁴ group is a group of formula (55), or (57), or (76), and (IV) said R¹ group is a group of formula (93).

In another embodiment of this invention: (I) said A ring is oxadiazolyl, and (II) said B ring is piperidinyl, and (III) said R⁴ group is a substituted —CH₂-phenyl, wherein said substitutents are as described in the definition of R⁴ in formula (1) and any embodiments thereof, and (IV) said R¹ group is selected from the group consisting of: pyridyl, substituted pyridyl, substituted phenyl, indazolyl, substituted indazolyl, imidazopyridyl and substituted imidazopyridyl, wherein said substitutents are as described in the definition of R¹ in formula (1) and any embodiments thereof.

In another embodiment of this invention: (I) said A ring is a ring selected form the group consisting of rings of the formula (5), (25) and (26), and (II) said B ring is a ring selected from the group consisting of rings of the formula (27), (35), (35.1), (35.2), (42), (46) and (49), and (III) said R⁴ group is a group of formula (55) or (61), and (IV) said R¹ group is selected from the group consisting of groups of the formula (93), (97), (106), (111) and (125).

In another embodiment of this invention: (I) said A ring is pyrazolyl, and (II) said B ring is piperidinyl, and (III) said R⁴ group is a substituted —CH₂-phenyl, wherein said substitutents are as described in the definition of R⁴ in formula (1) and any embodiments thereof, and (IV) said R¹ group is pyridyl.

In another embodiment of this invention: (I) said A ring is a ring selected form the group consisting of rings of the formula (8) and (21), and (II) said B ring is a ring selected from the group consisting of rings of the formula (27), (35) and (35.1), and (III) said R⁴ group is selected from the group consisting of groups of the formula (55), (57) and (58), and (IV) said R¹ group is (93).

Another embodiment of this invention is directed to the compounds of formulas (200) to (384) as described in Table 1 below.

Another embodiment of this invention is directed to the compounds of formulas (200)-(246), (249)-(252), (257), (260)-(297), (306), (308), (310)-(315), (317)-(320), (322)-(327), (330)-(338), (340), (343), (344), (346), (355), (356), (363)-(366), and (369)-(384) as described in Table 1 below.

Another embodiment of this invention is directed to compounds (200)-(214), (249), (251), (260)-(267), (276)-(280), (306), (310)-(312), (314), (322), (330) and (336).

Embodiments of this invention also include an independent embodiment to each individual compound of compounds 200 to 384 as if said embodiments were each individually written out here. Thus, other embodiments of this invention include an embodiment to compound (200), an embodiment to compound (201), an embodiment to compound (202), an embodiment to compound (203), etc.

Another embodiment of this invention is directed to a pharmaceutically acceptable salt of a compound of formula (1).

Another embodiment of this invention is directed to a pharmaceutically acceptable salt of a compound selected from the group consisting of compounds (200) to (384). Another embodiment is directed to a pharmaceutically acceptable salt of a compound selected from the group consisting of compounds (200)-(214), (249), (251), (260)-(267), (276)-(280), (306), (310)-(312), (314), (322), (330) and (336).

Another embodiment of this invention is directed to a solvate of a compound of formula (1). Another embodiment of this invention is directed to a solvate of a compound selected from the group consisting of compounds (200) to (384). Another embodiment is directed to a solvate of a compound selected from the group consisting of compounds (200)-(214), (249), (251), (260)-(267), (276)-(280), (306), (310)-(312), (314), (322), (330) and (336).

Other embodiments of this invention are directed to any one of the embodiments of formula (1) wherein the compound is in pure and isolated form. Other embodiments of this invention are directed to any one of the embodiments of formula (1) wherein the compound is in pure form. Other embodiments of this invention are directed to any one of the embodiments of formula (1) wherein the compound is in isolated form.

Another embodiment of this invention is directed to a pharmaceutical composition comprising an effective amount of at least one compound (e.g., 1, 2 or 3, or 1 or 2, or 1, and usually 1) of formula (1) and a pharmaceutically acceptable carrier. Another embodiment of this invention is directed to a pharmaceutical composition comprising an effective amount of a compound of formula (1) and a pharmaceutically acceptable carrier.

Another embodiment of this invention is directed to a pharmaceutical composition comprising an effective amount of a compound selected from the group consisting of: (200) to (384), and a pharmaceutically acceptable carrier. Another embodiment of this invention is directed to a pharmaceutical composition comprising an effective amount of a compound selected from the group consisting of (200)-(214), (249), (251), (260)-(267), (276)-(280), (306), (310)-(312), (314), (322), (330) and (336), and a pharmaceutically acceptable carrier.

Another embodiment of this invention is directed to a pharmaceutical composition comprising an effective amount of a compound of formula (1), a chemotherapeutic agent, and a pharmaceutically acceptable carrier.

The compounds of the invention are useful in preparing a medicament that is useful in treating cancer.

The compounds of this invention inhibit the activity of ERK1 and ERK2 Thus, this invention further provides a method of inhibiting ERK in mammals, especially humans, by the administration of an effective amount of one or more (e.g., one) compounds of this invention. The administration of the compounds of this invention to patients, to inhibit ERK1 and/or ERK2, is useful in the treatment of cancer.

In any of the methods of treating cancer described herein, unless stated otherwise, the methods can optionally include the administration of an effective amount of one or more (e.g., 1, 2 or 3, or 1 or 2, or 1) chemotherapeutic agents. The chemotherapeutic agents can be administered currently or sequentially with the compounds of this invention. In the treatment of breast cancer, the compounds of formula (1) can be be administered in a treatment protocol which also includes the administration of an effective amount of at least one (e.g., 1-3, or 1-2, or 1) antihormonal agent (i.e., the methods of treating breast cancer can include hormonal therapies).

The methods of treating cancer described herein include methods wherein a combination of drugs (i.e., compounds, or pharmaceutically active ingredients, or pharmaceutical compositions) are used (i.e., the methods of treating cancer of this invention include combination therapies). Those skilled in the art will appreciate that the drugs are generally administered individually as a pharmaceutical composition. The use of a pharmaceutical composition comprising more than one drug is within the scope of this invention.

The methods of treating cancer described herein include methods of treating cancer that comprise administering a therapeutically effective amount of a compound of the instant invention in combination with radiation therapy and/or in combination with a second compound selected from: an estrogen receptor modulator, an androgen receptor modulator, a retinoid receptor modulator, a cytotoxiccytostatic agent, an antiproliferative agent, a prenyl-protein transferase inhibitor, an HMG-CoA reductase inhibitor, an HIV protease inhibitor, a reverse transcriptase inhibitor, an angiogenesis inhibitor, PPAR-γ agonists, PPAR-δ agonists, an inhibitor of inherent multidrug resistance, an anti-emetic agent, an agent useful in the treatment of anemia, an agent useful in the treatment of neutropenia, an immunologic-enhancing drug, an inhibitor of cell proliferation and survival signaling, a bisphosphonate, an aromatase inhibitor, an siRNA therapeutic, γ-secretase and/or NOTCH inhibitors, agents that interfere with receptor tyrosine kinases (RTKs), an agent that interferes with a cell cycle checkpoint, and any of the therapeutic agents listed herein.

In any of the methods of treating cancer described herein, unless stated otherwise, the methods can optionally include the administration of an effective amount of radiation therapy. For radiation therapy, γ-radiation is preferred.

Thus, another embodiment of this invention is directed to a method of treating cancer in a patient in need of such treatment, said method comprising administering an effective amount of a compound of formula (1). Another embodiment of this invention is directed to a method of treating cancer in a patient in need of such treatment, said method comprising administering to said patient an effective amount of a compound of formula (1), and an effective amount of at least one (e.g., 1-3, 1-2, or 1) chemotherapeutic agent.

The compounds, compositions and methods provided herein are useful for the treatment of cancer. Cancers that may be treated by the compounds, compositions and methods of the invention include, but are not limited to: (1) Cardiac: sarcoma (angiosarcoma, fibrosarcoma, rhabdomyosarcoma, liposarcoma), myxoma, rhabdomyoma, fibroma, lipoma and teratoma; (2) Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hamartoma, mesothelioma, non-small cell; (3) Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Karposi's sarcoma, leiomyoma, hemangioma, lipoma, neurofibroma, fibroma), large bowel (adenocarcinoma, tubular adenoma, villous adenoma, hamartoma, leiomyoma), colon, colorectal, rectal; (4) Genitourinary tract: kidney (adenocarcinoma, Wilm's tumor [nephroblastoma], lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); (5) Liver: hepatoma (hepatocellular carcinoma), cholangiocarcinoma, hepatoblastoma, angiosarcoma, hepatocellular adenoma, hemangioma; (6) Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; (7) Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma [pinealoma], glioblastoma multiform, oligodendroglioma, schwannoma, retinoblastoma, congenital tumors), spinal cord neurofibroma, meningioma, glioma, sarcoma); (8) Gynecological: uterus (endometrial carcinoma), cervix (cervical carcinoma, pre-tumor cervical dysplasia), ovaries (ovarian carcinoma [serous cystadenocarcinoma, mucinous cystadenocarcinoma, unclassified carcinoma], granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma), breast; (9) Hematologic: blood (myeloid leukemia [acute and chronic], acute lymphoblastic leukemia, chronic lymphocytic leukemia, chronic myelomonocytic (CMML), myeloproliferative diseases, multiple myeloma, myelodysplastic syndrome), Hodgkin's disease, non-Hodgkin's lymphoma [malignant lymphoma]; (10) Skin: malignant melanoma, basal cell carcinoma, squamous cell carcinoma, Karposi's sarcoma, moles dysplastic nevi, lipoma, angioma, dermatofibroma, keloids, psoriasis; and (11) Adrenal glands: neuroblastoma. Examples of cancer that may be treated by the compounds, compositions and methods of the invention include thyroid cancer, anaplastic thyroid carcinoma, epidermal cancer, head and neck cancer (e.g., squamous cell cancer of the head and neck), sarcoma, tetracarcinoma, hepatoma and multiple myeloma. Thus, the term "cancerous cell" as provided herein, includes a cell afflicted by any one of the above-identified conditions.

In the treatment of breast cancer (e.g., postmenopausal and premenopausal breast cancer, e.g., hormone-dependent breast cancer) the compound of formula (1) may be used with an effective amount of at least one antihormonal agent selected from the group consisting of: (a) aromatase inhibitors, (b) antiestrogens, and (c) LHRH analogues; and optionally an effective amount of at least one chemotherapeutic agent. Examples of aromatase inhibitors include but are not limited to: Anastrozole (e.g., Arimidex), Letrozole (e.g., Femara), Exemestane (Aromasin), Fadrozole and Formestane (e.g., Lentaron). Examples of antiestrogens include but are not limited to: Tamoxifen (e.g., Nolvadex), Fulvestrant (e.g., Faslodex), Raloxifene (e.g., Evista), and Acolbifene. Examples of LHRH analogues include but are not limited to: Goserelin (e.g., Zoladex) and Leuprolide (e.g., Leuprolide Acetate, such as Lupron or Lupron Depot). Examples of chemotherapeutic agents include but are not limited to: Trastuzumab (e.g., Herceptin), Gefitinib (e.g., Iressa), Erlotinib (e.g., Erlotinib HCl, such as Tarceva), Bevacizumab (e.g., Avastin), Cetuximab (e.g., Erbitux), and Bortezomib (e.g., Velcade).

In one embodiment of this invention the cancer treated is colo-rectal cancer (such as, for example, colon adenocarcinoma and colon adenoma). Thus, another embodiment of this invention is directed to a method of treating colo-rectal cancer in a patient in need of such treatment, said method comprising administering an effective of a compound of formula (1) to said patient. Another embodiment is directed to a method of treating colo-rectal cancer in a patient in need of such treatment, said method comprising administering to said patient an effective amount of a compound selected from the group consisting of: compounds of formulas (200)-(214), (249), (251), (260)-(267), (276)-(280), (306), (310)-(312), (314), (322), (330) and (336). Another embodiment of this invention is directed to a method of treating colo-rectal cancer in a patient in need of such treatment, said method comprising administering to said patient an effective amount of a compound of formula (1), and an effective amount of at least one (e.g., 1-3, or 1-2, or 1) chemotherapeutic agent.

In one embodiment of this invention the cancer treated is melanoma. Thus, another embodiment of this invention is directed to a method of treating melanoma in a patient in need of such treatment, said method comprising administering an effective amount of a compound of formula (1) to said patient. Another embodiment is directed to a method of treating melanoma in a patient in need of such treatment, said method comprising administering to said patient an effective amount of a compound selected from the group consisting of: compounds of formulas (200)-(214), (249), (251), (260)-(267), (276)-(280), (306), (310)-(312), (314), (322), (330) and (336). Another embodiment of this invention is directed to a method of treating melanoma in a patient in need of such treatment, said method comprising administering to said patient an effective amount of a compound of formula (1), and an effective amount of at least one (e.g., 1-3, or 1-2, or 1) chemotherapeutic agent.

The compounds of the invention are also useful in preparing a medicament that is useful in treating cancer.

The compounds of this invention may be administered to mammals, including humans, either alone or, in combination with pharmaceutically acceptable carriers, excipients or diluents, in a pharmaceutical composition, according to standard pharmaceutical practice. The compounds can be administered orally or parenterally, including the intravenous, intramuscular, intraperitoneal, subcutaneous, rectal and topical routes of administration.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, microcrystalline cellulose, sodium crosscarmellose, corn starch, or alginic acid; binding agents, for example starch, gelatin, polyvinyl-pyrrolidone or acacia, and lubricating agents, for example, magnesium stearate, stearic acid or talc. The tablets may be uncoated or they may be coated by known techniques to mask the unpleasant taste of the drug or delay disintegration and absorption in the gastrointestinal tract and thereby provide a sustained action over a longer period. For example, a water soluble taste masking material such as hydroxypropylmethyl-cellulose or hydroxypropylcellulose, or a time delay material such as ethyl cellulose, cellulose acetate buryrate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water soluble carrier such as polyethyleneglycol or an oil medium, for example peanut oil, liquid paraffin, or olive oil.

Aqueous suspensions contain the active material in admixture with excipients suitable for the manufacture of aqueous suspensions. Such excipients are suspending agents, for example sodium carboxymethylcellulose, methylcellulose, hydroxypropylmethyl-cellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethylene-oxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose, saccharin or aspartame.

Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as butylated hydroxyanisol or alpha-tocopherol.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present. These compositions may be preserved by the addition of an anti-oxidant such as ascorbic acid.

The pharmaceutical compositions of the invention may also be in the form of an oil-in-water emulsion. The oily phase may be a vegetable oil, for example olive oil or arachis oil, or a mineral oil, for example liquid paraffin or mixtures of these. Suitable emulsifying agents may be naturally-occurring phosphatides, for example soy bean lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening, flavouring agents, preservatives and antioxidants.

Syrups and elixirs may be formulated with sweetening agents, for example glycerol, propylene glycol, sorbitol or sucrose. Such formulations may also contain a demulcent, a preservative, flavoring and coloring agents and antioxidant.

The pharmaceutical compositions may be in the form of sterile injectable aqueous solutions. Among the acceptable vehicles and solvents that may be employed are water, Ringer's solution and isotonic sodium chloride solution.

The sterile injectable preparation may also be a sterile injectable oil-in-water microemulsion where the active ingredient is dissolved in the oily phase. For example, the active ingredient may be first dissolved in a mixture of soybean oil and lecithin. The oil solution then introduced into a water and glycerol mixture and processed to form a microemulsion.

The injectable solutions or microemulsions may be introduced into a patient's blood-stream by local bolus injection.

Alternatively, it may be advantageous to administer the solution or microemulsion in such a way as to maintain a constant circulating concentration of the instant compound. In order to maintain such a constant concentration, a continuous intravenous delivery device may be utilized. An example of such a device is the Deltec CADD-PLUS™ model 5400 intravenous pump.

The pharmaceutical compositions may be in the form of a sterile injectable aqueous or oleagenous suspension for intramuscular and subcutaneous administration. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Compounds of the instant invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials include cocoa butter, glycerinated gelatin, hydrogenated vegetable oils, mixtures of polyethylene glycols of various molecular weights and fatty acid esters of polyethylene glycol.

For topical use, creams, ointments, jellies, solutions or suspensions, etc., containing the compound of the instant invention are employed. (For purposes of this application, topical application shall include mouth washes and gargles.)

The compounds for the present invention can be administered in intranasal form via topical use of suitable intranasal vehicles and delivery devices, or via transdermal routes, using those forms of transdermal skin patches well known to those of ordinary skill in the art. To be administered in the form of a transdermal delivery system, the dosage administration will, of course, be continuous rather than intermittent throughout the dosage regimen. Compounds of the present invention may also be delivered as a suppository employing bases such as cocoa butter, glycerinated gelatin, hydrogenated vegetable oils, mixtures of polyethylene glycols of various molecular weights and fatty acid esters of polyethylene glycol.

When a composition according to this invention is administered into a human subject, the daily dosage will normally be determined by the prescribing physician with the dosage generally varying according to the age, weight, and response of the individual patient, as well as the severity of the patient's symptoms.

The dosage regimen utilizing the compounds of the instant invention can be selected in accordance with a variety of factors including type, species, age, weight, sex and the type of cancer being treated; the severity (i.e., stage) of the cancer to be treated; the route of administration; the renal and hepatic function of the patient; and the particular compound or salt thereof employed. An ordinarily skilled physician or veterinarian can readily determine and prescribe the effective amount of the drug required to treat, for example, to prevent, inhibit (fully or partially) or arrest the progress of the disease. Compounds of this invention can be administered in a total daily dose of 10 mg to 3000 mg. For example, compounds of the instant invention can be administered in a total daily dose of up to 3000 mg. Compounds of the instant invention can be administered once daily (QD), or divided into multiple daily doses such as twice daily (BID), and three times daily (TID). Compounds of the instant invention can be administered at a total daily dosage of up to 3000 mg, e.g., 200 mg, 300 mg, 400 mg, 600 mg, 800 mg, 1000 mg, 2000 mg or 3000 mg, which can be administered in one daily dose or can be divided into multiple daily doses as described above.

In addition, the administration can be continuous, i.e., every day, or intermittently. The terms "intermittent" or "intermittently" as used herein means stopping and starting at either regular or irregular intervals. For example, intermittent administration of a compound of the instant invention may be administration one to six days per week or it may mean administration in cycles (e.g. daily administration for two to eight consecutive weeks, then a rest period with no administration for up to one week) or it may mean administration on alternate days. The compounds of this invention may be administered discontinuously rather than continuously during the treatment cycle. Thus, the compounds of this invention may be administered daily for one or more weeks during the cycle and discontinued for one or more weeks during the cycle, with this pattern of administration repeating during the treatment cycle (e.g., administration for a week and then discontinued for a week). This discontinuous treatment may also be based upon numbers of days rather than a full week. The number of days (or weeks) that the compounds of this invention are not dosed do not have to equal the number of days (or weeks) wherein the compounds of this invention are dosed. Usually, if a discontinuous dosing protocol is used, the number of days or weeks that the compounds of this invention are dosed is at least equal to or greater than the number of days or weeks that the compounds of this invention are not dosed.

In addition, the compounds of the instant invention may be administered according to any of the schedules described above, consecutively for a few weeks, followed by a rest period. For example, the compounds of the instant invention may be administered according to any one of the schedules described above from two to eight weeks, followed by a rest period of one week, or twice daily at a dose of 100-500 mg for three to five days a week. In another particular embodiment, the compounds of the instant invention may be administered three times daily for two consecutive weeks, followed by one week of rest.

Any one or more of the specific dosages and dosage schedules of the compounds of the instant invention, may also be applicable to any one or more of the therapeutic agents to be used in the combination treatment (hereinafter referred to as the "second therapeutic agent").

Moreover, the specific dosage and dosage schedule of this second therapeutic agent can further vary, and the optimal dose, dosing schedule and route of administration will be determined based upon the specific second therapeutic agent that is being used.

Of course, the route of administration of the compounds of the instant invention is independent of the route of administration of the second therapeutic agent. In an embodiment, the administration for a compound of the instant invention is oral administration. In another embodiment, the administration for a compound of the instant invention is intravenous administration. Thus, in accordance with these embodiments, a compound of the instant invention is administered orally or intravenously, and the second therapeutic agent can be administered orally, parenterally, intraperitoneally, intravenously, intraarterially, transdermally, sublingually, intramuscularly, rectally, transbuccally, intranasally, liposomally, via inhalation, vaginally, intraoccularly, via local delivery by catheter or stent, subcutaneously, intraadiposally, intraarticularly, intrathecally, or in a slow release dosage form.

In addition, a compound of the instant invention and second therapeutic agent may be administered by the same mode of administration, i.e. both agents administered e.g. orally, by IV. However, it is also within the scope of the present invention to administer a compound of the instant invention by one mode of administration, e.g. oral, and to administer the second therapeutic agent by another mode of administration, e.g. IV or any other ones of the administration modes described hereinabove.

The first treatment procedure, administration of a compound of the instant invention, can take place prior to the second treatment procedure, i.e., the second therapeutic agent, after the treatment with the second therapeutic agent, at the same time as the treatment with the second therapeutic agent, or a combination thereof. For example, a total treatment period can be decided for a compound of the instant invention. The second therapeutic agent can be administered prior to onset of treatment with a compound of the instant invention or following treatment with a compound of the instant invention. In addition, anti-cancer treatment can be administered during the period of administration of a compound of the instant invention but does not need to occur over the entire treatment period of a compound of the instant invention.

The instant compounds are also useful in combination with therapeutic, chemotherapeutic and anti-cancer agents. Combinations of the presently disclosed compounds with therapeutic, chemotherapeutic and anti-cancer agents are within the scope of the invention. Examples of such agents can be found in *Cancer Principles and Practice of Oncology* by V. T. Devita and S. Hellman (editors), 6$^{th}$ edition (Feb. 15, 2001), Lippincott Williams & Wilkins Publishers. A person of ordinary skill in the art would be able to discern which combinations of agents would be useful based on the particular characteristics of the drugs and the cancer involved. Such agents include the following: estrogen receptor modulators, androgen receptor modulators, retinoid receptor modulators, cytotoxic/cytostatic agents, antiproliferative agents, prenyl-protein transferase inhibitors, HMG-CoA reductase inhibitors and other angiogenesis inhibitors, HIV protease inhibitors, reverse transcriptase inhibitors, inhibitors of cell proliferation and survival signaling, bisphosphonates, aromatase inhibitors, siRNA therapeutics, γ-secretase inhibitors, agents that interfere with receptor tyrosine kinases (RTKs) and agents that interfere with cell cycle checkpoints. The instant compounds are particularly useful when co-administered with radiation therapy.

"Estrogen receptor modulators" refers to compounds that interfere with or inhibit the binding of estrogen to the receptor, regardless of mechanism. Examples of estrogen receptor modulators include, but are not limited to, tamoxifen, raloxifene, idoxifene, LY353381, LY117081, toremifene, fulvestrant, 4-[7-(2,2-dimethyl-1-oxopropoxy-4-methyl-2-[4-[2-(1-piperidinyl)ethoxy]phenyl]-2H-1-benzopyran-3-yl]-phenyl-2,2-dimethylpropanoate, 4,4'-dihydroxybenzophenone-2,4-dinitrophenyl-hydrazone, and SH646.

"Androgen receptor modulators" refers to compounds which interfere or inhibit the binding of androgens to the receptor, regardless of mechanism. Examples of androgen receptor modulators include finasteride and other 5α-reductase inhibitors, nilutamide, flutamide, bicalutamide, liarozole, and abiraterone acetate.

"Retinoid receptor modulators" refers to compounds which interfere or inhibit the binding of retinoids to the receptor, regardless of mechanism. Examples of such retinoid receptor modulators include bexarotene, tretinoin, 13-cis-retinoic acid, 9-cis-retinoic acid, α-difluoromethylomithine, ILX23-7553, trans-N-(4'-hydroxyphenyl)retinamide, and N-4-carboxyphenyl retinamide.

"Cytotoxic/cytostatic agents" refer to compounds which cause cell death or inhibit cell proliferation primarily by interfering directly with the cell's functioning or inhibit or interfere with cell myosis, including alkylating agents, tumor necrosis factors, intercalators, hypoxia activatable compounds, microtubule inhibitors/microtubule-stabilizing agents, inhibitors of mitotic kinesins, histone deacetylase inhibitors, inhibitors of kinases involved in mitotic progression, inhibitors of kinases involved in growth factor and cytokine signal transduction pathways, antimetabolites, biological response modifiers, hormonal/anti-hormonal therapeutic agents, haematopoietic growth factors, monoclonal antibody targeted therapeutic agents, topoisomerase inhibitors, proteosome inhibitors, ubiquitin ligase inhibitors, and aurora kinase inhibitors.

Examples of cytotoxic/cytostatic agents include, but are not limited to, sertenef, cachectin, ifosfamide, tasonermin, lonidamine, carboplatin, altretamine, prednimustine, dibromodulcitol, ranimustine, fotemustine, nedaplatin, oxaliplatin, temozolomide, heptaplatin, estramustine, improsulfan tosilate, trofosfamide, nimustine, dibrospidium chloride, pumitepa, lobaplatin, satraplatin, profiromycin, cisplatin, irofulven, dexifosfamide, cis-aminedichloro(2-methyl-pyridine)platinum, benzylguanine, glufosfamide, GPX100, (trans, trans, trans)-bis-mu-(hexane-1,6-diamine)-mu-[diamine-platinum(II)]bis[diamine(chloro)platinum (II)]tetrachloride, diarizidinylspermine, arsenic trioxide, 1-(11-dodecylamino-10-hydroxyundecyl)-3,7-dimethylxanthine, zorubicin, idarubicin, daunorubicin, bisantrene, mitoxantrone, pirarubicin, pinafide, valrubicin, amrubicin, antineoplaston, 3'-deamino-3'-morpholino-13-deoxo-10-hydroxycarminomycin, annamycin, galarubicin, elinafide, MEN10755, 4-demethoxy-3-deamino-3-aziridinyl-4-methylsulphonyl-daunorubicin (see WO 00/50032), Raf kinase inhibitors (such as Bay43-9006) and mTOR inhibitors (such as Wyeth's CCI-779).

An example of a hypoxia activatable compound is tirapazamine.

Examples of proteosome inhibitors include but are not limited to lactacystin and MLN-341 (Velcade).

Examples of microtubule inhibitors/microtubule-stabilising agents include paclitaxel, vindesine sulfate, 3',4'-didehydro-4'-deoxy-8'-norvincaleukoblastine, docetaxol, rhizoxin, dolastatin, mivobulin isethionate, auristatin, cemadotin, RPR109881, BMS184476, vinflunine, cryptophycin, 2,3,4,5, 6-pentafluoro-N-(3-fluoro-4-methoxyphenyl)benzene sulfonamide, anhydrovinblastine, N,N-dimethyl-L-valyl-L-valyl-N-methyl-L-valyl-L-prolyl-L-proline-t-butylamide, TDX258, the epothilones (see for example U.S. Pat. Nos. 6,284,781 and 6,288,237) and BMS188797. In an embodiment the epothilones are not included in the microtubule inhibitors/microtubule-stabilising agents.

Some examples of topoisomerase inhibitors are topotecan, hycaptamine, irinotecan, rubitecan, 6-ethoxypropionyl-3',4'-O-exo-benzylidene-chartreusin, 9-methoxy-N,N-dimethyl-5-nitropyrazolo[3,4,5-kl]acridine-2-(6H) propanamine, 1-amino-9-ethyl-5-fluoro-2,3-dihydro-9-hydroxy-4-methyl-1H,12H-benzo[de]pyrano[3',4':b,7]-indolizino[1,2b]quinoline-10,13(9H,15H)dione, lurtotecan, 7-[2-(N-isopropylamino)ethyl]-(20S)camptothecin, BNP1350, BNPI1100, BN80915, BN80942, etoposide phosphate, teniposide, sobuzoxane, 2'-dimethylamino-2'-deoxy-etoposide, GL331, N-[2-(dimethylamino)ethyl]-9-hydroxy-5,6-dimethyl-6H-pyrido[4,3-b]carbazole-1-carboxamide, asulacrine, (5a,5aB,8aa,9b)-9-[2-[N-[2-(dimethylamino)ethyl]-N-methylamino]ethyl]-5-[4-hydroOxy-3,5-dimethoxyphenyl]-5,5a,6,8,8a,9-hexohydrofuro(3',4':6,7)naphtho(2,3-d)-1,3-dioxol-6-one, 2,3-(methylenedioxy)-5-methyl-7-hydroxy-8-methoxybenzo[c]-phenanthridinium, 6,9-bis[(2-aminoethyl)amino]benzo[g]isoquinoline-5,10-dione, 5-(3-aminopropylamino)-7,10-dihydroxy-2-(2-hydroxyethylaminomethyl)-6H-pyrazolo[4,5,1-de]acridin-6-one, N-[1-[2(diethylamino)ethylamino]-7-methoxy-9-oxo-9H-thioxanthen-4-ylmethyl]formamide, N-(2-(dimethylamino)ethyl)acridine-4-carboxamide, 6-[[2-(dimethylamino)ethyl]amino]-3-hydroxy-7H-indeno[2,1-c]quinolin-7-one, and dimesna.

Examples of inhibitors of mitotic kinesins, and in particular the human mitotic kinesin KSP, are described in Publications WO03/039460, WO03/050064, WO03/050122, WO03/049527, WO03/049679, WO03/049678, WO04/039774, WO03/079973, WO03/099211, WO03/105855, WO03/106417, WO04/037171, WO04/058148, WO04/058700, WO04/126699, WO05/018638, WO05/019206, WO05/019205, WO05/018547, WO05/017190, US2005/0176776. In an embodiment inhibitors of mitotic kinesins include, but are not limited to inhibitors of KSP, inhibitors of MKLP1, inhibitors of CENP-E, inhibitors of MCAK and inhibitors of Rab6-KIFL.

Examples of "histone deacetylase inhibitors" include, but are not limited to, SAHA, TSA, oxamflatin, PXD101, MG98 and scriptaid. Further reference to other histone deacetylase inhibitors may be found in the following manuscript; Miller, T. A. et al. *J. Med. Chem.* 46(24):5097-5116 (2003).

"Inhibitors of kinases involved in mitotic progression" include, but are not limited to, inhibitors of aurora kinase, inhibitors of Polo-like kinases (PLK; in particular inhibitors of PLK-1), inhibitors of bub-1 and inhibitors of bub-R1. An example of an "aurora kinase inhibitor" is VX-680.

"Antiproliferative agents" includes antisense RNA and DNA oligonucleotides such as G3139, ODN698, RVASK-RAS, GEM231, and INX3001, and antimetabolites such as enocitabine, carmofur, tegafur, pentostatin, doxifluridine, trimetrexate, fludarabine, capecitabine, galocitabine, cytarabine ocfosfate, fosteabine sodium hydrate, raltitrexed, paltitrexid, emitefur, tiazofurin, decitabine, nolatrexed, pemetrexed, nelzarabine, 2'-deoxy-2'-methylidenecytidine, 2'-fluoromethylene-2'-deoxycytidine, N-[5-(2,3-dihydrobenzo[i]yl)sulfonyl]-N'-(3,4-dichlorophenyl)urea, N6-[4-deoxy-4-[N2-[2(E),4(E)-tetradecadienoyl]glycylamino]-L-glycero-B-L-manno-heptopyranosyl]adenine, aplidine, ecteinascidin, troxacitabine, 4-[2-amino-4-oxo-4,6,7,8-tetrahydro-3H-pyrimidino[5,4-b][1,4]thiazin-6-yl-(S)-ethyl]-2,5-thienoyl-L-glutamic acid, aminopterin, 5-fluorouracil, alanosine, 11-acetyl-8-(carbamoyloxymethyl)-4-formyl-6-methoxy-14-oxa-1,11-diazatetracyclo(7.4.1.0.0)-tetradeca-2,4,6-trien-9-yl acetic acid ester, swainsonine, lometrexol, dexrazoxane, methioninase, 2'-cyano-2'-deoxy-N4-palmitoyl-1-B-D-arabino furanosyl cytosine, 3-aminopyridine-2-carboxaldehyde thiosemicarbazone and trastuzumab.

Examples of monoclonal antibody targeted therapeutic agents include those therapeutic agents which have cytotoxic agents or radioisotopes attached to a cancer cell specific or target cell specific monoclonal antibody. Examples include Bexxar.

"HMG-CoA reductase inhibitors" refers to inhibitors of 3-hydroxy-3-methylglutaryl-CoA reductase. Examples of HMG-CoA reductase inhibitors that may be used include but are not limited to lovastatin (MEVACOR®; see U.S. Pat. Nos. 4,231,938, 4,294,926 and 4,319,039), simvastatin (ZO-COR®; see U.S. Pat. Nos. 4,444,784, 4,820,850 and 4,916,239), pravastatin (PRAVACHOL®; see U.S. Pat. Nos. 4,346,227, 4,537,859, 4,410,629, 5,030,447 and 5,180,589), fluvastatin (LESCOL®; see U.S. Pat. Nos. 5,354,772, 4,911,165, 4,929,437, 5,189,164, 5,118,853, 5,290,946 and 5,356,896), atorvastatin (LIPITOR®; see U.S. Pat. Nos. 5,273,995, 4,681,893, 5,489,691 and 5,342,952) and cerivastatin (also known as rivastatin and BAYCHOL®); see U.S. Pat. No. 5,177,080). The structural formulas of these and additional HMG-CoA reductase inhibitors that may be used in the instant methods are described at page 87 of M. Yalpani, "Cholesterol Lowering Drugs", *Chemistry & Industry*, pp. 85-89 (5 Feb. 1996) and U.S. Pat. Nos. 4,782,084 and 4,885,314. The term HMG-CoA reductase inhibitor as used herein includes all pharmaceutically acceptable lactone and open-acid forms (i.e., where the lactone ring is opened to form the free acid) as well as salt and ester forms of compounds which have HMG-CoA reductase inhibitory activity, and therefor the use of such salts, esters, open-acid and lactone forms is included within the scope of this invention.

"Prenyl-protein transferase inhibitor" refers to a compound which inhibits any one or any combination of the prenyl-protein transferase enzymes, including farnesyl-protein transferase (FPTase), geranylgeranyl-protein transferase type I (GGPTase-I), and geranylgeranyl-protein transferase type-II (GGPTase-II, also called Rab GGPTase).

Examples of prenyl-protein transferase inhibitors can be found in the following publications and patents: WO 96/30343, WO 97/18813, WO 97/21701, WO 97/23478, WO 97/38665, WO 98/28980, WO 98/29119, WO 95/32987, U.S. Pat. Nos. 5,420,245, 5,523,430, 5,532,359, 5,510,510, 5,589,485, 5,602,098, European Patent Publ. 0 618 221, European Patent Publ. 0 675 112, European Patent Publ. 0 604 181, European Patent Publ. 0 696 593, WO 94/19357, WO 95/08542, WO 95/11917, WO 95/12612, WO 95/12572, WO 95/10514, U.S. Pat. No. 5,661,152, WO 95/10515, WO 95/10516, WO 95/24612, WO 95/34535, WO 95/25086, WO 96/05529, WO 96/06138, WO 96/06193, WO 96/16443, WO 96/21701, WO 96/21456, WO 96/22278, WO 96/24611, WO 96/24612, WO 96/05168, WO 96/05169, WO 96/00736, U.S. Pat. No. 5,571,792, WO 96/17861, WO 96/33159, WO 96/34850, WO 96/34851, WO 96/30017, WO 96/30018, WO 96/30362, WO 96/30363, WO 96/31111, WO 96/31477, WO 96/31478, WO 96/31501, WO 97/00252, WO 97/03047, WO 97/03050, WO 97/04785, WO 97/02920, WO 97/17070, WO 97/23478, WO 97/26246, WO 97/30053, WO 97/44350, WO 98/02436, and U.S. Pat. No. 5,532,359. For an example of the role of a prenyl-protein transferase inhibitor on angiogenesis see *European J. of Cancer*, Vol. 35, No. 9, pp. 1394-1401 (1999).

"Angiogenesis inhibitors" refers to compounds that inhibit the formation of new blood vessels, regardless of mechanism. Examples of angiogenesis inhibitors include, but are not limited to, tyrosine kinase inhibitors, such as inhibitors of the tyrosine kinase receptors Flt-1 (VEGFR1) and Flk-1/KDR (VEGFR2), inhibitors of epidermal-derived, fibroblast-derived, or platelet derived growth factors, MMP (matrix metalloprotease) inhibitors, integrin blockers, interferon-α, interleukin-12, pentosan polysulfate, cyclooxygenase inhibitors, including nonsteroidal anti-inflammatories (NSAIDs) like aspirin and ibuprofen as well as selective cyclooxygenase-2 inhibitors like celecoxib and rofecoxib (*PNAS*, Vol. 89, p. 7384 (1992); *JNCI*, Vol. 69, p. 475 (1982); *Arch. Opthalmol.*, Vol. 108, p. 573 (1990); *Anat. Rec.*, Vol. 238, p. 68 (1994); *FEBS Letters*, Vol. 372, p. 83 (1995); *Clin, Orthop.* Vol. 313, p. 76 (1995); *J. Mol. Endocrinol.*, Vol. 16, p. 107 (1996); *Jpn. J. Pharmacal.*, Vol. 75, p. 105 (1997); *Cancer*

Res., Vol. 57, p. 1625 (1997); Cell, Vol. 93, p. 705 (1998); Intl. J. Mol. Med., Vol. 2, p. 715 (1998); J. Biol. Chem., Vol. 274, p. 9116 (1999)), steroidal anti-inflammatories (such as corticosteroids, mineralocorticoids, dexamethasone, prednisone, prednisolone, methylpred, betamethasone), carboxyamidotriazole, combretastatin A-4, squalamine, 6-O-chloroacetylcarbonyl)-fumagillol, thalidomide, angiostatin, troponin-1, angiotensin II antagonists (see Fernandez et al., J. Lab. Clin. Med. 105:141-145 (1985)), and antibodies to VEGF (see, Nature Biotechnology, Vol. 17, pp. 963-968 (October 1999); Kim et al., Nature, 362, 841-844 (1993); WO 00/44777; and WO 00/61186).

Other therapeutic agents that modulate or inhibit angiogenesis and may also be used in combination with the compounds of the instant invention include agents that modulate or inhibit the coagulation and fibrinolysis systems (see review in Clin. Chem. La. Med. 38:679-692 (2000)). Examples of such agents that modulate or inhibit the coagulation and fibrinolysis pathways include, but are not limited to, heparin (see Thromb. Haemost. 80:10-23 (1998)), low molecular weight heparins and carboxypeptidase U inhibitors (also known as inhibitors of active thrombin activatable fibrinolysis inhibitor [TAFIa]) (see Thrombosis Res. 101:329-354 (2001)). TAFIa inhibitors have been described in U.S. Ser. Nos. 60/310,927 (filed Aug. 8, 2001) and 60/349,925 (filed Jan. 18, 2002).

"Agents that interfere with cell cycle checkpoints" refer to compounds that inhibit protein kinases that transduce cell cycle checkpoint signals, thereby sensitizing the cancer cell to DNA damaging agents. Such agents include inhibitors of ATR, ATM, the CHK1 and CHK2 kinases and cdk and cdc kinase inhibitors and are specifically exemplified by 7-hydroxystaurosporin, flavopiridol, CYC202 (Cyclacel) and BMS-387032.

"Agents that interfere with receptor tyrosine kinases (RTKs)" refer to compounds that inhibit RTKs and therefore mechanisms involved in oncogenesis and tumor progression. Such agents include inhibitors of c-Kit, Eph, PDGF, Flt3 and c-Met. Further agents include inhibitors of RTKs as described by Bume-Jensen and Hunter, Nature, 411:355-365, 2001.

"Inhibitors of cell proliferation and survival signalling pathway" refer to compounds that inhibit signal transduction cascades downstream of cell surface receptors. Such agents include inhibitors of serine/threonine kinases (including but not limited to inhibitors of Akt such as described in WO 02/083064, WO 02/083139, WO 02/083140, US 2004-0116432, WO 02/083138, US 2004-0102360, WO 03/086404, WO 03/086279, WO 03/086394, WO 03/084473, WO 03/086403, WO 2004/041162, WO 2004/096131, WO 2004/096129, WO 2004/096135, WO 2004/096130, WO 2005/100356, WO 2005/100344, US 2005/029941, US 2005/44294, US 2005/43361, 60/734,188, 60/652,737, 60/670,469), inhibitors of Raf kinase (for example BAY-43-9006), inhibitors of MEK (for example CI-1040 and PD-098059), inhibitors of mTOR (for example Wyeth CCI-779), and inhibitors of PI3K (for example LY294002).

As described above, the combinations with NSAID's are directed to the use of NSAID's which are potent COX-2 inhibiting agents. For purposes of this specification an NSAID is potent if it possesses an $IC_{50}$ for the inhibition of COX-2 of 1 μM or less as measured by cell or microsomal assays.

The invention also encompasses combinations with NSAID's which are selective COX-2 inhibitors. For purposes of this specification NSAID's which are selective inhibitors of COX-2 are defined as those which possess a specificity for inhibiting COX-2 over COX-1 of at least 100 fold as measured by the ratio of $IC_{50}$ for COX-2 over $IC_{50}$ for COX-1 evaluated by cell or microsomal assays. Such compounds include, but are not limited to those disclosed in U.S. Pat. Nos. 5,474,995, 5,861,419, 6,001,843, 6,020,343, 5,409,944, 5,436,265, 5,536,752, 5,550,142, 5,604,260, 5,698,584, 5,710,140, WO 94/15932, U.S. Pat. Nos. 5,344,991, 5,134,142, 5,380,738, 5,393,790, 5,466,823, 5,633,272 and 5,932,598, all of which are hereby incorporated by reference.

Inhibitors of COX-2 that are particularly useful in the instant method of treatment are: 3-phenyl-4-(4-(methylsulfonyl)phenyl)-2-(5H)-furanone; and 5-chloro-3-(4-methylsulfonyl)-phenyl-2-(2-methyl-5-pyridinyl)pyridine; or a pharmaceutically acceptable salt thereof.

Compounds that have been described as specific inhibitors of COX-2 and are therefore useful in the present invention include, but are not limited to, the following: parecoxib, BEXTRA® and CELEBREX® or a pharmaceutically acceptable salt thereof.

Other examples of angiogenesis inhibitors include, but are not limited to, endostatin, ukrain, ranpirnase, IM862, 5-methoxy-4-[2-methyl-3-(3-methyl-2-butenyl)oxiranyl]-1-oxaspiro[2,5]oct-6-yl(chloroacetyl)carbamate, acetyldinanaline, 5-amino-1-[[3,5-dichloro-4-(4-chlorobenzoyl)phenyl]methyl]-1H-1,2,3-triazole-4-carboxamide, CM101, squalamine, combretastatin, RPI4610, NX31838, sulfated mannopentaose phosphate, 7,7-(carbonyl-bis[imino-N-methyl-4,2-pyrrolocarbonylimino[N-methyl-4,2-pyrrole]-carbonylimino]-bis-(1,3-naphthalene disulfonate), and 3-[(2,4-dimethylpyrrol-5-yl)methylene]-2-indolinone (SU5416).

As used above, "integrin blockers" refers to compounds which selectively antagonize, inhibit or counteract binding of a physiological ligand to the $\alpha_v\beta_3$ integrin, to compounds which selectively antagonize, inhibit or counteract binding of a physiological ligand to the αvβ5 integrin, to compounds which antagonize, inhibit or counteract binding of a physiological ligand to both the $\alpha_v\beta_3$ integrin and the $\alpha_v\beta_5$ integrin, and to compounds which antagonize, inhibit or counteract the activity of the particular integrin(s) expressed on capillary endothelial cells. The term also refers to antagonists of the $\alpha_v\beta_6$, $\alpha_v\beta_8$, $\alpha_1\beta_1$, $\alpha_2\beta_1$, $\alpha_5\beta_1$, $\alpha_6\beta_1$ and $\alpha_6\beta_4$ integrins. The term also refers to antagonists of any combination of $\alpha_v\beta_3$, $\alpha_v\beta_5$, $\alpha_v\beta_6$, $\alpha_v\beta_8$, $\alpha_1\beta_1$, $\alpha_2\beta_1$, $\alpha_5\beta_1$, $\alpha_6\beta_1$ and $\alpha_6\beta_4$ integrins.

Some specific examples of tyrosine kinase inhibitors include N-(trifluoromethylphenyl)-5-methylisoxazol-4-carboxamide, 3-[(2,4-dimethylpyrrol-5-yl)methylidenyl)indolin-2-one, 17-(allylamino)-17-demethoxygeldanamycin, 4-(3-chloro-4-fluorophenylamino)-7-methoxy-6-[3-(4-morpholinyl)propoxyl]quinazoline, N-(3-ethynylphenyl)-6,7-bis (2-methoxyethoxy)-4-quinazolinamine, BIBX1382, 2,3,9, 10,11,12-hexahydro-10-(hydroxymethyl)-10-hydroxy-9-methyl-9,12-epoxy-1H-diindolo[1,2,3-fg:3',2',1'-kl]pyrrolo [3,4-i][1,6]benzodiazocin-1-one, SH268, genistein, ST1571, CEP2563, 4-(3-chlorophenylamino)-5,6-dimethyl-7H-pyrrolo[2,3-d]pyrimidinemethane sulfonate, 4-(3-bromo-4-hydroxyphenyl)amino-6,7-dimethoxyquinazoline, 4-(4'-hydroxyphenyl)amino-6,7-dimethoxyquinazoline, SU6668, ST1571A, N-4-chlorophenyl-4-(4-pyridylmethyl)-1-phthalazinamine, and EMD121974.

Combinations with compounds other than anti-cancer compounds are also encompassed in the instant methods. For example, combinations of the instantly claimed compounds with PPAR-γ (i.e., PPAR-gamma) agonists and PPAR-δ (i.e., PPAR-delta) agonists are useful in the treatment of certain malignancies. PPAR-γ and PPAR-δ are the nuclear peroxisome proliferator-activated receptors γ and δ. The expression of PPAR-γ on endothelial cells and its involvement in angiogenesis has been reported in the literature (see J. Cardiovasc. Pharmacol. 1998; 31:909-913; J. Biol. Chem. 1999; 274:

9116-9121; *Invest. Ophthalmol Vis. Sci.* 2000; 41:2309-2317). More recently, PPAR-γ agonists have been shown to inhibit the angiogenic response to VEGF in vitro; both troglitazone and rosiglitazone maleate inhibit the development of retinal neovascularization in mice. (*Arch. Ophthamol.* 2001; 119:709-717). Examples of PPAR-γ agonists and PPAR-γ/α agonists include, but are not limited to, thiazolidinediones (such as DRF2725, CS-011, troglitazone, rosiglitazone, and pioglitazone), fenofibrate, gemfibrozil, clofibrate, GW2570, SB219994, AR-11039242, JTT-501, MCC-555, GW2331, GW409544, NN2344, KRP297, NP0110, DRF4158, NN622, GI262570, PNU182716, DRF552926, 2-[(5,7-dipropyl-3-trifluoromethyl-1,2-benzisoxazol-6-yl)oxy]-2-methylpropionic acid (disclosed in U.S. Ser. No. 09/782,856), and 2(R)-7-(3-(2-chloro-4-(4-fluorophenoxy) phenoxy)propoxy)-2-ethylchromane-2-carboxylic acid (disclosed in U.S. Ser. No. 60/235,708 and 60/244,697).

Another embodiment of the instant invention is the use of the presently disclosed compounds in combination with gene therapy for the treatment of cancer. For an overview of genetic strategies to treating cancer see Hall et al (*Am. J. Hum. Genet.* 61:785-789, 1997) and Kufe et al (Cancer Medicine, 5th Ed, pp 876-889, BC Decker, Hamilton 2000). Gene therapy can be used to deliver any tumor suppressing gene. Examples of such genes include, but are not limited to, p53, which can be delivered via recombinant virus-mediated gene transfer (see U.S. Pat. No. 6,069,134, for example), a uPA/uPAR antagonist ("Adenovirus-Mediated Delivery of a uPA/uPAR Antagonist Suppresses Angiogenesis-Dependent Tumor Growth and Dissemination in Mice," Gene Therapy, August 1998; 5(8):1105-13), and interferon gamma (*J. Immunol.* 2000; 164:217-222).

The compounds of the instant invention may also be administered in combination with an inhibitor of inherent multidrug resistance (MDR), in particular MDR associated with high levels of expression of transporter proteins. Such MDR inhibitors include inhibitors of p-glycoprotein (P-gp), such as LY335979, XR9576, OC144-093, R101922, VX853 and PSC833 (valspodar).

A compound of the present invention may be employed in conjunction with anti-emetic agents to treat nausea or emesis, including acute, delayed, late-phase, and anticipatory emesis, which may result from the use of a compound of the present invention, alone or with radiation therapy. For the prevention or treatment of emesis, a compound of the present invention may be used in conjunction with other anti-emetic agents, especially neurokinin-1 receptor antagonists, 5HT3 receptor antagonists, such as ondansetron, granisetron, tropisetron, and zatisetron, GABAB receptor agonists, such as baclofen, a corticosteroid such as Decadron (dexamethasone), Kenalog, Aristocort, Nasalide, Preferid, Benecorten or others such as disclosed in U.S. Pat. Nos. 2,789,118, 2,990,401, 3,048,581, 3,126,375, 3,929,768, 3,996,359, 3,928,326 and 3,749,712, an antidopaminergic, such as the phenothiazines (for example prochlorperazine, fluphenazine, thioridazine and mesoridazine), metoclopramide or dronabinol. In another embodiment, conjunctive therapy with an anti-emesis agent selected from a neurokinin-1 receptor antagonist, a 5HT3 receptor antagonist and a corticosteroid is disclosed for the treatment or prevention of emesis that may result upon administration of the instant compounds.

Neurokinin-1 receptor antagonists of use in conjunction with the compounds of the present invention are fully described, for example, in U.S. Pat. Nos. 5,162,339, 5,232,929, 5,242,930, 5,373,003, 5,387,595, 5,459,270, 5,494,926, 5,496,833, 5,637,699, 5,719,147; European Patent Publication Nos. EP 0 360 390, 0 394 989, 0 428 434, 0 429 366, 0 430 771, 0 436 334, 0 443 132, 0 482 539, 0 498 069, 0 499 313, 0 512 901, 0 512 902, 0 514 273, 0 514 274, 0 514 275, 0 514 276, 0 515 681, 0 517 589, 0 520 555, 0 522 808, 0 528 495, 0 532 456, 0 533 280, 0 536 817, 0 545 478, 0 558 156, 0 577 394, 0 585 913, 0 590 152, 0 599 538, 0 610 793, 0 634 402, 0 686 629, 0 693 489, 0 694 535, 0 699 655, 0 699 674, 0 707 006, 0 708 101, 0 709 375, 0 709 376, 0 714 891, 0 723 959, 0 733 632 and 0 776 893; PCT International Patent Publication Nos. WO 90/05525, 90/05729, 91/09844, 91/18899, 92/01688, 92/06079, 92/12151, 92/15585, 92/17449, 92/20661, 92/20676, 92/21677, 92/22569, 93/00330, 93/00331, 93/01159, 93/01165, 93/01169, 93/01170, 93/06099, 93/09116, 93/10073, 93/14084, 93/14113, 93/18023, 93/19064, 93/21155, 93/21181, 93/23380, 93/24465, 94/00440, 94/01402, 94/02461, 94/02595, 94/03429, 94/03445, 94/04494, 94/04496, 94/05625, 94/07843, 94/08997, 94/10165, 94/10167, 94/10168, 94/10170, 94/11368, 94/13639, 94/13663, 94/14767, 94/15903, 94/19320, 94/19323, 94/20500, 94/26735, 94/26740, 94/29309, 95/02595, 95/04040, 95/04042, 95/06645, 95/07886, 95/07908, 95/08549, 95/11880, 95/14017, 95/15311, 95/16679, 95/17382, 95/18124, 95/18129, 95/19344, 95/20575, 95/21819, 95/22525, 95/23798, 95/26338, 95/28418, 95/30674, 95/30687, 95/33744, 96/05181, 96/05193, 96/05203, 96/06094, 96/07649, 96/10562, 96/16939, 96/18643, 96/20197, 96/21661, 96/29304, 96/29317, 96/29326, 96/29328, 96/31214, 96/32385, 96/37489, 97/01553, 97/01554, 97/03066, 97/08144, 97/14671, 97/17362, 97/18206, 97/19084, 97/19942 and 97/21702; and in British Patent Publication Nos. 2 266 529, 2 268 931, 2 269 170, 2 269 590, 2 271 774, 2 292 144, 2 293 168, 2 293 169, and 2 302 689. The preparation of such compounds is fully described in the aforementioned patents and publications, which are incorporated herein by reference.

In an embodiment, the neurokinin-1 receptor antagonist for use in conjunction with the compounds of the present invention is selected from: 2-(R)-(1-(R)-(3,5-bis(trifluoromethyl)phenyl)ethoxy)-3-(S)-(4-fluorophenyl)-4-(3-(5-oxo-1H,4H-1,2,4-triazolo)methyl)morpholine, or a pharmaceutically acceptable salt thereof, which is described in U.S. Pat. No. 5,719,147.

A compound of the instant invention may also be administered with an agent useful in the treatment of anemia. Such an anemia treatment agent is, for example, a continuous erythropoiesis receptor activator (such as epoetin alfa).

A compound of the instant invention may also be administered with an agent useful in the treatment of neutropenia. Such a neutropenia treatment agent is, for example, a hematopoietic growth factor which regulates the production and function of neutrophils such as a human granulocyte colony stimulating factor, (G-CSF). Examples of a G-CSF include filgrastim.

A compound of the instant invention may also be administered with an immunologic-enhancing drug, such as levamisole, isoprinosine and Zadaxin.

A compound of the instant invention may also be useful for treating or preventing cancer in combination with P450 inhibitors including: xenobiotics, quinidine, tyramine, ketoconazole, testosterone, quinine, methyrapone, caffeine, phenelzine, doxorubicin, troleandomycin, cyclobenzaprine, erythromycin, cocaine, furafyline, cimetidine, dextromethorphan, ritonavir, indinavir, amprenavir, diltiazem, terfenadine, verapamil, cortisol, itraconazole, mibefradil, nefazodone and nelfinavir.

A compound of the instant invention may also be useful for treating or preventing cancer in combination with Pgp and/or BCRP inhibitors including: cyclosporin A, PSC833, GF120918, cremophorEL, fumitremorgin C, Ko132, Ko134, Iressa, Imatnib mesylate, EKI-785, Cl1033, novobiocin, diethylstilbestrol, tamoxifen, resperpine, VX-710, tryprostatin A, flavonoids, ritonavir, saquinavir, nelfinavir, omeprazole, quinidine, verapamil, terfenadine, ketoconazole, nifidepine, FK506, amiodarone, XR9576, indinavir, amprenavir, cortisol, testosterone, LY335979, OC144-093, erythromycin, vincristine, digoxin and talinolol.

A compound of the instant invention may also be useful for treating or preventing cancer, including bone cancer, in combination with bisphosphonates (understood to include bisphosphonates, diphosphonates, bisphosphonic acids and diphosphonic acids). Examples of bisphosphonates include but are not limited to: etidronate (Didronel), pamidronate (Aredia), alendronate (Fosamax), risedronate (Actonel), zoledronate (Zometa), ibandronate (Boniva), incadronate or cimadronate, clodronate, EB-1053, minodronate, neridronate, piridronate and tiludronate including any and all pharmaceutically acceptable salts, derivatives, hydrates and mixtures thereof.

A compound of the instant invention may also be useful for treating or preventing breast cancer in combination with aromatase inhibitors. Examples of aromatase inhibitors include but are not limited to: anastrozole, letrozole and exemestane.

A compound of the instant invention may also be useful for treating or preventing cancer in combination with siRNA therapeutics.

The compounds of the instant invention may also be administered in combination with γ-secretase inhibitors and/or inhibitors of NOTCH signaling. Such inhibitors include compounds described in WO 01/90084, WO 02/30912, WO 01/70677, WO 03/013506, WO 02/36555, WO 03/093252, WO 03/093264, WO 03/093251, WO 03/093253, WO 2004/039800, WO 2004/039370, WO 2005/030731, WO 2005/014553, U.S. Ser. No. 10/957,251, WO 2004/089911, WO 02/081435, WO 02/081433, WO 03/018543, WO 2004/031137, WO 2004/031139, WO 2004/031138, WO 2004/101538, WO 2004/101539 and WO 02/47671 (including LY-450139).

A compound of the instant invention may also be useful for treating or preventing cancer in combination with PARP inhibitors.

A compound of the instant invention may also be useful for treating cancer in combination with the following therapeutic agents: abarelix (Plenaxis Depot®); aldesleukin (Prokine®); Aldesleukin (Proleukin®); Alemtuzumabb (Campath®); alitretinoin (Panretin®), allopurinol (Zyloprim®); altretamine (Hexylen®); amifostine (Ethyol®); anastrozole (Arimidex®); arsenic trioxide (Trisenox®); asparaginase (Elspar®); azacitidine (Vidaza®); bevacuzimab (Avastin); bexarotene capsules (Targretin®); bexarotene gel (Targretin®); bleomycin (Blenoxane®); bortezomib (Velcade®); busulfan intravenous (Busulfex); busulfan oral (Myleran®); calusterone (Methosarb®); capecitabine (Xeloda); carboplatin (Paraplatin®); carmustine (BCNU®, BiCNU®); carmustine (Gliadel®); carmustine with Polifeprosan 20 Implant (Gliadel Wafer®); celecoxib (Celebrex®); cetuximab (Erbitux®); chlorambucil (Leukeran®); cisplatin (Platinol®); cladribine (Leustatin®, 2-CdA®); clofarabine (Clolar®); cyclophosphamide (Cytoxan®, Neosar®); cyclophosphamide (Cytoxan Injection®); cyclophosphamide (Cytoxan Tablet®); cytarabine (Cytosar-U®); cytarabine liposomal (DepoCyt®); dacarbazine (DTIC-Dome®); dactinomycin, actinomycin D (Cosmegen®); Darbepoetin alfa (Aranesp®); daunorubicin liposomal (DanuoXome®); daunorubicin, daunomycin (Daunorubicin®); daunorubicin, daunomycin (Cerubidine®); Denileukin diftitox (Ontak®); dexrazoxane (Zinecard®); docetaxel (Taxotere®); doxorubicin (Adriamycin PFS®); doxorubicin (Adriamycin®, Rubex®); doxorubicin (Adriamycin PFS Injection®); doxorubicin liposomal (Doxil®); DROMOSTANOLONE PROPIONATE (DROMOSTANOLONE®); DROMOSTANOLONE PROPIONATE (MASTERONE INJECTION®); Elliott's B Solution (Elliott's B Solution®); epirubicin (Ellence®); Epoetin alfa (Epogen®); erlotinib (Tarceva); estramustine (Emcyt®); etoposide phosphate (Etopophos®); etoposide, VP-16 (Vepesid®); exemestane (Aromasin®); Filgrastim (Neupogen®); floxuridine (intraarterial) (FUDR®); fludarabine (Fludara®); fluorouracil, 5-FU (Adrucil®); fulvestrant (Faslodex®); gefitinib (Iressa®); gemcitabine (Gemzar®); gemtuzumab ozogamicin (Mylotarg®); goserelin acetate (Zoladex Implant®); goserelin acetate (Zoladex®); histrelin acetate (Histrelin Implant®); hydroxyurea (Hydrea®); Ibritumomab Tiuxetan (Zevalin®); idarubicin (Idamycin®); ifosfamide (IFEX®); imatinib mesylate (Gleevec®); interferon alfa 2a (Roferon A®); Interferon alfa-2b (Intron A®); irinotecan (Camptosar®); lenalidomide (Revlimid®); letrozole (Femara®); leucovorin (Wellcovorin®, Leucovorin®); Leuprolide Acetate (Eligard®); levamisole (Ergamisol®); lomustine, CCNU (CeeBU®); rneclorethamine, nitrogen mustard (Mustargen®); megestrol acetate (Megace®); melphalan, L-PAM (Alkeran®); mercaptopurine, 6-MP (Purinethol®); mesna (Mesnex®); mesna (Mesnex Tabs®); methotrexate (Methotrexate®); methoxsalen (Uvadex®); mitomycin C (Mutamycin®); mitotane (Lysodren®); mitoxantrone (Novantrone®); nandrolone phenpropionate (Durabolin-50®); nelarabine (Arranon®); Nofetumomab (Verluma®); Oprelvekin (Neumega®); oxaliplatin (Eloxatin®); paclitaxel (Paxene®); paclitaxel (Taxol®); paclitaxel protein-bound particles (Abraxane®); palifermin (Kepivance®); pamidronate (Aredia®); pegademase (Adagen (Pegademase Bovine)®); pegaspargase (Oncaspar®); Pegfilgrastim (Neulasta®); pemetrexed disodium (Alimta®); pentostatin (Nipent®); pipobroman (Vercyte®); plicamycin, mithramycin (Mithracin®); porfimer sodium (Photofrin®); procarbazine (Matulane®); quinacrine (Atabrine®); Rasburicase (Elitek®); Rituximab (Rituxan®); Ridaforolimus; sargramostim (Leukine®); Sargramostim (Prokine®); sorafenib (Nexavar®); streptozocin (Zanosar®); sunitinib maleate (Sutent®); talc (Sclerosol®); tamoxifen (Nolvadex®); temozolomide (Temodar®); teniposide, VM-26 (Vumon®); testolactone (Teslac®); thioguanine, 6-TG (Thioguanine®); thiotepa (Thioplex®); topotecan (Hycamtin®); toremifene (Fareston®); Tositumomab (Bexxar®); Tositumomab/I-131 tositumomab (Bexxar®); Trastuzumab (Herceptin®); tretinoin, ATRA (Vesanoid®); Uracil Mustard (Uracil Mustard Capsules®); valrubicin (Valstar®); vinblastine (Velban®); vincristine (Oncovin®); vinorelbine (Navelbine®); vorinostat (Zolinza®) and zoledronate (Zometa®).

In an embodiment, the angiogenesis inhibitor to be used as the second compound is selected from a tyrosine kinase inhibitor, an inhibitor of epidermal-derived growth factor, an inhibitor of fibroblast-derived growth factor, an inhibitor of platelet derived growth factor, an MMP (matrix metalloprotease) inhibitor, an integrin blacker, interferon-α, interleukin-12, pentosan polysulfate, a cyclooxygenase inhibitor, carboxyamidotriazole, combretastatin A-4, squalamine, 6-O-chloroacetyl-carbonyl)-fumagillol, thalidomide, angiostatin, troponin-1, or an antibody to VEGF. In an embodiment, the estrogen receptor modulator is tamoxifen or raloxifene.

Thus, the scope of the instant invention encompasses the use of the instantly claimed compounds in combination with a second compound selected from: an estrogen receptor modulator, an androgen receptor modulator, a retinoid receptor modulator, a cytotoxic/cytostatic agent, an antiproliferative agent, a prenyl-protein transferase inhibitor, an HMG-CoA reductase inhibitor, an HIV protease inhibitor, a reverse transcriptase inhibitor, an angiogenesis inhibitor, PPAR-γ agonists, PPAR-δ agonists, an inhibitor of inherent multidrug resistance, an anti-emetic agent, an agent useful in the treatment of anemia, an agent useful in the treatment of neutropenia, an immunologic-enhancing drug, an inhibitor of cell proliferation and survival signaling, a bisphosphonate, an aromatase inhibitor, an siRNA therapeutic, γ-secretase and/or NOTCH inhibitors, agents that interfere with receptor tyrosine kinases (RTKs), an agent that interferes with a cell cycle checkpoint, and any of the therapeutic agents listed above.

Also included in the scope of the claims is a method of treating cancer that comprises administering a therapeutically effective amount of a compound of the instant invention in combination with radiation therapy and/or in combination with a second compound selected from: an estrogen receptor modulator, an androgen receptor modulator, a retinoid receptor modulator, a cytotoxiccytostatic agent, an antiproliferative agent, a prenyl-protein transferase inhibitor, an HMG-CoA reductase inhibitor, an HIV protease inhibitor, a reverse transcriptase inhibitor, an angiogenesis inhibitor, PPAR-γ agonists, PPAR-δ agonists, an inhibitor of inherent multidrug resistance, an anti-emetic agent, an agent useful in the treatment of anemia, an agent useful in the treatment of neutropenia, an immunologic-enhancing drug, an inhibitor of cell proliferation and survival signaling, a bisphosphonate, an aromatase inhibitor, an siRNA therapeutic, γ-secretase and/or NOTCH inhibitors, agents that interfere with receptor tyrosine kinases (RTKs), an agent that interferes with a cell cycle checkpoint, and any of the therapeutic agents listed above.

And yet another embodiment of the invention is a method of treating cancer that comprises administering a therapeutically effective amount of a compound of the instant invention in combination with paclitaxel or trastuzumab.

The invention further encompasses a method of treating or preventing cancer that comprises administering a therapeutically effective amount of a compound of the instant invention in combination with a COX-2 inhibitor.

The instant invention also includes a pharmaceutical composition useful for treating or preventing cancer that comprises a therapeutically effective amount of a compound of the instant invention and a second compound selected from: an estrogen receptor modulator, an androgen receptor modulator, a retinoid receptor modulator, a cytotoxic/cytostatic agent, an antiproliferative agent, a prenyl-protein transferase inhibitor, an HMG-CoA reductase inhibitor, an HIV protease inhibitor, a reverse transcriptase inhibitor, an angiogenesis inhibitor, a PPAR-γ agonist, a PPAR-γ agonist, an inhibitor of cell proliferation and survival signaling, a bisphosphonate, an aromatase inhibitor, an siRNA therapeutic, γ-secretase and/or NOTCH inhibitors, agents that interfere with receptor tyrosine kinases (RTKs), an agent that interferes with a cell cycle checkpoint, and any of the therapeutic agents listed above.

Methods for the safe and effective administration of most of these chemotherapeutic agents are known to those skilled in the art. In addition, their administration is described in the standard literature. For example, the administration of many of the chemotherapeutic agents is described in the "Physicians' Desk Reference" (PDR), e.g., 1996 edition (Medical Economics Company, Montvale, N.J. 07645-1742, USA), the Physicians' Desk Reference, 56$^{th}$ Edition, 2002 (published by Medical Economics company, Inc. Montvale, N.J. 07645-1742), the Physicians' Desk Reference, 57$^{th}$ Edition, 2003 (published by Thompson PDR, Montvale, N.J. 07645-1742), the Physicians' Desk Reference, 60$^{th}$ Edition, 2006 (published by Thompson PDR, Montvale, N.J. 07645-1742), and the Physicians' Desk Reference, 64$^{th}$ Edition, 2010 (published by PDR Network, LLC at Montvale, N.J. 07645-1725); the disclosures of which are incorporated herein by reference thereto.

If the patient is responding, or is stable, after completion of the therapy cycle, the therapy cycle can be repeated according to the judgment of the skilled clinician. Upon completion of the therapy cycles, the patient can be continued on the compounds of this invention at the same dose that was administered in the treatment protocol. This maintenance dose can be continued until the patient progresses or can no longer tolerate the dose (in which case the dose can be reduced and the patient can be continued on the reduced dose).

Those skilled in the art will recognize that the actual dosages and protocols for administration employed in the methods of this invention may be varied according to the judgment of the skilled clinician. The actual dosage employed may be varied depending upon the requirements of the patient and the severity of the condition being treated. Determination of the proper dosage for a particular situation is within the skill of the art. A determination to vary the dosages and protocols for administration may be made after the skilled clinician takes into account such factors as the patient's age, condition and size, as well as the severity of the cancer being treated and the response of the patient to the treatment.

The amount and frequency of administration of the compound of formula (1) and the chemotherapeutic agents will be regulated according to the judgment of the attending clinician (physician) considering such factors as age, condition and size of the patient as well as severity of the cancer being treated.

The chemotherapeutic agent can be administered according to therapeutic protocols well known in the art. It will be apparent to those skilled in the art that the administration of the chemotherapeutic agent can be varied depending on the cancer being treated and the known effects of the chemotherapeutic agent on that disease. Also, in accordance with the knowledge of the skilled clinician, the therapeutic protocols (e.g., dosage amounts and times of administration) can be varied in view of the observed effects of the administered therapeutic agents on the patient, and in view of the observed responses of the cancer to the administered therapeutic agents.

The initial administration can be made according to established protocols known in the art, and then, based upon the observed effects, the dosage, modes of administration and times of administration can be modified by the skilled clinician.

The particular choice of chemotherapeutic agent will depend upon the diagnosis of the attending physicians and their judgement of the condition of the patient and the appropriate treatment protocol.

The determination of the order of administration, and the number of repetitions of administration of the chemotherapeutic agent during a treatment protocol, is well within the knowledge of the skilled physician after evaluation of the cancer being treated and the condition of the patient.

Thus, in accordance with experience and knowledge, the practicing physician can modify each protocol for the administration of a chemotherapeutic agent according to the individual patient's needs, as the treatment proceeds. All such modifications are within the scope of the present invention.

The attending clinician, in judging whether treatment is effective at the dosage administered, will consider the general well-being of the patient as well as more definite signs such as relief of cancer-related symptoms (e.g., pain), inhibition of tumor growth, actual shrinkage of the tumor, or inhibition of metastasis. Size of the tumor can be measured by standard methods such as radiological studies, e.g., CAT or MRI scan, and successive measurements can be used to judge whether or not growth of the tumor has been retarded or even reversed. Relief of disease-related symptoms such as pain, and improvement in overall condition can also be used to help judge effectiveness of treatment.

The compounds of this invention may be prepared by employing reactions as shown in the following Reaction Schemes, in addition to other standard manipulations that are known in the literature or exemplified in the experimental procedures. The illustrative Reaction Schemes below, therefore, are not limited by the compounds listed or by any particular substituents employed for illustrative purposes. Substituent numbering as shown in the Reaction Schemes do not necessarily correlate to that used in the claims and often, for clarity, a single substituent is shown attached to the compound where multiple substituents are optionally allowed under the definitions of formula (1) hereinabove.

The LCMS conditions are: (1) column: C-18 reverse phase, 5um, 4.6×50 mm, (2) MS:PE Sciex API-150EX, and (3) HPLC: Shimadzu LC-10 ADvp, 1 ml/min, linear gradient 10% acetonitrile in water to 95% acetonitrile in water, both contain 0.05% TFA

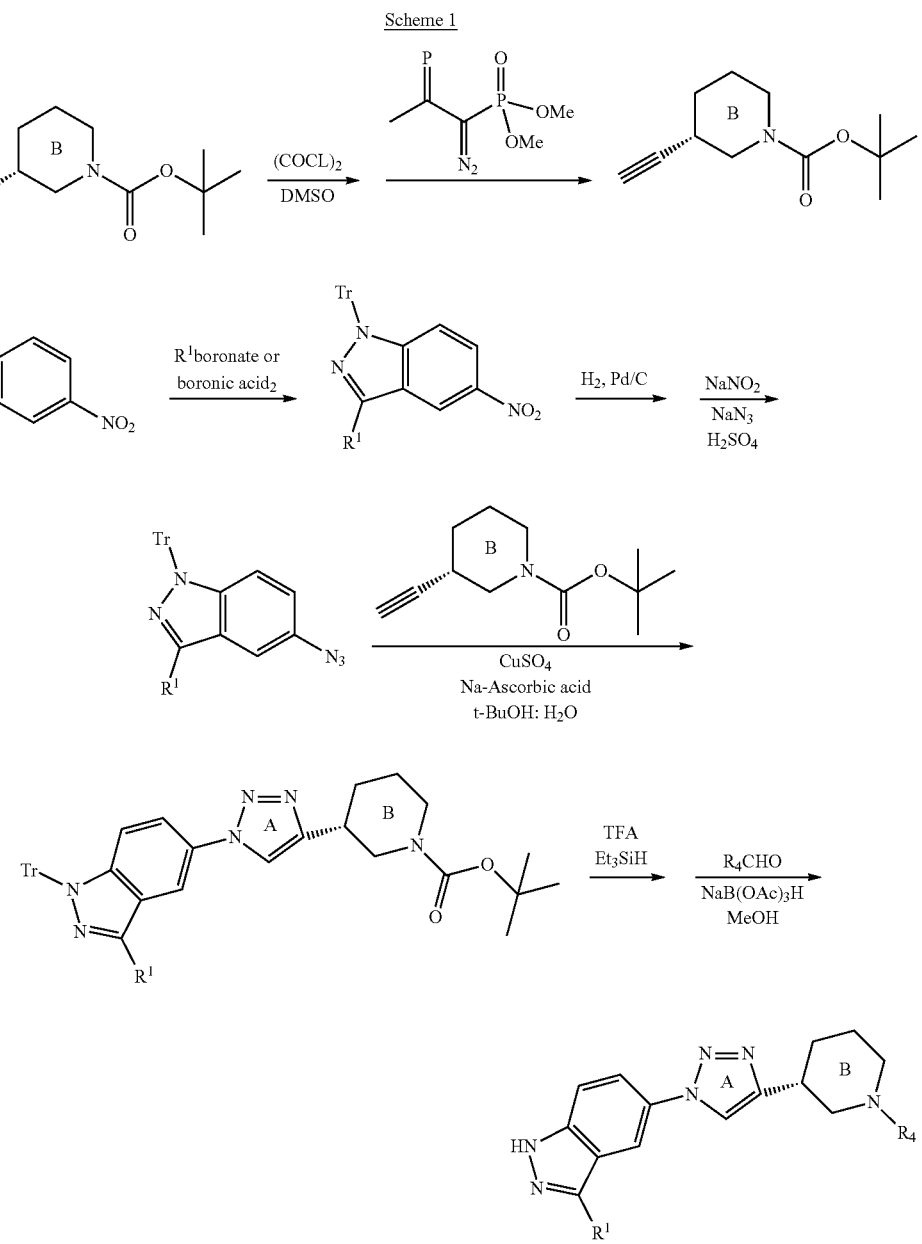

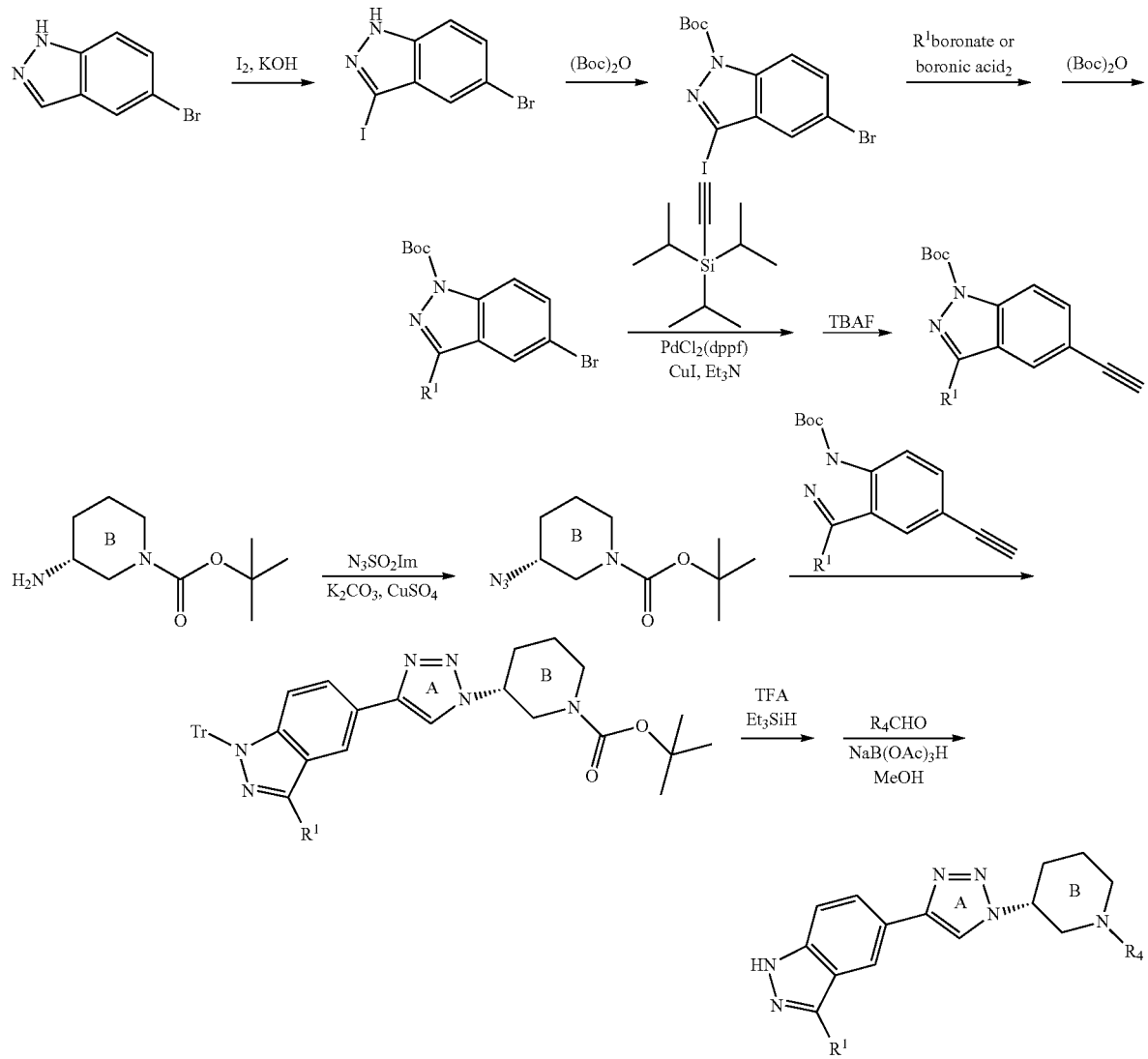
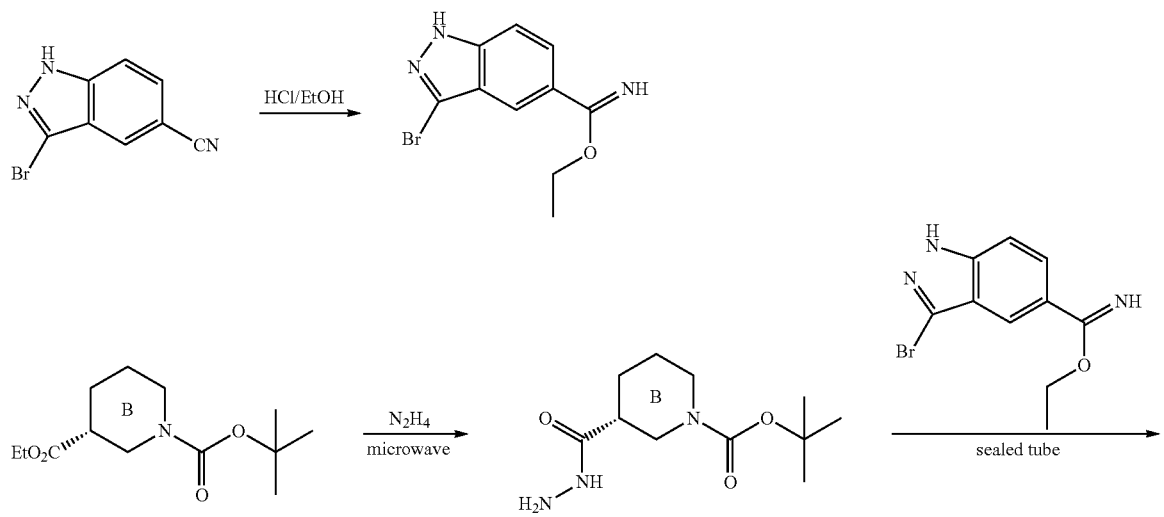

63 64
-continued
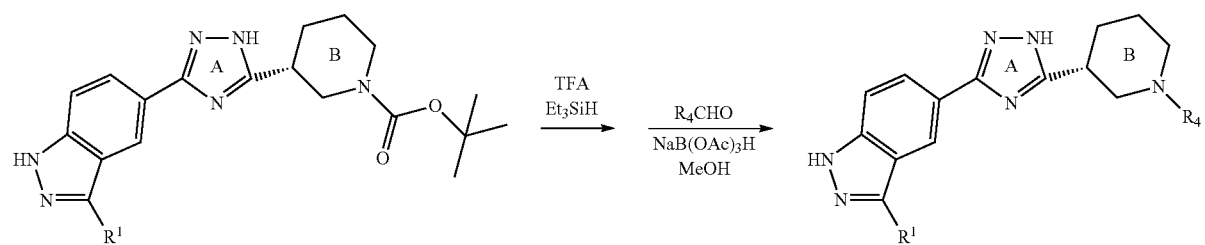
Scheme 4
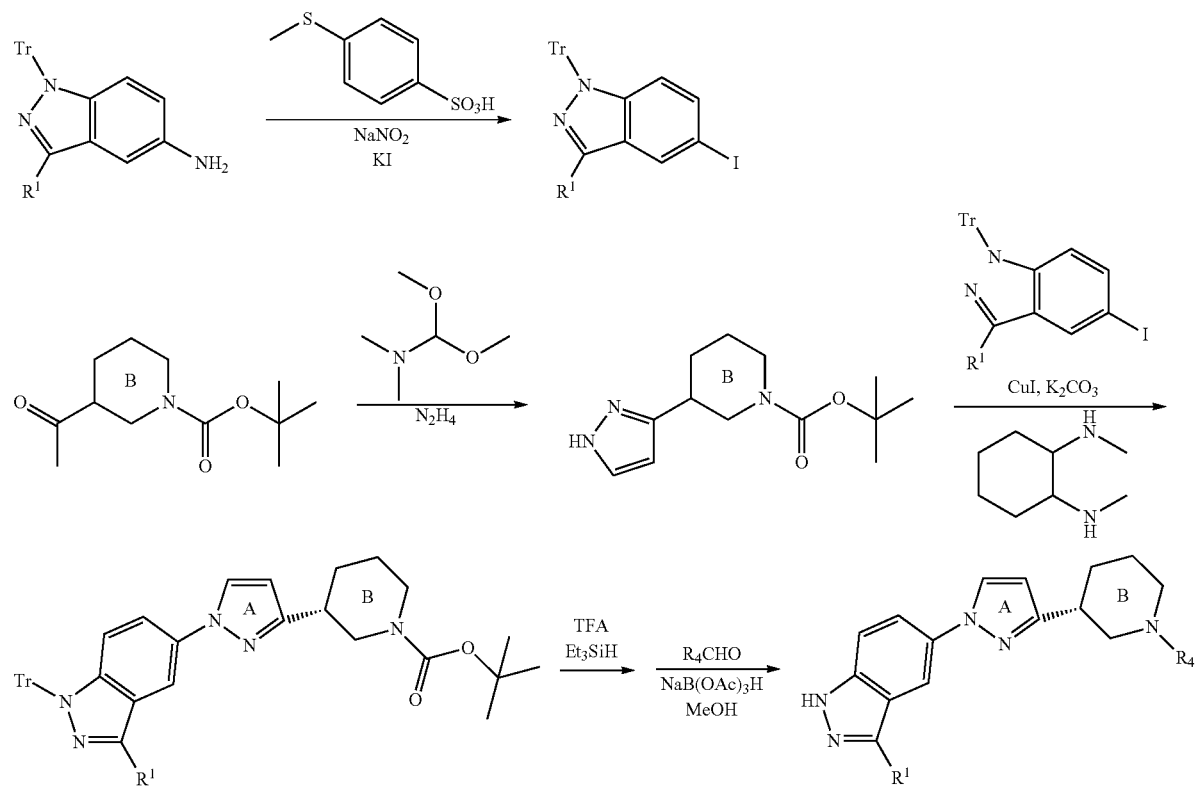
Scheme 5
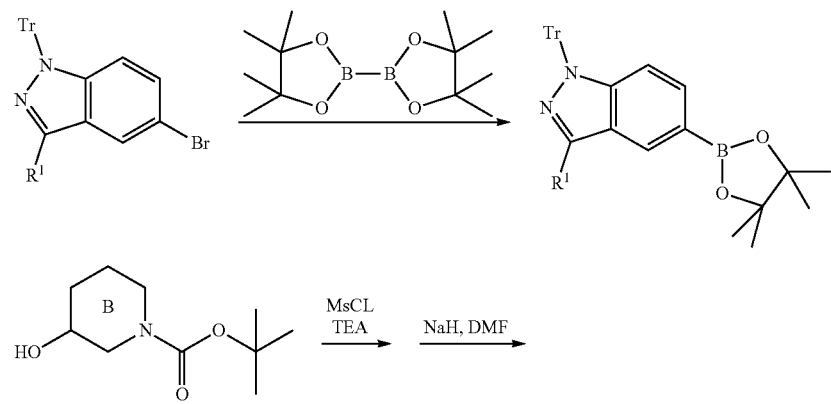

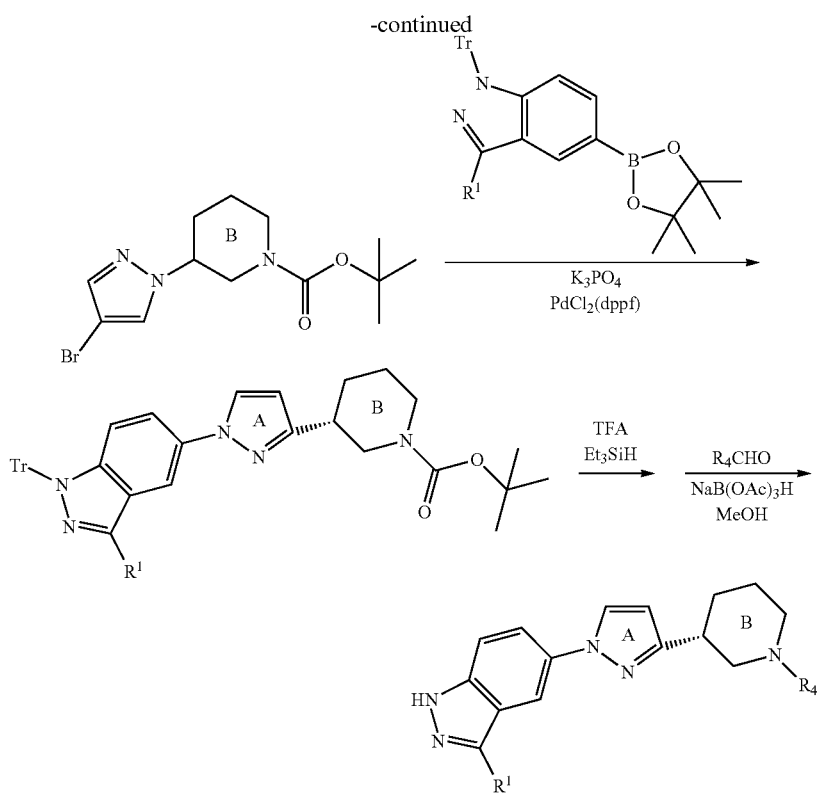

Scheme 6

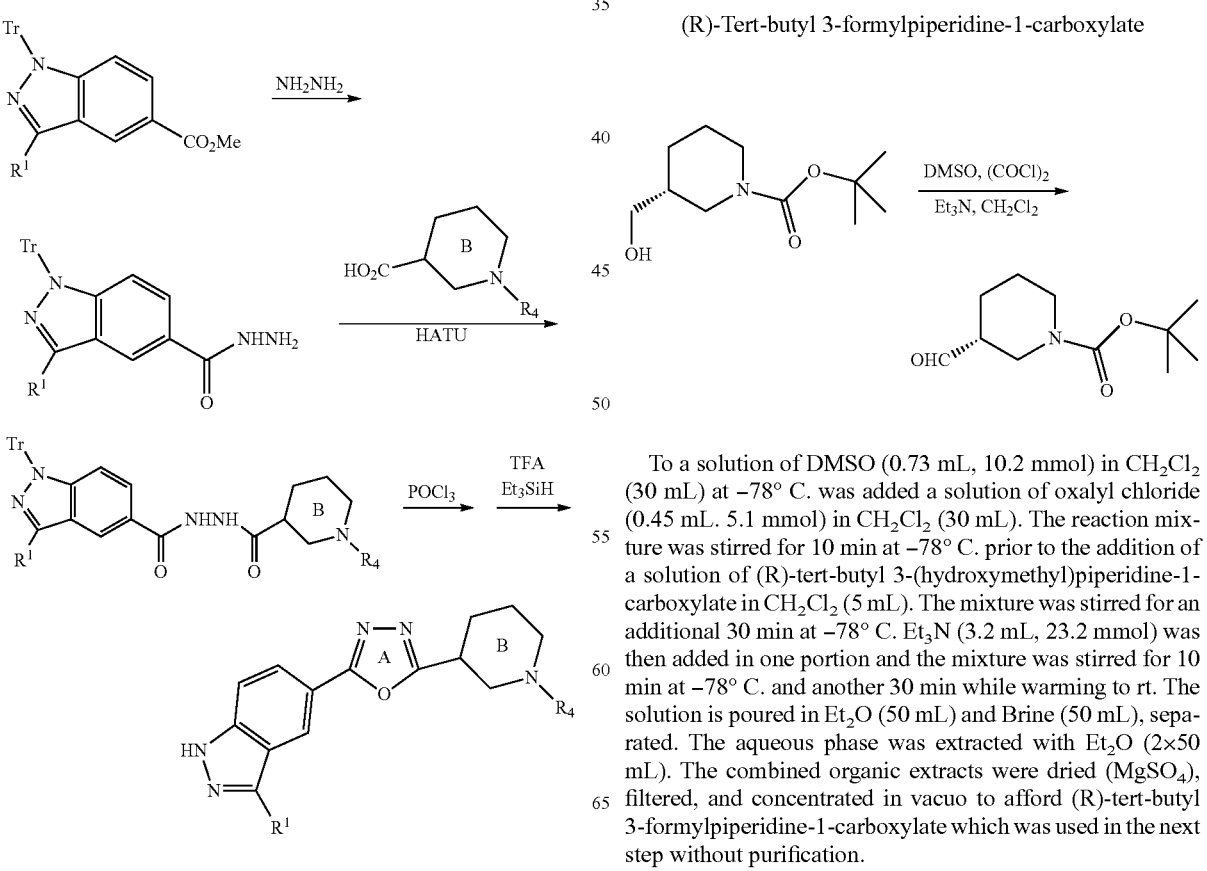

Example 1

(R)-Tert-butyl 3-formylpiperidine-1-carboxylate

To a solution of DMSO (0.73 mL, 10.2 mmol) in $CH_2Cl_2$ (30 mL) at −78° C. was added a solution of oxalyl chloride (0.45 mL. 5.1 mmol) in $CH_2Cl_2$ (30 mL). The reaction mixture was stirred for 10 min at −78° C. prior to the addition of a solution of (R)-tert-butyl 3-(hydroxymethyl)piperidine-1-carboxylate in $CH_2Cl_2$ (5 mL). The mixture was stirred for an additional 30 min at −78° C. $Et_3N$ (3.2 mL, 23.2 mmol) was then added in one portion and the mixture was stirred for 10 min at −78° C. and another 30 min while warming to rt. The solution is poured in $Et_2O$ (50 mL) and Brine (50 mL), separated. The aqueous phase was extracted with $Et_2O$ (2×50 mL). The combined organic extracts were dried ($MgSO_4$), filtered, and concentrated in vacuo to afford (R)-tert-butyl 3-formylpiperidine-1-carboxylate which was used in the next step without purification.

(S)-Tert-butyl 3-ethynylpiperidine-1-carboxylate

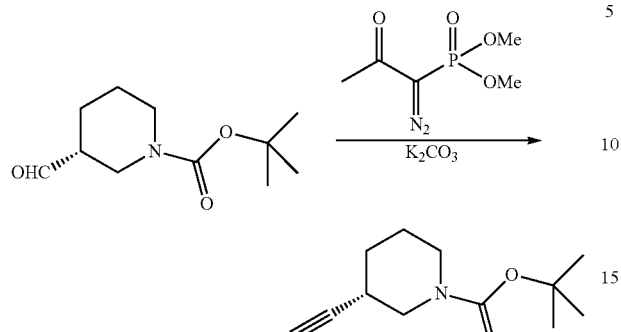

To crude (R)-tert-butyl 3-formylpiperidine-1-carboxylate in MeOH (20 mL) was added dimethyl 1-diazo-2-oxopropylphosphonate (1.28 g, 5.6 mmol), cooled to 0° C. and then added $K_2CO_3$ (2.56 g, 18.6 mmol), followed by MS, TLC. Added water (60 mL), extracted with EtOAc (3×50 mL), organic layer were evaporated and dried to give the desired product (S)-tert-butyl 3-ethynylpiperidine-1-carboxylate (0.86 g).

5-Nitro-3-(pyridin-4-yl)-1-trityl-1H-indazole

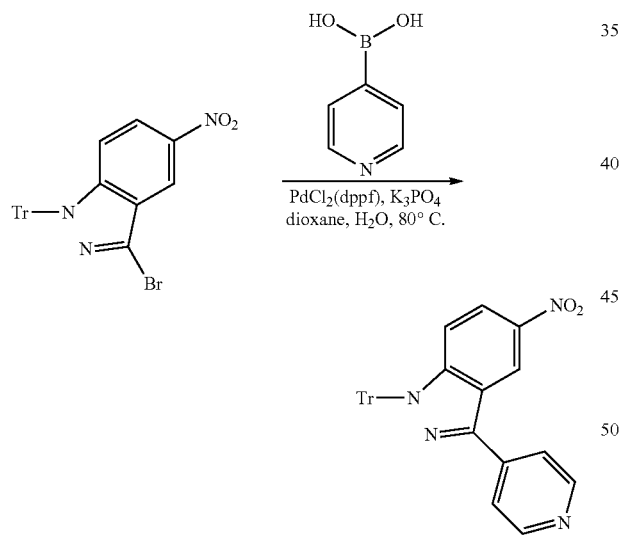

To a 500 ml round bottom flask equipped with a magnetic stir bar was added 3-bromo-5-nitro-1-trityl-1H-indazole (13.13 g, 27.1 mmol), followed by the additions of 4-pyridine boronic acid (5.00 g, 40.7 mmol), $PdCl_2(dppf)$ (2.21 g, 2.7 mmol) and $K_3PO_4$ (14.39 g, 67.8 mmol). The mixture was dissolved in a mixture of 160 ml of dioxane and 40 ml of $H_2O$ and stirred overnight at 80° C. Upon completion, the reaction mixture was filtered through a pad of celite and washed with water (3×100 ml). The organic phase was then dried over anhydrous $MgSO_4$, filtered and concentrated to give a crude product. The crude product was column purified (30% EtAOc/Hexane) to give 5-nitro-3-(pyridin-4-yl)-1-trityl-1H-indazole (10.7 g) as a yellow solid.

3-(Pyridin-4-yl)-1-trityl-4H-indazol-5-amine

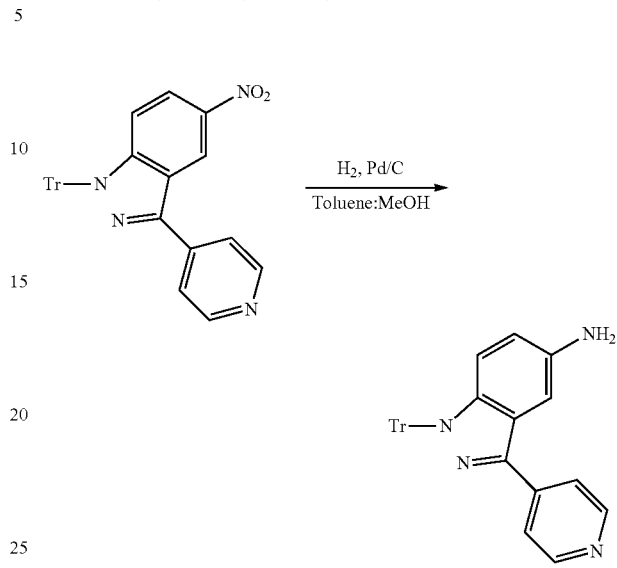

To a 500 ml round bottom flask equipped with a magnetic stir bar was added 5-nitro-3-(pyridin-4-yl)-1-trityl-1H-indazole (1332 g, 27.6 mmol) and dissolved in a mixture of toluene:MeOH (120 ml: 40 ml). While stirring, Pd/C (1.5 g, 10% wet) was added. The mixture was then subjected to a hydrogen balloon and stirred overnight. Upon completion of the reaction, which was determined by LC/MS, the mixture was filtered through celite and concentrated under vacuum to give 3-(pyridin-4-yl)-1-trityl-1H-indazol-5-amine (13.21 g) as a yellow solid.

5-Azido-3-(pyridin-4-yl)-1-trityl-1H-indazole

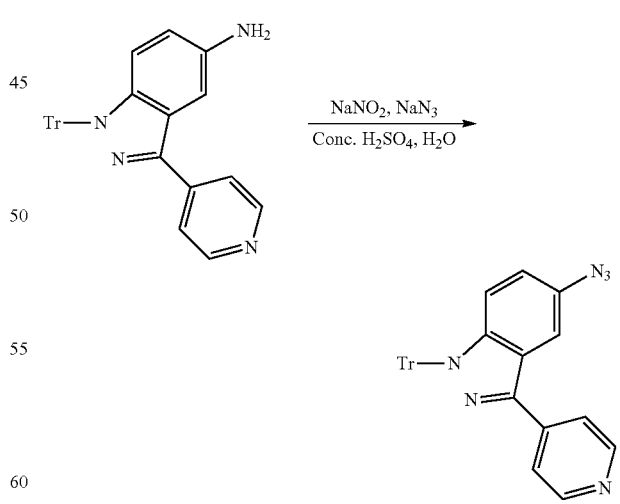

To a 1 L round bottom flask equipped with a magnetic stir bar was suspended 3-(pyridin-4-yl)-1-trityl-1H-indazol-5-amine (13.00 g, 28.7 mmol) in 400.00 ml of water and cooled to 0° C. 80 ml of conc. $H_2SO_4$ was added slowly over a period of 15 min at 0° C. A solution of $NaNO_2$ (2.48 g, 35.9 mmol) in 15 ml of water was added to the mixture and allowed to stir at 0° C. for 30 min. A solution of NaN₃ (3.36 g, 51.7 mmol) in water was then added dropwise over a period of 15 min. The mixture was slowly warmed to room temperature and stirred overnight. Upon completion, the precipitate was filtered, washed with water and dried to give 5-azido-3-(pyridin-4-yl)-1-trityl-1H-indazole (12.62 g) as a yellow solid.

(R)-5-(4-(Piperidin-3-yl)-1H-1,2,3-triazol-1-yl)-3-(pyridin-4-yl)-1H-indazole

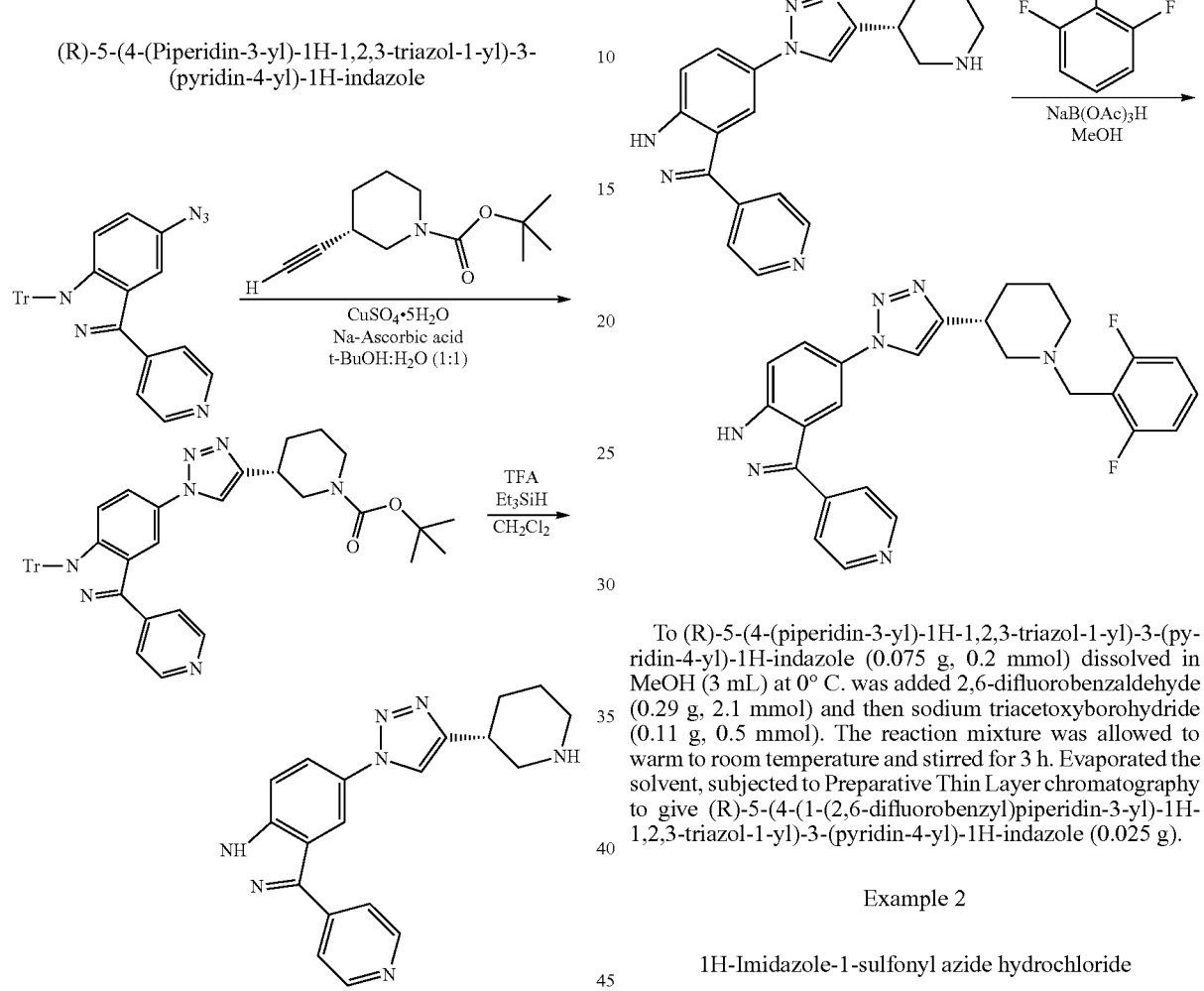

5-azido-3-(pyridin-4-yl)-1-trityl-1H-indazole (1.0 g, 2.1 mmol) and (S)-tert-butyl 3-ethynylpiperidine-1-carboxylate (0.43 g, 2.1 mmol) were suspended in t-BuOH:H₂O (1:1 10 mL:10 mL) and then CuSO₄·5H₂O (5 mg, 0.002 mmol) and Na-Ascorbic acid (40 mg, 0.21 mmol) were added sequentially. Reaction mixture was stirred vigorously at room temperature overnight. After the completion of reaction, added sat. NaCl (30 mL), extracted with EtOAc (3×50 mL), evaporated the organic solvent to give (R)-tert-butyl 3-(1-(3-(pyridin-4-yl)-1-trityl-1H-indazol-5-yl)-1H-1,2,3-triazol-4-yl)piperidine-1-carboxylate (1.26 g) which was used for next step with out purification.

To the crude (R)-tert-butyl 3-(1-(3-(pyridin-4-yl)-1-trityl-1H-indazol-5-yl)-1H-1,2,3-triazol-4-yl)piperidine-1-carboxylate dissolved in CH₂Cl₂ (30 mL) was added TFA (2 mL and Et₃SiH (0.2 mL) and stirred at room temperature overnight under a stream of nitrogen. Evaporated the solvent and column purified (10% MeOH in CH₂Cl₂) to give the (R)-5-(4-(piperidin-3-yl)-1H-1,2,3-triazol-1-yl)-3-(pyridin-4-yl)-1H-indazole (0.61 g).

(R)-5-(4-(1-(2,6-difluorobenzyl)piperidin-3-yl)-1H-1,2,3-triazol-1-yl)-3-(pyridin-4-yl)-1H-indazole

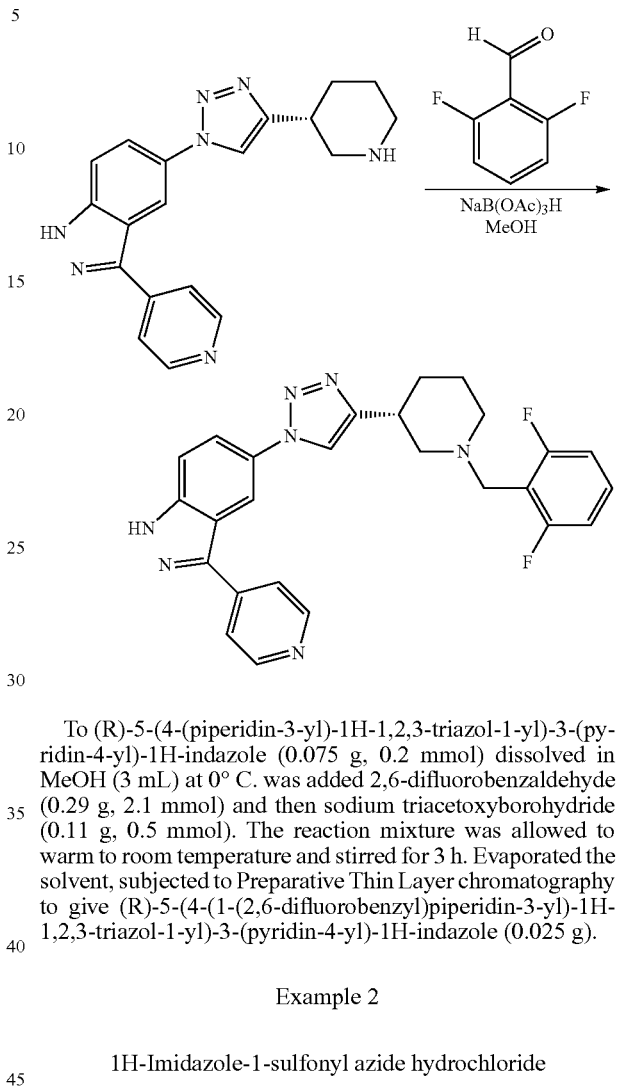

To (R)-5-(4-(piperidin-3-yl)-1H-1,2,3-triazol-1-yl)-3-(pyridin-4-yl)-1H-indazole (0.075 g, 0.2 mmol) dissolved in MeOH (3 mL) at 0° C. was added 2,6-difluorobenzaldehyde (0.29 g, 2.1 mmol) and then sodium triacetoxyborohydride (0.11 g, 0.5 mmol). The reaction mixture was allowed to warm to room temperature and stirred for 3 h. Evaporated the solvent, subjected to Preparative Thin Layer chromatography to give (R)-5-(4-(1-(2,6-difluorobenzyl)piperidin-3-yl)-1H-1,2,3-triazol-1-yl)-3-(pyridin-4-yl)-1H-indazole (0.025 g).

Example 2

1H-Imidazole-1-sulfonyl azide hydrochloride

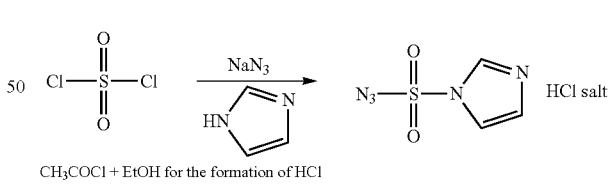

CH₃COCl + EtOH for the formation of HCl

Sulfuryl chloride (16.1 mL, 200 mol) was added drop-wise to an ice-cooled suspension of NaN₃ (13.0 g, 200 mmol) in MeCN (200 mL) and the mixture stirred overnight at room temperature. Imidazole (25.9 g, 380 mmol) was added portion-wise to the ice-cooled mixture and the resulting slurry stirred for 3 h at room temperature. The mixture was diluted with EtOAc (600 mL), washed with H₂O (2×400 mL) then saturated aqueous NaHCO₃ (2×400 mL), dried over MgSO₄ and filtered. A solution of HCl in EtOH [obtained by the drop-wise addition of AcCl (42.6 mL, 300 mmol) to ice-cooled dry ethanol (150 mL)] was added drop-wise to the filtrate with stirring, the mixture chilled in an ice-bath, filtered and the filter cake washed with EtOAc (3×100 mL) to give 1H-Imidazole-1-sulfonyl azide hydrochloride as colourless needles (24 g).

(R)-Tert-butyl 3-azidopiperidine-1-carboxylate

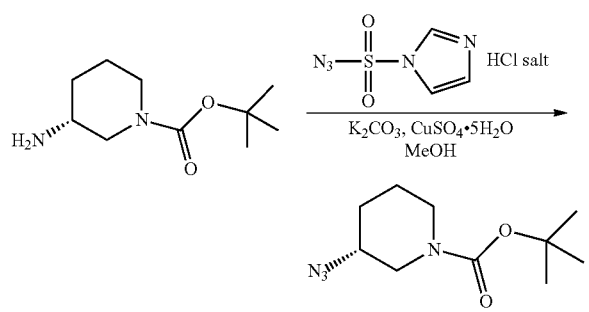

Imidazole-1-sulfonyl azide hydrochloride (1.03 g, 6.0 mmol) was added to (R)-tert-butyl 3-aminopiperidine-1-carboxylate (1.0 g, 5.0 mmol), $K_2CO_3$ (1.33 g, 10.0 mmol) and $CuSO_4 \cdot 5H_2O$ (0.012 g, 0.05 mmol) in MeOH (30 mL) and the mixture was stirred at room temperature for 12 h. The mixture was concentrated, diluted with $H_2O$ (50 mL), extracted with EtOAc (3×60 mL). The combined organic layers were dried ($MgSO_4$), filtered and concentrated to give (R)-tert-butyl 3-azidopiperidine-1-carboxylate (0.65 g).

Tert-butyl 5-bromo-3-iodo-1H-indazole-1-carboxylate

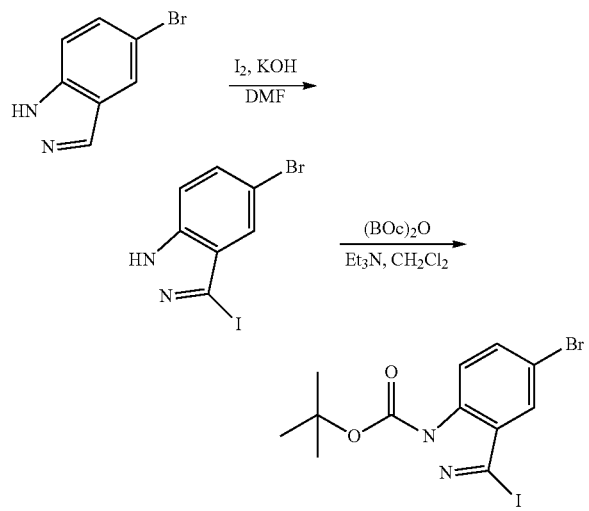

To a solution of 5-bromo-1H-indazole (8.00 g, 40.6 mmol) in DMF (200 ml), was added $I_2$ (20.61 g, 81.2 mmol) and KOH (8.54 g, 152.3 mmol) successively. The reaction was stirred at room temperature for 3 h. The mixture was then poured into aqueous $NaHSO_3$ and extracted with $Et_2O$ (3×150 ml). The combined organic layers were washed with water (3×150 ml) and brine (3×150 ml). It was dried over anhydrous $Na_2SO_4$ and evaporated to dryness to give crude product 5-bromo-3-iodo-1H-indazole (17.21 g).

The crude product of 5-bromo-3-iodo-1H-indazole was dissolved in $CH_2Cl_2$ (200 ml) under $N_2$. $Et_3N$ (14.00 ml, 100.6 mmol) was added followed by $(Boc)_2O$ (10.98 g, 50.3 mmol). The reaction was stirred at room temperature overnight. After completion of the reaction, the mixture was diluted with $CH_2Cl_2$ (150 ml) and washed with sat. $NaHCO_3$ (200 ml) and sat. NaCl (200 ml). The organic phase was dried over anhydrous $MgSO_4$, and evaporated to dryness. The residue was purified by column (30% EtAOc/Hexane) to give tert-butyl 5-bromo-3-iodo-1H-indazole-1-carboxylate (16.20 g).

5-bromo-3-(pyridin-4-yl)-1H-indazole

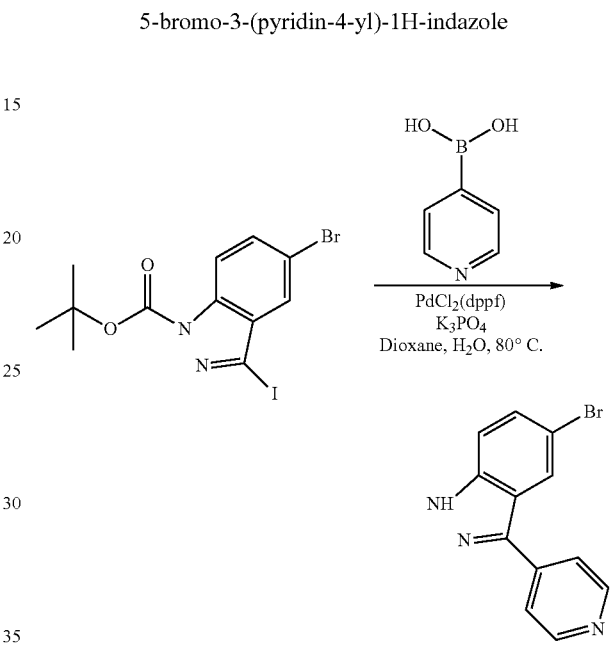

To a 500 ml round bottom flask equipped with a magnetic stir bar was added tert-butyl 5-bromo-3-iodo-1H-indazole-1-carboxylate (6.00 g, 14.2 mmol), followed by the additions of 4-pyridineboronic acid (1.92 g, 15.6 mmol), $PdCl_2(dppf)$ (1.16 g, 1.4 mmol) and $K_3PO_4$ (9.03 g, 42.5 mmol). The mixture was dissolved in a mixture of 160 ml of dioxane and 40 ml of $H_2O$ and stirred overnight at 80° C. Upon completion, the reaction mixture was filtered through celite and washed with water (3×100 ml). The organic phase was then dried over anhydrous $MgSO_4$, filtered and concentrated to dryness to give a crude product. The crude product was column purified to give 5-bromo-3-(pyridin-4-yl)-1H-indazole (2.74 g) as a de-BOc product.

Tert-butyl 5-bromo-3-(pyridin-4-yl)-1H-indazole-1-carboxylate

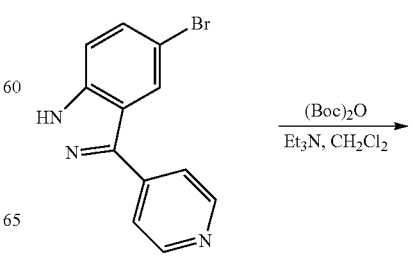

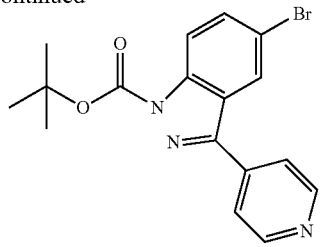

To a solution of 5-bromo-3-(pyridin-4-yl)-1H-indazole (2.74 g, 10.0 mmol) in CH$_2$Cl$_2$ (100 ml) under N$_2$ was added Et$_3$N (3.5 ml, 25.0 mmol) followed by (Boc)$_2$O (2.73 g, 12.5 mmol). The reaction was stirred at room temperature overnight. After completion of the reaction, the mixture was diluted with CH$_2$Cl$_2$ (100 ml) and washed with sat. NaHCO$_3$ (100 ml) and sat. NaCl (100 ml). The organic phase was dried over anhydrous MgSO$_4$, and evaporated to dryness. It was then purified by column (20% EtAOc/Hexane) to give tert-butyl 5-bromo-3-(pyridin-4-yl)-1H-indazole-1-carboxylate (2.71 g).

Tert-butyl 3-(pyridin-4-yl)-5-(((triisopropylsilyl)ethynyl)-1H-indazole-1-carboxylate

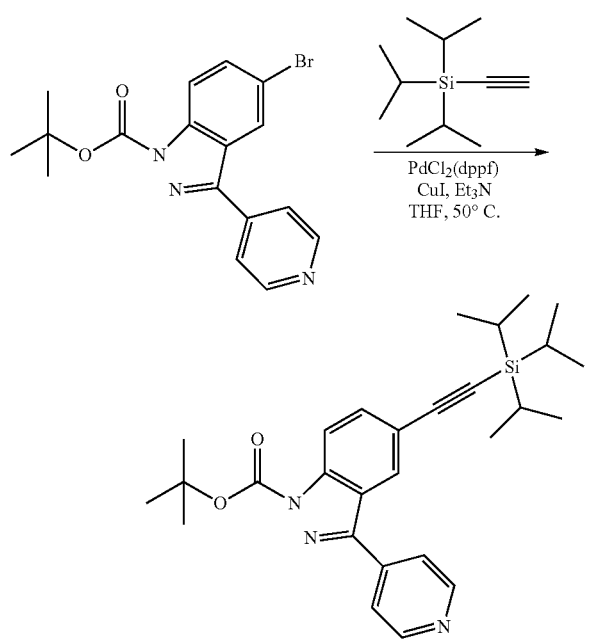

To a 250 ml round bottom flask equipped with a magnetic stir bar was added tert-butyl 5-bromo-3-(pyridin-4-yl)-1H-indazole-1-carboxylate (2.70 g, 7.2 mmol), TIPS-Aacetylene (3.2 ml, 14.4 mmol), dppf (1.47 g, 1.80 mmol), CuI (0.34 g, 1.8 mmol) and Et$_3$N (4.5 ml, 32.5 mmol). The mixture was dissolved in THF (100 ml) and heated at 50° C. for 3 h. The completion of the reaction was determined by LC/MS. After completion, the reaction mixture was washed with brine and dried over anhydrous MgSO$_4$. It was column purified with (30% EtAOc/Hexane) to give tert-butyl 3-(pyridin-4-yl)-5-(((triisopropylsilyl)ethynyl)-1H-indazole-1-carboxylate (3.16 g).

Tert-butyl 5-ethynyl-3-(pyridin-4-yl)-1H-indazole-1-carboxylate

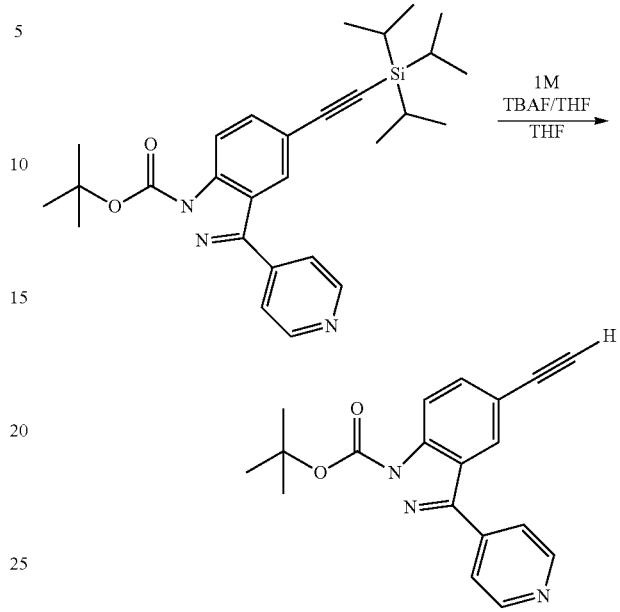

To a solution of tert-butyl 3-(pyridin-4-yl)-5-(((triisopropylsilyl)ethynyl)-1H-indazole-1-carboxylate (3.10 g, 6.5 mmol) in THF (100 ml) was added 1M TBAF in THF (7.2 ml, 7.2 mmol). The reaction was stirred for 3 h at room temperature. Upon completion, the reaction mixture was quenched with the addition of saturated aqueous NH$_4$Cl (50 ml) and extracted with Et$_2$O (3×100 ml). The combined organic extracts were washed with saturated aqueous NaCl (100 ml) and dried with anhydrous Na$_2$SO$_4$. The organic phase was concentrated under reduced pressure and column purified (20-80% EtAOc/Hexane) to give the desired product of tert-butyl 5-ethynyl-3-(pyridin-4-yl)-1H-indazole-1-carboxylate (0.77 g) and the de-Boc product of 5-ethynyl-3-(pyridin-4-yl)-1H-indazole (0.40 g).

(R)-5-(1-(piperidin-3-yl)-1H-1,2,3-triazol-4-yl)-3-(pyridin-4-yl)-1H-indazole

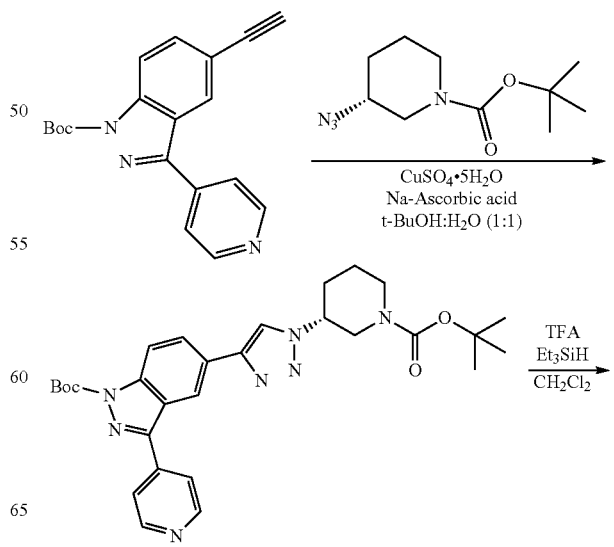

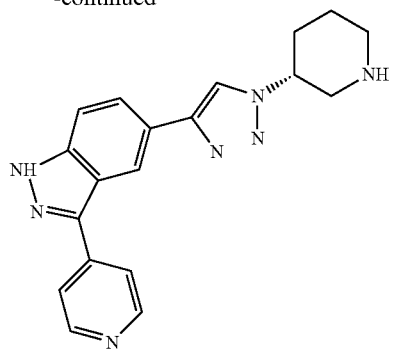

Tert-butyl 5-ethynyl-3-(pyridin-4-yl)-1H-indazole-1-carboxylate (0.385 g, 1.2 mmol) and (R)-tert-butyl 3-azidopiperidine-1-carboxylate (0.273 g, 1.2 mmol) were suspended in t-BuOH:H₂O (1:1, 15 mL:15 mL) and then CuSO4.5H2O (0.060 g, 0.24 mmol) and Na-Ascorbic acid (0.048 g, 0.48 mmol) were added sequentially. Reaction mixture was stirred vigorously at room temperature overnight. After the completion of reaction, added sat. NaCl (30 mL), extracted with EtOAc (3×50 mL), evaporated the organic solvent to give (R)-tert-butyl 5-(1-(1-(tert-butoxycarbonyl)piperidin-3-yl)-1H-1,2,3-triazol-4-yl)-3-(pyridin-4-yl)-1H-indazole-1-carboxylate (0.81 g) which was used for next step without purification.

To the crude (R)-tert-butyl 5-(1-(1-(tert-butoxycarbonyl)piperidin-3-yl)-1H-1,2,3-triazol-4-yl)-3-(pyridin-4-yl)-1H-indazole-1-carboxylate in CH₂Cl₂ (40 mL), added TFA (2.5 mL) and stirred at room temperature overnight under a stream of nitrogen. Evaporated the solvents and column purified (5-10% MeOH in CH₂Cl₂) to give (R)-5-(1-(piperidin-3-yl)-1H-1,2,3-triazol-4-yl)-3-(pyridin-4-yl)-1H-indazole (0.4 g).

(R)-5-(1-(1-(2-fluoro-6-methylbenzyl)piperidin-3-yl)-1H-1,2,3-triazol-4-yl)-3-(pyridin-4-yl)-1H-indazole

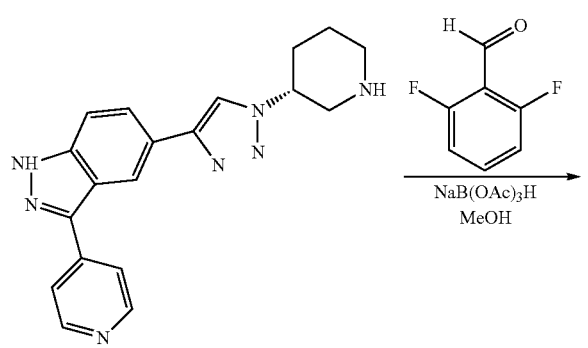

(R)-5-(1-(piperidin-3-yl)-1H-1,2,3-triazol-4-yl)-3-(pyridin-4-yl)-1H-indazole (0.05 g, 0.14 mmol) was dissolved in MeOH (3 mL) at 0° C., added 2,6-difluorobenzaldehyde (0.2 g, 1.4 mmol) and then sodium triacetoxyborohydride (0.0761 g, 0.37 mmol). The reaction mixture was allowed to warm to room temperature and stirred for 3 h. Evaporated the solvent, subjected to Preparative Thin Layer chromatography to give (R)-5-(1-(1-(2-fluoro-6-methylbenzyl)piperidin-3-yl)-1H-1,2,3-triazol-4-yl)-3-(pyridin-4-yl)-1H-indazole (0.034 g).

Example 3

Ethyl 3-bromo-1H-indazole-5-carbimidate hydrochloride

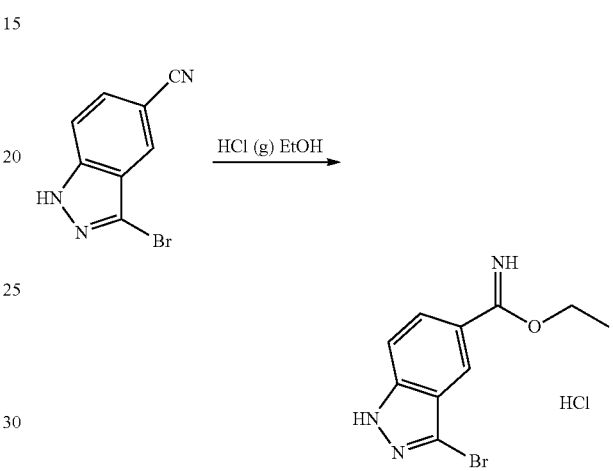

Passed HCl (g) slowly into a suspension of indazole 3-bromo-1H-indazole-5-carbonitrile (7 g) in EtOH (USP, 300 ml) at 0° C. Stirred at 0° C.-5° C. for approximately 2 hours until precipitation occurred, and stirred overnight at room temperature. Diluted with Ether (ca. 300 ml) and filtered out white solid, dried at room temperature to yield ethyl 3-bromo-1H-indazole-5-carbimidate hydrochloride (7.5 g).

(R)-tert-butyl 3-(hydrazinecarbonyl)piperidine-1-carboxylate

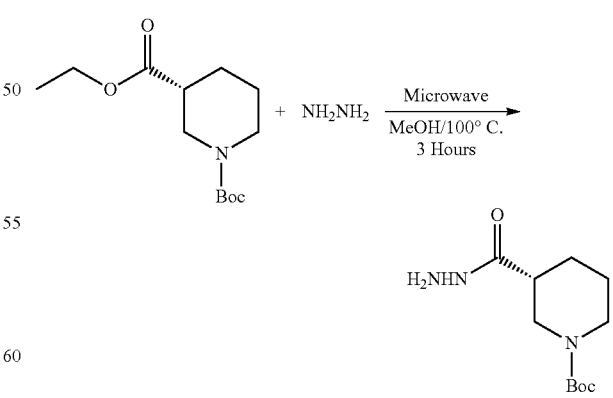

Stirred a solution of (R)-1-tert-butyl 3-ethyl piperidine-1,3-dicarboxylate (5 g, 19.4 mmol), hydrazine (anhydrous; 2 ml) in MeOH (5 ml) in a microwave oven at 100° C. for 3 hours. Cooled and solvent was evaporated. Chromatographed residue on silica gel eluting with 3% MeOH: DCM to yield (R)-tert-butyl 3-(hydrazinecarbonyl)piperidine-1-carboxylate as colorless oil (5.1 g).

(R)-tert-butyl 3-(3-(3-bromo-1H-indazol-5-yl)-1H-1,2,4-triazol-5-yl)piperidine-1-carboxylase

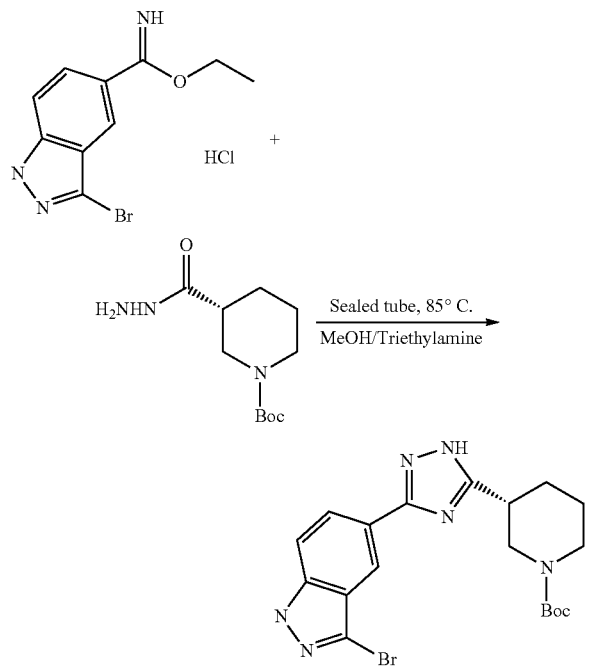

Mixture of ethyl 3-bromo-1H-indazole-5-carbimidate hydrochloride (4.1 g, 13.5 mmol) and (R)-tert-butyl 3-(hydrazinecarbonyl)piperidine-1-carboxylate (5.1 g, 20 mmol) in MeOH (25 ml) was heated in a sealed tube at 85° C. overnight. After solvent was evaporated, the residue was diluted with DCM (200 ml) and washed with H₂O (50 ml), Dried over Na₂SO₄; filtered and evaporated solvent. Chromatographed residue eluting with 5% MeOH/DCM to yield (R)-tert-butyl 3-(3-(3-bromo-1H-indazol-5-yl)-1H-1,2,4-triazol-5-yl)piperidine-1-carboxylate as a white solid (6 g).

(R)-tert-butyl 3-(3-(3-bromo-1-trityl-1H-indazol-5-yl)-1H-1,2,4-triazol-5-yl)piperidine-1-carboxylate

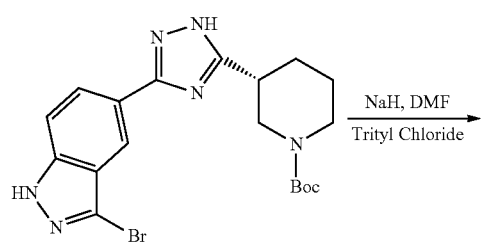

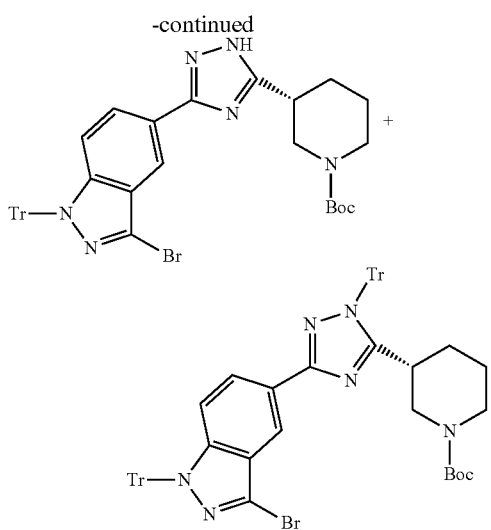

Added Sodium Hydride (100 mg; 2.5 mmol) to a solution of (R)-tert-butyl 3-(3-(3-bromo-1H-indazol-5-yl)-1H-1,2,4-triazol-5-yl)piperidine-1-carboxylate (530 mg, 0.988 mmol) in DMF (5 ml) at 0° C., then stirred for 30 minutes. Trityl Chloride (570 mg, 2.05 mmol) was added, and stirred at room temperature overnight. Added water (100 ml), filtered precipitated solid, washed with water, dried, then chromatographed on silica gel eluting with 30% v/v EtOAc/Hexanes to yield a mixture of mono and dialkylated products (560 mg, 8:2 mono/dialkylation).

(R)-tert-butyl 3-(3-(3-(pyridin-4-yl)-1-trityl-1H-indazol-5-yl)-1H-1,2,4-triazol-5-yl)piperidine-1-carboxylate

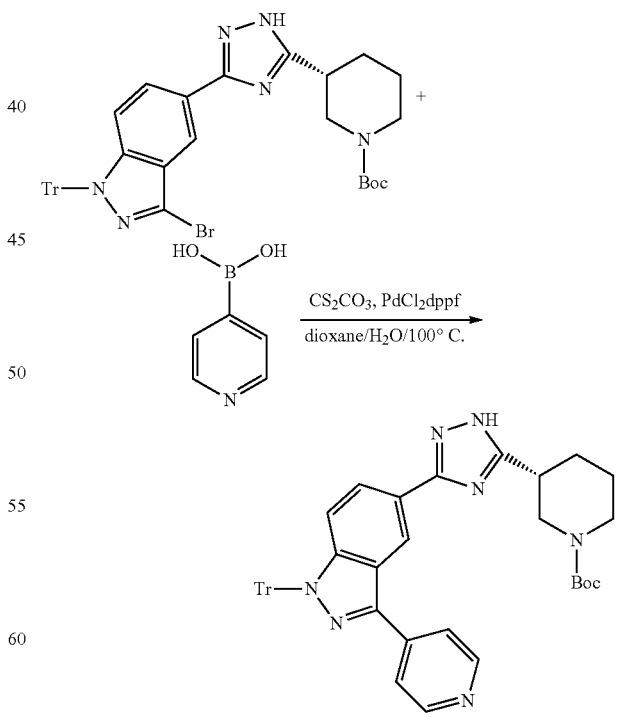

Stirred a mixture of (R)-tert-butyl 3-(3-(3-bromo-1-trityl-1H-indazol-5-yl)-1H-1,2,4-triazol-5-yl)piperidine-1-carboxylate (500 mg, 0.72 mmol), pyridine 4-boronic acid (150 mg, 1.22 mmol), PdCl₂dppf (30 mg, 0.036 mmol) and Cesium carbonate (400 mg, 1.23 mmol) in dioxane (9 mL) and water (1 mL) at 100° C. in a microwave oven for 2 hours. After cooling, diluted with water (50 ml), then extracted with DCM (100 ml). The combined organic layer was dried (Na₂SO₄), filtered and evaporated to yield crude product, which chromatographed on silica gel eluting with 30% v/v EtOAc/Hexanes to yield (R)-tert-butyl 3-(3-(3-(pyridin-4-yl)-1-trityl-1H-indazol-5-yl)-1H-1,2,4-triazol-5-yl)piperidine-1-carboxylate as a white solid (430 mg).

(R)-5-(5-(piperidin-3-yl)-1H-1,2,4-triazol-3-yl)-3-(pyridin-4-yl)-1H-indazole

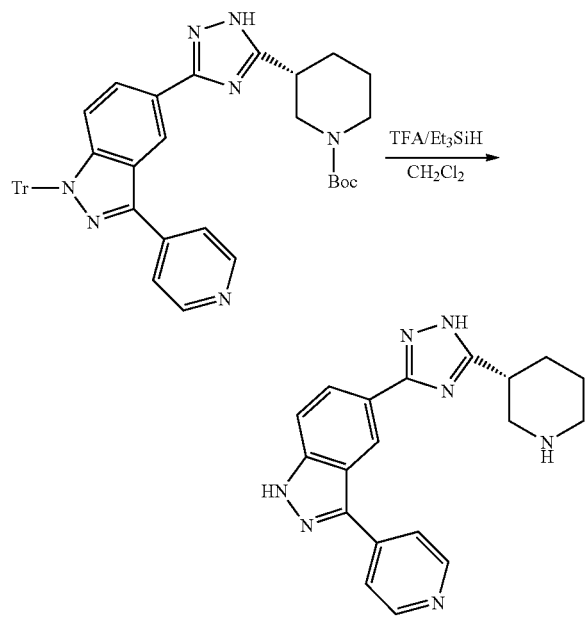

Added Triethylsilane (1 ml, 6.26 mmol) and Trifluoroacetic acid (2 ml, 26.8 mmol) to a solution of (R)-tert-butyl 3-(3-(3-(pyridin-4-yl)-1-trityl-1H-indazol-5-yl)-1H-1,2,4-triazol-5-yl)piperidine-1-carboxylate (430 mg, 0.62 mmol) in DCM (10 ml), stirred overnight at room temperature. Evaporated solvent then added ether (100 ml) and filtered out the solid to give the TFA salt of (R)-5-(5-(piperidin-3-yl)-1H-1,2,4-triazol-3-yl)-3-(pyridin-4-yl)-1H-indazole as a yellow solid (205 mg).

(R)-5-(5-(1-(2-fluoro-6-methoxybenzyl)piperidin-3-yl)-1H-1,2,4-triazol-3-yl)-3-(pyridin-4-yl)-1H-indazole

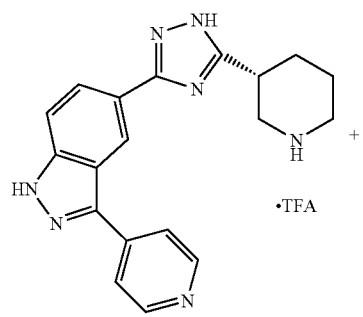

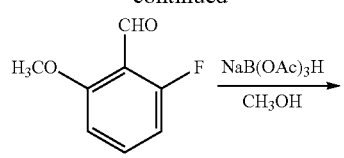

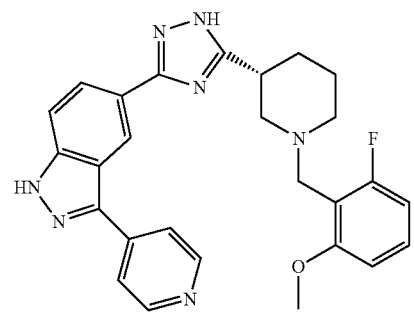

Added 2-Fluoro-6-methoxy benzaldehyde (69 mg, 0.44 mmol) to a mixture of (R)-5-(5-(piperidin-3-yl)-1H-1,2,4-triazol-3-yl)-3-(pyridin-4-yl)-1H-indazole (96 mg, 0.277 mmol) and sodium triacetoxy borohydride (176 mg, 0.833 mmol) in MeOH (8 ml) at room temperature. After stirred for 30 minutes, the solvent was evaporated. Diluted with EtOAc (150 ml), washed with H₂O (50 ml), dried (Na₂SO₄) and concentrated. Crude product was purified on silica gel eluting with 5% v/v MeOH/CH₂Cl₂ to yield (R)-5-(5-(1-(2-fluoro-6-methoxybenzyl)piperidin-3-yl)-1H-1,2,4-triazol-3-yl)-3-(pyridin-4-yl)-1H-indazole as a white solid (54 mg).

Example 4

(R)-1-(piperidin-1-yl)-2-(3-(3-(3-(pyridin-4-yl)-1H-indazol-5-yl)-1H-1,2,4-triazol-5-yl)piperidin-1-yl)ethanone

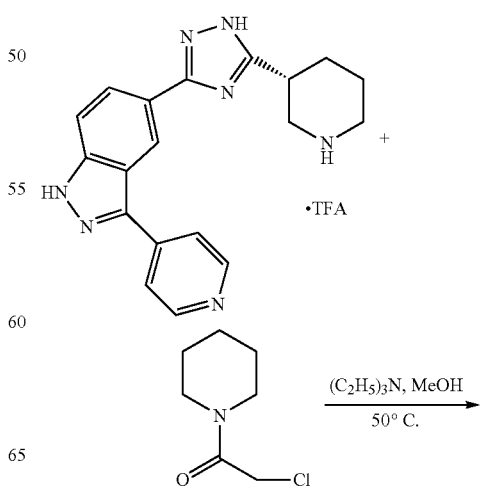

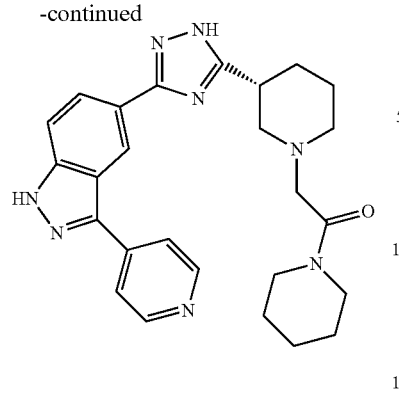

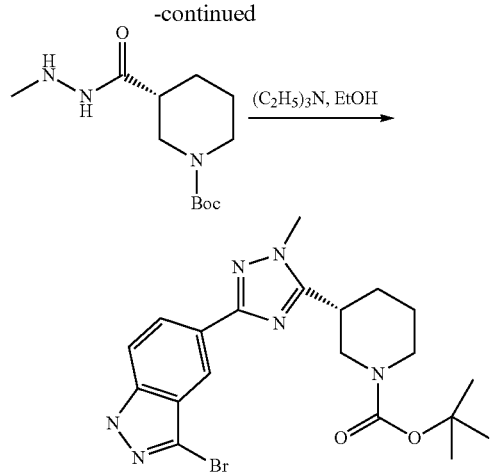

Added 2-chloro-1-(piperidin-1-yl)ethanone (50 mg, 0.31 mmol) to a solution of (R)-5-(5-(-(piperidin-3-yl)-1H-1,2,4-triazol-3-yl)-3-(pyridin-4-yl)-1H-indazole (47 mg, 0.106 mmol) and triethylamine (0.3 ml, 2.1 mmol) in MeOH (10 ml). After stirred at 50° C. overnight, reaction mixture was concentrated then purified on preparative TLC (20×20 cm) eluting with 10% v/v MeOH/MeCl₂ saturated with NH₄OH to yield (R)-1-(piperidin-1-yl)-2-(3-(3-(3-(pyridin-4-yl)-1H-indazol-5-yl)-1H-1,2,4-triazol-5-yl)piperidin-1-yl)ethanone as a white solid (23 mg).

Example 5

(R)-tert-butyl 3-(2-methylhydrazinecarbonyl)piperidine-1-carboxylate

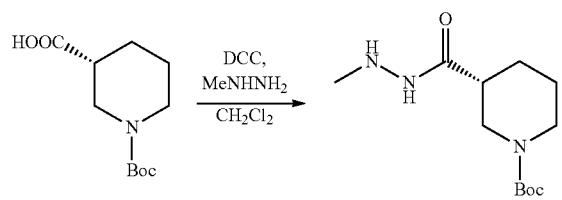

Added a solution of N,N-dicyclohexylcarbodiimide (1 M in CH₂Cl₂, 5 ml, 5 mmol) to a solution of (R)-1-(tert-butoxycarbonyl)piperidine-3-carboxylic acid (1 g, 4.36 mmol) and N-methyl hydrazine (0.3 g, 6.51 mmol) in CH₂Cl₂ (20 ml) then stirred for 1 hour. The precipitated solid was filtered, mother liquors were concentrated and residue purified by chromatography on silica gel eluting with 3% v/v MeOH/CH₂Cl₂ to yield (R)-tert-butyl 3-(2-methylhydrazinecarbonyl)piperidine-1-carboxylate as a white solid (0.85 g).

(R)-tert-butyl 3-(3-(3-bromo-1H-indazol-5-yl)-1-methyl-1H-1,2,4-triazol-5-yl)piperidine-1-carboxylate

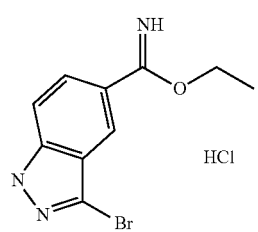

Added triethylamine (0.5 ml, 3.59 mmol) to a solution of ethyl 3-bromo-1H-indazole-5-carbimidate hydrochloride (200 mg, 0.658 mmol) and (R)-tert-butyl 3-(2-methylhydrazine-carbonyl)piperidine-1-carboxylate (200 mg, 0.78 mmol) in EtOH (USP, 5 ml) and heated in a microwave oven at 100° C. for 12 hours. Evaporated solvent then chromatographed residue on silica gel eluting with 1/1 v/v EtOAc/Hexanes to yield (R)-tert-butyl 3-(3-(3-bromo-1H-indazol-5-yl)-1-methyl-1H-1,2,4-triazol-5-yl)piperidine-1-carboxylate as a white solid (100 mg).

(R)-tert-butyl 3-(1-methyl-3-(3-(pyridin-4-yl)-1H-indazol-5-yl)-1H-1,2,4-triazol-5-yl)piperidine-1-carboxylate Stirred a mixture of (R)-tert-butyl 3-(3-(3-bromo-1H-indazol-5-yl)-1-methyl-1H-1,2,4-triazol-5-yl)piperidine-1-carboxylate (50 mg, 0.0108 mmol), 4-pyridyl boronic acid (50 mg, 0.409 mmol), PdCl₂dppf (10 mg, 0.0136 mmol), cesium carbonate (60 mg, 0.1846 mmol) in dioxane/H₂O (v/v 3/1, 4 ml) at 100° C. in a microwave oven for 2 hours. Reaction was cooled, extracted with DCM (50 ml), washed with H₂O (20 ml). Dried (Na₂SO₄), filtered and solvent evaporated to yield (R)-tert-butyl 3-(1-methyl-3-(3-(pyridin-4-yl)-1H-indazol-5-yl)-1H-1,2,4-triazol-5-yl)piperidine-1-carboxylate as a white solid (30 mg).

(R)-5-(1-methyl-5-(piperidin-3-yl)-1H-1,2,4-triazol-3-yl)-3-(pyridin-4-yl)-1H-indazole

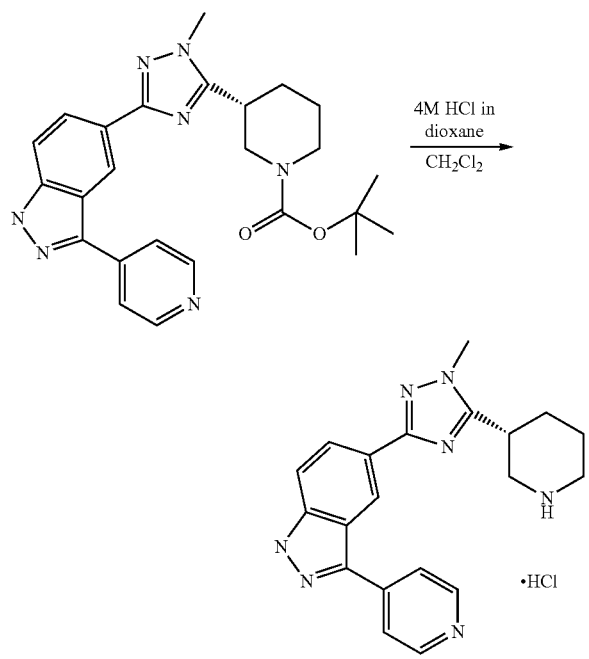

Added 4M HCl in dioxane (2 ml) to a solution of (R)-tert-butyl 3-(1-methyl-3-(3-(pyridin-4-yl)-1H-indazol-5-yl)-1H-1,2,4-triazol-5-yl)piperidine-1-carboxylate (25 mg, 0.054 mmol) in DCM (5 ml), then stirred 4 hours at room temperature. The solvent was evaporated to yield (R)-5-(1-methyl-5-(piperidin-3-yl)-1H-1,2,4-triazol-3-yl)-3-(pyridin-4-yl)-1H-indazole as a white solid (15 mg).

(R)-5-(5-(1-(2-fluoro-6-methoxybenzyl)piperidin-3-yl)-1-methyl-4H-1,2,4-triazol-3-yl)-3-(pyridin-4-yl)-1H-indazole

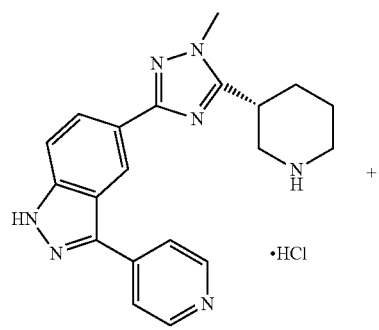

Added 2-Fluoro-6-methoxy benzaldehyde (20 mg, 0.129 mmol) to a solution of (R)-5-(1-methyl-5-(piperidin-3-yl)-1H-1,2,4-triazol-3-yl)-3-(pyridin-4-yl)-1H-indazole (15 mg, 0.0379 mmol) and sodium triacetoxyborohydride (25 mg, 0.118 mmol) in MeOH (4 ml) at room temperature, then stirred for 2 hours. Reaction was diluted with CH₂Cl₂ (50 ml) and H₂O (25 ml), organic layer was separated, dried over Na₂SO₄, filtered and solvent evaporated. The residue was chromatographed on silica gel eluting with 5% v/v MeOH/CH₂Cl₂/NH₄OH to yield (R)-5-(5-(1-(2-fluoro-6-methoxybenzyl)piperidin-3-yl)-1-methyl-1H-1,2,4-triazol-3-yl)-3-(pyridin-4-yl)-1H-indazole as a white solid (12 mg).

Example 6

Tert-butyl 3-(methoxy(methyl)carbamoyl)piperidine-1-carboxylate

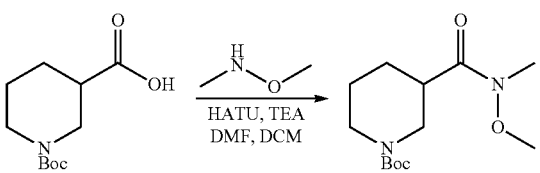

To the solution of 1-Boc-piperidine-3-carboxylic acid (6.9 g, 30 mmol) in DMF (10 mL) and dichloromethane (40 mL) were added N,O-dimethylhydroxylamine hydrochloride (3.22 g, 33 mmol), HATU (12 g, 31.5 mmol) and triethylamine (9 mL). The reaction mixture was stirred overnight. After most of the solvent was removed and diluted with EtOAc, the organic layer was washed with water and brine, Dried and evaporation to give 10.2 g of crude product as light yellow oil.

Tert-butyl 3-acetylpiperidine-1-carboxylate

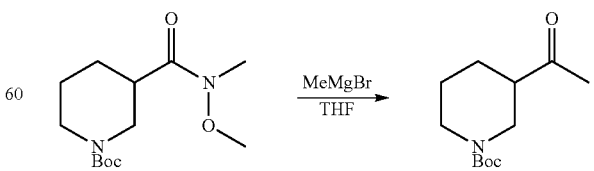

Tert-butyl 3-(methoxy(methyl)carbamoyl)piperidine-1-carboxylate (8.17 g, 30 mmol) was dissolved in THF (100 mL) and cooled to 0° C., methylmagnesium bromide (3.0 M in Et₂O, 11 mL, 33 mmol) was added dropwise. The reaction mixture was warmed to room temperature and stirred overnight. After quench with saturated NH₄Cl, the reaction mixture was extracted with EtOAc, dried and concentrated. The crude product was column purified with mixture of hexane and EtOAc to give tert-butyl 3-acetylpiperidine-1-carboxylate (4.8 g).

Tert-butyl 3-(1H-pyrazol-3-yl)piperidine-1-carboxylate

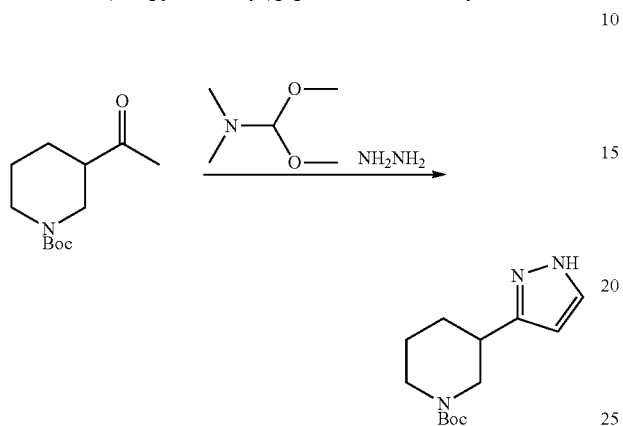

The solution of tert-butyl 3-acetylpiperidine-1-carboxylate (1.2 g, 6 mmol) and N,N-dimethylformamide dimethyl acetal (1.2 g, 10 mmol) in toluene (15 mL) was refluxed overnight. After azotropic evaporation with MeOH, EtOH (14 mL) and hydrazine hydrate (2 mL) were added and refluxed for 3 h. The reaction mixture was concentrated and column purified with mixture of hexane and EtOAc to give tert-butyl 3-(1H-pyrazol-3-yl)piperidine-1-carboxylate (125 mg).

5-iodo-3-(pyridin-4-yl)-1-trityl-1H-indazole

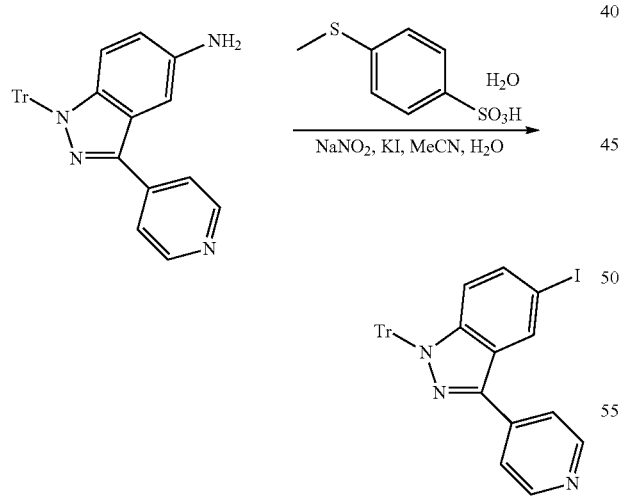

To the stirred solution of 3-(pyridin-4-yl)-1-trityl-1H-indazol-5-amine (6.02 g, 13.3 mmol) in MeCN (45 mL) was added p-toluenesulfonic acid monohydrate (3.37 g, 17.7 mmol). After cooled to 10° C., a solution of sodium nitrite (1.84 g, 26.6 mmol), potassium iodide (5.52 g, 33.2 mmol) in water (9 mL) was added dropwise. The resulting dark brown solution was stirred at room temperature for 4 hours. The mixture was diluted with EtOAc and washed with water and 1N Na₂S₂O₃. After dried and concentrated, the crude mixture was column purified with mixture of hexane and EtOAc to give 5-iodo-3-(pyridin-4-yl)-1-trityl-1H-indazole (3.95 g).

Tert-butyl 3-(1-(3-(pyridin-4-yl)-1-trityl-1H-indazol-5-yl)-1H-pyrazol-3-yl)piperidine-1-carboxylate

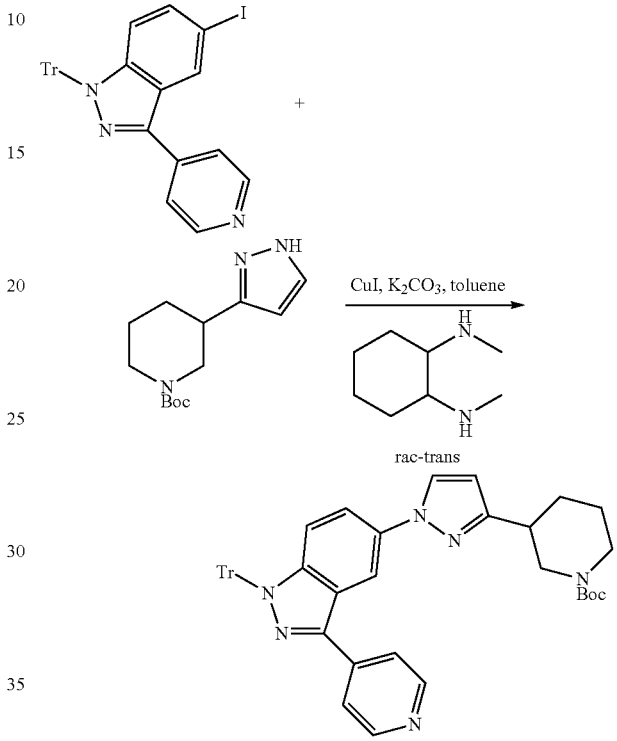

The mixture of 5-iodo-3-(pyridin-4-yl)-1-trityl-1H-indazole (281 mg, 0.5 mmol), tert-butyl 3-(1H-pyrazol-3-yl)piperidine-1-carboxylate (151 mg, 0.6 mmol), copper (I) iodide (19 mg, 0.1 mmol), rac-trans-N,N-dimethylcyclohexane-1,2-diamine (57 mg, 0.4 mmol), K₂CO₃ (552 mg, 4 mmol) in toluene (3 mL) was heated at 100° C. for 4 days. After cooling to room temperature, the reaction mixture was filtered through a pad of celite, and washed with EtOAc. The filtrate was concentrated and column purified with mixture of methanol, dichloromethane and ammonia to give tert-butyl 3-(1-(3-(pyridin-4-yl)-1-trityl-1H-indazol-5-yl)-1H-pyrazol-3-yl)piperidine-1-carboxylate (380 mg).

Tert-butyl 3-(1-(3-(pyridin-4-yl)-1H-indazol-5-yl)-1H-pyrazol-3-yl)piperidine-1-carboxylate

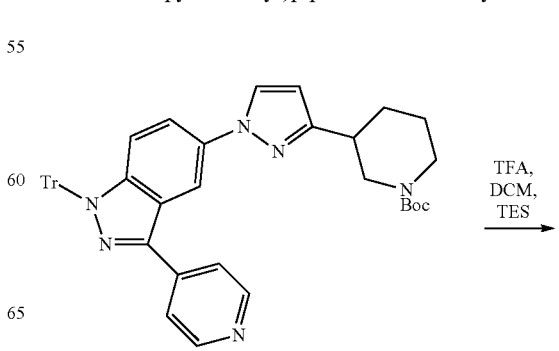

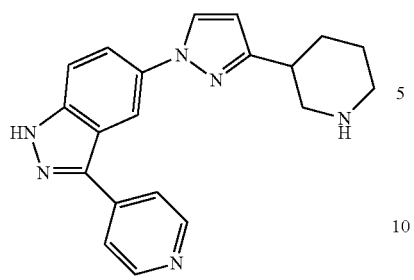

To tert-butyl 3-(1-(3-(pyridin-4-yl)-1-trityl-1H-indazol-5-yl)-1H-pyrazol-3-yl)piperidine-1-carboxylate (140 mg, 0.2 mmol) in DCM (5 mL) were added triethylsilane (40 mg, 0.34 mmol) and trifluoroacetic acid (1 mL), the reaction mixture was stirred at room temperature for 3 h. After concentration, crude mixture was column purified with mixture of methanol, dichloromethane and ammonia to give tert-butyl 3-(1-(3-(pyridin-4-yl)-1H-indazol-5-yl)-1H-pyrazol-3-yl)piperidine-1-carboxylate (120 mg).

5-(3-(1-(2-Fluoro-6-methoxybenzyl)piperidin-3-yl)-1H-pyrazol-1-yl)-3-(pyridin-4-yl)-1H-indazole

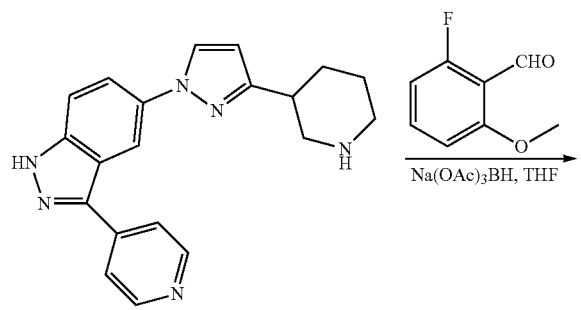

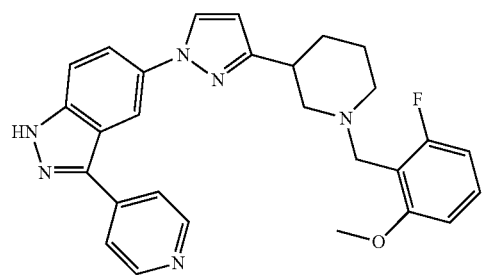

To tert-butyl 3-(1-(3-(pyridin-4-yl)-1H-indazol-5-yl)-1H-pyrazol-3-yl)piperidine-1-carboxylate (30 mg, 0.09 mmol) in THF (2 mL) were added 2-fluoro-6-methoxybenzaldehyde (20 mg, 0.13 mmol) and sodium triacetoxyborohydride (30 mg, 0.14 mmol). After 3 h, the reaction mixture was quenched with saturated NaHCO₃ and extracted with EtOAc. After concentration, crude mixture was column purified with mixture of methanol, dichloromethane and ammonia to give 5-(3-(1-(2-fluoro-6-methoxybenzyl)piperidin-3-yl)-1H-pyrazol-1-yl)-3-(pyridin-4-yl)-1H-indazole (37 mg).

Example 7

Tert-butyl 3-hydroxypiperidine-1-carboxylate

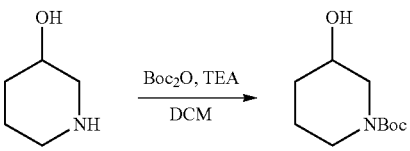 [SMILES: OC1CCCNC1 ; CC(C)(C)OC(=O)N1CCCC(O)C1]

To 3-hydroxypiperidine (3.03 g, 30 mmol) in dichloromethane (30 mL) was added triethylamine (6 mL) and Boc₂O (7 g, 32 mmol). After stirring for 3 h, the reaction mixture was quenched with saturated NaHCO₃, and extracted with dichloromethane. The combined organic layer was washed with H₂O, dried and concentrated to give crude product, which was washed with hexane to give tert-butyl 3-hydroxypiperidine-1-carboxylate as white power (5.4 g).

Tert-butyl 3-(methylsulfonyloxy)piperidine-1-carboxylate

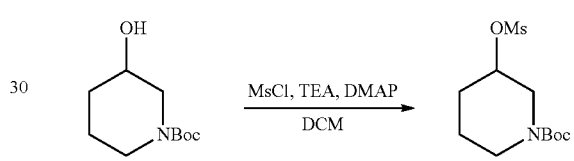

Tert-butyl 3-hydroxypiperidine-1-carboxylate (3.6 g, 18 mmol) was dissolved in dichloromethane (20 mL) and cooled to 0° C., triethylamine (4 mL) was added, followed by dropwise addition of methanesulfonyl chloride (2.28 g, 20 mmol) and DMAP (10 mg). The reaction mixture was warmed to room temperature and stirred overnight. The reaction mixture was quenched with saturated NaHCO₃, and extracted with dichloromethane. The organic layer was washed with H₂O, dried and concentrated to give crude product (5.5 g).

Tert-butyl 3-(4-bromo-1H-pyrazol-1-yl)piperidine-1-carboxylate

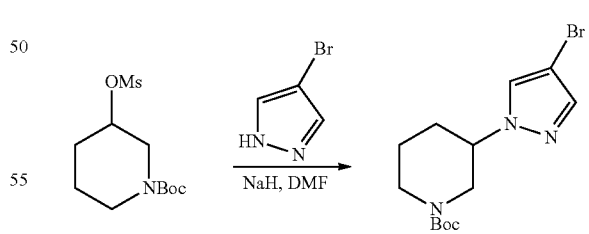

4-Bromopyrazole (2.94 g, 20 mmol) dissolved in DMF (20 mL) was cooled to 0° C., sodium hydride (900 mg, 22.5 mmol) was added portion-wise over 1 h. After warmed to room temperature and stirred for 1 h, tert-butyl 3-(methylsulfonyloxy)-piperidine-1-carboxylate (5.03 g, 20 mmol) was added, and the reaction mixture was heated at 100° C. overnight. The reaction mixture was quenched with saturated NH₄Cl, and extracted with EtOAc. The organic layer was washed with H₂O, brine, dried and concentrated. Crude mixture was column purified with mixture of EtOAc and hexane to give tert-butyl 3-(4-bromo-1H-pyrazol-1-yl)piperidine-1-carboxylate (1.97 g) as white solid.

3-(Pyridin-4-yl)-5-(4,4,5,5-tetramethyl-4,3,2-dioxaborolan-2-yl)-1-trityl-1H-indazole

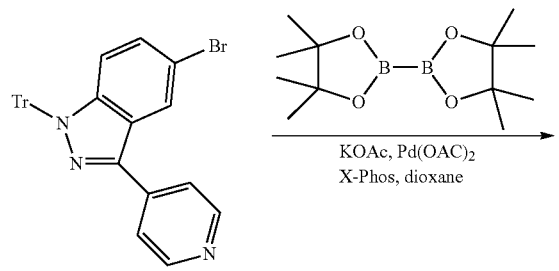

To the suspension of 5-bromo-3-(pyridin-4-yl)-1-trityl-1H-indazole (1.03 g, 2 mmol) in dioxane (25 mL) were added bis(pinacolato)diboron (1.27 g, 5 mmol), potassium acetate (588 mg, 6 mmol), palladium acetate (45 mg, 0.2 mmol) and X-phos (95 mg, 0.2 mmol). The reaction mixture was degassed with nitrogen and stirred under nitrogen at 80° C. overnight. After cooled to room temperature, the reaction mixture was filtered and washed with EtOAc. The filtrate was washed with water, dried and concentrated. Crude mixture was column purified with mixture of EtOAc and Hexane to give 3-(pyridin-4-yl)-5-(4,4,5,5-tetramethyl-1,3,2-dioxaborolan-2-yl)-1-trityl-4H-indazole (0.83 g) as brown solid.

Tert-butyl 3-(4-(3-(pyridin-4-yl)-1-trityl-1H-indazol-5-yl)-1H-pyrazol-1-yl)piperidine-1-carboxylate

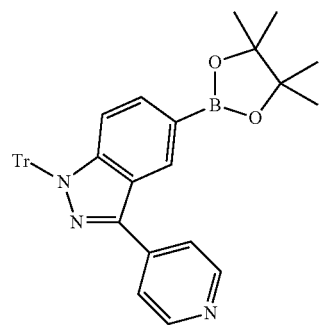

+

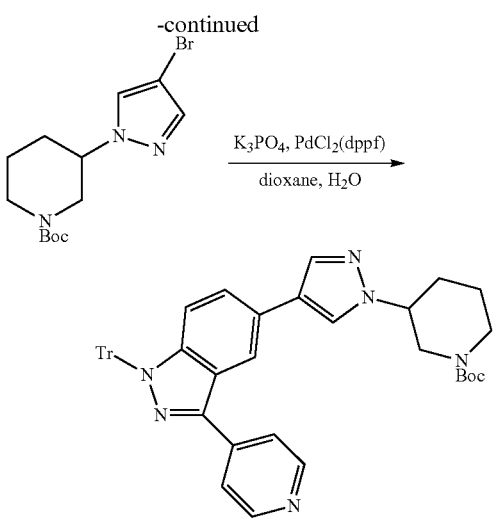

To tert-butyl 3-(4-bromo-1H-pyrazol-1-yl)piperidine-1-carboxylate (0.66 g, 2 mmol) and 3-(pyridin-4-yl)-5-(4,4,5,5-tetramethyl-1,3,2-dioxaborolan-2-yl)-1-trityl-1H-indazole (1.13 g, 2 mmol) in dioxane (8 mL) and water (2 mL) was added potassium phosphate (848 mg, 4 mmol) and PdCl$_2$(dppf) (120 mg, 0.16 mmol). The reaction mixture was stirred at 80° C. for 24 h. After filtered through a pad of celite, and washed with EtOAc, the filtrate was washed with brine, dried and concentrated. The crude mixture was column purified with mixture of methanol, dichloromethane and ammonia to give tert-butyl 3-(4-(3-(pyridin-4-yl)-1-trityl-1H-indazol-5-yl)-1H-pyrazol-1-yl)piperidine-1-carboxylate (420 mg) as light yellow solid.

5-[1-[1-[(2,6-Difluorophenyl)methyl]-3-piperidinyl]-1H-pyrazol-1-yl]-3-(4-pyridinyl)-1H-indazole

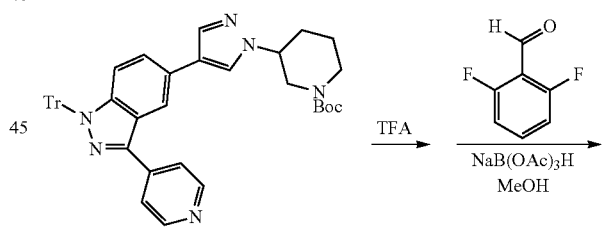

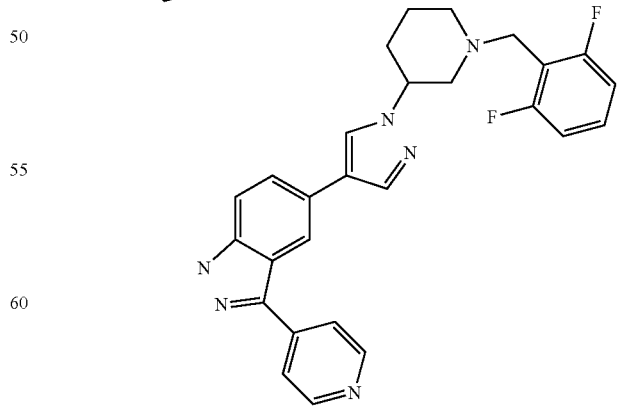

Following the procedure for the preparation of Tert-butyl 3-(1-(3-(pyridin-4-yl)-1H-indazol-5-yl)-1H-pyrazol-3-yl)

piperidine-1-carboxylate and 5-(3-(1-(2-Fluoro-6-methoxy-benzyl)piperidin-3-yl)-1H-pyrazol-1-yl)-3-(pyridin-4-yl)-1H-indazole the title compound was prepared Example 8

(1S,5R)-8-Tert-butyl 2-methyl 3-oxo-8-azabicyclo[3.2.1]octane-2,8-dicarboxylate

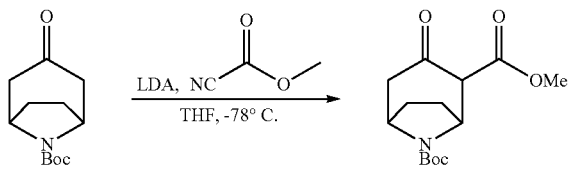

N-Boc-nortropinone (10 g, 44.4 mmol) was dissolved in THF (55 mL) and cooled to −78° C., LDA (2M in THF, 24.4 mL, 48.8 mmol) was added dropwise. After 1 h at −78° C., cyanoformate (4.22 mL, 53.2 mmol) was added, and the reaction mixture was warmed up to room temperature and stirred for 5 hours. After quench with saturated NH₄Cl, the reaction mixture was extracted with EtOAc. The combined EtOAc layer was washed with water and brine. Dried and concentrated. The crude product was column purified with mixture of Hexane and EtOAc to give 10 g of (1S,5R)-8-tert-butyl 2-methyl 3-oxo-8-azabicyclo[3.2.1]octane-2,8-dicarboxylate.

(1S,5R)-8-Tert-butyl 2-methyl 3-hydroxy-8-azabicyclo[3.2.1]octane-2,8-dicarboxylate

(1S,5R)-8-Tert-butyl 2-methyl 3-oxo-8-azabicyclo[3.2.1]octane-2,8-dicarboxylate (2 g, 7.04 mmol) was dissolved in MeOH (26 mL), sodium borohydride (280 mg, 7.39 mmol) was added portionwise. The reaction mixture was stirred at room temperature for 1.5 hours. After evaporation, the crude mixture was dissolved in EtOAc, washed with saturated NaHCO₃ and water. Dried and concentrate to give 1.75 g of crude product. The crude was carried over the next step without further purification.

(1S,5R)-8-Tert-butyl 2-methyl 3-(methylsulfonyloxy)-8-azabicyclo[3.2.1]octane-2,8-dicarboxylate

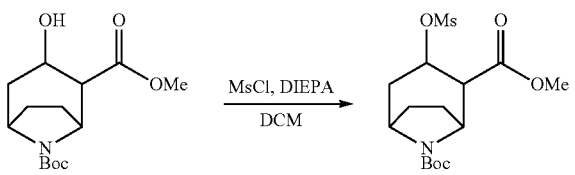 [SMILES: COC(=O)C1C(O)CC2CCC1N2C(=O)OC(C)(C)C ; COC(=O)C1C(OS(C)(=O)=O)CC2CCC1N2C(=O)OC(C)(C)C]

(1S,5R)-8-Tert-butyl 2-methyl 3-hydroxy-8-azabicyclo[3.2.1]octane-2,8-dicarboxylate (1.75 g, 6.14 mmol) was dissolved in dichloromethane (30 mL), methanesulfonyl chloride (0.95 mL, 123 mmol) was added, followed by dropwise addition of N,N-diisopropylethyl-amine (5.29 mL, 30.7 mmol). The reaction mixture was stirred at room temperature overnight. After quench with saturated NaHCO₃, the reaction mixture was extracted with dichloro-methane. The combined organic layer was washed with water and brine. Dried and concentrated to give 2.23 g of crude product. The crude was carried over the next step without further purification.

(1S,5R)-8-Tert-butyl 2-methyl 8-azabicyclo[3.2.1]oct-2-ene-2,8-dicarboxylate

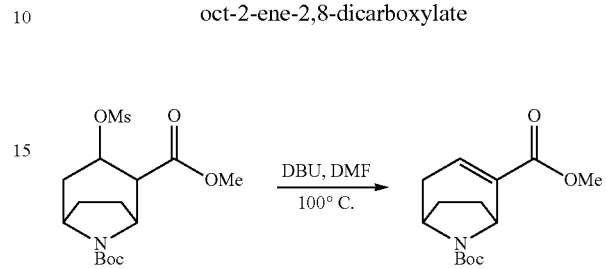

(1S,5R)-8-tert-butyl 2-methyl 3-(methylsulfonyloxy)-8-azabicyclo[3.2.1]octane-2,8-dicarboxylate (14.22 g, 39.15 mmol) and DBU (58.55 mL, 391.15 mmol) in DMF (73.87 mL) were heated at 100° C. for 10 hours. The reaction was quenched with saturated sodium bicarbonate solution and extracted with ethyl acetate. The organic fractions were combined, dried with sodium sulfate and concentrated to give crude product. The crude was purified using flash chromatography (0-100% Ethyl Acetate in Hexane) to give 5.45 g of (1S,5R)-8-tert-butyl 2-methyl 8-azabicyclo[3.2.1]oct-2-ene-2,8-dicarboxylate.

(1S,5S)-8-Tert-butyl 2-methyl 8-azabicyclo[3.2.1]octane-2,8-dicarboxylate

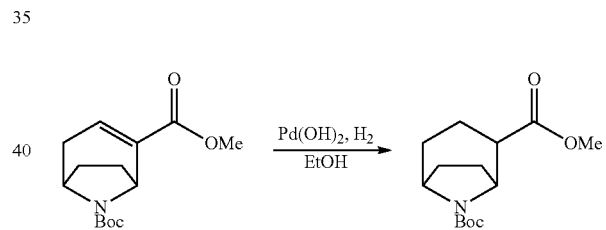

(1S,5R)-8-tert-butyl 2-methyl 8-azabicyclo[3.2.1]oct-2-ene-2,8-dicarboxylate (5.45 g) was dissolved in ethanol (200 mL), Palladium hydroxide (20% wt, 2.73 g) was added. After vacuum degassed, the reaction mixture was hydrogenated under hydrogen balloon overnight. After filter through a pad of celite, washed with ethanol, the filtrate was concentrated to give 5.49 g of crude product. The crude was brought to next step without further purification.

(1S,5S)-Methyl 8-azabicyclo[3.2.1]octane-2-carboxylate

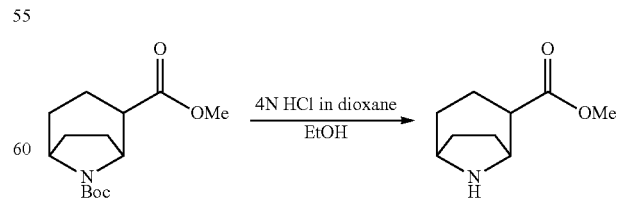

To (1S,5S)-8-tert-butyl 2-methyl 8-azabicyclo[3.2.1]octane-2,8-dicarboxylate (5.49 g) in EtOH (1 mL) was added 4M HCl in dioxane (5 mL). The reaction mixture was stirred at room temperature for 2 hours. Concentrated to give crude product (3.45 g).

(1S,5S)-Methyl 8-(2-fluorobenzyl)-8-azabicyclo[3.2.1]octane-2-carboxylate

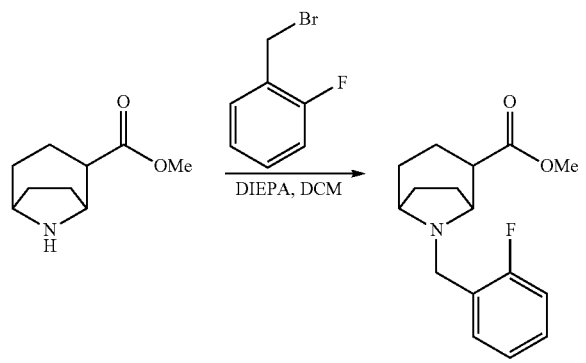 [SMILES: COC(=O)C1CCC2CCC1N2 ; Fc1ccccc1CBr ; COC(=O)C1CCC2CCC1N2Cc1ccccc1F]

To (1S,5S)-methyl 8-azabicyclo[3.2.1]octane-2-carboxylate (185 mg, 1.1 mmol) dissolved in DCM (11 mL) was added 2-fluorobenzylbromide (206 mg, 1.1 mmol), followed by N,N-diisopropylethylamine (424 mg, 3.3 mmol). After stirring for 1 hour, the reaction mixture was quenched with water, and extracted with DCM. Dried and concentrated to give 186 mg of crude product. The crude was carried over the next step without further purification.

(1S,5S)-8-(2-Fluorobenzyl)-8-azabicyclo[3.2.1]octane-2-carboxylic acid

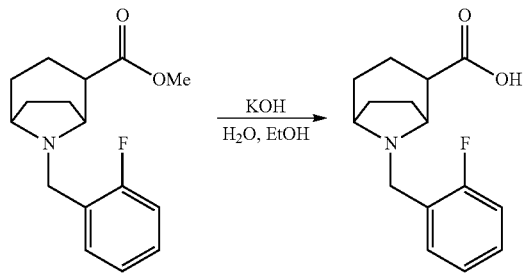 [SMILES: COC(=O)C1CCC2CCC1N2Cc1ccccc1F ; "KOH" ; O=C(O)C1CCC2CCC1N2Cc1ccccc1F]

Potassium hydroxide (113 mg, 0.201 mmol) was dissolved in ethanol (6.722 mL). The basic solution then water (1 mL) was added consecutively to the SM (186 mg, 0.672 mmol). The reaction was stirred at room temperature for 3 hours. Using 1N HCl the reaction was neutralized to pH 7 then concentrated. The resulting residue was dissolved in dichloromethane and washed with water. The organic layer was dried with sodium sulfate and concentrated to yield 176 mg of crude product. The crude was carried over the next step without further purification.

3-(2-Methylpyridin-4-yl)-1-trityl-1H-indazole-5-carbohydrazide

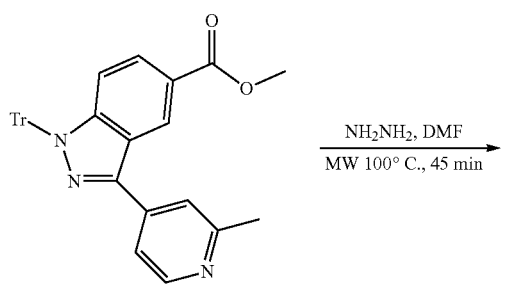

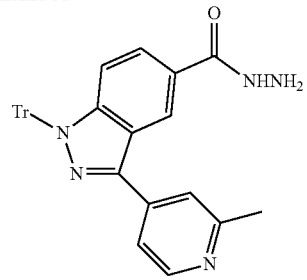

The mixture of methyl 3-(2-methylpyridin-4-yl)-1-trityl-1H-indazole-5-carboxylate (50 mg, 0.1 mmol) and hydrazine (6.3 mg, 0.2 mmol) in DMF (0.23 mL) was heated at 100° C. under microwave condition for 45 min. The reaction mixture was quenched with water, and extracted with EtOAc. The combined organic layer was dried and concentrated to give 52 mg of crude product. The crude was brought to next step without further purification.

N'-(8-(2-Fluorobenzyl)-8-azabicyclo[3.2.1]octane-2-carbonyl)-3-(2-methylpyridin-4-yl)-1-trityl-1H-indazole-5-carbohydrazide

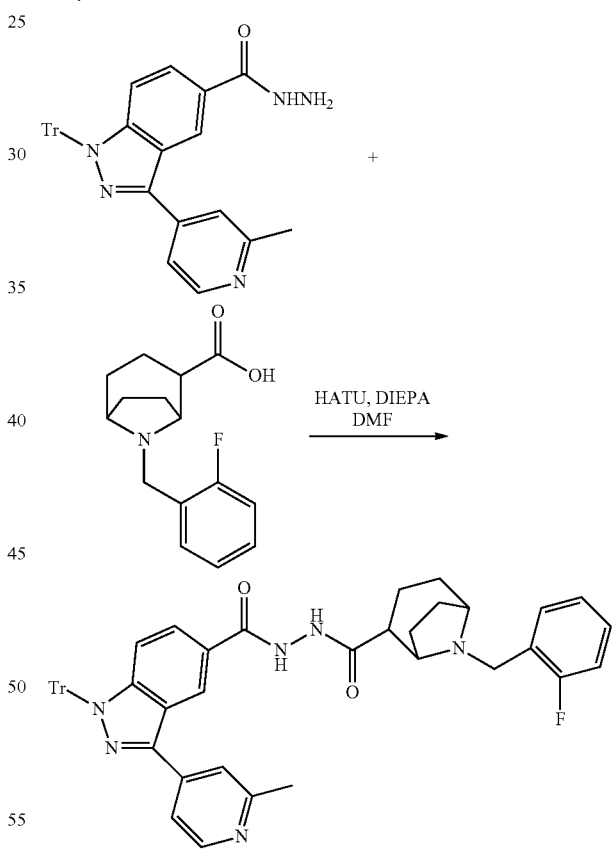

The mixture of 3-(2-methylpyridin-4-yl)-1-trityl-1H-indazole-5-carbohydrazide (50 mg, 0.1 mmol), HATU (56 mg, 0.15 mmol), N,N-diisopropylethylamine (25 mg, 0.2 mmol), and acid (26 mg, 0.1 mmol) in DMF (1 mL) was stirred at room temperature for 2 hours. The reaction mixture was quenched with water, and extracted with EtOAc. The combined organic layer was dried and concentrated to give 142 mg of crude product. The crude was brought to next step without further purification.

2-(8-(2-Fluorobenzyl)-8-azabicyclo[3.2.1]octan-2-yl)-5-(3-(2-methylpyridin-4-yl)-1-trityl-1H-indazol-5-yl)-1,3,4-oxadiazole

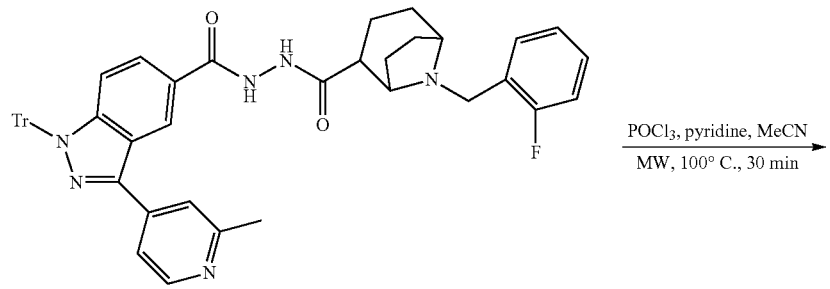

To N'-(8-(2-fluorobenzyl)-8-azabicyclo[3.2.1]octane-2-carbonyl)-3-(2-methylpyridin-4-yl)-1-trityl-1H-indazole-5-carbohydrazide (142 mg, 0.19 mmol) in acetonitrile (1.6 mL) was added pyridine (44 mg, 0.56 mmol), followed by phosphoryl trichloride (86 mg, 0.56 mmol). The reaction mixture was heated at 100° C. under microwave condition for 30 min. After quench with saturated NaHCO₃, the mixture was extracted with EtOAc. The combined organic layer was dried and concentrated to give 40 mg crude product. The crude was brought to next step without further purification.

2-(8-(2-fluorobenzyl)-8-azabicyclo[3.2.1]octan-2-yl)-5-(3-(2-methylpyridin-4-yl)-1H-indazol-5-yl)-1,3,4-oxadiazole

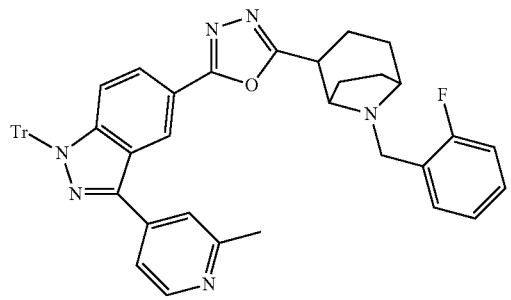

To 2-(8-(2-Fluorobenzyl)-8-azabicyclo[3.2.1]octan-2-yl)-5-(3-(2-methylpyridin-4-yl)-1-trityl-1H-indazol-5-yl)-1,3,4-oxadiazole (40 mg, 0.054 mmol) 95% trifluoroacetic acid (3 mL) was added. The reaction was stirred at room temperature for 30 minutes. After reaction completion, triethylsilane (0.1 mL) was added. The reaction was concentrated and submitted for prep LC/MS. A total of 6 mg of purified compound was retrieved.

Methyl 5-methoxypiperidine-3-carboxylate

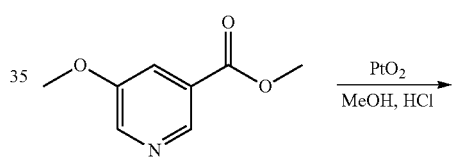

Methyl 5-methoxypyridine 3-carboxylate (1 g, 6.02 mmol) and platinum (IV) oxide (50 mg) suspended in 1.25 M HCl in methyl alcohol (10 mL) were hydrogenated in Parr shaker under 40 psi overnight. The reaction mixture was filtered through a pad of celite, washed with MeOH and concentrated to give crude product.

Methyl 1-(2-fluoro-6-methoxybenzyl)-5-methoxypiperidine-3-carboxylate

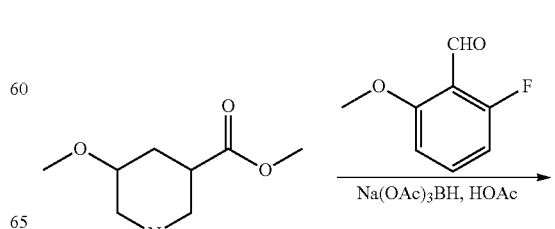

-continued

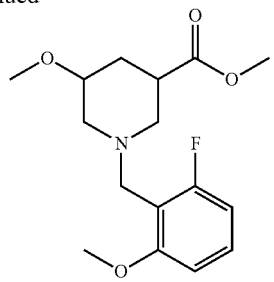

To Methyl 5-methoxypiperidine-3-carboxylate (500 mg, 2.9 mmol) in DCM (10 mL) was added 2-fluoro-6-methoxybenzaldehyde (890 mg, 5.8 mmol) and 10 drops of acetic acid. After stirring for 15 min, sodium triacetoxyborohydride (2.4 g, 11.6 mmol) was added. The reaction mixture was stirred at room temperature overnight. After quench with saturated $Na_2CO_3$, the mixture was extracted with DCM. Dried and concentrated to give crude product.

1-(2-Fluoro-6-methoxybenzyl)-5-methoxypiperidine-3-carboxylic acid

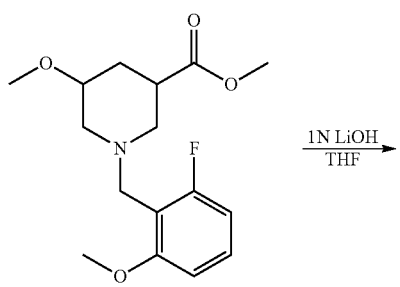

Methyl 1-(2-fluoro-6-methoxybenzyl)-5-methoxypiperidine-3-carboxylate in THF and 1 N LiOH (v:v=1:1) was stirred at room temperature overnight. After neutralized with 1N aqueous HCl to pH~6, the solvent was evaporated to give crude product.

The following compounds were prepared as above using 1-(2-Fluoro-6-methoxybenzyl)-5-methoxypiperidine-3-carboxylic acid:

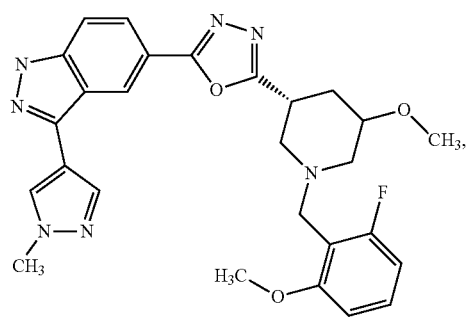

-continued

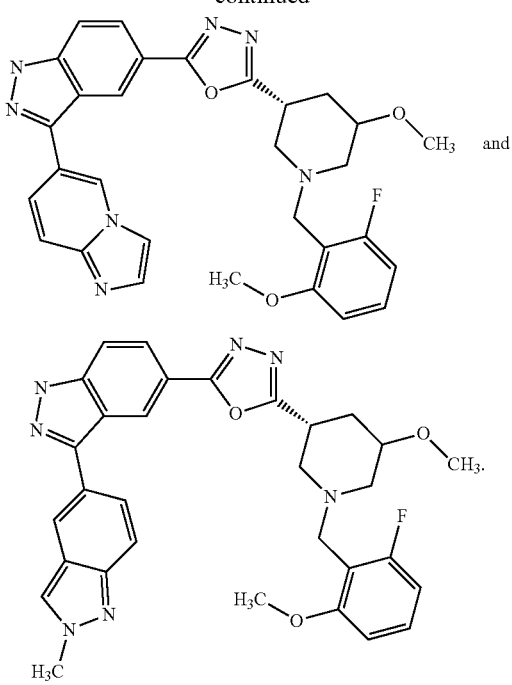

Example 9

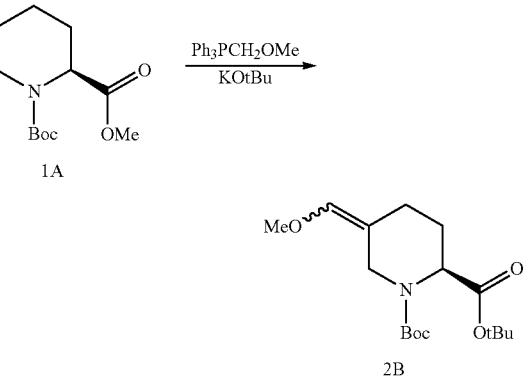

Compound 1A was prepared by following literature procedures [(a) Organic Process Research & Development, 13(4), 739-746; 2009; (b) Bioorganic & Medicinal Chemistry Letters (2002), 12(10), 1387-1390. (c) PCT Int. Appl. (2006), 111 pp. CODEN: PIXXD2 WO 2006125974A1 20061130 (page 40, 58-60)].

A suspension of (methoxymethyl)triphenylphosphonium chloride (6 g) and t-BuOK (1.6 g) in toluene was stirred at room temperature for 5 h, to which a solution of compound 1A (514 mg) in THF (30 mL) was added dropwise. The reaction mixture was stirred at room temperature for 16 h, and diluted with ethyl acetate 150 mL). The resulting mixture was washed with $H_2O$, brine, dried ($K_2CO_3$) and concentrated. The crude was purified on silica gel column (hexanes/ethyl acetate 12:1) to give compound 2A (520 mg).

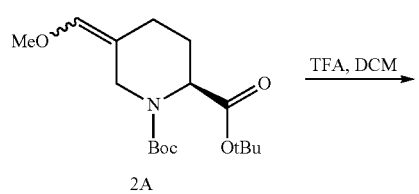

2A

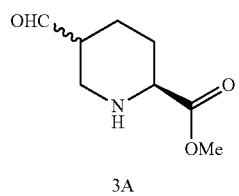

3A

To a stirred mixture of compound 2A (1 g) in methylene chloride (10 mL) was added 5 mL of TFA. The resulting mixture was stirred at room temperature for 2 h and concentrated to give compound 3A (1.4 g). The crude product was used in the next step without further purification.

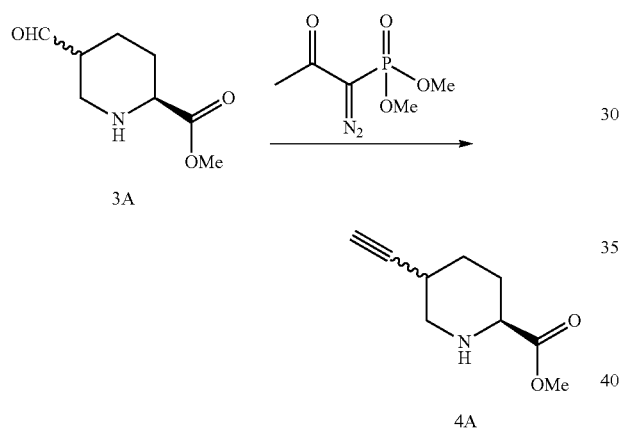

To a stirred mixture of crude 3A (1.4 g) and $K_2CO_3$ (2.4 g, 5 eqiv.) in MeOH (10 mL) was added dimethyl-1-diazo-2-oxypropylphosphate (534 ml, 1 equiv.) in MeOH (10 mL) dropwise. The reaction mixture was stirred at room temperature for 16 h and diluted with methylene chloride (150 mL), which was washed with 1 N HCl. The organic layer was separated and the aqueous layer was basified with $NaHCO_3$. The resulting mixture was extracted with methylene chloride (15 mL×3), which was dried ($Na_2SO_4$) and filtered to give a methylene chloride solution of compound 4A, which was used in the next step without further workup.

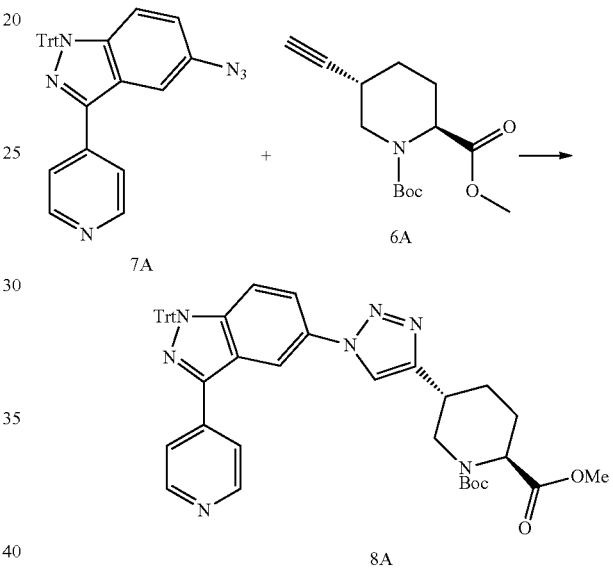

To the methylene chloride solution of 4A obtained from last step was added triethylamine (2.9 mL) followed by (Boc)2O (3.8 g). The reaction mixture was stirred at room temperature for overnight and diluted with $CH_2Cl_2$, which was washed with sat. $NaHCO_3$, brine, dried ($MgSO_4$) and concentrated. Purification on silica gel column (hexanes/ethyl acetate 25/1) gave compound 5A (150 mg) followed by compound 6A (224 mg).

To a stirred mixture of compound 5-Azido-3-(pyridin-4-yl)-1-trityl-1H-indazole (prepared as in Example 1 the 5th step), 7A (481 mg) and 6A (224 mg) in THF (5 mL) and t-BuOH/$H_2O$ (40 mL) was added sodium ascorbate (67 mg) followed by $CuSO_4.5H_2O$ (42 mg)). The resulting mixture was stirred at room temperature for 16 h, to which additional 67 mg of sodium ascorbate and 42 mg of $CuSO_4.5H2O$ was added. The reaction mixture was stirred at room temperature for another 16 h and diluted with ethyl acetate (150 mL), which was washed with sat. $NH_4Cl$, dried ($MgSO_4$) and concentrated. Purifaction on silica gel column ($CH_2Cl_2$/MeOH, 100/0.25) gave compound 8A (540 mg).

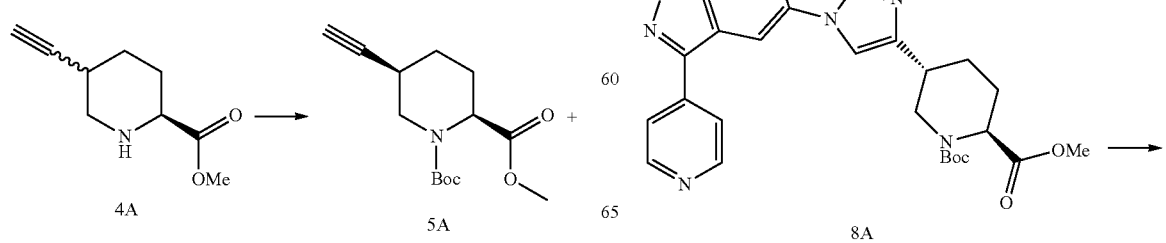

101

-continued

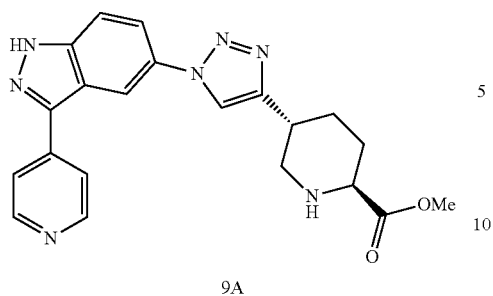
9A

A mixture of 8A (540 mg), TFA (10 mL) and TES (0.5 mL) was stirred at room temperature for 30 min and concentrated. Purifaction on silica gel column (CH₂Cl₂/2N ammonium in MeOH, 15/1) gave compound 9A (290 mg).

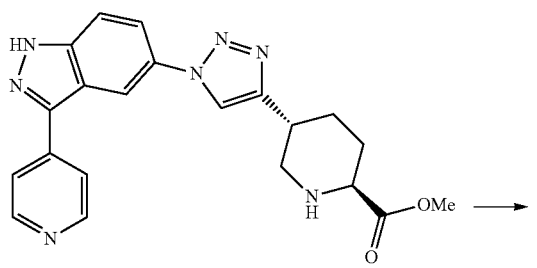
9A

To a stirred mixture of 9A (130 mg) and 2-F-6-MeO-benzaldehyde (246 mg) in MeOH (5 mL) was added NaBH(OAc)₃ (342 mg). The reaction mixture was stirred at room temperature for 16 h and concentrated. To the crude was added CH₂Cl₂. The resulting mixture was then filtered, and filtrate was transferred to a silica gel column and purified (CH₂Cl₂/2N ammonium in MeOH, 25/1) to give 10A (130 mg) followed by 30 mg recovered 9A.

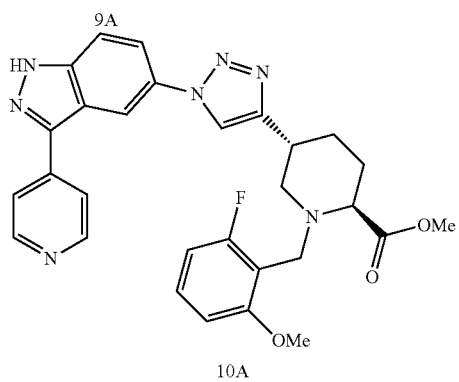
10A

102

-continued

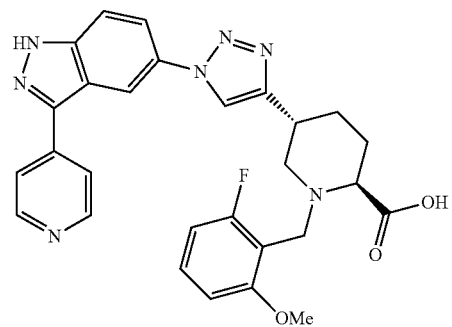
11A

A mixture of 10A (130 mg) and 1 N LiOH (1 mL) was stirred at 50° C. for 16 h and concentrated. The crude was purified on a silica gel column (CH₂Cl₂/MeOH, 10:1, followed by MeOH) to give 11A (119 mg).

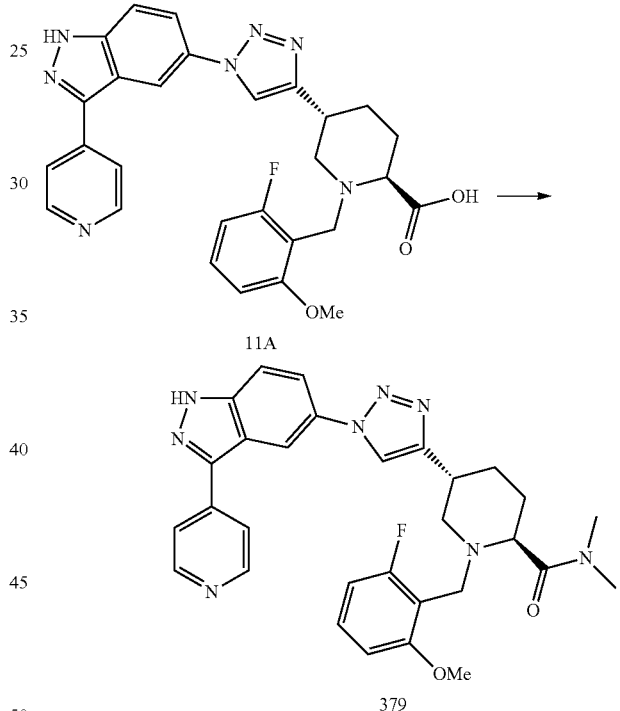

A mixture of 11A, dimethyl amine HCl salt (16 mg), HATU (60 mg) and DIPEA (100 mL) in DMF/CH₂Cl₂ (4/2 mL) was stirred at room temperature for 3 h and concentrated. The crude was purified on a silica gel column (CH₂Cl₂/2N ammonium in MeOH, 20/1) to give 379 (22.1 mg).

Compounds 380 to 384 in Table 1 were prepared by following routes similar to those described above.

Table 1 below provides data for compounds of Examples 1 to 8, as well as for other compounds of this invention which are prepared by methods similar to those of Examples 1 to 9. In Table 1 "D" represents deuterium. A ∿∿∿ bond represents a racemic mixture.

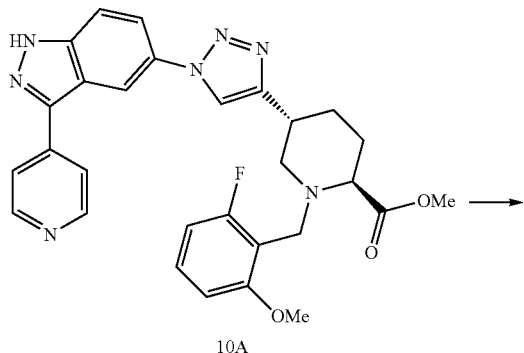
10A

TABLE 1

| Structure | Name | cacld M + H | obs. M + H | HPLC Retention Time min. |
|---|---|---|---|---|
| (200) | 5-[4-[1-[(2-FLUORO-6-METHOXYPHENYL)METHYL]-3(R)-PIPERIDINYL]-1H-1,2,3-TRIAZOL-1-YL]-3-(4-PYRIDINYL)-1H-INDAZOLE (PURE ISOMER) | 484.6 | 484.2 | 1.62 |
| (201) | DEUTERATED-5-[4-[1-[(2-FLUORO-6-METHOXYPHENYL)METHYL-(D)]-3(R)-PIPERIDINYL]-1H-1,2,3-TRIAZOL-1-YL]-3-(4-PYRIDINYL)-1H-INDAZOLE | 485.6 | 485.2 | 1.27 |
| (202) | 5-[4-[1-[(2-FLUORO-6-METHOXYPHENYL)METHYL]-3(R)-PIPERIDINYL]-1H-1,2,3-TRIAZOL-1-YL]-3-IMIDAZO[1,2-a]PYRIDIN-6-YL-1H-INDAZOLE | 523.6 | 523.2 | 1.67 |
| (203) | 5-[4-[1-[(2,6-DIFLUOROPHENYL)METHYL]3(R)-PIPERIDINYL]-1H-1,2,3-TRIAZOL-1-YL]-3-(4-PYRIDINYL)-1H-INDAZOLE (PURE ISOMER) | 472.5 | 472 | 1.54 |

TABLE 1-continued

| Structure | Name | cacld M + H | obs. M + H | HPLC Retention Time min. |
|---|---|---|---|---|
| (204) | 5-[4-[1-[[2-FLUORO-6-(2-METHOXYETHOXY)PHENYL]METHYL]-3(R)-PIPERIDINYL]-1H-1,2,3-TRIAZOL-1-YL]-3-(4-PYRIDINYL)-1H-INDAZOLE | 528.6 | 528.3 | 1.67 |
| (205) | DEUTERATED-5-[4-[1-[(2-FLUORO-6-METHOXYPHENYL)METHYL-(D2)]-3(R)-PIPERIDINYL]-1H-1,2,3-TRIAZOL-1-YL]-3-(4-PYRIDINYL)1H-INDAZOLE | 486.6 | 486.2 | 1.27 |
| (206) | 5-[4-[1-[(2-FLUORO-6-METHOXYPHENYL)METHYL]-3(R)-PIPERIDINYL]-1H-1,2,3-TRIAZOL-1-YL]-3-(2-METHYL-4-PYRIDINYL)-1H-INDAZOLE (PURE ISOMER) | 498.6 | 498.2 | 1.64 |
| (207) | 6-[5-[4-[1-[(2-FLUORO-6-METHOXYPHENYL)METHYL]-3(R)-PIPERIDINYL]-1H-1,2,3-TRIAZOL-1-YL]-1H-INDAZOL-3-YL][1,2,4]TRIAZOLO[1,5-a]PYRIDINE | 524.6 | 524.2 | 1.87 |

TABLE 1-continued

| Structure | Name | cacld M + H | obs. M + H | HPLC Retention Time min. |
|---|---|---|---|---|
| (208) | DEUTERATED-5-[4-[1-[(2,6-DIFLUOROPHENYL)METHYL]-(D)]-3(R)-PIPERIDINYL]-1H-1,2,3-TRIAZOL-1-YL]-3-(4-PYRIDINYL)-1H-INDAZOLE | 473.5 | 473 | 1.64 |
| (209) | DEUTERATED-5-[4-[1-[(2,6-DIFLUOROPHENYL)METHYL-(D2)]-3(R)-PIPERIDINYL]-1H-1,2,3-TRIAZOL-1-YL]-3-(4-PYRIDINYL)-1H-INDAZOLE | 474.5 | 474 | 1.68 |
| (210) | 5-[4-[1-[(2-FLUORO-6-METHOXYPHENYL)METHYL]-3(R)-PIPERIDINYL]-1H-1,2,3-TRIAZOL-1-YL]-3-(2-METHYL-2H-INDAZOL-5-YL)-1H-INDAZOLE | 537.6 | 537.2 | 1.83 |
| (211) | 5-[4-[1-[(2,6-DIFLUOROPHENYL)METHYL]-3(R)-PIPERIDINYL]-1H-1,2,3-TRIAZOL-1-YL]-3-IMIDAZO[1,2-a]PYRIDIN-6-YL-1H-INDAZOLE (PURE ISOMER) | 511.6 | 511 | 1.61 |

TABLE 1-continued

| Structure | Name | cacld M + H | obs. M + H | HPLC Retention Time min. |
|---|---|---|---|---|
| (212) | 6-[5-[4-[1-[(2-FLUOROPHENYL)METHYL]-3(R)-PIPERIDINYL]-1H-1,2,3-TRIAZOL-1-YL]-1H-INDAZOL-3-YL][1,2,4]TRIAZOLO[1,5-a]PYRIDINE | 494.6 | 494.2 | 1.82 |
| (213) | 5-[4-[1-[(2,6-DIFLUOROPHENYL)METHYL]-3(R)-PIPERIDINYL]-1H-1,2,3-TRIAZOL-1-YL]-3-(2-METHYL-4-PYRIDINYL)-1H-INDAZOLE (PURE ISOMER) | 486.5 | 486 | 1.63 |
| (214) | 6-[5-[4-[1-[(2,6-DIFLUOROPHENYL)METHYL]-3(R)-PIPERIDINYL]-1H-1,2,3-TRIAZOL-1-YL]-1H-INDAZOL-3-YL][1,2,4]TRIAZOLO[1,5-a]PYRIDINE | 512.5 | 512.2 | 1.81 |

TABLE 1-continued

| Structure | Name | cacld M + H | obs. M + H | HPLC Retention Time min. |
|---|---|---|---|---|
| (215) | 5-[4-[1-[[2-FLUORO-6-(3-METHOXYPROPOXY)PHEN-YL]METHYL]-3(R)-PIPERIDINYL]-1H-1,2,3-TRIAZOL-1-YL]-3-(4-PYRIDINYL)-1H-INDAZOLE | 542.6 | 542 | 1.7 |
| (216) | 6-[5-[4-[1-[(2-FLUORO-6-METHOXYPHENYL)METHYL]-3(R)-PIPERIDINYL]-1H-1,2,3-TRIAZOL-1-YL]-1H-INDAZOL-3-YL]-2-METHYLBENZOTHIAZOLE | 554.7 | 554.2 | 1.99 |
| (217) | 5-[4-[1-[(2,6-DIFLUOROPHENYL)METHYL]-3(R)-PIPERIDINYL]-1H-1,2,3-TRIAZOL-1-YL]-3-(2-METHYL-2H-INDAZOL-5-YL)-1H-INDAZOLE | 525.6 | 525 | 1.77 |
| (218) | 5-[4-[1-[(2-FLUORO-4-METHOXYPHENYL)METHYL]-3(R)-PIPERIDINYL]-1H-1,2,3-TRIAZOL-1-YL]-3-(4-PYRIDINYL)-1H-INDAZOLE | 484.6 | 484 | 1.04 |

TABLE 1-continued
| Structure | Name | cacld M + H | obs. M + H | HPLC Retention Time min. |
|---|---|---|---|---|
| 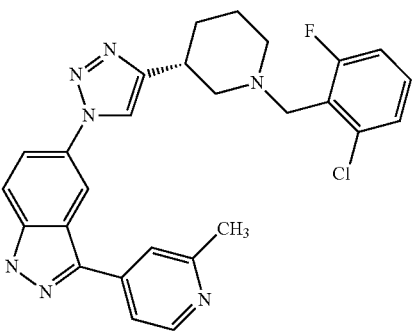 (219) | 5-[4-[1-[(2-CHLORO-6-FLUOROPHENYL)METHYL]-3(R)-PIPERIDINYL]-1H-1,2,3-TRIAZOL-1-YL]-3-(2-METHYL-4-PYRIDINYL)-1H-INDAZOLE (PURE ISOMER) | 503 | 502.2 | 1.61 |
| 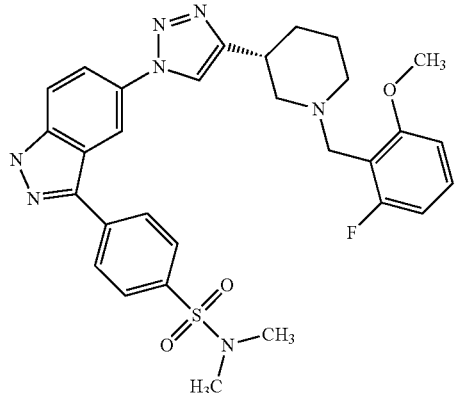 (220) | 4-[5-[4-[1-[(2-FLUORO-6-METHOXYPHENYL)METHYL]-3(R)-PIPERIDINYL]-1H-1,2,3-TRIAZOL-1-YL]-1H-INDAZOL-3-YL]-N,N-DIMETHYLBENZENESULFON-AMIDE | 590.7 | 590.2 | 1.96 |
| 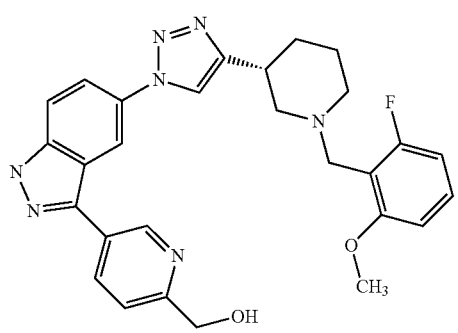 (221) | 5-[5-[4-[1-[(2-FLUORO-6-METHOXYPHENYL)METHYL]-3(R)-PIPERIDINYL]-1H-1,2,3-TRIAZOL-1-YL]-1H-INDAZOL-3-YL]-2-PYRIDINEMETHANOL | 514.6 | 514.2 | 1.66 |

TABLE 1-continued

| Structure | Name | cacld M + H | obs. M + H | HPLC Retention Time min. |
|---|---|---|---|---|
| 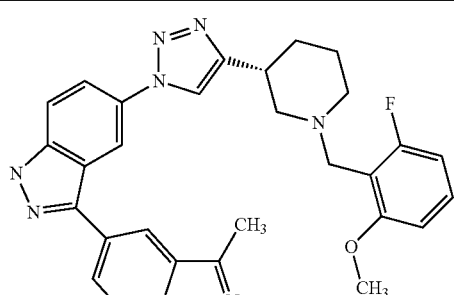 (222) | 5-[4-[1-[(2-FLUORO-6-METHOXYPHENYL)METHYL]-3(R)-PIPERIDINYL]-1H-1,2,3-TRIAZOL-1-YL]-3'-METHYL-3,5'-BI-1H-INDAZOLE | 537.6 | 537.2 | 1.49 |
| 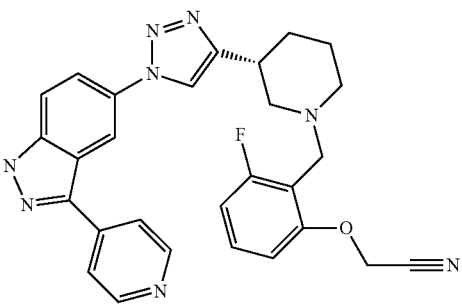 (223) | [3-FLUORO-2-[[3(R)-[1-[3-(4-PYRIDINYL)-1H-INDAZOL-5-YL]-1H-1,2,3-TRIAZOL-4-YL]-1-PIPERIDINYL]METHYL]PHENOXY]ACETONITRILE | 509.6 | 509 | 0.68 |
| 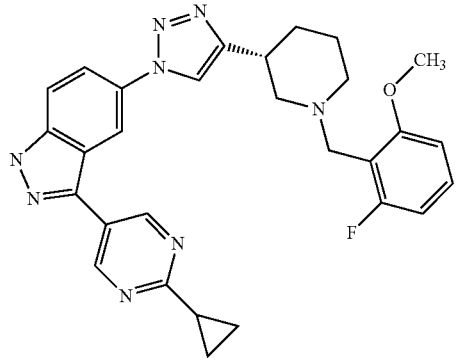 (224) | 3-(2-CYCLOPROPYL-5-PYRIMIDINYL)-5-[4-[1-[(2-FLUORO-6-METHOXYPHENYL)METHYL]-3(R)-PIPERIDINYL]-1H-1,2,3-TRIAZOL-1-YL]-1H-INDAZOLE | 525.6 | 525.2 | 1.94 |
| 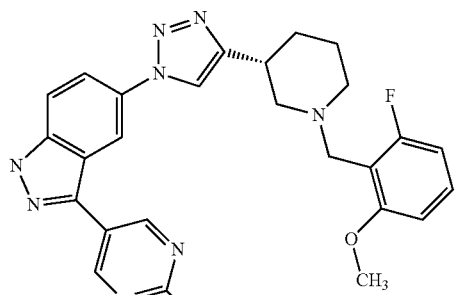 (225) | 5-[4-[1-[(2-FLUORO-6-METHOXYPHENYL)METHYL]-3(R)-PIPERIDINYL]-1H-1,2,3-TRIAZOL-1-YL]-3-(2-METHOXY-5-PYRIMIDINYL)-1H-INDAZOLE | 515.6 | 515.2 | 1.89 |

TABLE 1-continued
| Structure | Name | cacld M + H | obs. M + H | HPLC Retention Time min. |
|---|---|---|---|---|
| 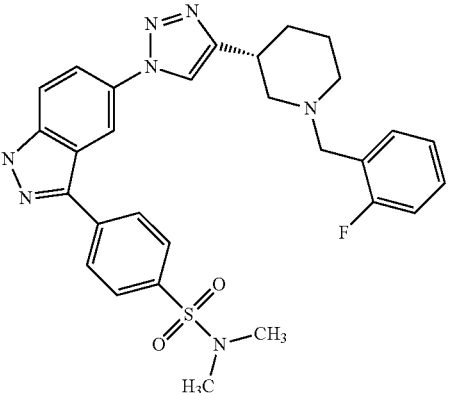 (226) | 4-[5-[4-[1-[(2-FLUOROPHENYL)METHYL]-3(R)-PIPERIDINYL]-1H-1,2,3-TRIAZOL-1-YL]-1H-INDAZOL-3-YL]-N,N-DIMETHYLBENZENESULFON-AMIDE | 560.7 | 560.2 | 1.93 |
| 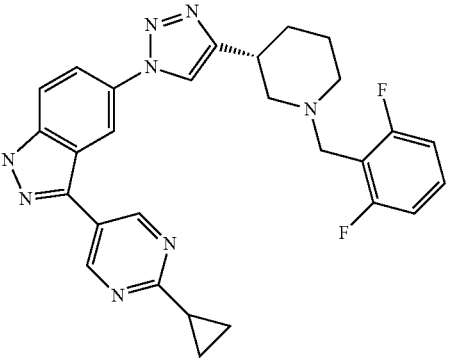 [SMILES: COc1ncc(-c2n[nH]c3ccc(-n4cc([C@@H]5CCCN(Cc6c(F)cccc6F)C5)nn4)cc23)cn1] (227) | 3-(2-CYCLOPROPYL-5-PYRIMIDINYL)-5-[4-[1-[(2,6-DIFLUOROPHENYL)METHYL]-3(R)-PIPERIDINYL]-1H-1,2,3-TRIAZOL-1-YL]-1H-INDAZOLE | 513.6 | 513.2 | 1.89 |
| 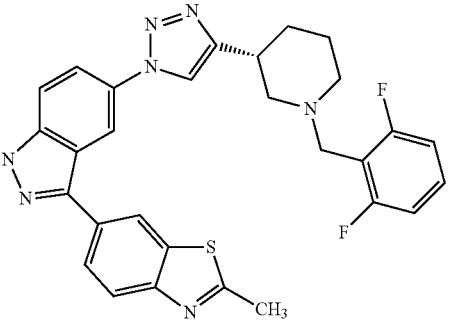 (228) | 6-[5-[4-[1-[(2,6-DIFLUOROPHENYL)METHYL]-3(R)-PIPERIDINYL]-1H-1,2,3-TRIAZOL-1-YL]-1H-INDAZOL-3-YL]-2-METHYLBENZOTHIAZOLE | 542.6 | 542.2 | 1.94 |

TABLE 1-continued

| Structure | Name | cacld M + H | obs. M + H | HPLC Retention Time min. |
|---|---|---|---|---|
| (229) | 4-[5-[4-[1-[(2-FLUORO-6-METHOXYPHENYL)METHYL]-3(R)-PIPERIDINYL]-1H-1,2,3-TRIAZOL-1-YL]-1H-INDAZOL-3-YL]-1-METHYL-2(1H)-PYRIDINONE | 514.6 | 514.2 | 1.74 |
| (230) | 6-[5-[4-[1-[(2-FLUOROPHENYL)METHYL]-3(R)-PIPERIDINYL]-1H-1,2,3-TRIAZOL-1-YL]-1H-INDAZOL-3-YL]-2-METHYLBENZOTHIAZOLE | 524.6 | 524.2 | 1.95 |
| (231) | 5-[5-[4-[1-[(2,6-DIFLUOROPHENYL)METHYL]-3(R)-PIPERIDINYL]-1H-1,2,3-TRIAZOL-1-YL]-1H-INDAZOL-3-YL]-2-PYRIDINEMETHANOL | 502.5 | 502 | 1.62 |
| (232) | 5-[4-[1-[(2,6-DIFLUOROPHENYL)METHYL]-3(R)-PIPERIDINYL]-1H-1,2,3-TRIAZOL-1-YL]-3-(2-METHOXY-5-PYRIMIDINYL)-1H-INDAZOLE | 503.5 | 503.2 | 1.84 |

TABLE 1-continued
| Structure | Name | cacld M + H | obs. M + H | HPLC Retention Time min. |
|---|---|---|---|---|
| 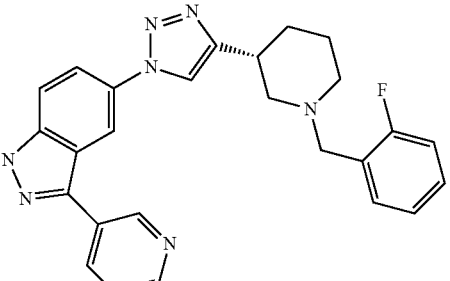 (233) | 5-[4-[1-[(2-FLUOROPHENYL)METHYL]-3(R)-PIPERIDINYL]-1H-1,2,3-TRIAZOL-1-YL]-3-(2-METHOXY-5-PYRIMIDINYL)-1H-INDAZOLE | 485.5 | 485.2 | 1.84 |
| 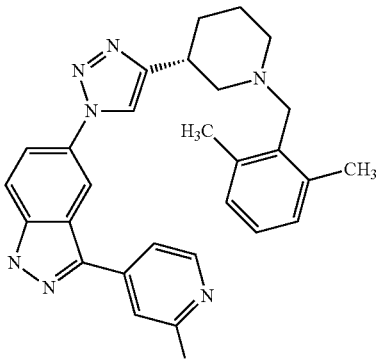 (234) | 5-[4-[1-[(2,6-DIMETHYLPHENYL)METHYL]-3(R)-PIPERIDINYL]-1H-1,2,3-TRIAZOL-1-YL]-3-(2-METHYL-4-PYRIDINYL)-1H-INDAZOLE (PURE ISOMER) | 478.6 | 478 | 1.68 |
| 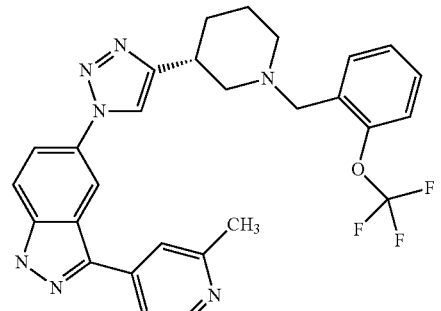 (235) | 3-(2-METHYL-4-PYRIDINYL)-5-[4-[1-[[2-(TRIFLUOROMETHOXY)PHEN-YL]METHYL]-3(R)-PIPERIDINYL]-1H-1,2,3-TRIAZOL-1-YL]-1H-INDAZOLE (PURE ISOMER) | 534.6 | 534.2 | 1.71 |

TABLE 1-continued

| Structure | Name | cacld M + H | obs. M + H | HPLC Retention Time min. |
|---|---|---|---|---|
| (236) | 4-[5-[4-[1-[(2,6-DIFLUOROPHENYL)METHYL]-3(R)-PIPERIDINYL]-1H-1,2,3-TRIAZOL-1-YL]-1H-INDAZOL-3-YL]-N,N-DIMETHYLBENZENESULFON-AMIDE | 578.7 | 578.2 | 1.92 |
| (237) | 4-[5-[4-[1-[(2,6-DIFLUOROPHENYL)METHYL]-3(R)-PIPERIDINYL]-1H-1,2,3-TRIAZOL-1-YL]-1H-INDAZOL-3-YL]-1-METHYL-2(1H)-PYRIDINONE (PURE ISOMER) | 502.5 | 502 | 1.67 |
| (238) | 3-(2-CYCLOPROPYL-5-PYRIMIDINYL)-5-[4-[1-[(2-FLUOROPHENYL)METHYL]-3(R)-PIPERIDINYL]-1H-1,2,3-TRIAZOL-1-YL]-1H-INDAZOLE | 495.6 | 495.2 | 1.9 |
| (239) | 5-[4-[1-[(2-FLUORO-6-METHOXYPHENYL)METHYL]-3(R)-PIPERIDINYL]-1H-1,2,3-TRIAZOL-1-YL]-3-(1H-PYRROLO[2,3-b]PYRIDIN-4-YL)-1H-INDAZOLE | 523.6 | 523.2 | 1.79 |

TABLE 1-continued

| Structure | Name | cacld M + H | obs. M + H | HPLC Retention Time min. |
|---|---|---|---|---|
| 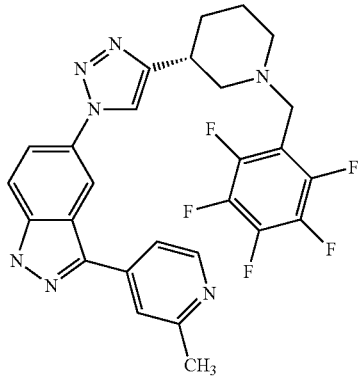 (240) | 3-(2-METHYL-4-PYRIDINYL)-5-[4-[1-[(PENTAFLUOROPHENYL)METHYL]-3(R)-PIPERIDINYL]-1H-1,2,3-TRIAZOL-1-YL]-1H-INDAZOLE (PURE ISOMER) | 540.5 | 540 | 1.68 |
| 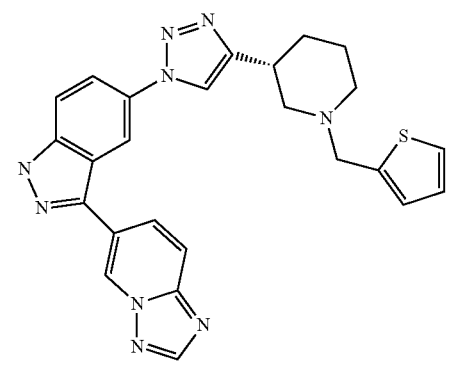 (241) | 6-[5-[4-[1-(2-THIENYLMETHYL)-3(R)-PIPERIDINYL]-1H-1,2,3-TRIAZOL-1-YL]-1H-INDAZOL-3-YL][1,2,4]TRIAZOLO[1,5-a]PYRIDINE | 482.6 | 482.2 | 1.82 |
| 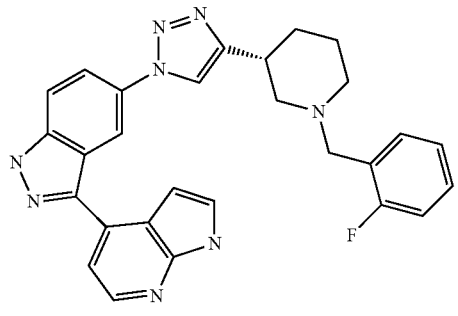 (242) | 5-[4-[1-[(2-FLUOROPHENYL)METHYL]-3(R)-PIPERIDINYL]-1H-1,2,3-TRIAZOL-1-YL]-3-(1H-PYRROLO[2,3-b]PYRIDIN-4-YL)-1H-INDAZOLE | 493.6 | 493.2 | 1.74 |
| 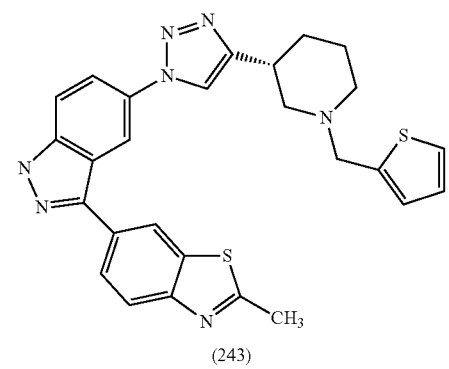 [SMILES: Cc1nc2ccc(-c3n[nH]c4ccc(-n5cc([C@@H]6CCCN(Cc7cccs7)C6)nn5)cc34)cc2s1] (243) | 2-METHYL-6-[5-[4-[1-(2-THIENYLMETHYL)-3(R)-PIPERIDINYL]-1H-1,2,3-TRIAZOL-1-YL]-1H-INDAZOL-3-YL]BENZOTHIAZOLE | 512.7 | 512 | 1.96 |

TABLE 1-continued
| Structure | Name | cacld M + H | obs. M + H | HPLC Retention Time min. |
|---|---|---|---|---|
| 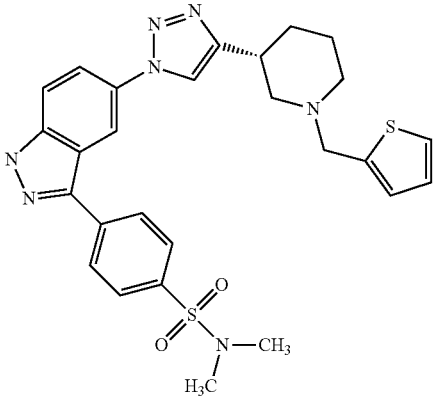 (244) | N,N-DIMETHYL-4-[5-[4-[1-(2-THIENYLMETHYL)-3(R)-PIPERIDINYL]-1H-1,2,3-TRIAZOL-1-YL]-1H-INDAZOL-3-YL]BENZENESULFONAMIDE | 548.7 | 548.1 | 1.93 |
| 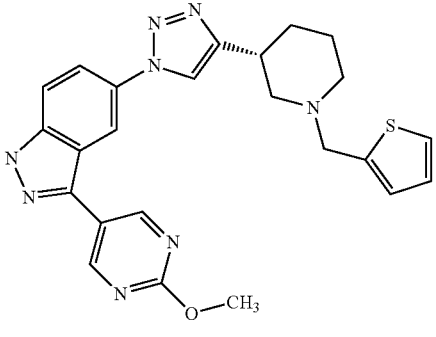 (245) | 3-(2-METHOXY-5-PYRIMIDINYL)-5-[4-[1-(2-THIENYLMETHYL)-3(R)-PIPERIDINYL]-1H-1,2,3-TRIAZOL-1-YL]-1H-INDAZOLE | 473.6 | 473.2 | 1.87 |
| 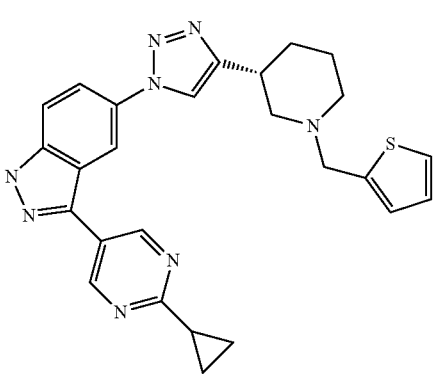 [SMILES: COc1ncc(-c2n[nH]c3ccc(-n4cc([C@@H]5CCCN(Cc6cccs6)C5)nn4)cc23)cn1] (246) | 3-(2-CYCLOPROPYL-5-PYRIMIDINYL)-5-[4-[1-(2-THIENYLMETHYL)-3(R)-PIPERIDINYL]-1H-1,2,3-TRIAZOL-1-YL]-1H-INDAZOLE | 483.6 | 483.2 | 1.91 |

TABLE 1-continued

| Structure | Name | cacld M + H | obs. M + H | HPLC Retention Time min. |
|---|---|---|---|---|
| 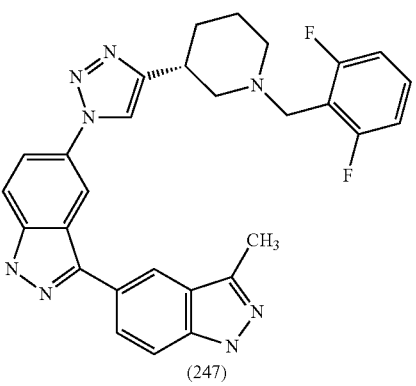 [SMILES: Cc1n[nH]c2ccc(-c3n[nH]c4ccc(-n5cc([C@@H]6CCCN(Cc7c(F)cccc7F)C6)nn5)cc34)cc12] (247) | 5-[4-[1-[(2,6-DIFLUOROPHENYL)METHYL]-3(R)-PIPERIDINYL]-1H-1,2,3-TRIAZOL-1-YL]-3'-METHYL-3,5'-BI-1H-INDAZOLE (PURE ISOMER) | 525.6 | 525 | 1.76 |
| 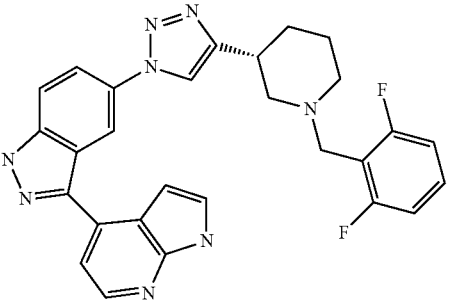 (248) | 5-[4-[1-[(2,6-DIFLUOROPHENYL)METHYL]-3(R)-PIPERIDINYL]-1H-1,2,3-TRIAZOL-1-YL]-3-(1H PYRROLO[2,3-b]PYRIDIN-4-YL)-1H-INDAZOLE | 511.6 | 511.2 | 1.74 |
| 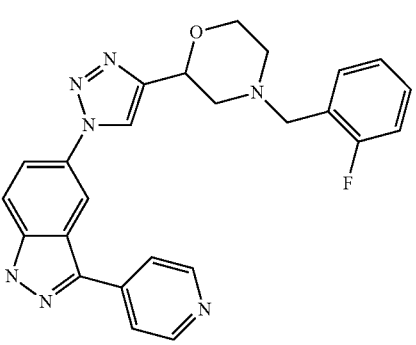 (249) | 5-[4-[4-[(2-FLUOROPHENYL)METHYL]-2-MORPHOLINYL]-1H-1,2,3-TRIAZOL-1-YL]-3-(4-PYRIDINYL)-1H-INDAZOLE | 456.5 | 456.2 | 1.61 |
| 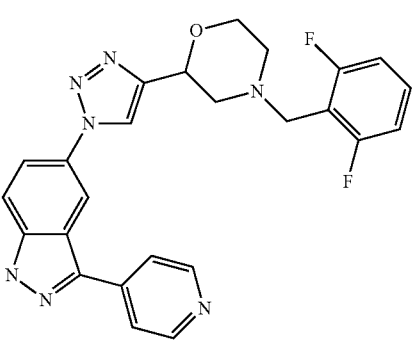 (250) | 5-[4-[4-[(2,6-DIFLUOROPHENYL)METHYL]-2-MORPHOLINYL]-1H-1,2,3-TRIAZOL-1-YL]-3-(4-PYRIDINYL)-1H-INDAZOLE | 474.5 | 474.2 | 1.61 |

TABLE 1-continued

| Structure | Name | cacld M + H | obs. M + H | HPLC Retention Time min. |
|---|---|---|---|---|
| (251) | 5-[4-[4-[(2-FLUORO-6-METHOXYPHENYL)METHYL]-2-MORPHOLINYL]-1H-1,2,3-TRIAZOL-1-YL]-3-(4-PYRIDINYL)-1H-INDAZOLE | 486.5 | 486.2 | 1.66 |
| (252) | 5-[4-[4-(2-PHENYLETHYL)-2-MORPHOLINYL]-1H-1,2,3-TRIAZOL-1-YL]-3-(4-PYRIDINYL)-1H-INDAZOLE | 452.5 | 452.2 | 1.66 |
| (253) | 3-(2,3-DIHYDRO-5-BENZOFURANYL)-5-[5-[1-[(2-FLUORO-6-METHOXYPHENYL)METHYL]-1,2,3,6-TETRAHYDRO-2(R)-PYRIDINYL]-1H-1,2,4-TRIAZOL-3-YL]-1H-INDAZOLE | 522.6 | 523.4 | 2.0 |
| (254) | 5-[5-[1-[(2,6-DIFLUOROPHENYL)METHYL]-1,2,3,6-TETRAHYDRO-2(R)-PYRIDINYL]-1H-1,2,4-TRIAZOL-3-YL]-3-(2,3-DIHYDRO-5-BENZOFURANYL)-1H-INDAZOLE | 510.5 | 511.4 | 1.9 |

TABLE 1-continued

| Structure | Name | cacld M + H | obs. M + H | HPLC Retention Time min. |
|---|---|---|---|---|
| 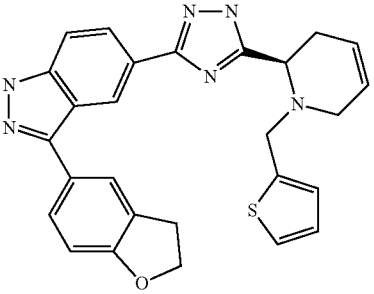 (255) (and Enantiomer) | 3-(2,3-DIHYDRO-5-BENZOFURANYL)-5-[5-[1,2,3,6-TETRAHYDRO-1-(2-THIENYLMETHYL)-2(R)-PYRIDINYL]-1H-1,2,4-TRIAZOL-3-YL]-1H-INDAZOLE | 480.6 | 481.1 | 2.3 |
| 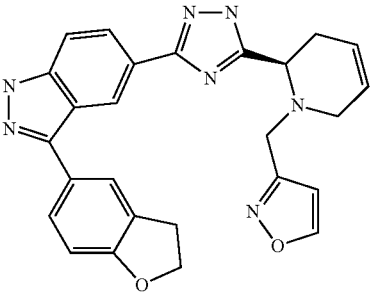 (256) (and enantiomer) | 3-(2,3-DIHYDRO-5-BENZOFURANYL)-5-[5-[1,2,3,6-TETRAHYDRO-1-(3-ISOXAZOLYLMETHYL)-2(R)-PYRIDINYL]-1H-1,2,4-TRIAZOL-3-YL]-1H-INDAZOLE | 465.5 | 466.2 | 2.4 |
| 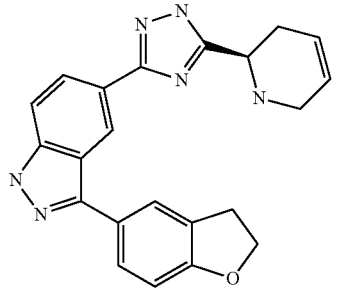 (257) (and enantiomer) | 3-(2,3-DIHYDRO-5-BENZOFURANYL)-5-[5-(1,2,3,6-TETRAHYDRO-2(R)-PYRIDINYL)-1H-1,2,4-TRIAZOL-3-YL]-1H-INDAZOLE | 472.5 | 472.3 | 2.1 |
| 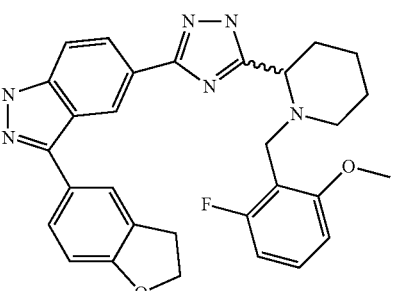 (258) | 3-(2,3-DIHYDRO-5-BENZOFURANYL)-5-[5-[1-[(2-FLUORO-6-METHOXYPHENYL)METHYL]-2-PIPERIDINYL]-1H-1,2,4-TRIAZOL-3-YL]-1H-INDAZOLE | 525.4 | 525.4 | 2.8 |

| Structure | Name | cacld M + H | obs. M + H | HPLC Retention Time min. |
|---|---|---|---|---|
| (259) | 5-[5-[1-[(2-FLUORO-6-METHOXYPHENYL)METHYL]-2-PIPERIDINYL]-1H-1,2,4-TRIAZOL-3-YL]-3-[4-(1-METHYLETHOXY)PHENYL]-1H-INDAZOLE | 541.0 | 541.4 | 2.2 |
| (260) | 5-[1-[1-[(2-FLUOROPHENYL)METHYL]-3(R)-PIPERIDINYL]-1H-1,2,3-TRIAZOL-4-YL]-3-(4-PYRIDINYL)-1H-INDAZOLE (PURE ISOMER) | 454.5 | 454.0 | 1.6 |
| (261) | 5-[1-[1-[(2-FLUORO-6-METHOXYPHENYL)METHYL]-3(R)-PIPERIDINYL]-1H-1,2,3-TRIAZOL-4-YL]-3-(4-PYRIDINYL)-1H-INDAZOLE (PURE ISOMER) | 484.6 | 484.0 | 1.6 |

TABLE 1-continued

| Structure | Name | cacld M + H | obs. M + H | HPLC Retention Time min. |
|---|---|---|---|---|
| (262) | 5-[1-[1-[(1-METHYL-1H-INDOL-3-YL)METHYL]-3(R)-PIPERIDINYL]-1H-1,2,3-TRIAZOL-4-YL]-3-(4-PYRIDINYL)-1H-INDAZOLE (PURE ISOMER) | 489.6 | 489.0 | 1.7 |
| (263) | 5-[1-[1-[(2,6-DIFLUOROPHENYL)METHYL]-3(R)-PIPERIDINYL]-1H-1,2,3-TRIAZOL-4-YL]-3-(4-PYRIDINYL)-1H-INDAZOLE (PURE ISOMER) | 472.5 | 472.0 | 1.6 |
| (264) | 5-[1-[1-(2-NAPHTHALENYLMETHYL)-3(R)-PIPERIDINYL]-1H-1,2,3-TRIAZOL-4-YL]-3-(4-PYRIDINYL)-1H-INDAZOLE (PURE ISOMER) | 486.6 | 486.0 | 1.7 |

TABLE 1-continued

| Structure | Name | cacld M + H | obs. M + H | HPLC Retention Time min. |
|---|---|---|---|---|
| (265) | 5-[1-[1-[(2-FLUORO-6-METHOXYPHENYL)METHYL]-3(R)-PIPERIDINYL]-1H-1,2,3-TRIAZOL-4-YL]-3-(2-METHYL-4-PYRIDINYL)-1H-INDAZOLE (PURE ISOMER) | 498.6 | 498.0 | 1.7 |
| (266) | 1-METHYL-3-[[3(R)-[4-[3-(4-PYRIDINYL)-1H-INDAZOL-5-YL]-1H-1,2,3-TRIAZOL-1-YL]-1-PIPERIDINYL]METHYL]-1H-INDAZOLE (PURE ISOMER) | 490.6 | 490.0 | 1.6 |
| (267) | 5-[1-[1-[(2,6-DIFLUOROPHENYL)METHYL]-3(R)-PIPERIDINYL]-1H-1,2,3-TRIAZOL-4-YL]-3-(2-METHYL-4-PYRIDINYL)-1H-INDAZOLE (PURE ISOMER) | 486.5 | 486.0 | 1.6 |

TABLE 1-continued

| Structure | Name | cacld M + H | obs. M + H | HPLC Retention Time min. |
|---|---|---|---|---|
| (268) | 1-(2-FLUORO-6-METHOXYBENZOYL)-3(R)-[4-[3-(4-PYRIDINYL)-1H-INDAZOL-5-YL]-1H-1,2,3-TRIAZOL-1-YL]PIPERIDINE | 498.5 | 498.2 | 1.8 |
| (269) | 1-[(2,6-DIFLUOROPHENYL)METHYL]-5(R)-[4-[3-(2-METHYL-4-PYRIDINYL)-1H-INDAZOL-5-YL]-1H-1,2,3-TRIAZOL-1-YL]-2-PIPERIDINONE | 500.5 | 500.0 | 1.7 |
| (270) | 1-(2-FLUOROBENZOYL)-3(R)-[4-[3-(4-PYRIDINYL)-1H-INDAZOL-5-YL]-1H-1,2,3-TRIAZOL-1-YL]PIPERIDINE (PURE ISOMER) | 468.5 | 468.0 | 1.8 |

TABLE 1-continued
| Structure | Name | cacld M + H | obs. M + H | HPLC Retention Time min. |
|---|---|---|---|---|
| 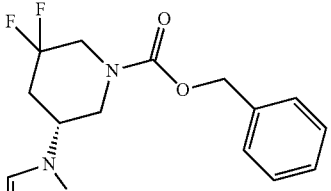 (271) | PHENYLMETHYL 3,3-DIFLUORO-5(R)-[4-[3-(4-PYRIDINYL)-1H-INDAZOL-5-YL]-1H-1,2,3-TRIAZOL-1-YL]-1-PIPERIDINECARBOXYLATE | 516.5 | 516.0 | 2.0 |
| 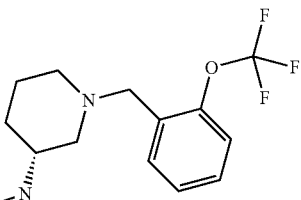 (272) | 3-(2-METHYL-4-PYRIDINYL)-5-[1-[1-[[2-(TRIFLUOROMETHOXY)PHENYL]METHYL]-3(R)-PIPERIDINYL]-1H-1,2,3-TRIAZOL-4-YL]-1H-INDAZOLE (PURE ISOMER) | 534.6 | 534.2 | 1.7 |
| 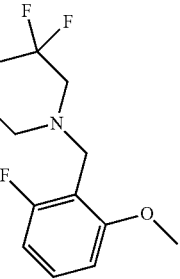 (273) | 5-[1-[5,5-DIFLUORO-1-[(2-FLUORO-6-METHOXYPHENYL)METHYL]-3-PIPERIDINYL]-1H-1,2,3-TRIAZOL-4-YL]-3-(4-PYRIDINYL)-1H-INDAZOLE | 520.5 | 520.2 | 0.9 |

TABLE 1-continued

| Structure | Name | cacld M + H | obs. M + H | HPLC Retention Time min. |
|---|---|---|---|---|
| 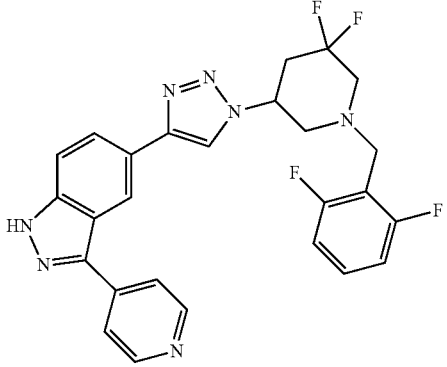 (274) | 5-[1-[1-[(2,6-DIFLUOROPHENYL)METHYL]-5,5-DIFLUORO-3-PIPERIDINYL]-1H-1,2,3-TRIAZOL-4-YL]-3-(4-PYRIDINYL)-1H-INDAZOLE | 508.5 | 508.2 | 0.9 |
| 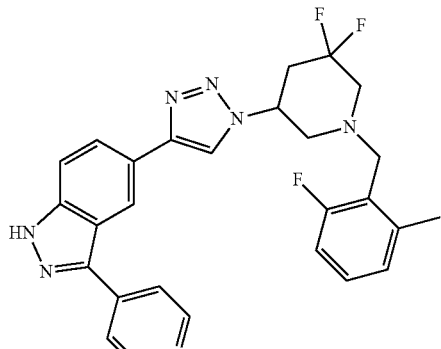 (275) | 5-[1-[5,5-DIFLUORO-1-[(2-FLUORO-6-METHYLPHENYL)METHYL]-3-PIPERIDINYL]-1H-1,2,3-TRIAZOL-4-YL]-3-(4-PYRIDINYL)-1H-INDAZOLE | 504.5 | 504.2 | 0.9 |
| 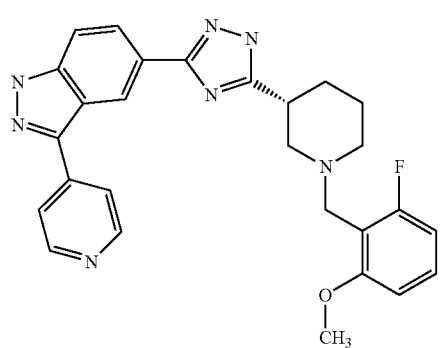 (276) | 5-[5-[1-[(2-FLUORO-6-METHOXYPHENYL)METHYL]-3(R)-PIPERIDINYL]-1H-1,2,4-TRIAZOL-3-YL]-3-(4-PYRIDINYL)-1H-INDAZOLE | 484.6 | 484.3 | 1.7 |
| 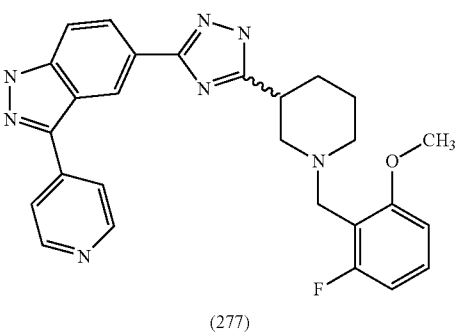 [SMILES: COc1cccc(F)c1CN1CCCC(c2nc(-c3ccc4[nH]nc(-c5ccncc5)c4c3)n[nH]2)C1] (277) | 5-[5-[1-[(2-FLUORO-6-METHOXYPHENYL)METHYL]-3(R/S)-PIPERIDINYL]-1H-1,2,4-TRIAZOL-3-YL]-3-(4-PYRIDINYL)-1H-INDAZOLE (RACEMIC) | 484.6 | 484.3 | 1.7 |

TABLE 1-continued

| Structure | Name | cacld M + H | obs. M + H | HPLC Retention Time min. |
|---|---|---|---|---|
| (278) | 3-(4-PYRIDINYL)-5-[5-[1-(2-THIENYLMETHYL)-3(R)-PIPERIDINYL]-1H-1,2,4-TRIAZOL-3-YL]-1H-INDAZOLE | 442.6 | 442.3 | 1.8 |
| (279) | 5-[5-[1-[(2,6-DIFLUOROPHENYL)METHYL]-3(R)-PIPERIDINYL]-1H-1,2,4-TRIAZOL-3-YL]-3-(4-PYRIDINYL)-1H-INDAZOLE | 472.5 | 472.3 | 1.9 |
| (280) | 5-[5-[1-[(2,6-DIFLUOROPHENYL)METHYL]-3(R/S)-PIPERIDINYL]-1H-1,2,4-TRIAZOL-3-YL]-3-(4-PYRIDINYL)-1H-INDAZOLE (RACEMIC) | 472.5 | 472.3 | 2.1 |
| (281) | 5-[5-[1-[(2,6-DIFLUOROPHENYL)METHYL]-3(R)-PIPERIDINYL]-1H-1,2,4-TRIAZOL-3-YL]-3-(2-METHYL-4-PYRIDINYL)-1H-INDAZOLE | 486.5 | 486.3 | 1.7 |

TABLE 1-continued

| Structure | Name | cacld M + H | obs. M + H | HPLC Retention Time min. |
|---|---|---|---|---|
| (282) | 5-[5-[1-(1,2,4-OXADIAZOL-3-YLMETHYL)-3(R/S)-PIPERIDINYL]-1H-1,2,4-TRIAZOL-3-YL]-3-(4-PYRIDINYL)-1H-INDAZOLE (RACEMIC) | 428.5 | 428.2 | 1.8 |
| (283) | 4-[5-[5-[1-[(2,6-DIFLUOROPHENYL)METHYL]-3(R)-PIPERIDINYL]-1H-1,2,4-TRIAZOL-3-YL]-1H-INDAZOL-3-YL]-2-PYRIDINAMINE | 487.5 | 487.2 | 2.1 |
| (284) | 3-(2,3-DIHYDRO-5-BENZOFURANYL)-5-[5-[1-[(2-FLUORO-6-METHOXYPHENYL)METHYL]-3(R)-PIPERIDINYL]-1H-1,2,4-TRIAZOL-3-YL]-1H-INDAZOLE | 525.6 | 525.3 | 2.8 |
| (285) | 6-[5-[5-[1-[(2,6-DIFLUOROPHENYL)METHYL]-3(R)-PIPERIDINYL]-1H-1,2,4-TRIAZOL-3-YL]-1H-INDAZOL-3-YL][1,2,4]TRIAZOLO[1,5-a]PYRIDINE | 512.5 | 512.2 | 1.8 |

TABLE 1-continued

| Structure | Name | cacld M + H | obs. M + H | HPLC Retention Time min. |
|---|---|---|---|---|
| 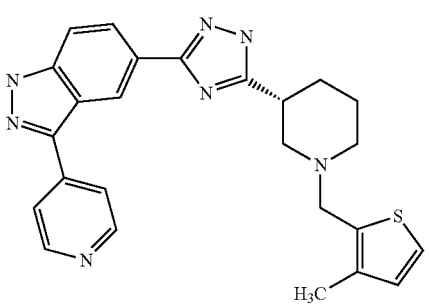 (286) | 5-[5-[1-[(3-METHYL-2-THIENYL)METHYL]-3(R)-PIPERIDINYL]-1H-1,2,4-TRIAZOL-3-YL]-3-(4-PYRIDINYL)-1H-INDAZOLE | 456.6 | 456.0 | 1.7 |
| 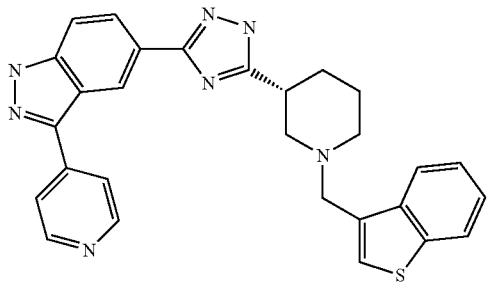 (287) | 5-[5-[1-(BENZO[b]THIEN-3-YLMETHYL)-3(R)-PIPERIDINYL]-1H-1,2,4-TRIAZOL-3-YL]-3-(4-PYRIDINYL)-1H-INDAZOLE | 492.6 | 492.3 | 1.7 |
| 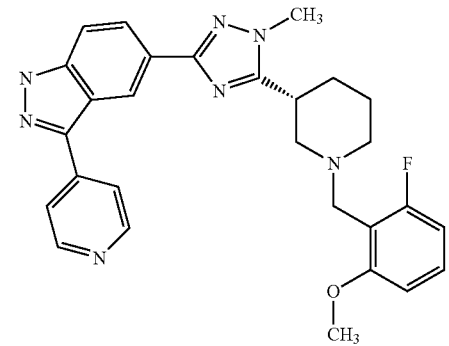 (288) | 5-[5-[1-[(2-FLUORO-6-METHOXYPHENYL)METHYL]-3(R)-PIPERIDINYL]-1-METHYL-1H-1,2,4-TRIAZOL-3-YL]-3-(4-PYRIDINYL)-1H-INDAZOLE | 498.6 | 498.3 | 2.1 |
| 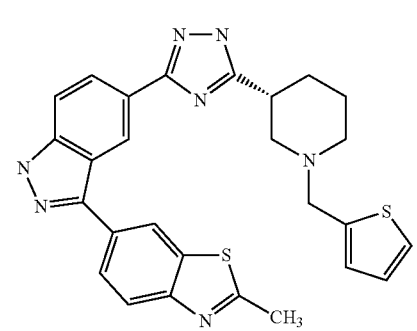 (289) | 2-METHYL-6-[5-[5-[1-(2-THIENYLMETHYL)-3(R)-PIPERIDINYL]-1H-1,2,4-TRIAZOL-3-YL]-1H-INDAZOL-3-YL]BENZOTHIAZOLE | 512.7 | 512.5 | 1.8 |

TABLE 1-continued

| Structure | Name | cacld M + H | obs. M + H | HPLC Retention Time min. |
|---|---|---|---|---|
| (290) | 3-(2-CYCLOPROPYL-4-PYRIDINYL)-5-[5-[1-[(2,6-DIFLUOROPHENYL)METHYL]-3(R)-PIPERIDINYL]-1H-1,2,4-TRIAZOL-3-YL]-1H-INDAZOLE | 512.6 | 512.3 | 2.4 |
| (291) | 5-[5-(1-[(2,6-DIFLUOROPHENYL)METHYL]-3(R)-PIPERIDINYL)-1H-1,2,4-TRIAZOL-3-YL]-3-(2,3-DIHYDRO-5-BENZOFURANYL)-1H-INDAZOLE | 513.6 | 513.3 | 2.7 |
| (292) | 5-[5-[5-[1-[(2-FLUORO-6-METHOXYPHENYL)METHYL]-3(R)-PIPERIDINYL]-1H-1,2,4-TRIAZOL-3-YL]-1H-INDAZOL-3-YL]-ALPHA,ALPHA-DIMETHYL-3-PYRIDINEMETHANOL | 542.6 | 542.4 | 2.2 |
| (293) | 5-[5-[1-[(2-FLUORO-6-METHOXYPHENYL)METHYL]-3(R)-PIPERIDINYL]-1H-1,2,4-TRIAZOL-3-YL]-3-[4-(1-METHYLETHOXY)PHENYL]-1H-INDAZOLE | 541.6 | 541.4 | 2.0 |

TABLE 1-continued

| Structure | Name | cacld M + H | obs. M + H | HPLC Retention Time min. |
|---|---|---|---|---|
| (294) | 5-[5-[1-[(2,6-DIFLUOROPHENYL)METHYL]-3(R/S)-PIPERIDINYL]-1H-1,2,4-TRIAZOL-3-YL]-3-(4-FLUOROPHENYL)-1H-INDAZOLE (RACEMIC) | 489.5 | 498.3 | 1.8 |
| (295) | 5-[5-[1-[(2,6-DIFLUOROPHENYL)METHYL]-3(R)-PIPERIDINYL]-1H-1,2,4-TRIAZOL-3-YL]-3-[4-[(1-METHYLETHYL)SULFONYL]PHENYL]-1H-INDAZOLE | 577.7 | 577.5 | 2.8 |
| (296) | 1-[[3(R/S)-[3-[3-(4-PYRIDINYL)-1H-INDAZOL-5-YL]-1H-1,2,4-TRIAZOL-5-YL]-1-PIPERIDINYL]ACETYL]-PIPERIDINE (RACEMIC) | 471.6 | 471.3 | 1.6 |
| (297) | 3-(1,3-BENZODIOXOL-5-YL)-5-[5-[1-[(2,6-DIFLUOROPHENYL)METHYL]-3(R)-PIPERIDINYL]-1H-1,2,4-TRIAZOL-3-YL]-1H-INDAZOLE | 515.5 | 515.3 | 1.9 |

TABLE 1-continued

| Structure | Name | cacld M + H | obs. M + H | HPLC Retention Time min. |
|---|---|---|---|---|
| (298) | 3-(2,3-DIHYDRO-5-BENZOFURANYL)-5-[5-[1-(2-THIENYLMETHYL)-3(R)-PIPERIDINYL]-1H-1,2,4-TRIAZOL-3-YL]-1H-INDAZOLE | 483.6 | 483.4 | 1.8 |
| (299) | 5-[5-[1-[(2,6-DIFLUOROPHENYL)METHYL]-3(R)-PIPERIDINYL]-1H-1,2,4-TRIAZOL-3-YL]-3-[4-(1-METHYLETHOXY)PHENYL]-1H-INDAZOLE | 529.6 | 529.3 | 2.9 |
| (300) | 5-[5-[1-[(2,6-DIFLUOROPHENYL)METHYL]-3(R)-PIPERIDINYL]-1H-1,2,4-TRIAZOL-3-YL]-3-(2,3-DIHYDRO-2,2-DIMETHYL-5-BENZOFURANYL)-1H-INDAZOLE | 541.6 | 541.3 | 2.0 |
| (301) | 5-[5-[1-[(2,6-DIFLUOROPHENYL)METHYL]-3(R)-PIPERIDINYL]-1H-1,2,4-TRIAZOL-3-YL]-3-[4-(TRIFLUOROMETHYL)PHENYL]-1H-INDAZOLE | 539.5 | 539.3 | 3.2 |

TABLE 1-continued

| Structure | Name | cacld M + H | obs. M + H | HPLC Retention Time min. |
|---|---|---|---|---|
| (302) | 5-[5-[1-[(2,6-DIFLUOROPHENYL)METHYL]-3(R)-PIPERIDINYL]-1H-1,2,4-TRIAZOL-3-YL]-3-(2,3-DIFLUORO-4-PYRIDINYL)-1H-INDAZOLE | 508.5 | 508.3 | 2.6 |
| (303) | 5-[5-[1-[(2,6-DIFLUOROPHENYL)METHYL]-3(R)-PIPERIDINYL]-1H-1,2,4-TRIAZOL-3-YL]-3-(3,5-DIMETHYL-4-ISOXAZOLYL)-1H-INDAZOLE | 490.5 | 490.2 | 1.8 |
| (304) | 3-[4-(1-METHYLETHOXY)PHENYL]-5-[5-[1-(2-THIENYLMETHYL)-3(R)-PIPERIDINYL]-1H-1,2,4-TRIAZOL-3-YL]-1H-INDAZOLE | 499.7 | 499.3 | 3.4 |
| (305) | 5-[5-[1-[(2,6-DIFLUOROPHENYL)METHYL]-3(R)-PIPERIDINYL]-1H-1,2,4-TRIAZOL-3-YL]-3-[4-[(1-METHYLETHYL)THIO]PHENYL]-1H-INDAZOLE | 545.7 | 545.4 | 3.9 |

TABLE 1-continued
| Structure | Name | cacld M + H | obs. M + H | HPLC Retention Time min. |
|---|---|---|---|---|
| 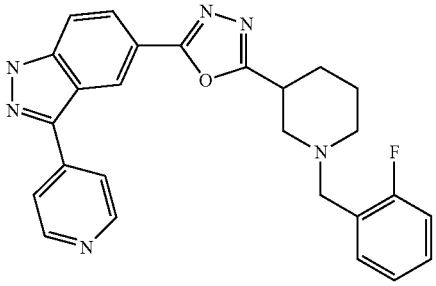 (306) | 5-[5-[1-[(2-FLUOROPHENYL)METHYL]-3-PIPERIDINYL]-1,3,4-OXADIAZOL-2-YL]-3-(4-PYRIDINYL)-1H-INDAZOLE | 455.5 | 455.2 | 2.2 |
| 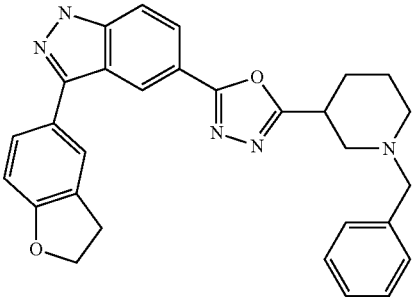 (307) | 3-(2,3-DIHYDRO-5-BENZOFURANYL)-5-[5-[1-(PHENYLMETHYL)-3-(PIPERIDINYL]-1,3,4-OXADIAZOL-2-YL]-1H-INDAZOLE | 478.6 | 478.7 | 3.4 |
| 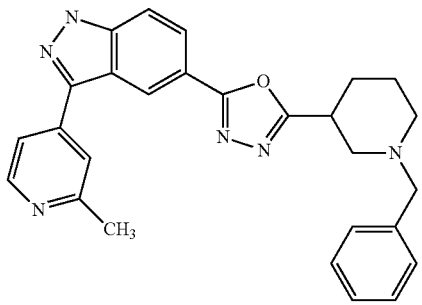 (308) | 3-(2-METHYL-4-PYRIDINYL)-5-[5-[1-(PHENYLMETHYL)-3-PIPERIDINYL]-1,3,4-OXADIAZOL-2-YL]-1H-INDAZOLE | 451.5 | 451.7 | 2.2 |
| 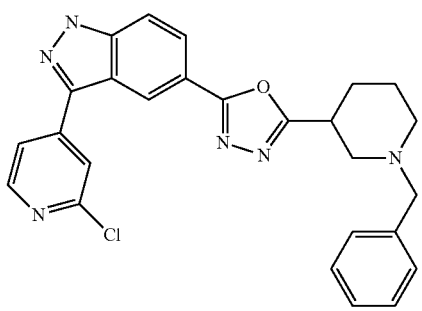 (309) | 3-(2-CHLORO-4-PYRIDINYL)-5-[5-[1-(PHENYLMETHYL)-3-PIPERIDINYL]-1,3,4-OXADIAZOL-2-YL]-1H-INDAZOLE | 472.0 | 471.6 | 3.3 |

TABLE 1-continued

| Structure | Name | cacld M + H | obs. M + H | HPLC Retention Time min. |
|---|---|---|---|---|
| (310) | 5-[5-[1-[(2-FLUOROPHENYL)METHYL]-5-METHYL-3-PIPERIDINYL]-1,3,4-OXADIAZOL-2-YL]-3-(4-PYRIDINYL)-1H-INDAZOLE | 469.5 | 469.2 | 2.4 |
| (311) | 5-[5-[1-[(2-FLUOROPHENYL)METHYL]-5(S)-METHYL-3(R)-PIPERIDINYL]-1,3,4-OXADIAZOL-2-YL]-3-(4-PYRIDINYL)-1H-INDAZOLE | 469.5 | 469.2 | 2.4 |
| (312) | 5-[5-[1-[(2-FLUOROPHENYL)METHYL]-5(R)-METHYL-3(R)-PIPERIDINYL]-1,3,4-OXADIAZOL-2-YL]-3-(4-PYRIDINYL)-1H-INDAZOLE | 469.5 | 469.2 | 2.4 |
| (313) | N-[5-[5-[5-[1-[(2,6-DIFLUOROPHENYL)METHYL]-3(R)-PIPERIDINYL]-1,3,4-OXADIAZOL-2-YL]-1H-INDAZOL-3-YL]-2-HYDROXYPHENYL]ACETAMIDE | 545.6 | 545.2 | 2.8 |

TABLE 1-continued

| Structure | Name | cacld M + H | obs. M + H | HPLC Retention Time min. |
|---|---|---|---|---|
| (314) | N-[5-[5-[5-[1-[(2-FLUORO-6-METHOXYPHENYL)METHYL]-3(R)-PIPERIDINYL]-1,3,4-OXADIAZOL-2-YL]-1H-INDAZOL-3-YL]-2-HYDROXYPHENYL] ACETAMIDE | 557.6 | 557.6 | 3.0 |
| (315) | N-[5-[5-[5-[1-[(2-FLUOROPHENYL)METHYL]-3(R)-PIPERIDINYL]-1,3,4-OXADIAZOL-2-YL]-1H-INDAZOL-3-YL]-2-HYDROXYPHENYL] ACETAMIDE | 527.6 | 527.2 | 2.8 |
| (316) | N-[2-HYDROXY-5-[5-[5-[1-(6-QUINOXALINYLMETHYL)-3(R)-PIPERIDINYL]-1,3,4-OXADIAZOL-2-YL]-1H-INDAZOL-3-YL]PHENYL]ACETAMIDE | 561.6 | 561.2 | 2.6 |
| (317) | 5-[5-[1-[(2-FLUOROPHENYL)METHYL]-3(R)-PIPERIDINYL]-1,3,4-OXADIAZOL-2-YL]-3-(2-METHYL-2H-INDAZOL-5-YL)-1H-INDAZOLE | 508.6 | 508.2 | 3.0 |

TABLE 1-continued
| Structure | Name | cacld M + H | obs. M + H | HPLC Retention Time min. |
|---|---|---|---|---|
| 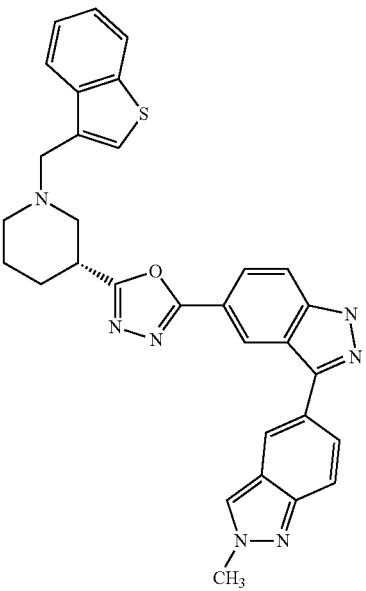 (318) | 5-[5-[1-(BENZO[b]THIEN-3-YLMETHYL)-3(R)-PIPERIDINYL]-1,3,4-OXADIAZOL-2-YL]-3-(2-METHYL-2H-INDAZOL-5-YL)-1H-INDAZOLE | 546.7 | 546.2 | 3.3 |
| 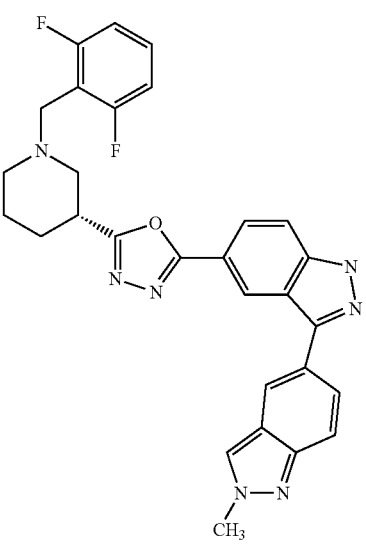 (319) | 5-[5-[1-[(2,6-DIFLUOROPHENYL)METHYL]-3(R)-PIPERIDINYL]-1,3,4-OXADIAZOL-2-YL]-3-(2-METHYL-2H-INDAZOL-5-YL)-1H-INDAZOLE | 543.6 | 543.2 | 2.9 |

| Structure | Name | cacld M + H | obs. M + H | HPLC Retention Time min. |
|---|---|---|---|---|
| 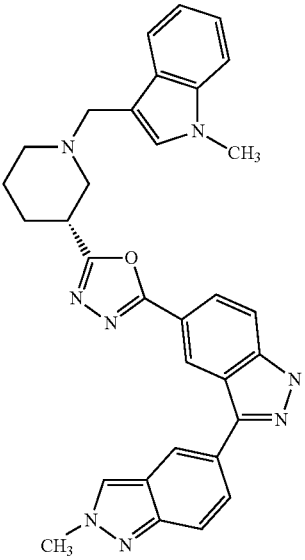 (320) | 3-(2-METHYL-2H-INDAZOL-5-YL)-5-[5-[1-[(1-METHYL-1H-INDOL-3-YL)METHYL]-3(R)-PIPERIDINYL]-1,3,4-OXADIAZOL-2-YL]-1H-INDAZOLE | 543.6 | 543.3 | 3.3 |
| 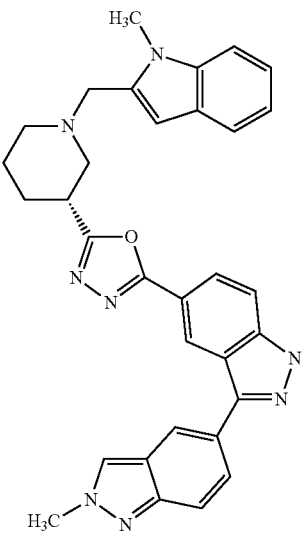 (321) | 3-(2-METHYL-2H-INDAZOL-5-YL)-5-[5-[1-[(1-METHYL-1H-INDOL-2-YL)METHYL]-3(R)-PIPERIDINYL]-1,3,4-OXADIAZOL-2-YL]-1H-INDAZOLE | 543.6 | 543.3 | 3.4 |

TABLE 1-continued

| Structure | Name | cacld M + H | obs. M + H | HPLC Retention Time min. |
|---|---|---|---|---|
| (322) | 5-[5-[1-[(2-FLUORO-6-METHOXYPHENYL)METHYL]-3(R)-PIPERIDINYL]-1,3,4-OXADIAZOL-2-YL]-3-(2-METHYL-2H-INDAZOL-5-YL)-1H-INDAZOLE | 538.6 | 538.2 | 3.1 |
| (323) | 5-[5-[1-(2-BENZOFURANYLMETHYL)-3(R)-PIPERIDINYL]-1,3,4-OXADIAZOL-2-YL]-3-(2-METHYL-2H-INDAZOL-5-YL)-1H-INDAZOLE | 530.6 | 530.2 | 3.2 |
| (324) | 5-[5-[1-(2,3-DIHYDRO-1H-INDEN-1-YL)-3(R)-PIPERIDINYL]-1,3,4-OXADIAZOL-2-YL]-3-(2-METHYL-2H-INDAZOL-5-YL)-1H-INDAZOLE | 516.6 | 516.2 | 3.2 |

TABLE 1-continued

| Structure | Name | cacld M + H | obs. M + H | HPLC Retention Time min. |
|---|---|---|---|---|
| (325) | 5-[5-[1-[(2-FLUOROPHENYL)METHYL]-3(R)-PIPERIDINYL]-1,3,4-OXADIAZOL-2-YL]-3-IMIDAZO[1,2-a]PYRIDIN-6-YL-1H-INDAZOLE | 494.5 | 494.2 | 2.3 |
| (326) | 5-[5-[1-(BENZO[b]THIEN-3-YLMETHYL)-3(R)-PIPERIDINYL]-1,3,4-OXADIAZOL-2-YL]-3-IMIDAZO[1,2-a]PYRIDIN-6-YL-1H-INDAZOLE | 532.6 | 532.2 | 2.6 |
| (327) | 5-[5-[1-[(2,6-DIFLUOROPHENYL)METHYL]-3(R)-PIPERIDINYL]-1,3,4-OXADIAZOL-2-YL]-3-IMIDAZO[1,2-a]PYRIDIN-6-YL-1H-INDAZOLE | 512.5 | 512.2 | 2.2 |

TABLE 1-continued

| Structure | Name | cacld M + H | obs. M + H | HPLC Retention Time min. |
|---|---|---|---|---|
| (328) | 3-IMIDAZO[1,2-a]PYRIDIN-6-YL-5-[5-[1-[(1-METHYL-1H-INDOL-3-YL)METHYL]-3(R)-PIPERIDINYL]-1,3,4-OXADIAZOL-2-YL]-1H-INDAZOLE | 529.6 | 529.2 | 2.6 |
| (329) | 3-IMIDAZO[1,2-a]PYRIDIN-6-YL-5-[5-[1-[(1-METHYL-1H-INDOL-2-YL)METHYL]-3(R)-PIPERIDINYL]-1,3,4-OXADIAZOL-2-YL]-1H-INDAZOLE | 529.6 | 529.2 | 2.7 |
| (330) | 5-[5-[1-[(2-FLUORO-6-METHOXYPHENYL)METHYL]-3(R)-PIPERIDINYL]-1,3,4-OXADIAZOL-2-YL]-3-IMIDAZO[1,2-a]PYRIDIN-6-YL-1H-INDAZOLE | 524.6 | 524.2 | 2.4 |

TABLE 1-continued

| Structure | Name | cacld M + H | obs. M + H | HPLC Retention Time min. |
|---|---|---|---|---|
| (331) | 5-[5-[1-(2-BENZOFURANYLMETHYL)-3(R)-PIPERIDINYL]-1,3,4-OXADIAZOL-2-YL]-3-IMIDAZO[1,2-a]PYRIDIN-6-YL-1H-INDAZOLE | 516.6 | 516.2 | 2.6 |
| (332) | 5-[5-[1-[(2-FLUOROPHENYL)METHYL]-3(R)-PIPERIDINYL]-1,3,4-OXADIAZOL-2-YL]-3-(2-METHYL-4-PYRIDINYL)-1H-INDAZOLE | 469.5 | 469.2 | 2.3 |

TABLE 1-continued
| Structure | Name | cacld M + H | obs. M + H | HPLC Retention Time min. |
|---|---|---|---|---|
| 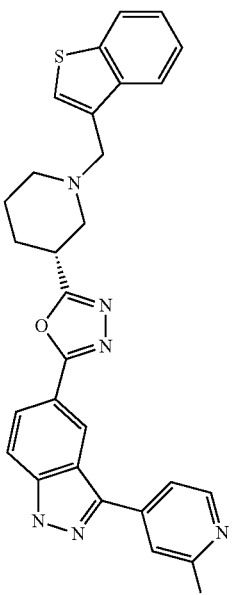<br>(333) | 5-[5-[1-(BENZO[b]THIEN-3-YLMETHYL)-3(R)-PIPERIDINYL]-1,3,4-OXADIAZOL-2-YL]-3-(2-METHYL-4-PYRIDINYL)-1H-INDAZOLE | 507.6 | 507.2 | 2.7 |
| 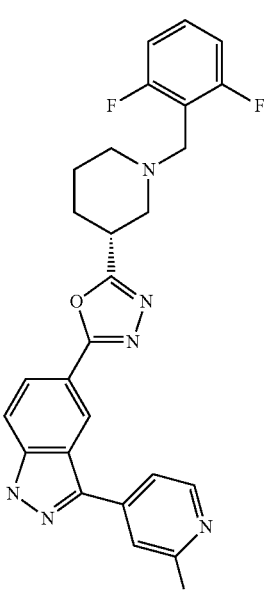<br>(334) | 5-[5-[1-[(2,6-DIFLUOROPHENYL)METHYL]-3(R)-PIPERIDINYL]-1,3,4-OXADIAZOL-2-YL]-3-(2-METHYL-4-PYRIDINYL)-1H-INDAZOLE | 487.5 | 487.2 | 2.3 |

TABLE 1-continued
| Structure | Name | cacld M + H | obs. M + H | HPLC Retention Time min. |
|---|---|---|---|---|
| 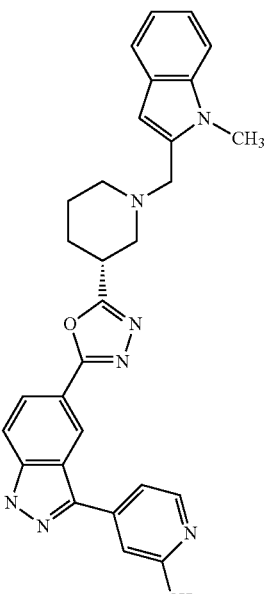 (335) | 5-[5-[1-[(1-METHYL-1H-INDOL-2-YL)METHYL]-3(R)-PIPERIDINYL]-1,3,4-OXADIAZOL-2-YL]-3-(2-METHYL-4-PYRIDINYL)-1H-INDAZOLE | 504.6 | 504.2 | 2.8 |
| 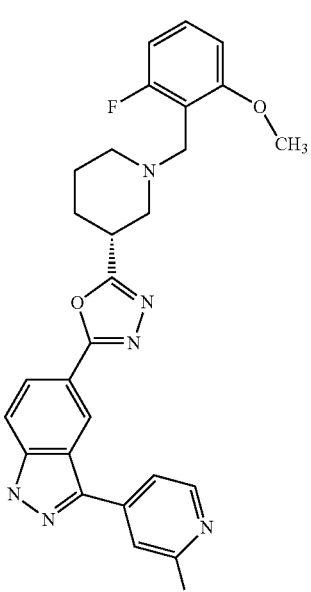 (336) | 5-[5-[1-[(2-FLUORO-6-METHOXYPHENYL)METHYL]-3(R)-PIPERIDINYL]-1,3,4-OXADIAZOL-2-YL]-3-(2-METHYL-4-PYRIDINYL)-1H-INDAZOLE | 499.6 | 499.2 | 2.5 |

TABLE 1-continued
| Structure | Name | cacld M + H | obs. M + H | HPLC Retention Time min. |
|---|---|---|---|---|
| 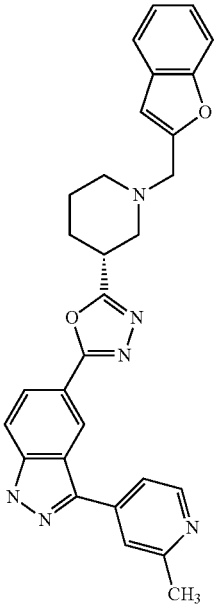 (337) | 5-[5-[1-(2-BENZOFURANYLMETHYL)-3(R)-PIPERIDINYL]-1,3,4-OXADIAZOL-2-YL]-3-(2-METHYL-4-PYRIDINYL)-1H-INDAZOLE | 491.6 | 491.2 | 2.6 |
| 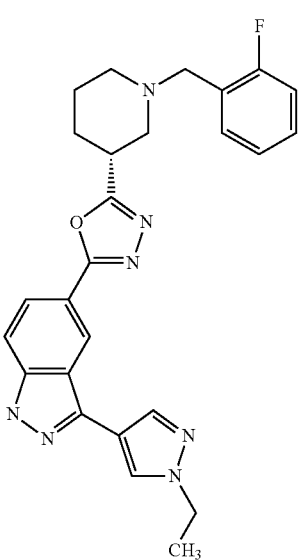 (338) | 3-(1-ETHYL-1H-PYRAZOL-4-YL)-5-[5-[1-[(2-FLUOROPHENYL)METHYL]-3(R)-PIPERIDINYL]-1,3,4-OXADIAZOL-2-YL]-1H-INDAZOLE | 472.5 | 472.2 | 3.0 |

TABLE 1-continued

| Structure | Name | cacld M + H | obs. M + H | HPLC Retention Time min. |
|---|---|---|---|---|
| (339) | 5-[5-[1-(BENZO[b]THIEN-3-YLMETHYL)-3(R)-PIPERIDINYL]-1,3,4-OXADIAZOL-2-YL]-3-(1-ETHYL-1H-PYRAZOL-4-YL)-1H-INDAZOLE | 510.6 | 510.2 | 3.4 |
| (340) | 5-[5-[1-[(2,6-DIFLUOROPHENYL)METHYL]-3(R)-PIPERIDINYL]-1,3,4-OXADIAZOL-2-YL]-3-(1-ETHYL-1H-PYRAZOL-4-YL)-1H-INDAZOLE | 490.5 | 490.2 | 3.0 |

TABLE 1-continued
| Structure | Name | cacld M + H | obs. M + H | HPLC Retention Time min. |
|---|---|---|---|---|
| 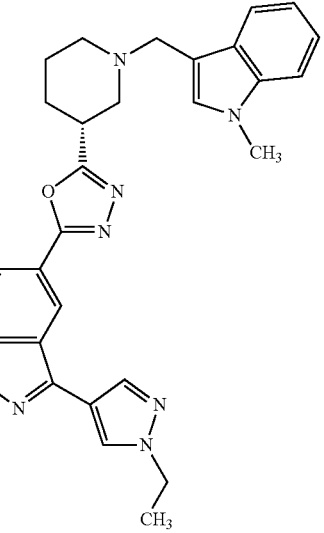 (341) | 3-(1-ETHYL-1H-PYRAZOL-4-YL)-5-[5-[1-[(1-METHYL-1H-INDOL-3-YL)METHYL]-3(R)-PIPERIDINYL]-1,3,4-OXADIAZOL-2-YL]-1H-INDAZOLE | 507.6 | 507.3 | 3.8 |
| 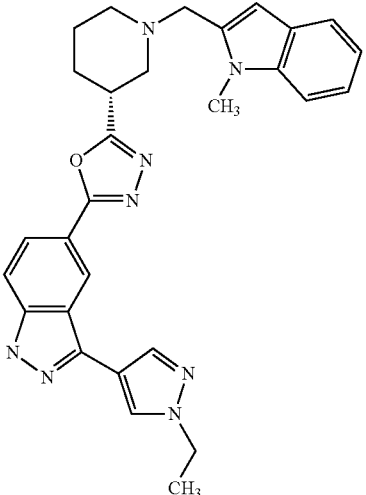 (342) | 3-(1-ETHYL-1H-PYRAZOL-4-YL)-5-[5-[1-[(1-METHYL-1H-INDOL-2-YL)METHYL]-3(R)-PIPERIDINYL]-1,3,4-OXADIAZOL-2-YL]-1H-INDAZOLE | 507.6 | 507.3 | 3.4 |

TABLE 1-continued
| Structure | Name | cacld M + H | obs. M + H | HPLC Retention Time min. |
|---|---|---|---|---|
| 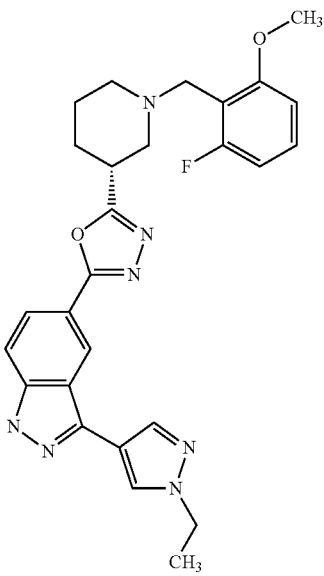 (343) | 3-(1-ETHYL-1H-PYRAZOL-4-YL)-5-[5-[1-[(2-FLUORO-6-METHOXYPHENYL)METHYL]-3(R)-PIPERIDINYL]-1,3,4-OXADIAZOL-2-YL]-1H-INDAZOLE | 502.6 | 502.2 | 3.2 |
| 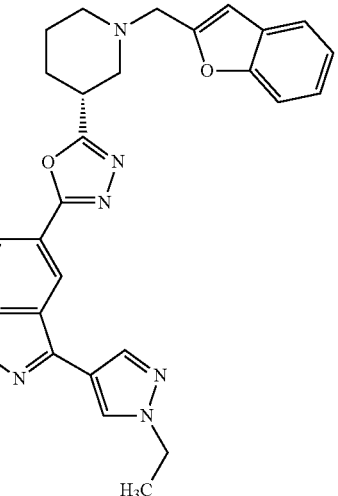 (344) | 5-[5-[1-(2-BENZOFURANYLMETHYL)-3(R)-PIPERIDINYL]-1,3,4-OXADIAZOL-2-YL]-3-(1-ETHYL-1H-PYRAZOL-4-YL)-1H-INDAZOLE | 494.6 | 494.2 | 3.3 |

TABLE 1-continued
| Structure | Name | cacld M + H | obs. M + H | HPLC Retention Time min. |
|---|---|---|---|---|
| 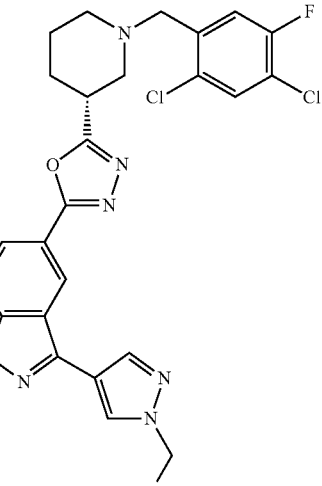 (345) | 5-[5-[1-[(2,4-DICHLORO-5-FLUOROPHENYL)METHYL]-3(R)-PIPERIDINYL]-1,3,4-OXADIAZOL-2-YL]-3-(1-ETHYL-1H-PYRAZOL-4-YL)-1H-INDAZOLE | 541.4 | 541.1 | 3.6 |
| 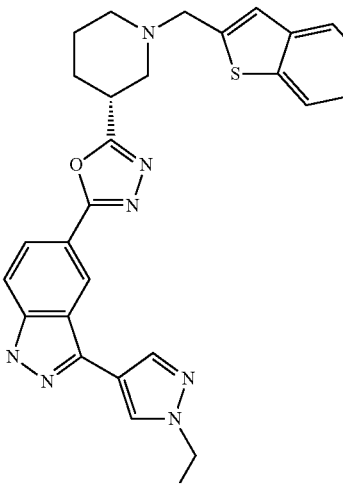 (346) | 5-[5-[1-(BENZO[b]THIEN-2-YLMETHYL)-3(R)-PIPERIDINYL]-1,3,4-OXADIAZOL-2-YL]-3-(1-ETHYL-1H-PYRAZOL-4-YL)-1H-INDAZOLE | 510.6 | 510.2 | 3.4 |
| 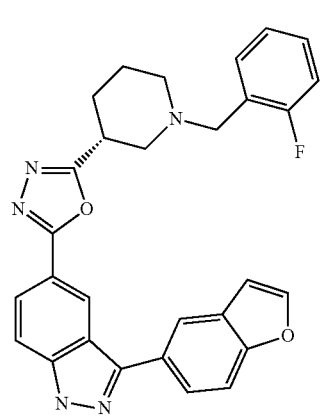 (347) | 3-(5-BENZOFURANYL)-5-[5-[1-[(2-FLUOROPHENYL)METHYL]-3(R)-PIPERIDINYL]-1,3,4-OXADIAZOL-2-YL]-1H-INDAZOLE | 494.5 | 494.2 | 3.7 |

TABLE 1-continued

| Structure | Name | cacld M + H | obs. M + H | HPLC Retention Time min. |
|---|---|---|---|---|
| (348) | 3-(5-BENZOFURANYL)-5-[5-[1-[(2,6-DIFLUOROPHENYL)METHYL]-3(R)-PIPERIDINYL]-1,3,4-OXADIAZOL-2-YL]-1H-INDAZOLE | 512.5 | 512.2 | 3.7 |
| (349) | 3-(5-BENZOFURANYL)-5-[5-[1-[(2-FLUORO-6-METHOXYPHENYL)METHYL]-3(R)-PIPERIDINYL]-1,3,4-OXADIAZOL-2-YL]-1H-INDAZOLE | 524.6 | 524.2 | 3.9 |
| (350) | 3-(5-BENZOFURANYL)-5-[5-[1-(2-BENZOFURANYLMETHYL)-3(R)-PIPERIDINYL]-1,3,4-OXADIAZOL-2-YL]-1H-INDAZOLE | 516.6 | 516.2 | 4.0 |

TABLE 1-continued

| Structure | Name | cacld M + H | obs. M + H | HPLC Retention Time min. |
|---|---|---|---|---|
| (351) | 3-(5-BENZOFURANYL)-5-[5-[1-(4-PYRIMIDINYLMETHYL)-3(R)-PIPERIDINYL]-1,3,4-OXADIAZOL-2-YL]-1H-INDAZOLE | 478.5 | 478.2 | 3.2 |
| (352) | 3-(5-BENZOFURANYL)-5-[5-[1-(CYCLOHEXYLMETHYL)-3(R)-PIPERIDINYL]-1,3,4-OXADIAZOL-2-YL]-1H-INDAZOLE | 482.6 | 482.2 | 4.0 |
| (353) | 3-(2-CHLORO-4-PYRIDINYL)-5-[5-[1-[(2-FLUOROPHENYL)METHYL]-3(R)-PIPERIDINYL]-1,3,4-OXADIAZOL-2-YL]-1H-INDAZOLE | 490.0 | 490.2 | 3.4 |

TABLE 1-continued
| Structure | Name | cacld M + H | obs. M + H | HPLC Retention Time min. |
|---|---|---|---|---|
| 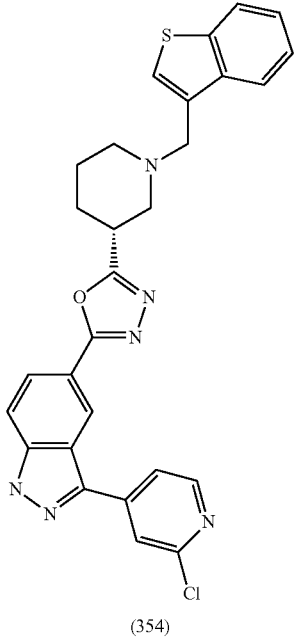 [SMILES: Clc1cc(-c2n[nH]c3ccc(-c4nnc([C@@H]5CCCN(Cc6csc7ccccc67)C5)o4)cc23)ccn1] (354) | 5-[5-[1-(BENZO[b]THIEN-3-YLMETHYL)-3(R)-PIPERIDINYL]-1,3,4-OXADIAZOL-2-YL]-3-(2-CHLORO-4-PYRIDINYL)-1H-INDAZOLE | 528.1 | 528.1 | 3.7 |
| 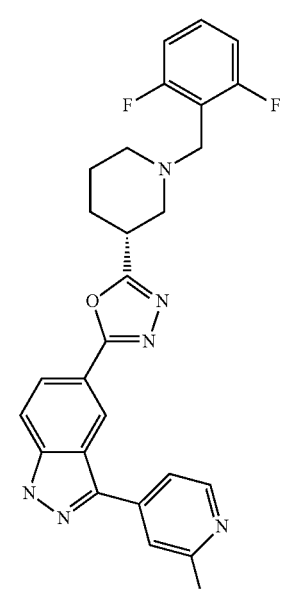 (355) | 3-(2-CHLORO-4-PYRIDINYL)-5-[5-[1-[(2,6-DIFLUOROPHENYL)METHYL]-3(R)-PIPERIDINYL]-1,3,4-OXADIAZOL-2-YL]-1H-INDAZOLE | 507.9 | 507.1 | 3.3 |

TABLE 1-continued
| Structure | Name | cacld M + H | obs. M + H | HPLC Retention Time min. |
|---|---|---|---|---|
| 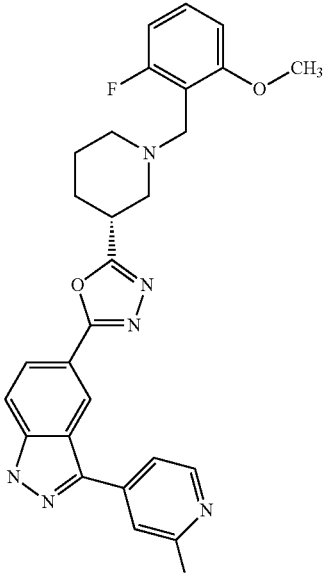 (356) | 3-(2-CHLORO-4-PYRIDINYL)-5-[5-[1-[(2-FLUORO-6-METHOXYPHENYL)METHYL]-3(R)-PIPERIDINYL]-1,3,4-OXADIAZOL-2-YL]-1H-INDAZOLE | 520.0 | 520.2 | 3.5 |
| 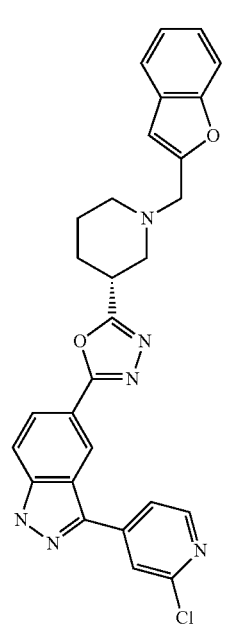 (357) | 5-[5-[1-(2-BENZOFURANYLMETHYL)-3(R)-PIPERIDINYL]-1,3,4-OXADIAZOL-2-YL]-3-(2-CHLORO-4-PYRIDINYL)-1H-INDAZOLE | 512.0 | 511.1 | 3.6 |

| Structure | Name | cacld M + H | obs. M + H | HPLC Retention Time min. |
|---|---|---|---|---|
| 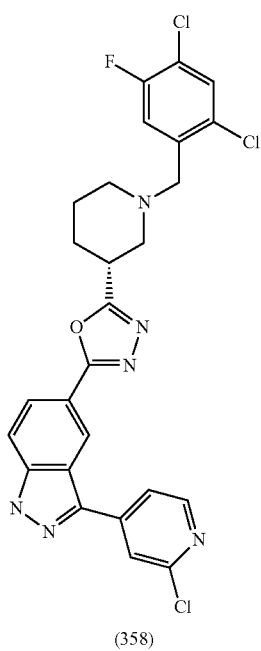 [SMILES: Fc1cc(CN2CCC[C@@H](c3nnc(-c4ccc5[nH]nc(-c6ccnc(Cl)c6)c5c4)o3)C2)c(Cl)cc1Cl] (358) | 3-(2-CHLORO-4-PYRIDINYL)-5-[5-[1-[(2,4-DICHLORO-5-FLUOROPHENYL)METHYL]-3(R)-PIPERIDINYL]-1,3,4-OXADIAZOL-2-YL]-1H-INDAZOLE | 558.8 | 557.1 | 4.0 |
| 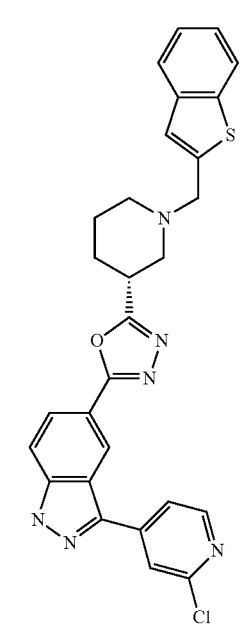 (359) | 5-[5-[1-(BENZO[b]THIEN-2-YLMETHYL)-3(R)-PIPERIDINYL]-1,3,4-OXADIAZOL-2-YL]-3-(2-CHLORO-4-PYRIDINYL)-1H-INDAZOLE | 528.1 | 528.1 | 3.8 |

TABLE 1-continued
| Structure | Name | cacld M + H | obs. M + H | HPLC Retention Time min. |
|---|---|---|---|---|
| 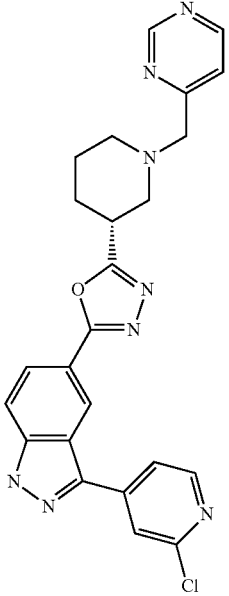 (360) | 3-(2-CHLORO-4-PYRIDINYL)-5-[5-[1-(4-PYRIMIDINYLMETHYL)-3(R)-PIPERIDINYL]-1,3,4-OXADIAZOL-2-YL]-1H-INDAZOLE | 473.9 | 473.2 | 2.9 |
| 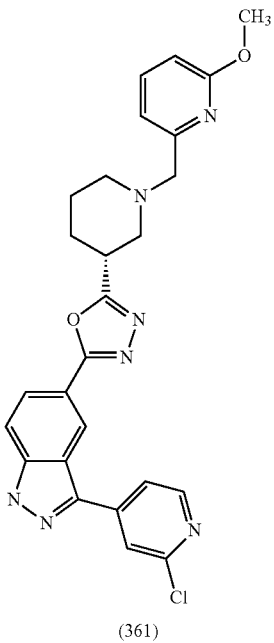 [SMILES: COc1cccc(CN2CCC[C@@H](c3nnc(-c4ccc5[nH]nc(-c6ccnc(Cl)c6)c5c4)o3)C2)n1] (361) | 3-(2-CHLORO-4-PYRIDINYL)-5-[5-[1-[(6-METHOXY-2-PYRIDINYL)METHYL]-3(R)-PIPERIDINYL]-1,3,4-OXADIAZOL-2-YL]-1H-INDAZOLE | 503.0 | 502.2 | 3.4 |

TABLE 1-continued

| Structure | Name | cacld M + H | obs. M + H | HPLC Retention Time min. |
|---|---|---|---|---|
| (362) | 3-(2-CHLORO-4-PYRIDINYL)-5-[5-[1-(CYCLOHEXYLMETHYL)-3(R)-PIPERIDINYL]-1,3,4-OXADIAZOL-2-YL]-1H-INDAZOLE | 478.0 | 477.2 | 3.7 |
| (363) | 5-[5-[1-[(2-FLUORO-6-METHOXYPHENYL)METHYL]-5-METHOXY-3(R)-PIPERIDINYL]-1,3,4-OXADIAZOL-2-YL]-3-(1-METHYL-1H-PYRAZOL-4-YL)-1H-INDAZOLE | 518.6 | 518.2 | 3.1 |
| (364) | 5-[5-[1-[(2-FLUORO-6-METHOXYPHENYL)METHYL]-5-METHOXY-3(R)-PIPERIDINYL]-1,3,4-OXADIAZOL-2-YL]-3-IMIDAZO[1,2-a]PYRIDIN-6-YL-1H-INDAZOLE | 554.6 | 554.2 | 2.6 |

TABLE 1-continued

| Structure | Name | cacld M + H | obs. M + H | HPLC Retention Time min. |
|---|---|---|---|---|
| (365) | 5-[5-[1-[(2-FLUORO-6-METHOXYPHENYL)METHYL]-5-METHOXY-3(R)-PIPERIDINYL]-1,3,4-OXADIAZOL-2-YL]-3-(2-METHYL-2H-INDAZOL-5-YL)-1H-INDAZOLE | 568.6 | 568.2 | 3.3 |
| (366) | ENDO/EXO-8-[(2-FLUOROPHENYL)METHYL]-2-[5-[3-(2-METHYL-4-PYRIDINYL)-1H-INDAZOL-5-YL]-1,3,4-OXADIAZOL-2-YL]-8-AZABICYCLO[3.2.1]OCTANE | 568.6 | 495.0 | 1.7 |
| (367) | 5-[3-[1-[(2,6-DIFLUOROPHENYL)METHYL]-3-PIPERIDINYL]-1H-PYRAZOL-1-YL]-3-(4-PYRIDINYL)-1H-INDAZOLE | 471.5 | 471.2 | 1.7 |
| (368) | 5-[3-[1-[(2-FLUORO-6-METHOXYPHENYL)METHYL]-3-PIPERIDINYL]-1H-PYRAZOL-1-YL]-3-(4-PYRIDINYL)-1H-INDAZOLE | 483.6 | 483.2 | 1.7 |

TABLE 1-continued
| Structure | Name | cacld M + H | obs. M + H | HPLC Retention Time min. |
|---|---|---|---|---|
| 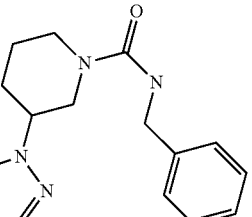 (369) | N-(PHENYLMETHYL)-3-[4-[3-(4-PYRIDINYL)-1H-INDAZOL-5-YL]-1H-PYRAZOL-1-YL]-1-PIPERIDINECARBOXAMIDE | 478.6 | 478.2 | 1.8 |
| 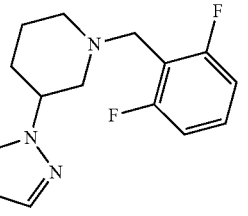 (370) | 5-[1-[1-[(2,6-DIFLUOROPHENYL)METHYL]-3-PIPERIDINYL]-1H-PYRAZOL-1-YL]-3-(4-PYRIDINYL)-1H-INDAZOLE | 471.5 | 471.2 | 1.6 |
| 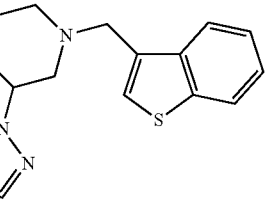 (371) | 5-[1-[1-(BENZO[b]THIEN-3-YLMETHYL)-3-PIPERIDINYL]-1H-PYRAZOL-4-YL]-3-(4-PYRIDINYL)-1H-INDAZOLE | 491.6 | 491.2 | 1.8 |

TABLE 1-continued

| Structure | Name | cacld M + H | obs. M + H | HPLC Retention Time min. |
|---|---|---|---|---|
| (372) | 5-[1-[1-[(2-FLUORO-6-METHOXYPHENYL)METHYL]-3-PIPERIDINYL]-1H-PYRAZOL-4-YL]-3-(4-PYRIDINYL)-1H-INDAZOLE | 483.6 | 483.2 | 1.7 |
| (373) | 5-[1-[1-[(2-FLUORO-6-METHOXYPHENYL)METHYL]-3(R)-PIPERIDINYL]-1H-PYRAZOL-4-YL]-3-(4-PYRIDINYL)-1H-INDAZOLE | 483.6 | 483.2 | 1.7 |
| (374) | 5-[1-[1-[[2-FLUORO-6-(2-METHOXYETHOXY)PHENYL]METHYL]-3(R)-PIPERIDINYL]-1H-PYRAZOL-4-YL]-3-(4-PYRIDINYL)-1H-INDAZOLE | 527.6 | 527.2 | 1.6 |

TABLE 1-continued

| Structure | Name | cacld M + H | obs. M + H | HPLC Retention Time min. |
|---|---|---|---|---|
| (375) | 5-[1-[1-[(2,6-DIFLUOROPHENYL)METHYL]-3(R)-PIPERIDINYL]-1H-PYRAZOL-4-YL]-3-(4-PYRIDINYL)-1H-INDAZOLE | 471.5 | 471.2 | 1.7 |
| (376) | 5-[1-[1-[[2-FLUORO-6-(1-METHYLETHOXY)PHENYL]METHYL]-3(R)-PIPERIDINYL]-1H-PYRAZOL-4-YL]-3-(4-PYRIDINYL)-1H-INDAZOLE | 511.6 | 511.2 | 1.8 |
| (377) | 5-[1-[1-[(2-FLUORO-4-METHOXYPHENYL)METHYL]-3(R)-PIPERIDINYL]-1H-PYRAZOL-4-YL]-3-(4-PYRIDINYL)-1H-INDAZOLE | 483.6 | 483.2 | 1.7 |

TABLE 1-continued

| Structure | Name | cacld M + H | obs. M + H | HPLC Retention Time min. |
|---|---|---|---|---|
| 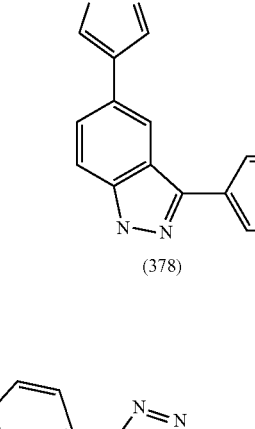 (378) | 5-[1-[1-[[2-FLUORO-6-(3-METHOXYPROPOXY)PHENYL]METHYL]-3(R)-PIPERIDINYL]-1H-PYRAZOL-4-YL]-3-(4-PYRIDINYL)-1H-INDAZOLE | 541.6 | 541.3 | 1.7 |
| 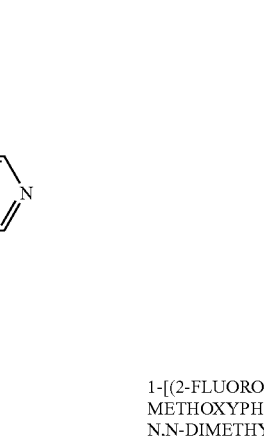 (379) | 1-[(2-FLUORO-6-METHOXYPHENYL)METHYL]-N,N-DIMETHYL-5(R)-[1-[3-(4-PYRIDINYL)-1H-INDAZOL-5-YL]-1H-1,2,3-TRIAZOL-4-YL]-2(S)-PIPERIDINECARBOXAMIDE | | 555 | 1.7 |
|  (380) | N,N-DIETHYL-1-[(2-FLUORO-6-METHOXYPHENYL)-METHYL]-5(R)-[1-[3-(4-PYRIDINYL)-1H-INDAZOL-5-YL]-1H-1,2,3-TRIAZOL-4-YL]-2(S)-PIPERIDINE-CARBOXAMIDE | | 583 | 1.8 |

TABLE 1-continued

| Structure | Name | cacld M + H | obs. M + H | HPLC Retention Time min. |
|---|---|---|---|---|
| (381) | 3,3-DIFLUORO-1-[[1-[(2-FLUORO-6-METHOXY-PHENYL)METHYL]-5(R)-[1-[3-(4-PYRIDINYL)-1H-INDAZOL-5-YL]-1H-1,2,3-TRIAZOL-4-YL]-2(S)-PIPERIDINYL]CARBONYL]AZETIDINE | | 603 | 1.7 |
| (382) | 1-[(2,6-DIFLUOROPHENYL)-METHYL]-N,N-DIMETHYL-5(R)-[1-[3-(4-PYRIDINYL)-1H-INDAZOL-5-YL]-1H-1,2,3-TRIAZOL-4-YL]-2(S)-PIPERIDINECARBOXAMIDE | | 543 | 1.6 |
| (383) | 1-[[1-[(2,6-DIFLUOROPHENYL)-METHYL]-5(R)-[1-[3-(4-PYRIDINYL)-1H-INDAZOL-5-YL]-1H-1,2,3-TRIAZOL-4-YL]-2(S)-PIPERIDINYL]-CARBONYL]-3,3-DIFLUOROAZETIDINE | | 590.9 | 1.7 |
| (384) | 1-[(2,6-DIFLUOROPHENYL)METHYL]-N,N-DIETHYL-5(R)-[1-[3-(4-PYRIDINYL)-1H-INDAZOL-5-YL]-1H-1,2,3-TRIAZOL-4-YL]-2(S)-PIPERIDINECARBOXAMIDE | | 571 | 1.7 |

Assays
Coupled ERK2 Assay:

Activity of compounds against inactive ERK2 can be tested in a coupled MEK1/ERK2 IMAP assay as follows: Compounds can be diluted to 25× final test concentration in 100% DMSO. 14 µl of kinase buffer (10 mM Tris.HCl pH 7.2, 10 mM $MgCl_2$, 0.01% Tween-20, 1 mM DTT) containing 0.4 ng unphosphorylated Mouse ERK2 protein can be added to each well of a black 384-well assay plate. 1 µl of 25× compound can be added to each well and incubated at room temperature for 30 minutes to allow an opportunity for the compound to bind to the inactive enzyme. DMSO concentration during initial incubation is 6.7%. ERK2 activity can be determined to be insensitive to DMSO concentrations up to 20%. ERK2 can then be activated and it's kinase activity can be measured by the addition of 10 µl kinase buffer with the following components (final concentration per reaction): 2 ng active (phosphorylated) human MEK1 protein and 4 µM (total) ERK2 IMAP substrate peptides (3.9 µM unlabeled IPT-TPITTTYFFFK-$CONH_2$ and 100 nM IPTTPITTTYFFFK (5-carboxyfluorescein)-$CONH_2$) and 30 µM ATP. DMSO concentration during ERK activation can be 4%. After one hour, reactions can be terminated by addition of 60 µl IMAP detections beads in binding buffer (Molecular Devices). Binding can be allowed to equilibrate for 30 minutes before reading the plate on an LJL Analyst Fluorescence Polarization plate reader. Compound inhibition can be calculated relative to DMSO and fully inhibited standards. Active compounds can be reconfirmed in an independent assay.

Active ERK2 Assay:

Activated ERK2 activity was also determined in the IMAP assay format using the procedure outlined above. 1 µl of 25× compound was added to 14 µl of kinase buffer containing 0.25 ng fully phosphorylated, active Mouse ERK2 protein. Following a 30 minute incubation, the reactions were initiated by addition of 10 µl of kinase buffer containing 1 µM ERK2 IMAP substrate peptide (0.9 µM unlabeled IPTTPITTTY-FFFK-$CONH_2$ and 100 nM IPTTPITTTYFFFK(5-carboxyfluorescein)-$CONH_2$) and 30 µM ATP. Reactions proceeded for 30 minutes before termination by addition of 60 µl IMAP detection beads in binding buffer. Plates were read as above after 30 minute binding equilibration. Active compounds were reconfirmed in an independent assay.

Soft Agar Assay:

Anchorage-independent growth is a characteristic of tumorigenic cell lines. Human tumor cells can be suspended in growth medium containing 0.3% agarose and an indicated concentration of a farnesyl transferase inhibitor. The solution can be overlayed onto growth medium solidified with 0.6% agarose containing the same concentration of ERK1 and ERK2 inhibitor as the top layer. After the top layer is solidified, plates can be incubated for 10-16 days at 37° C. under 5% $CO_2$ to allow colony outgrowth. After incubation, the colonies can be stained by overlaying the agar with a solution of MTT (3-[4,5-dimethyl-thiazol-2-yl]-2,5-diphenyltetrazolium bromide, Thiazolyl blue) (1 mg/mL in PBS). Colonies can be counted and the $IC_{50}$'s can be determined.

Plasma Sample and Standard Curve Preparation

A set of 12 rat plasma samples can be generated for each NCE (i.e. 6 timepoints and n=2 rats). These 12 samples can be pooled across the two rats at each timepoint to provide 6 pooled samples (one sample per time point) for each NCE. The pooled samples can be assayed as cassettes of six (36 samples total) to provide data on the six compounds. The 50-µL aliquots of the 36 plasma samples can be placed into individual wells of a 96-well plate. An additional compound (often a structural analog of the test compounds) can be selected as the internal standard. A mini-calibration curve can be prepared (three points plus a zero) for each compound assayed. Drug-free rat plasma can be measured into 1-mL aliquots and each aliquot can be spiked with known concentrations of the compounds to generate standards of the desired concentrations. The concentrations of the standards can be chosen to bracket the expected concentration of the pooled samples based on historical data from previous studies on other compounds. For this work, the standards can be set to contain concentrations of 25, 250 and 2500 ng NCE/mL plasma. The plasma standards can be precipitated in duplicate along with the samples. Protein precipitation may occur after addition of 150 µl, of acetonitrile containing the internal standard at a concentration of 1 ng/mL into each sample well using the Tomtec Quadra 96 system. The precipitated samples and standards can be vortexed and centrifuged in the 96-well plate. Approximately 50-100 µL of the supernatant can be removed and placed into a fresh 96-well plate using the Tomtec Quadra 96 system. A volume of 5-10 µl, of the supernatant can be used for analysis by HPLC-MS/MS. The mini-standard curve can be run in duplicate, once before and once after the samples. Thus, a total of 14 study samples plus standards can be analyzed per compound. In addition, solvent blanks can be injected before and after each set of 14 and after the highest calibration standard for each compound; therefore, a total of 103 injections can be made into each HPLC system for each set of six compounds. Multiple solvent blank injections can be be made from a single well. Twelve solvent blank wells can be designated in each 96-well plate. Thus, one batch (cassette) of six NCEs can be prepared and assayed using one 96-well plate format.

HPLC-MS/MS Analysis

All the compounds were analyzed using selected reaction monitoring (SRM) methods with LC/MS/MS instruments. Once the method development had been completed, the assay was quickly set up using a standard injection sequence template for the CARRS assay.

Compounds (200) to (378) had an AERK2 IC50 in the range of 0.3 to >1000 nM.

Compounds (200)-(214), (249), (251), (260)-(267), (276)-(280), (306), (310)-(312), (314), (322), (33) and (336) had an AERK2 IC50 in the range of 0.3 to 10.4 nM.

Compounds (247), (248), (253), (254), (255), (256), (258), (259), (298), (299), (300), (301), (302), (303), (304), (305), (307), (309), (316), (321), (328), (329), (339), (341), (342), (345), (347), (348), (349), (350), (351), (352), (353), (354), (357), (358), (359), (360), (361), (362), (367) and (368) had an AERK2 IC50 in the range of 504.3 to >1000 nM.

Compounds (253)-(255), (258), (259), (299)-(305), (307), (309), (321), (328), (329), (339), (341), (342), (345), (34), (348), (350), (351), (352), (354), (357)-(362), (367) and (368) had an AERK2 IC50 of >1000 nM.

While the present invention has been described in conjunction with the specific embodiments set forth above, many alternatives, modifications and variations thereof will be apparent to those of ordinary skill in the art. All such alternatives, modifications and variations are intended to fall within the spirit and scope of the present invention.

What is claimed is:
1. A compound of formula (1):
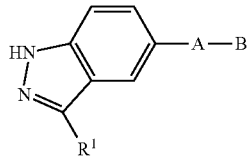
(1)
or a pharmaceutically acceptable salt thereof, wherein:
$R^1$ is selected from the group consisting of
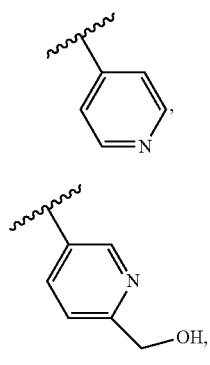
(93),
(94)
(95)
(96)
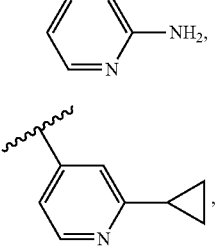
(97),
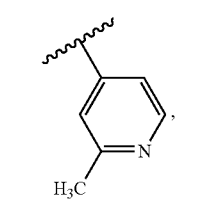
(98),
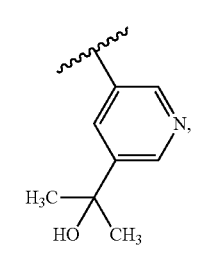
(99)
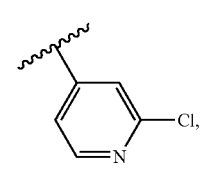
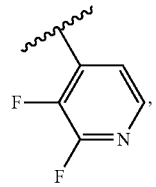
(100),
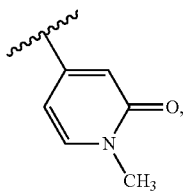
(101),
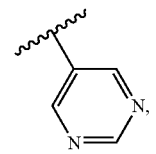
(102),
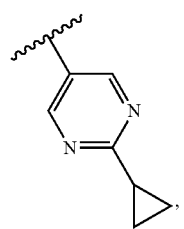
(103),
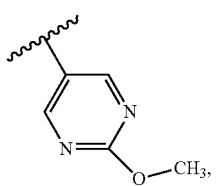
(104),
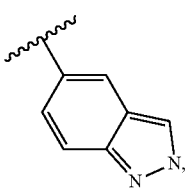
(105),
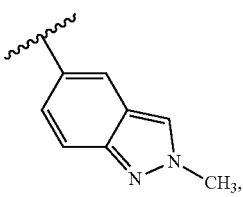
(106),
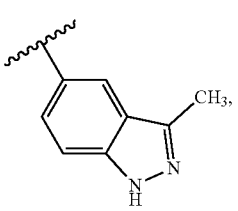
(107)

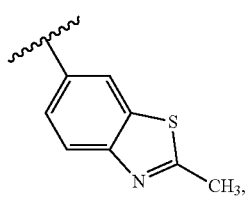 (108)
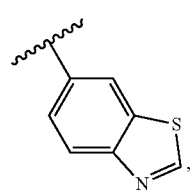 (109)
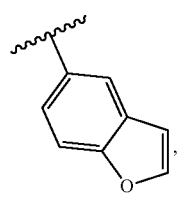 (110)
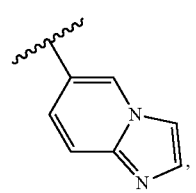 (111)
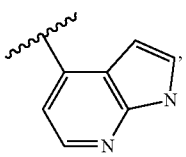 (112)
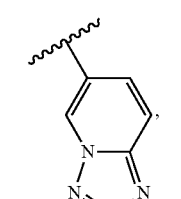 (113)
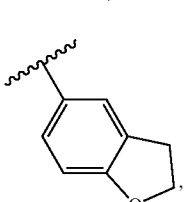 (114)
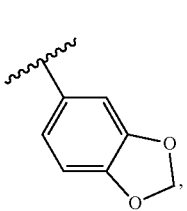 (115)
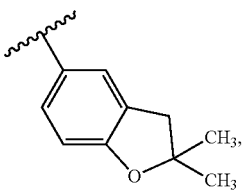 (116)
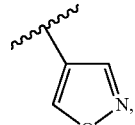 (117)
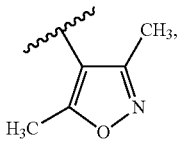 (118)
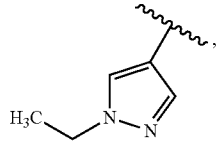 (119)
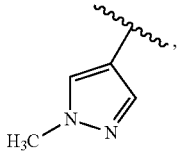 (120)
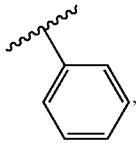 (121)
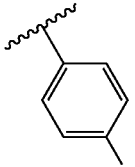 (122)
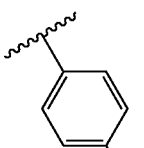 (123)
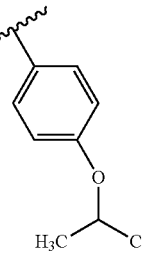 (124)

-continued
(125) 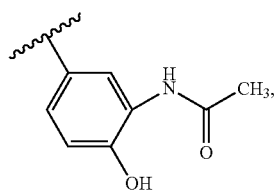
(126) 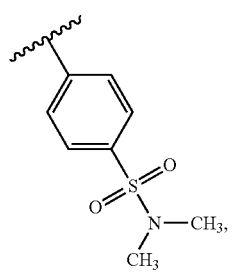
(127) 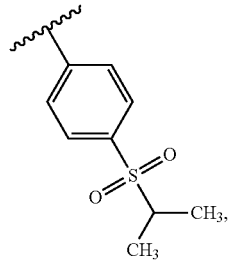
(128) 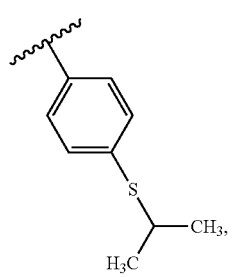
(129) 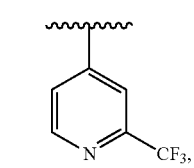
(130) 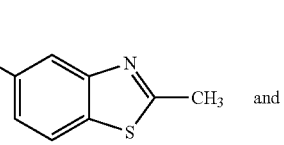 and
(131) 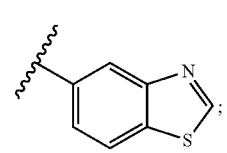;
A is selected from the group consisting of triazolyl, oxadiazolyl, thiadiazolyl, tetrazolyl, pyrazolyl, imidazolyl, and imidazolidinyl;
B is selected from the group consisting of
(27) 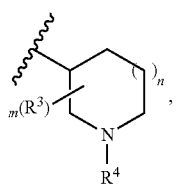
(28) 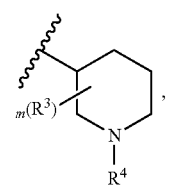
(29) 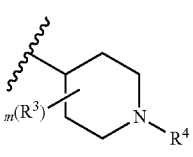
(30) 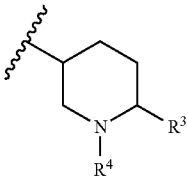
(31) 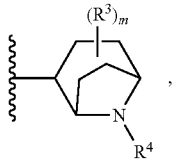
(32) 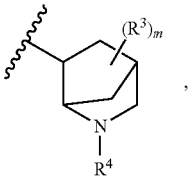
(33) 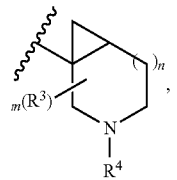
(34) 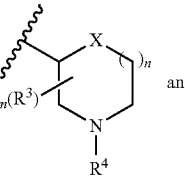 and -continued

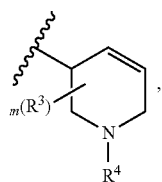
(34.1)

wherein R³ is selected from the group consisting of: (a) alkyl, (b) aryl, (c) —C(O)—(C₁-C₆)alkyl, (d) —SR¹⁸, (e) —C(O)—(C₃-C₆)cycloalkyl, (f) —N(R¹⁸)₂, (g) —NH—C(O)—R¹⁸, (h) —NH—S(O)₂R¹⁸, (i) —C(O)—N(R²⁰)₂ and (j) =O, m is 0 to 3, and n is 1 to 3, and X is selected from the group consisting of —NR⁵—, O, S, SO, SO₂ and C;

R⁴ is selected from the group consisting of: (1) —(C₁-C₂)alkylene-aryl, (2) —C(O)-aryl, (3) -(C₁-C₂)alkylene-heteroaryl, (4) —(C₁-C₂)alkylene-(fused heteroarylaryl), (5) —(C₁-C₂)alkylene-C(O)-heterocycloalkyl, (6) fused (arylcycloalkyl), (7) —(C₁-C₂)alkylene-cycloalkyl, (8) —(C₁-C₂)alkylene-(bridgedheterocycloalkyl), (9) —C(O)—(C₁-C₂)alkylene-aryl, and (10) —C(O)—(C₁-C₂)alkylene-aryl; and wherein said R⁴ groups are optionally substituted with 1 to 5 substitutents independently selected from the group consisting of: (a) alkyl, (b) alkoxy, (c) halo, (d) —O-alkylene-O-alkyl, (e) —O-alkylene-CN, (f) —O-(halo substituted alkyl), (g) —NH₂, (h) —O—(C₃-C₆)cycloalkyl, (i) —S-alkyl, (j) —N(R²²)₂, (k) —C(O)—(C₁-C₄)alkyl, (l) —C(O)—N(R¹⁸)₂, (m) cycloalkyl, (n) —CF₃, (o) —CF₂, and (p) —CF; and wherein said fused heteroarylaryl moiety of (4) is a fused monocyclic heteroaryl ring fused to an aryl ring, said heterocycloalkyl moiety of (5) is a monocyclic ring, said fused (arylcycloalkyl) in (6) is a monocyclic aryl ring fused to a monocyclic cycloalkyl ring, and said heterocycloalkyl moiety of (8) (not including the bridge) is a monocyclic ring; and provided that when R⁴ is substituted, and when the alkylene group of said R⁴ group (1), (3), (4), (5), (7), or (8) is substituted, then the alkylene carbon bound to the nitrogen of the B ring for said R⁴ groups (1), (3), (4), (5), (7), and (8) is not substituted with a heteroatom;

each R⁵ is independently selected from the group consisting of: (1) H, (2) (C₁-C₄)alkyl, (3) —C(O)—(C₁-C₄)alkyl, and (4) —C(O)—N(R¹⁸)₂;

each R⁶ is independently selected from the group consisting of: (1) alkyl, (2) cycloalkyl, (3) —CF₃, (4) —CF₂, and (5) —CF;

each R⁸ is independently selected from the group consisting of: (1) H, (2) alkyl, and (3) cycloalkyl;

each R¹⁰ is independently selected from the group consisting of: (1) alkyl, (2) cycloalkyl, and (3) —N(R¹⁸)₂;

each R¹² is independently selected from the group consisting of: (1) alkyl, and (2) cycloalkyl;

each R¹⁴ is independently selected from the group consisting of: (1) H, (2) alkyl, and (3) cycloalkyl;

each R¹⁶ is independently selected from the group consisting of: (1) alkyl, and (2) cycloalkyl;

each R¹⁸ is independently selected from the group consisting of: (1) H, (2) (C₁-C₄)alkyl, and (3) (C₃-C₆)cycloalkyl;

each R²⁰ is independently selected from the group consisting of: (1) H, and (2) (C₁-C₄) alkyl; and (3) wherein each R²⁰ can be taken together, along with the nitrogen to which they are bonded, to form a heterocycloalkyl ring, wherein said heterocycloalkyl ring is optionally substituted with 1-2 independently selected halo atoms; and each R²² is independently selected from the group consisting of: alkyl.

2. The compound of claim 1 wherein said B ring is selected from the group consisting of

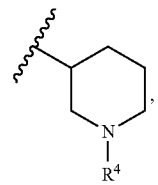
(35)

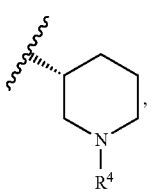
(35.1)

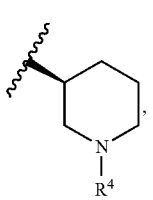
(35.2)

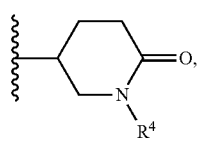
(36)

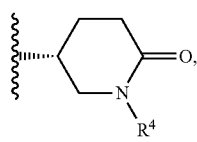
(37)

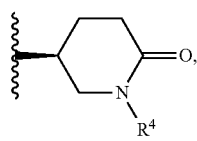
(38)

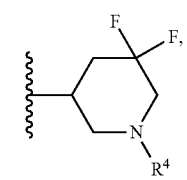
(39)

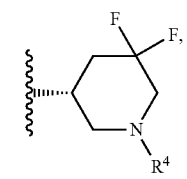
(40)

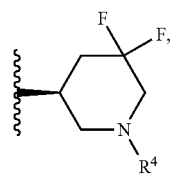 (41)
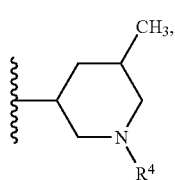 (42)
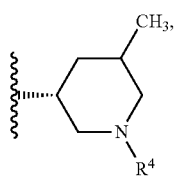 (43)
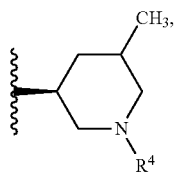 (44)
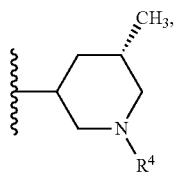 (45)
(46)
(47)
(48)
(49)
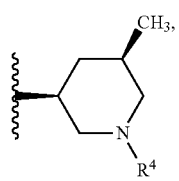 (50)
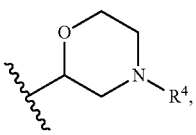 (51)
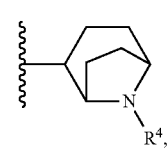 (52)
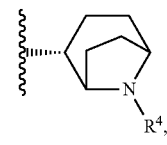 (53)
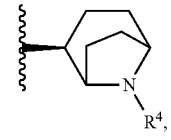 (54)
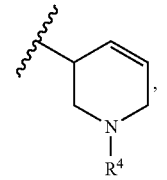 (54.1)
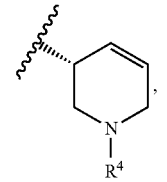 (54.2)
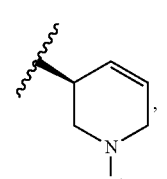 (54.3)
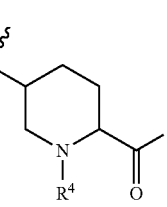 (54.4)

231
-continued
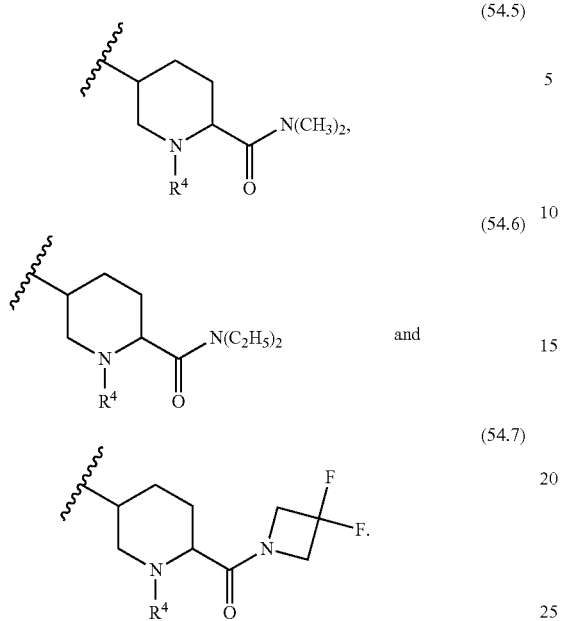
3. The compound of claim 1 wherein said R⁴ groups are selected from the group consisting of
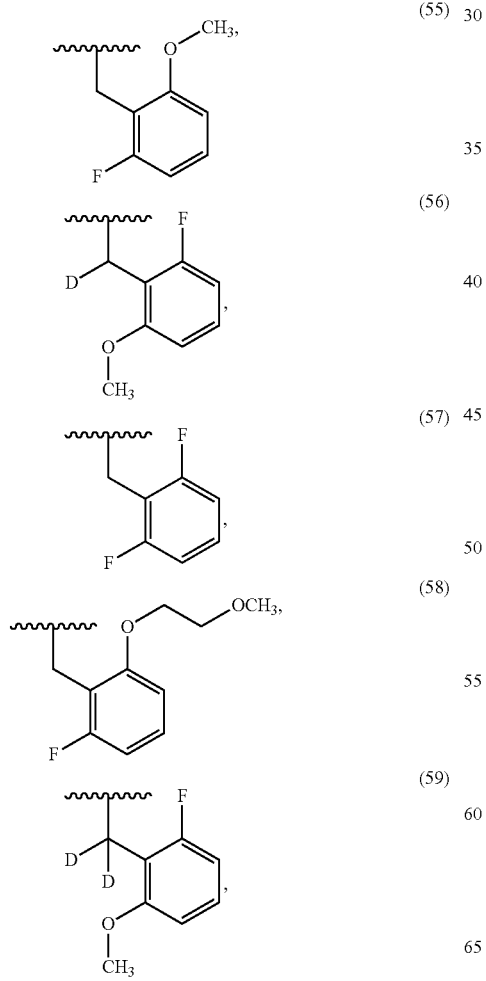
232
-continued
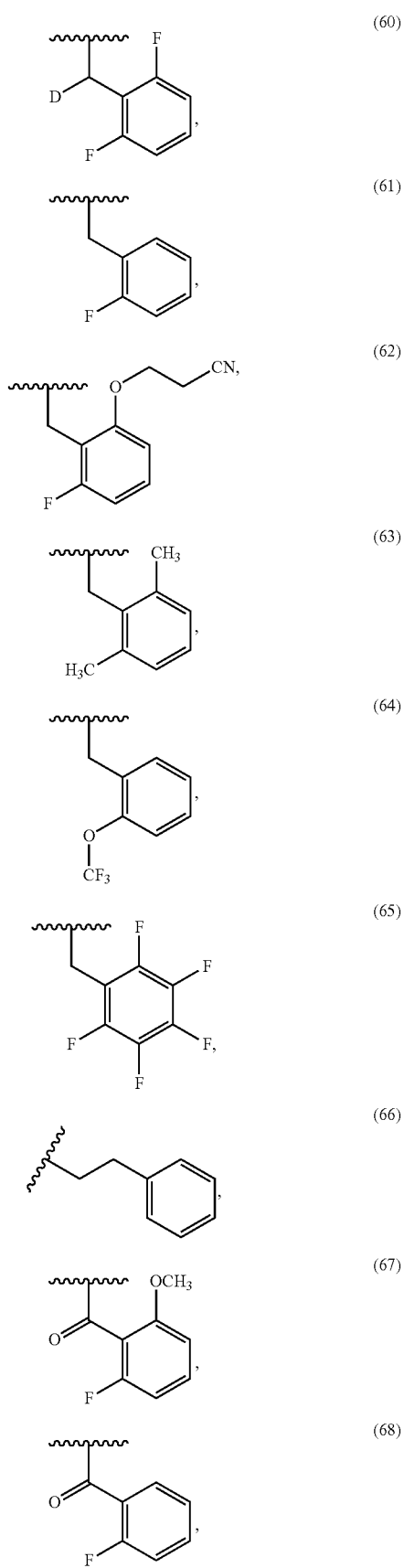

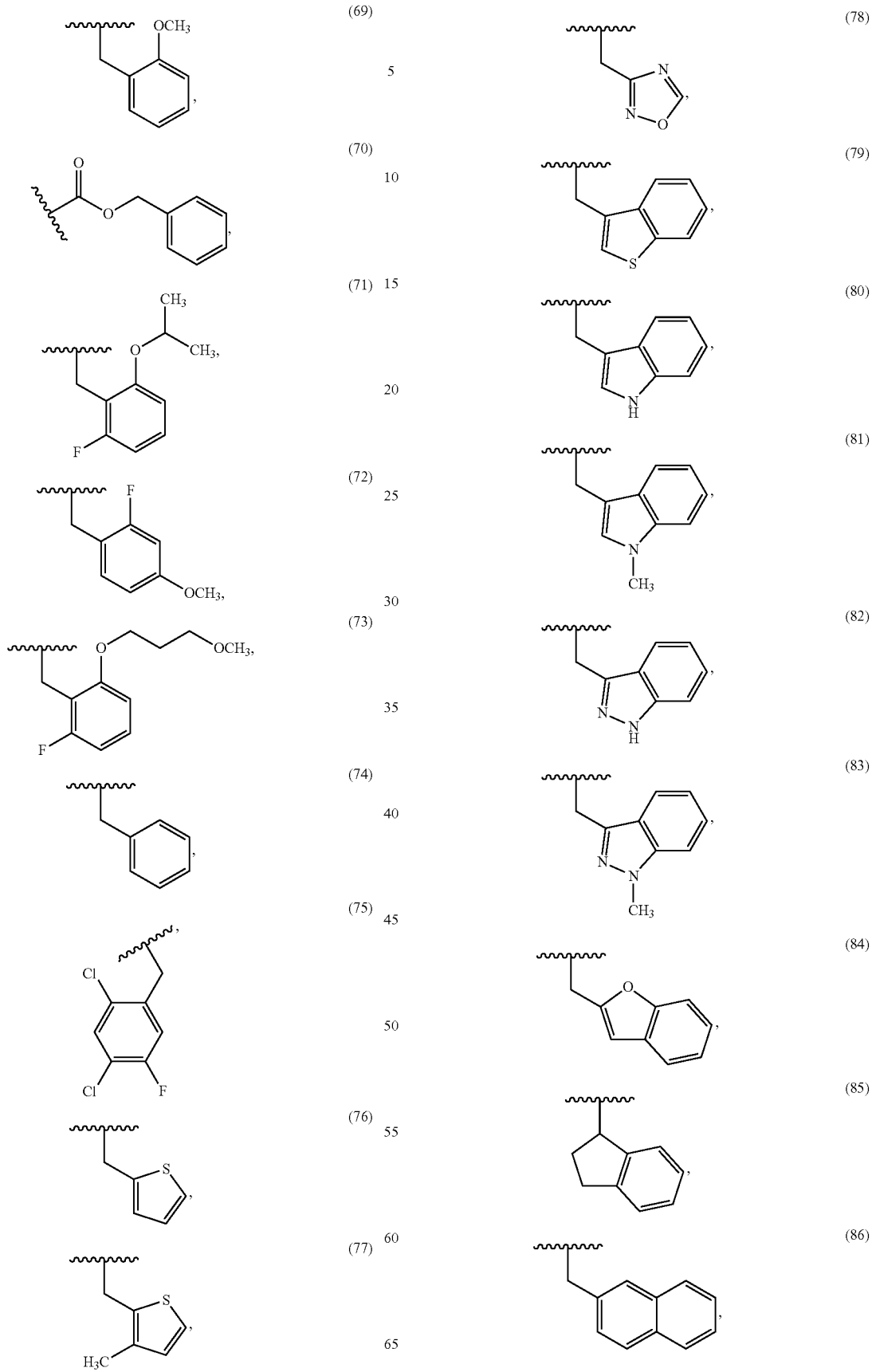

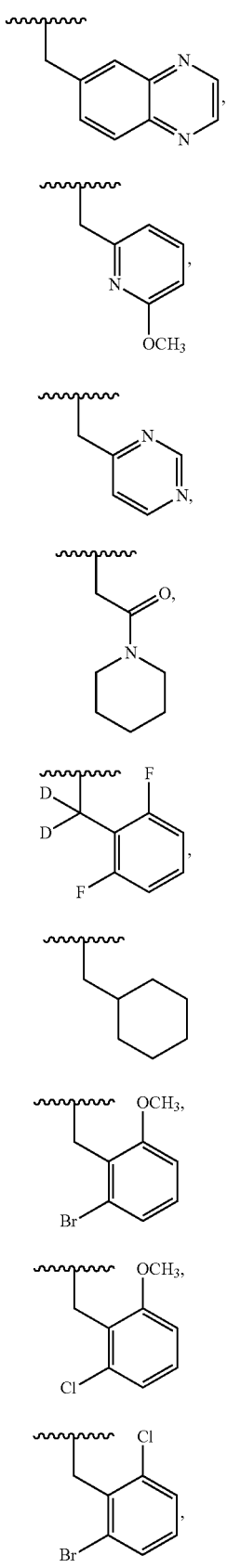
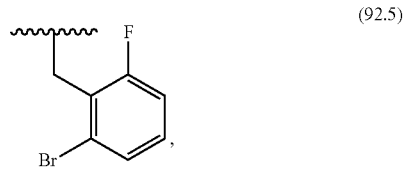
wherein D represents deuterium.
4. The compound of claim 1 selected from the group consisting of
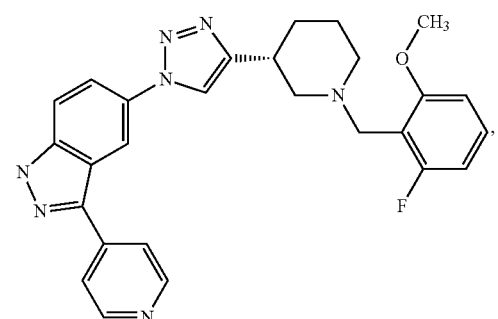
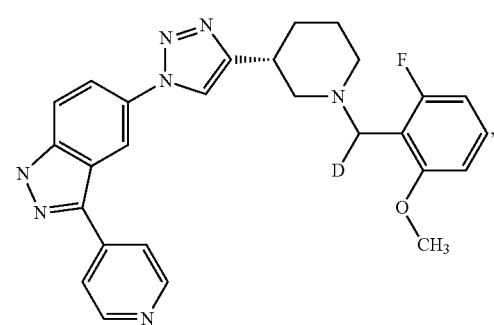
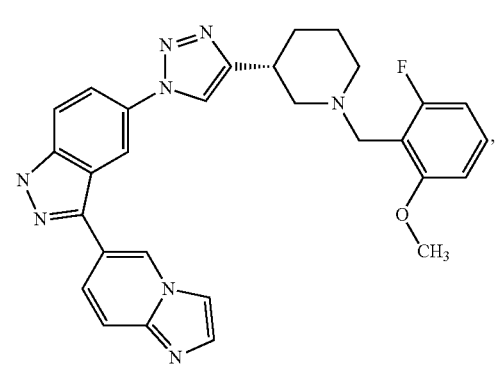

237
-continued
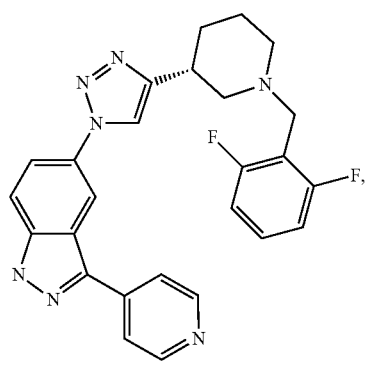
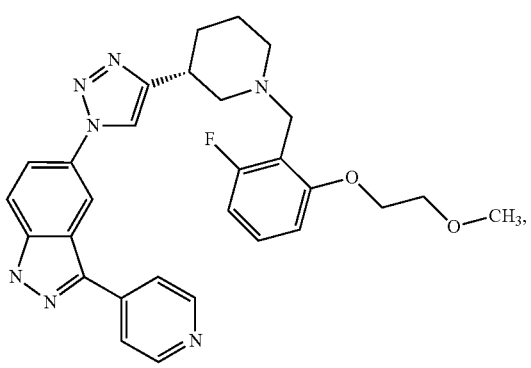
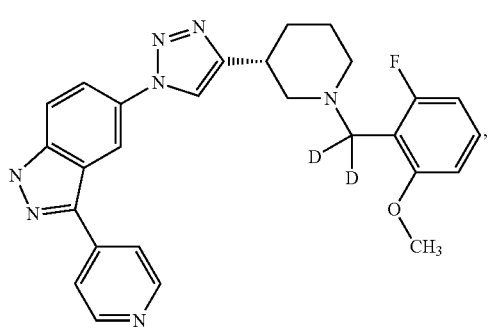
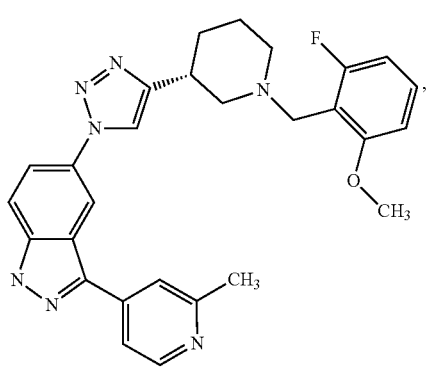
238
-continued
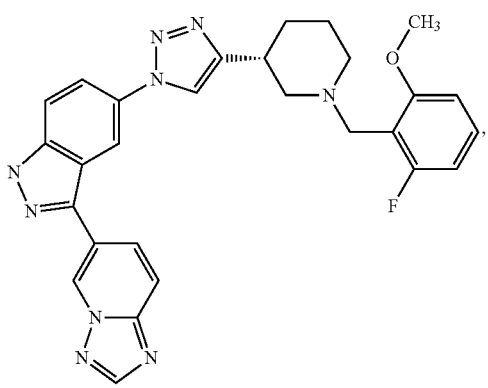
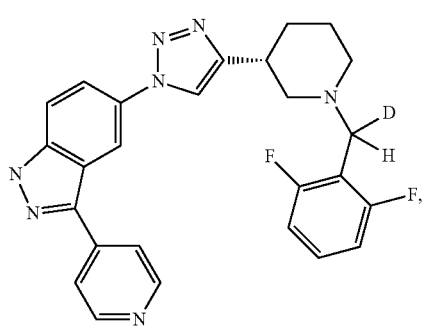
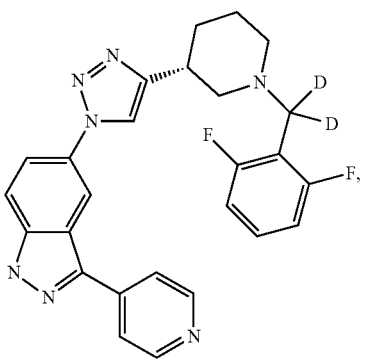
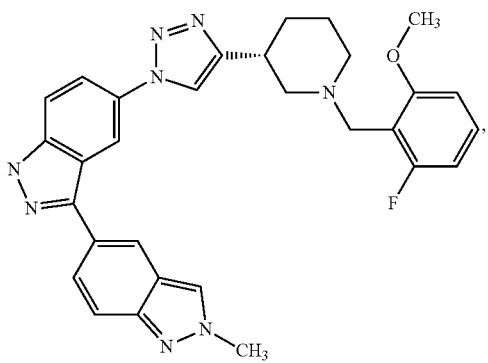

-continued
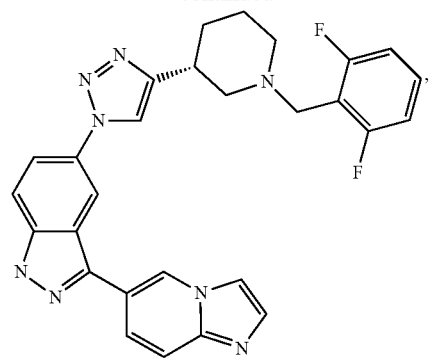 [SMILES: Fc1cccc(F)c1CN1CCC[C@@H](c2cn(-c3ccc4[nH]nc(-c5ccc6nccn6c5)c4c3)nn2)C1]
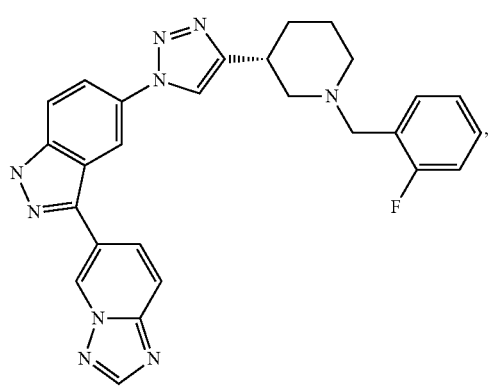
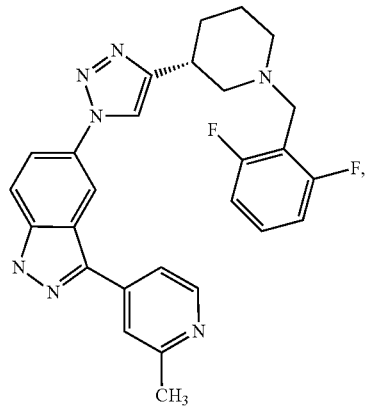
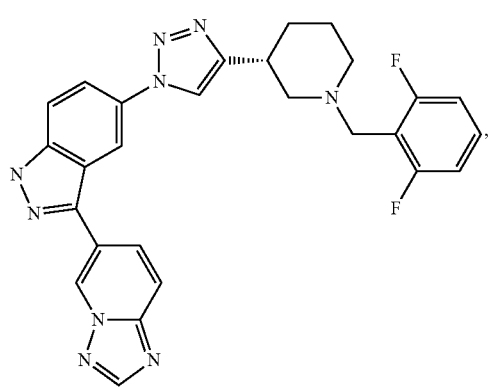
-continued
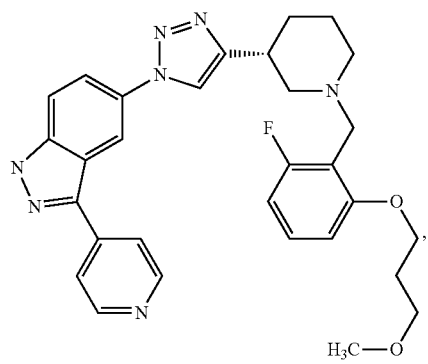
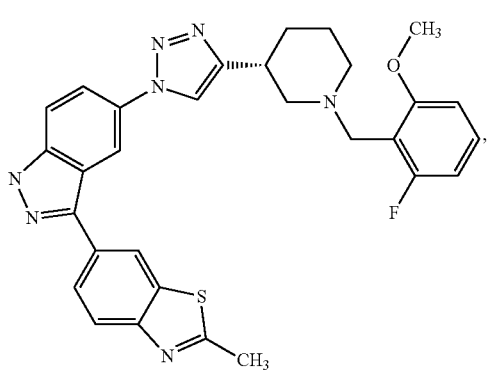
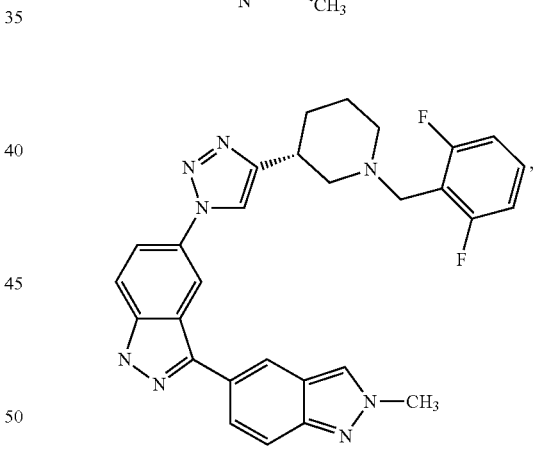
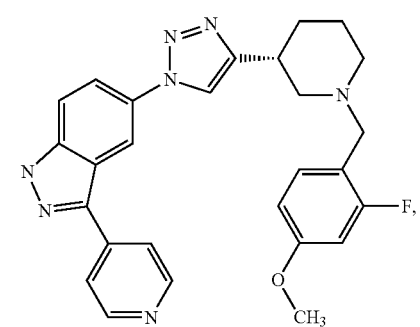

241
-continued
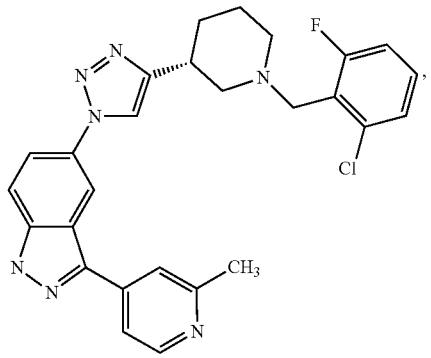
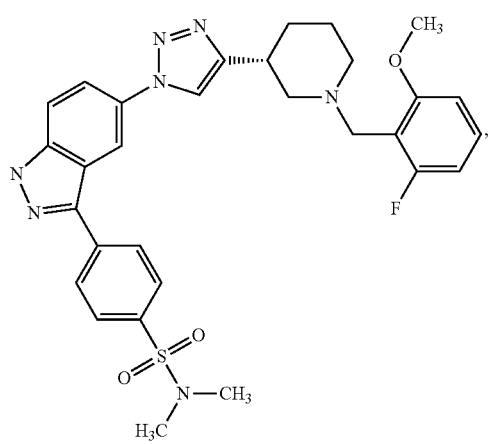
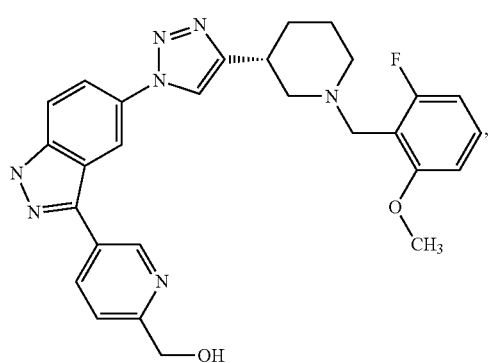
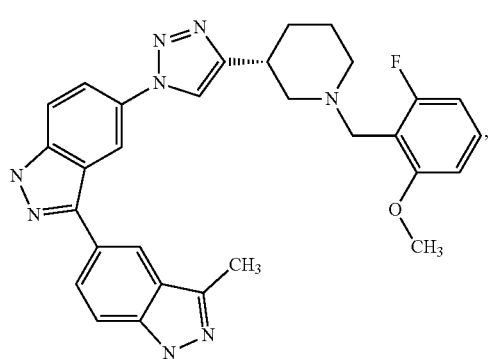
242
-continued
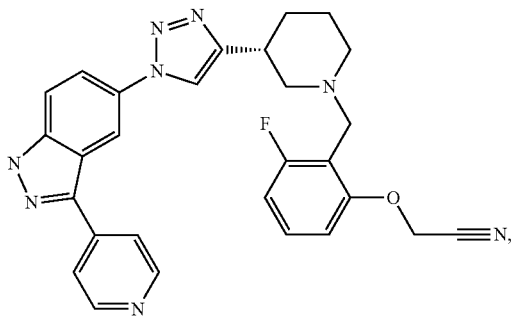
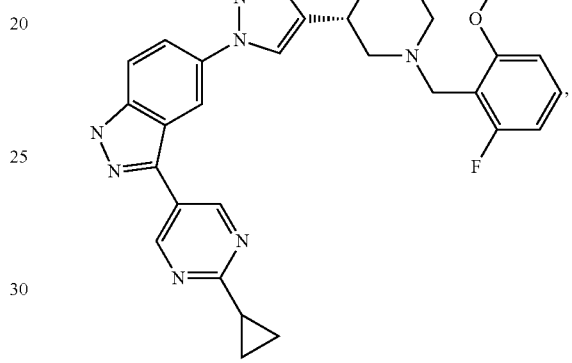
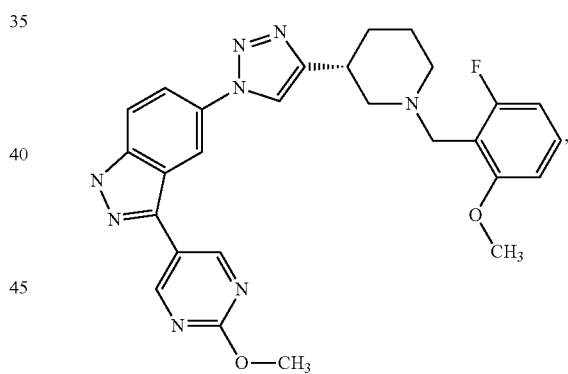
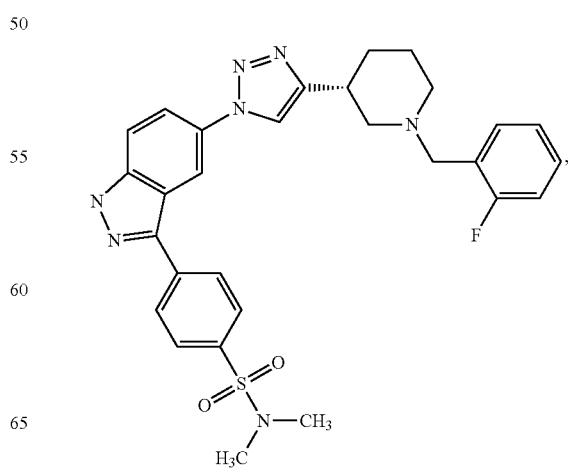

243
-continued
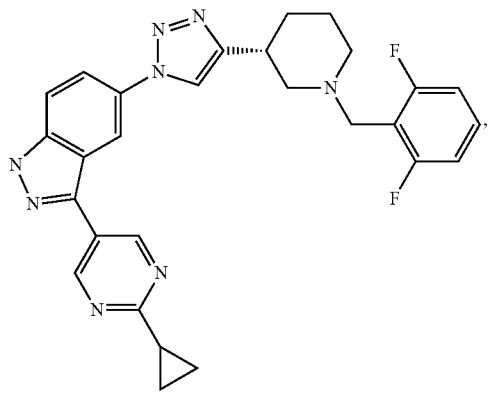
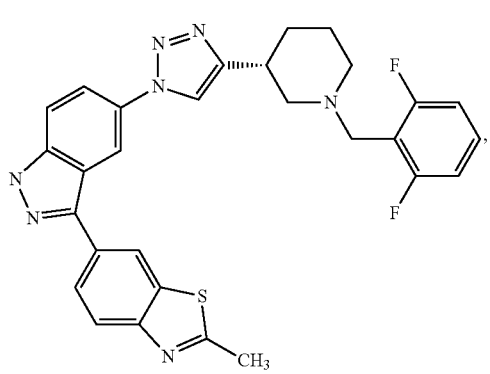
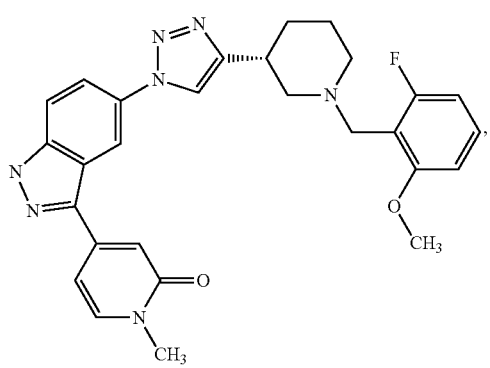
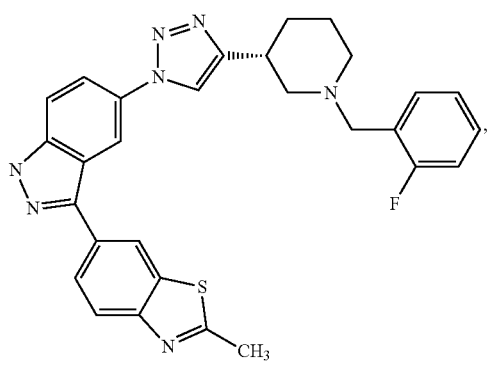
244
-continued
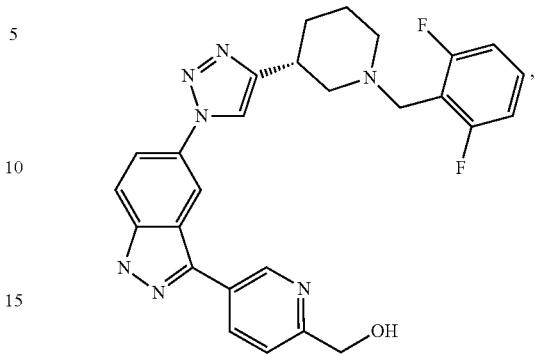
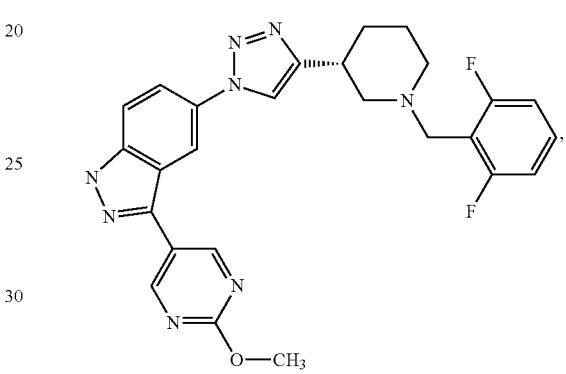
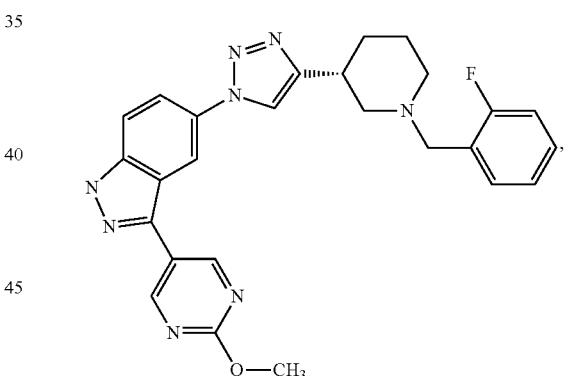
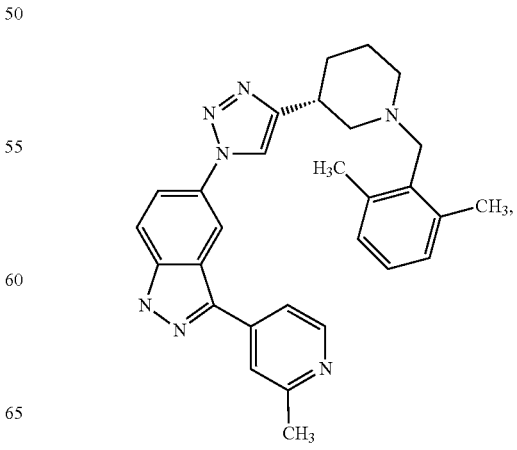

-continued

247
-continued
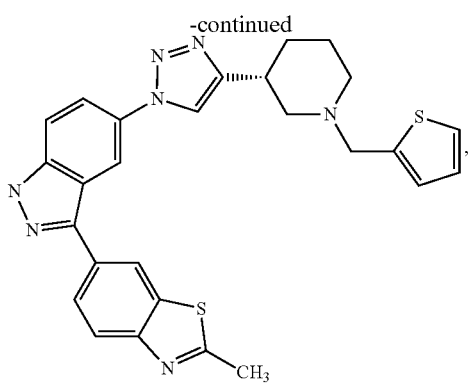
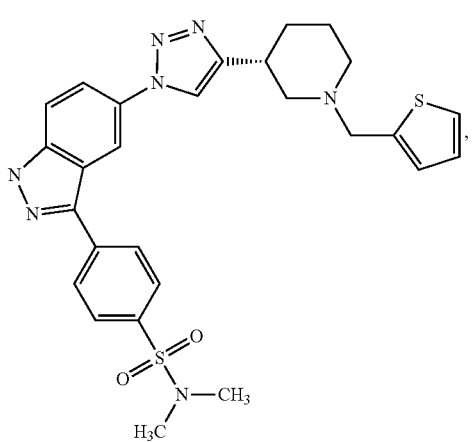
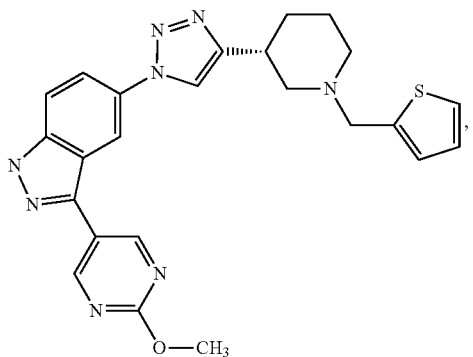
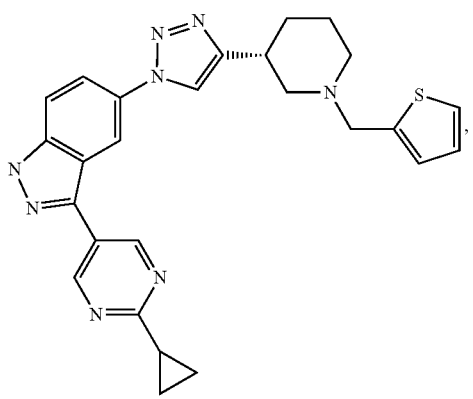
248
-continued
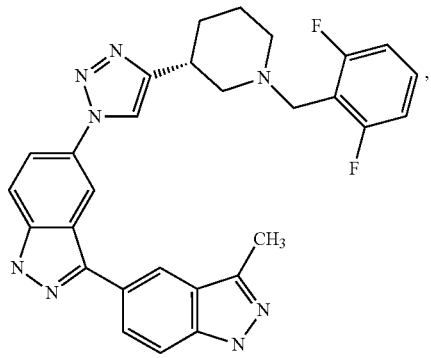
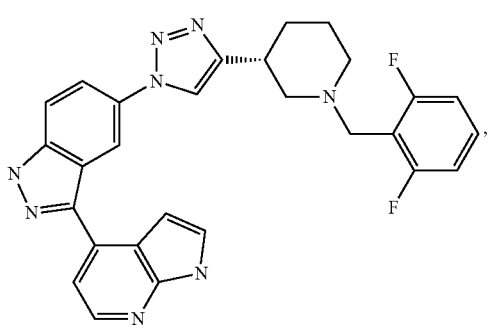
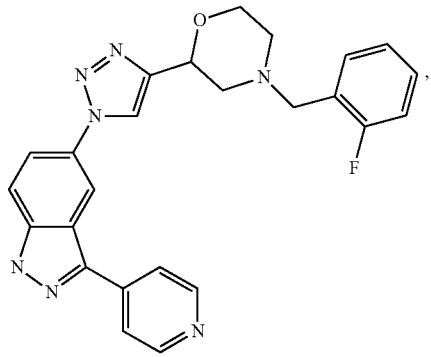
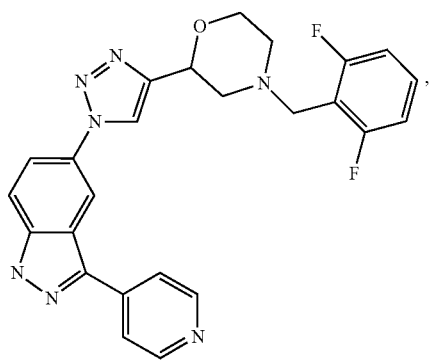

249
-continued
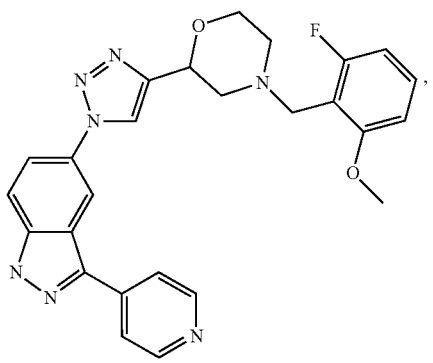
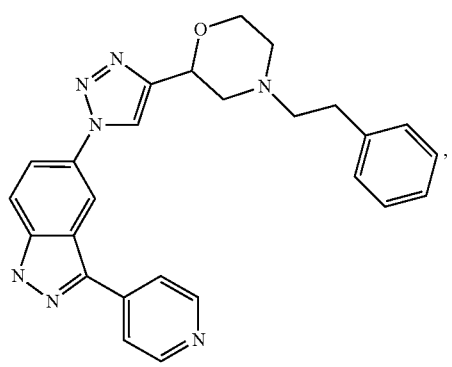
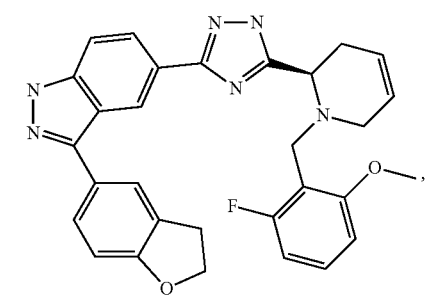
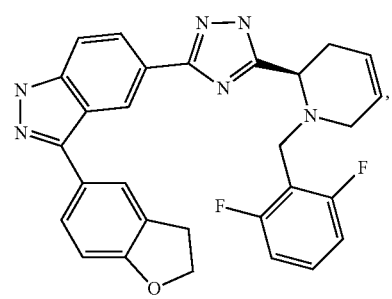
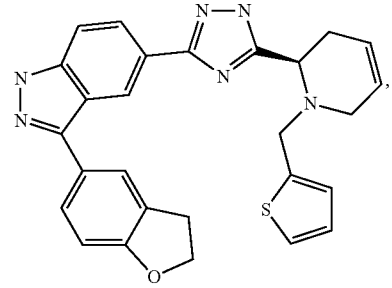
250
-continued
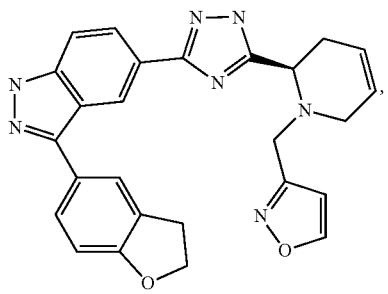
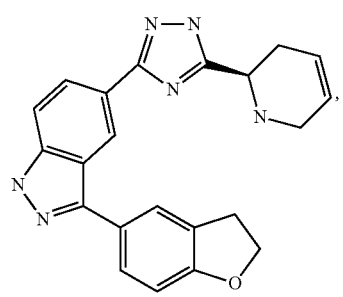
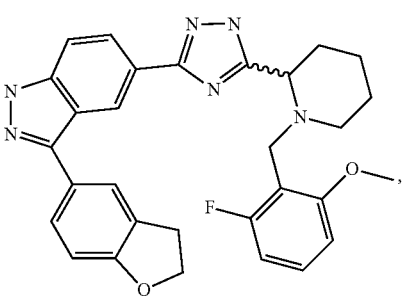
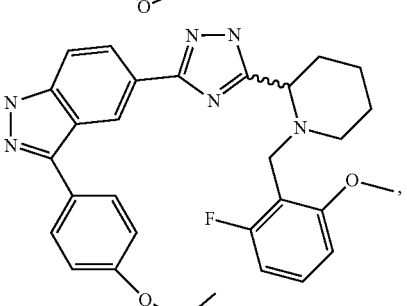

251
-continued
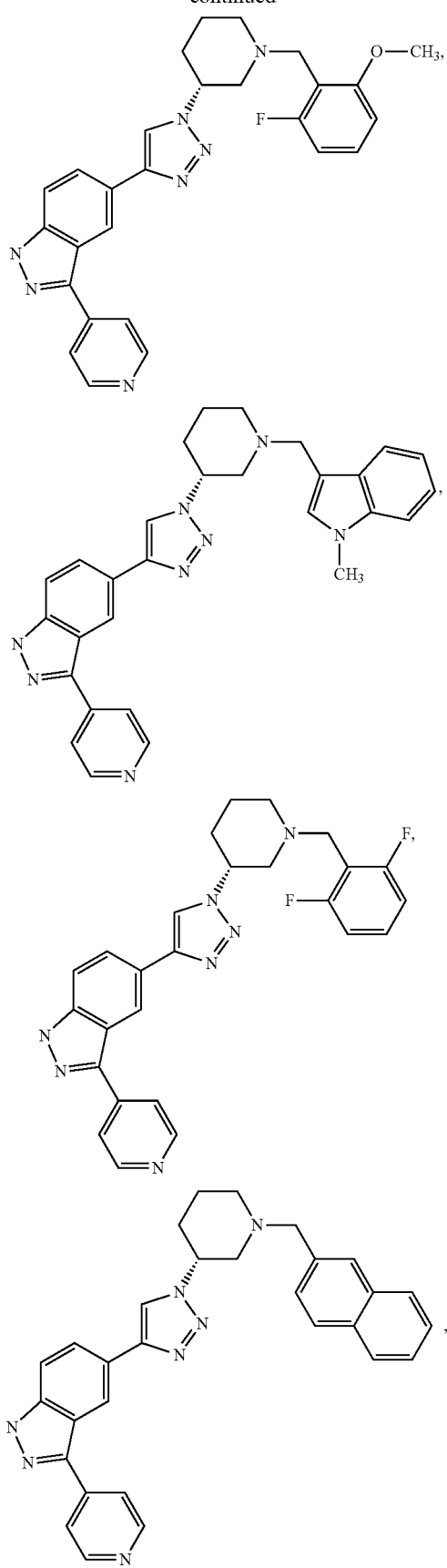
252
-continued
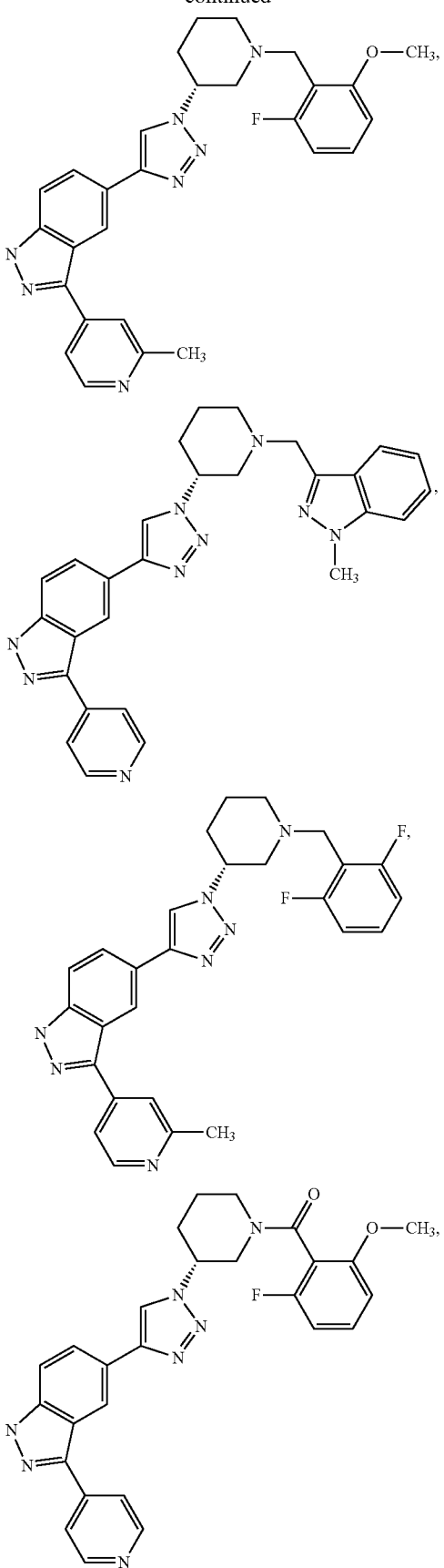

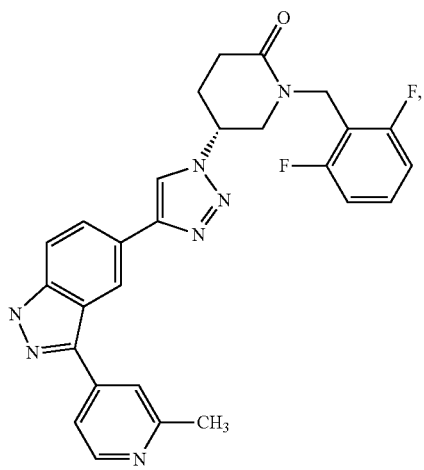
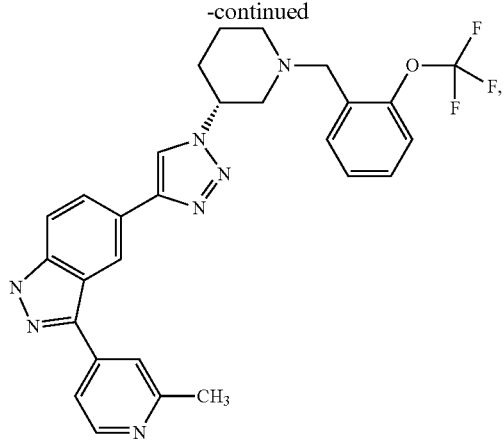
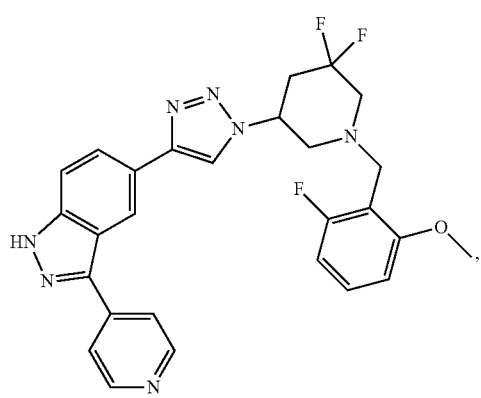
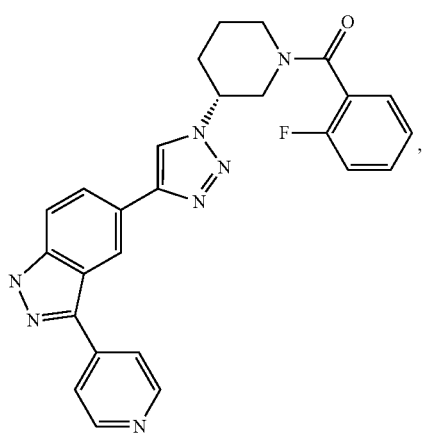
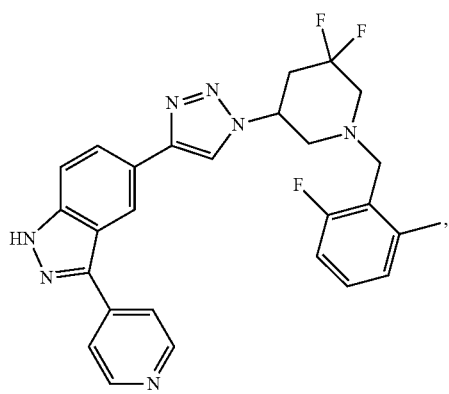
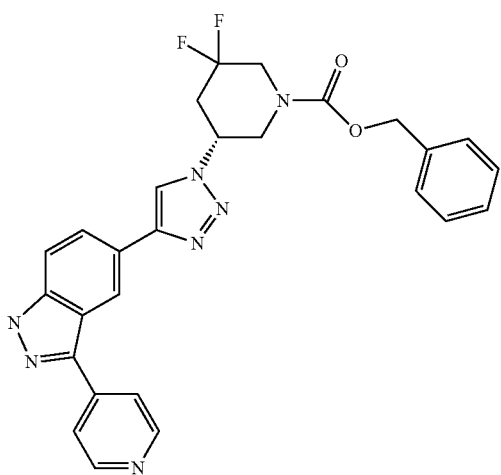
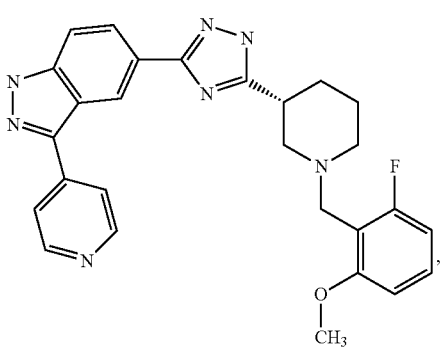

255
-continued
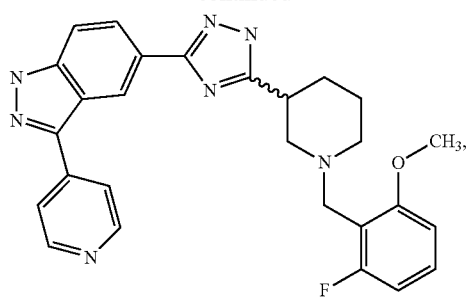
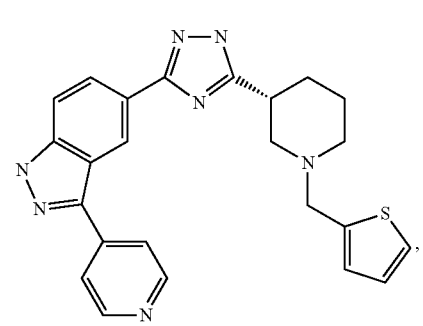
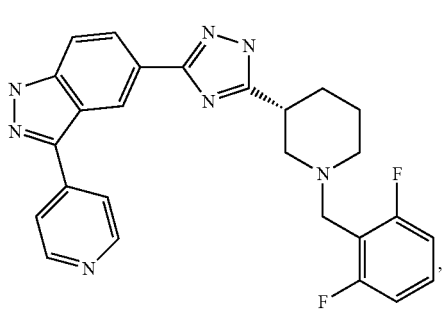
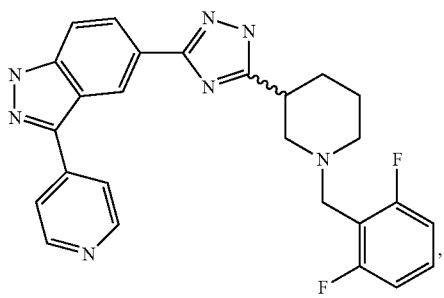
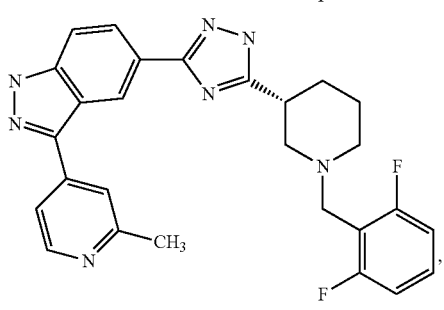
256
-continued
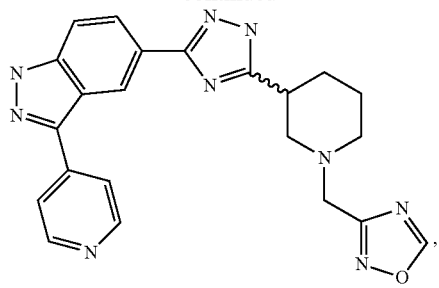
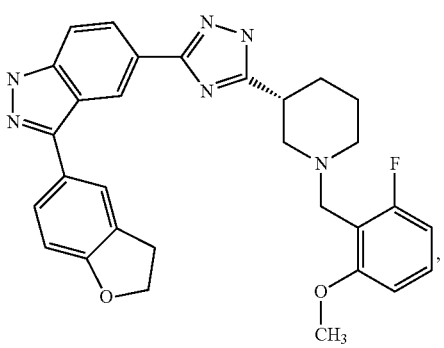
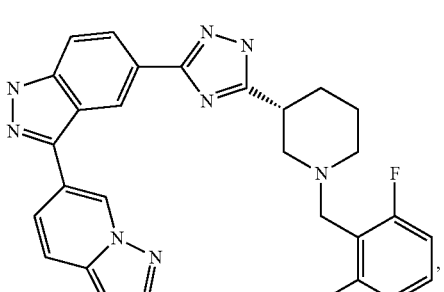
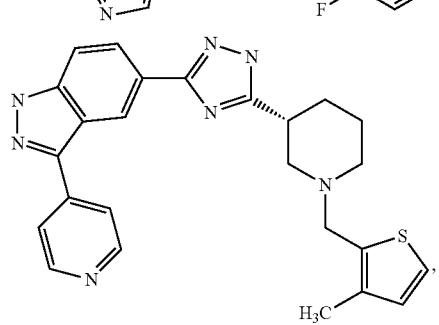

257
-continued
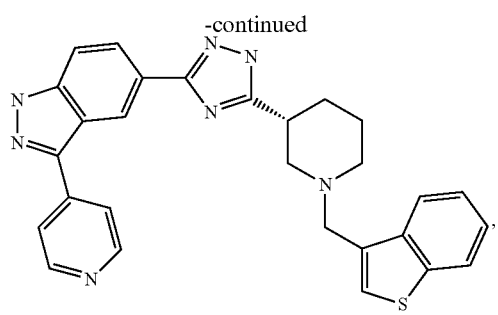
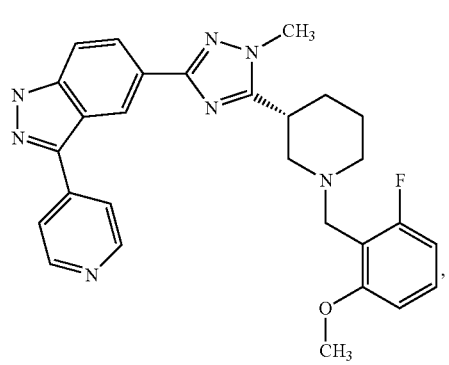
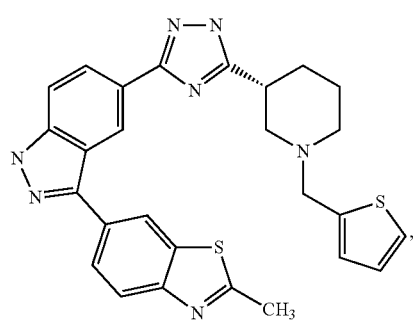
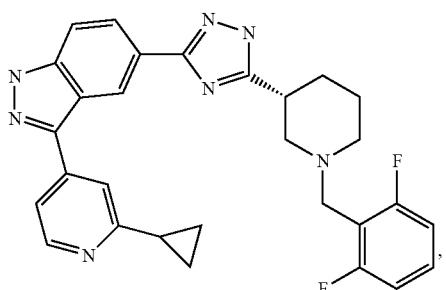
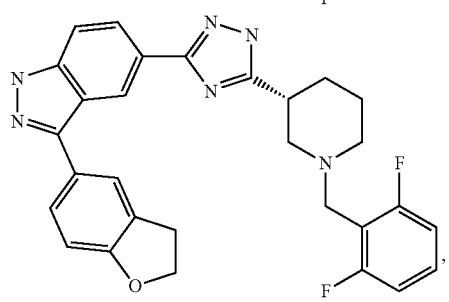
258
-continued
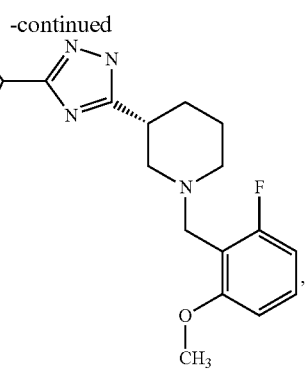
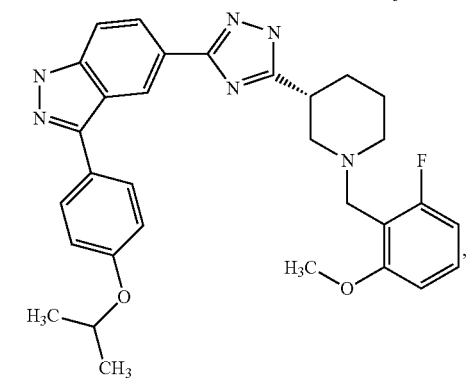
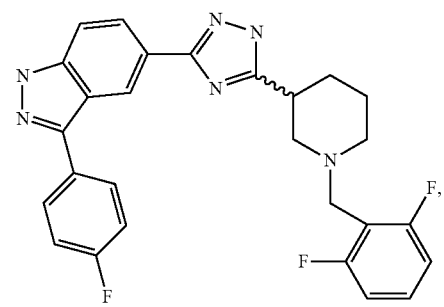
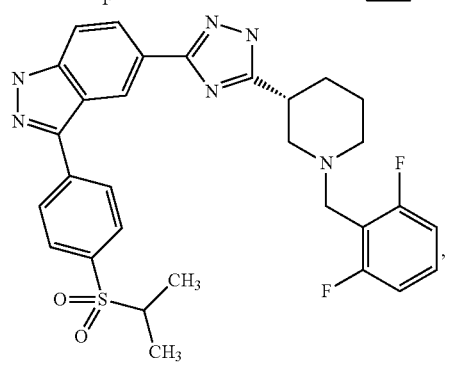
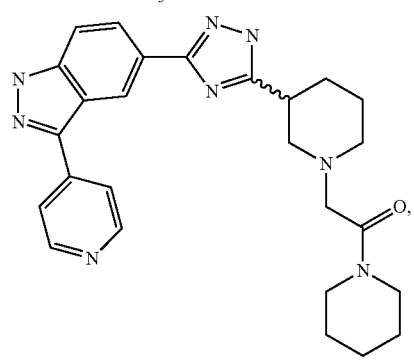

259
-continued
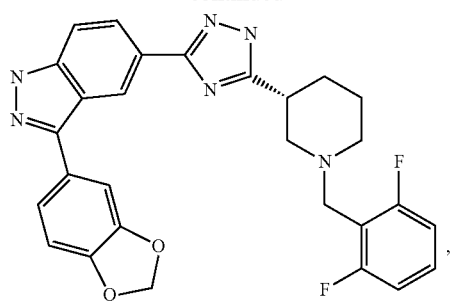
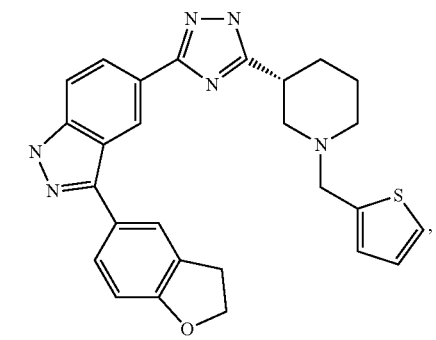
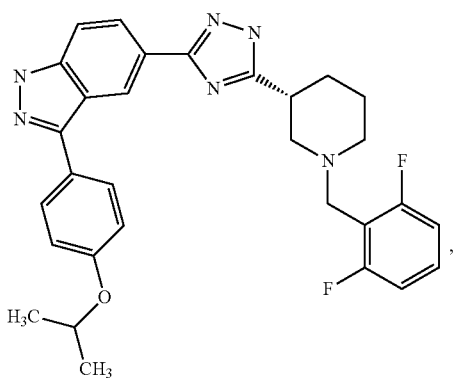
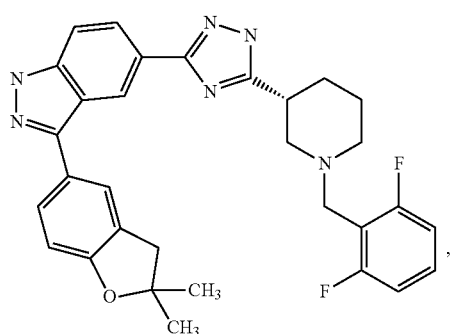
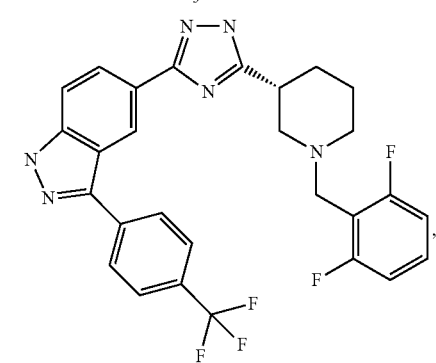
260
-continued
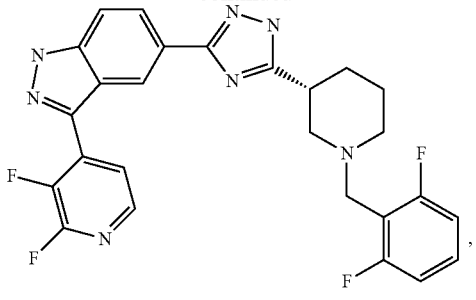
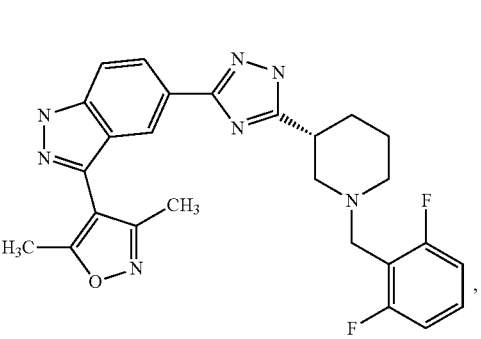
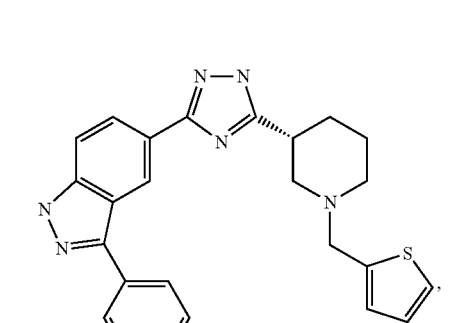
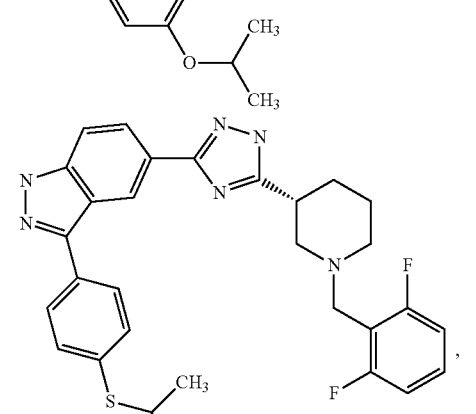
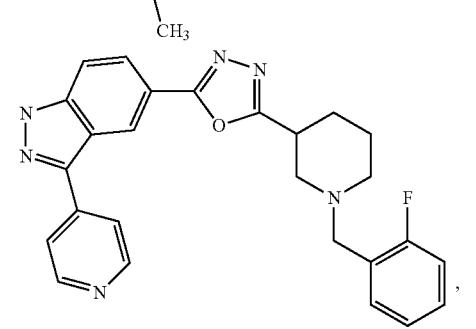

261
-continued
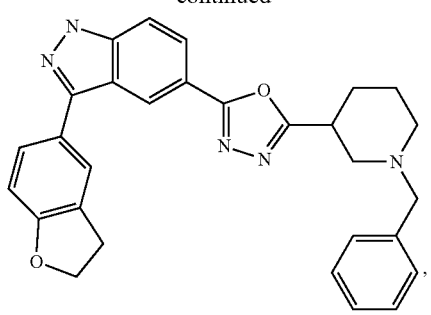
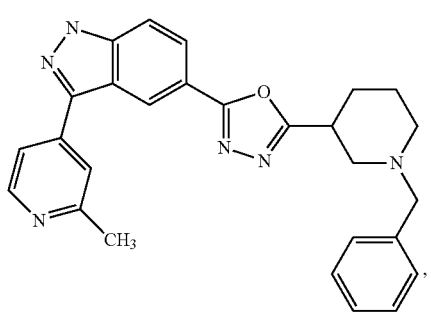
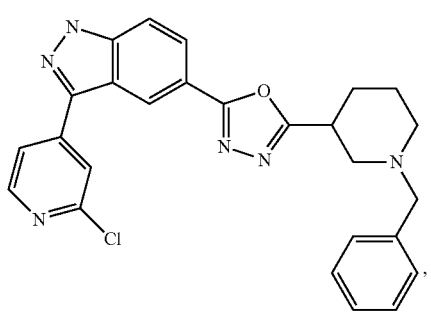
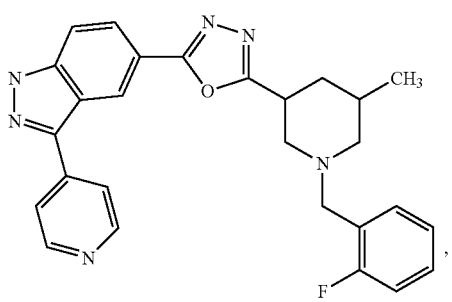
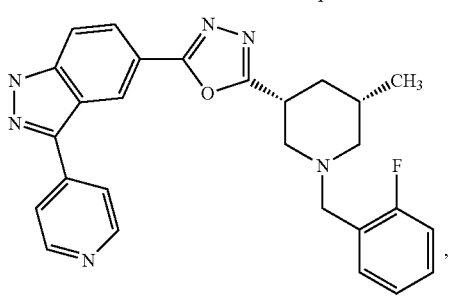
262
-continued
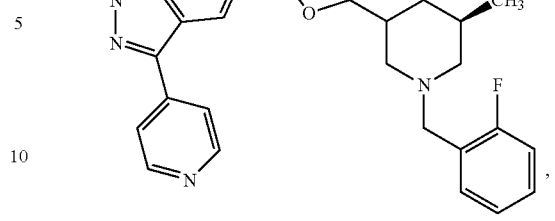
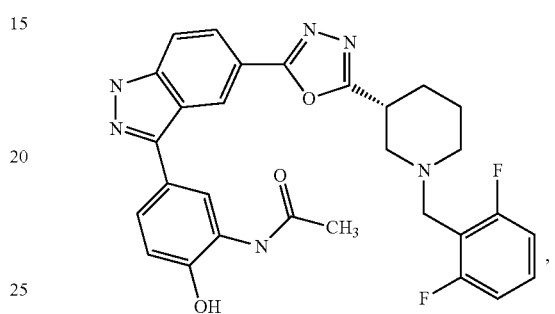
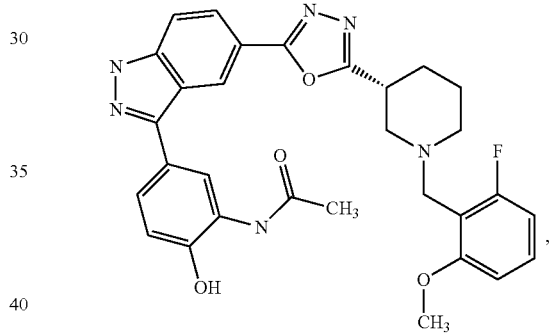
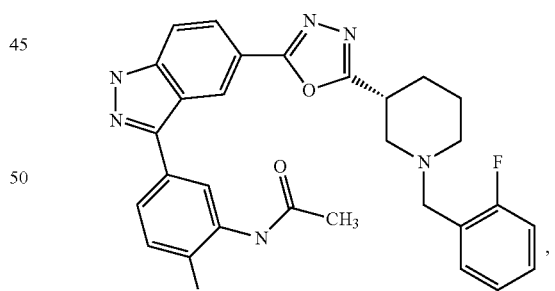
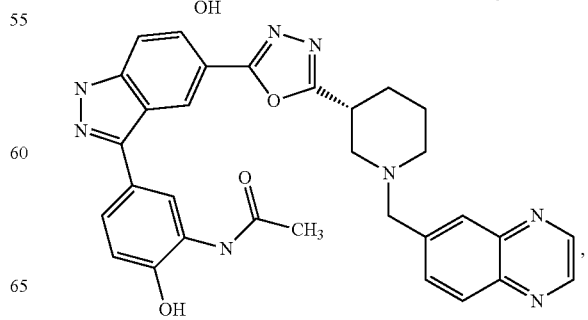

263
-continued
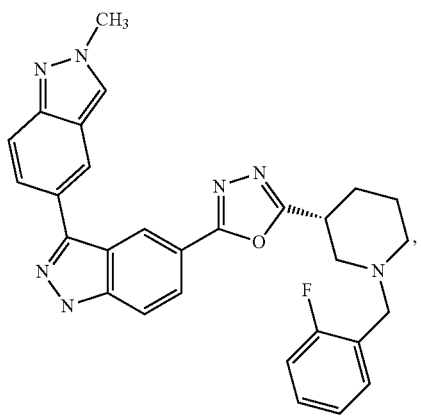
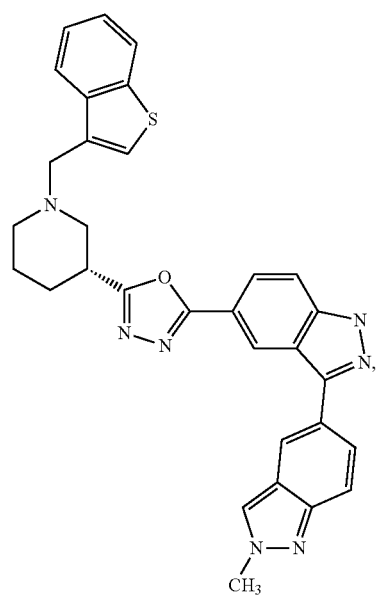
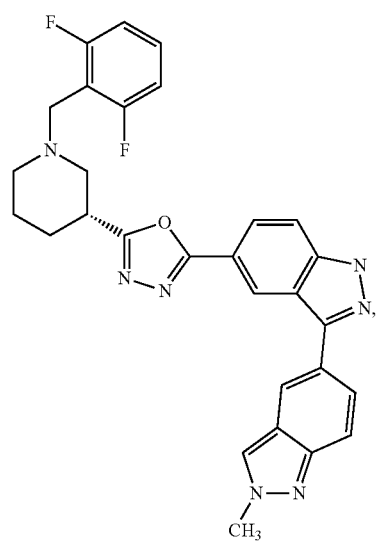
264
-continued
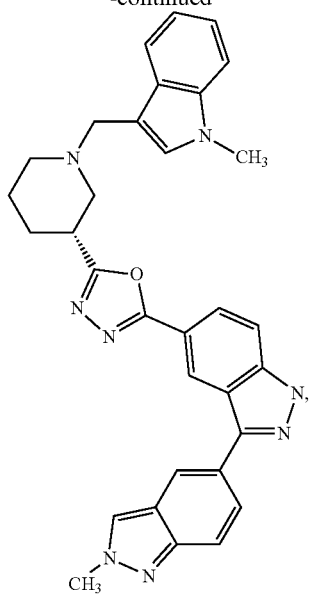
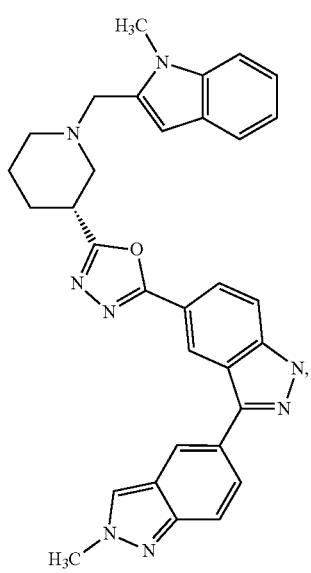
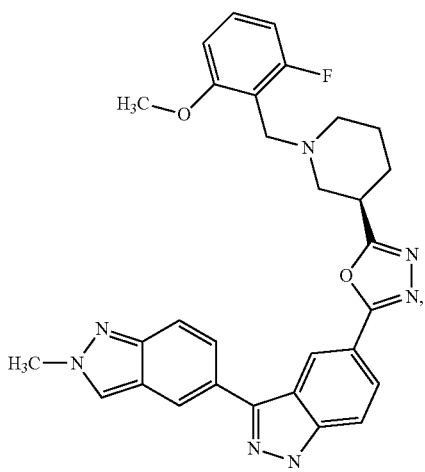

265
-continued
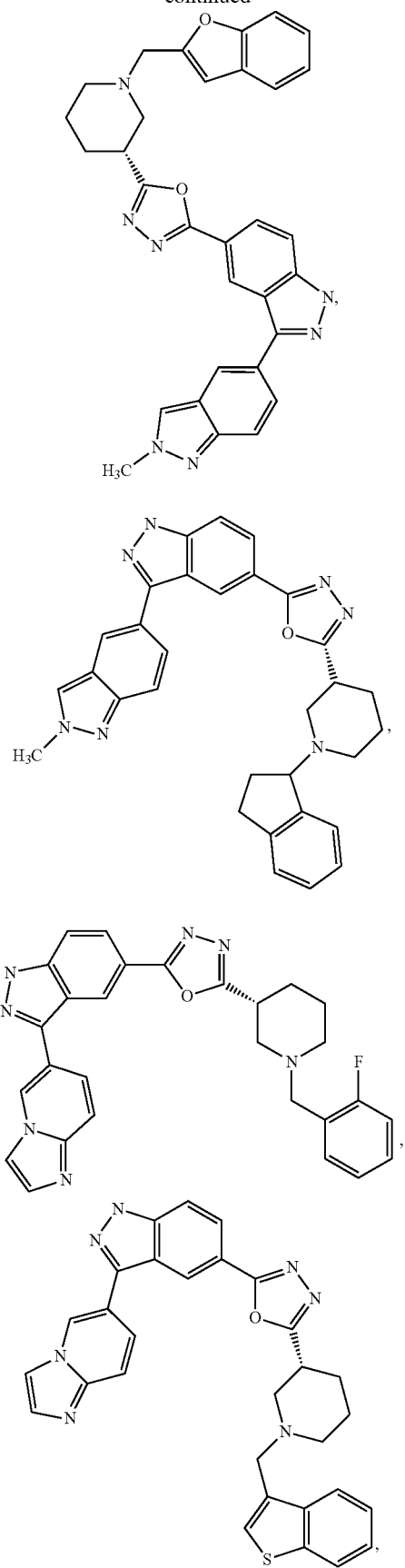
266
-continued
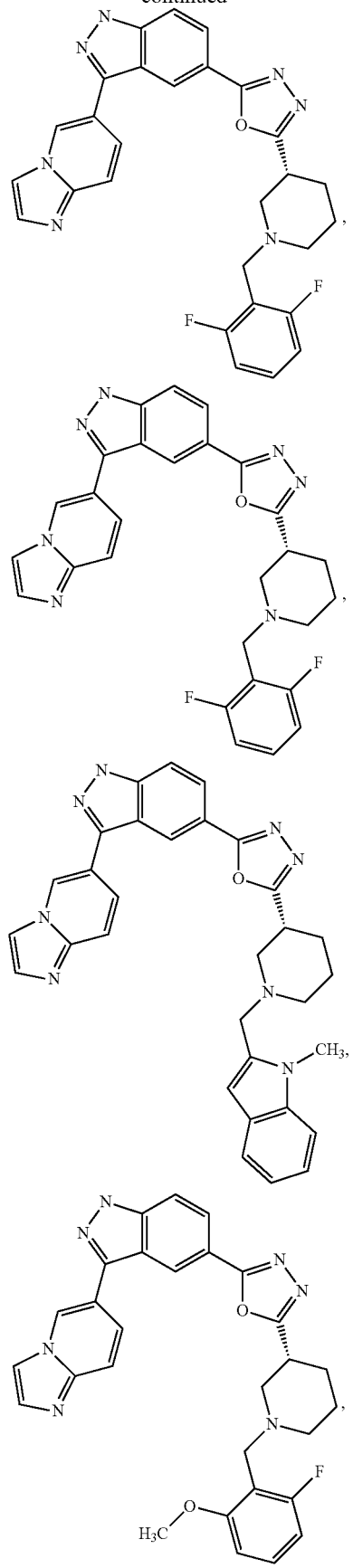

267
-continued
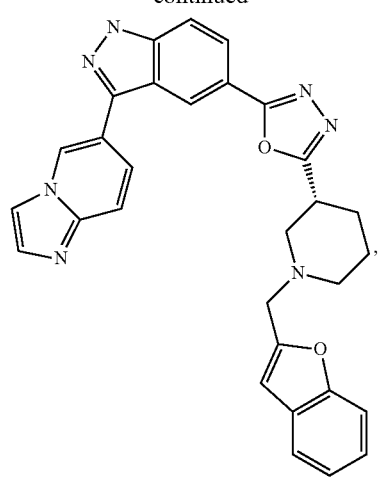
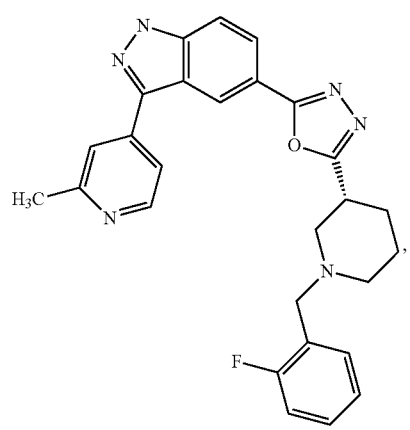
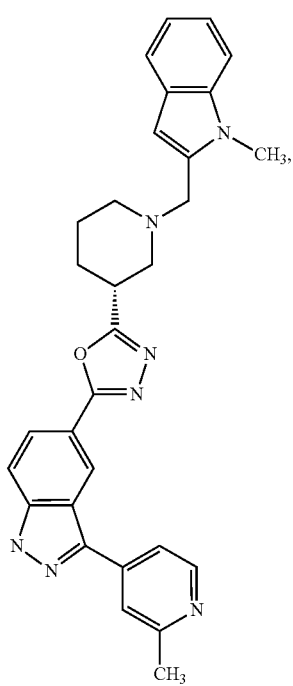
268
-continued
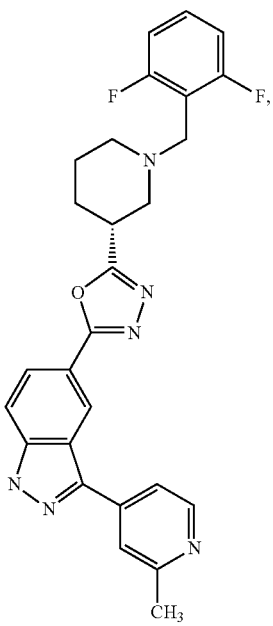

269
-continued
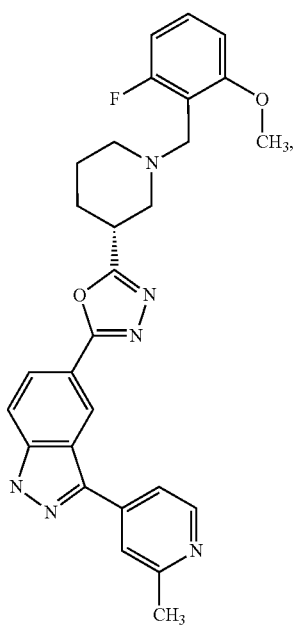
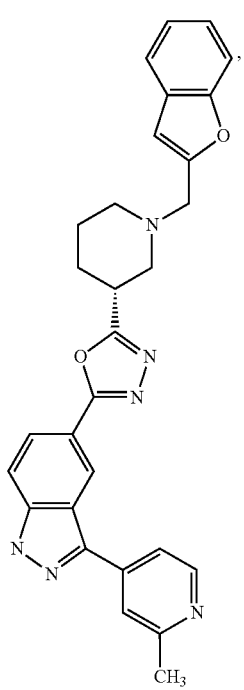
270
-continued
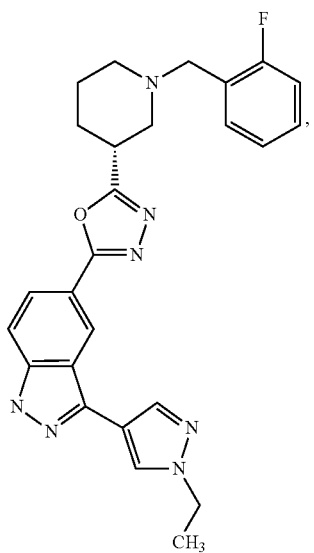
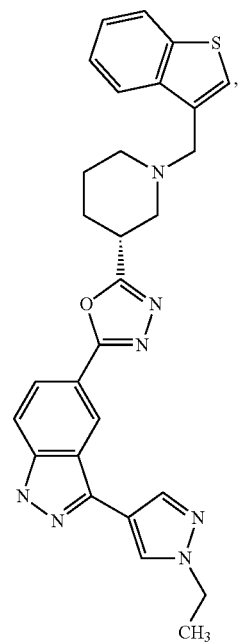

271
-continued
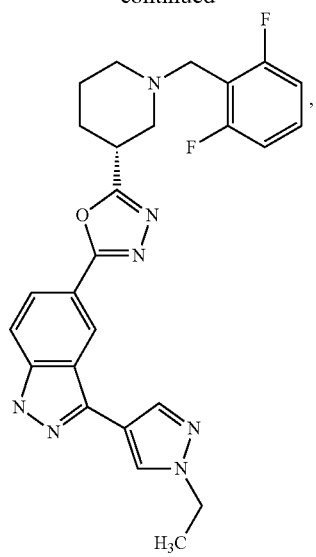
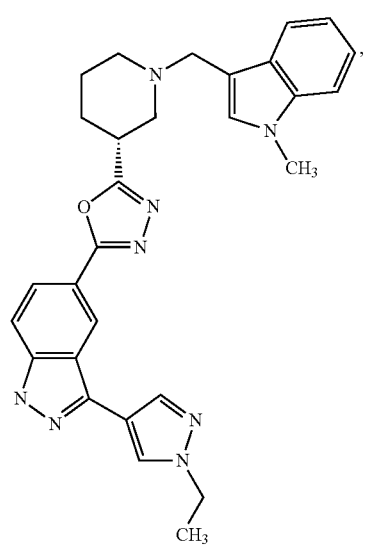
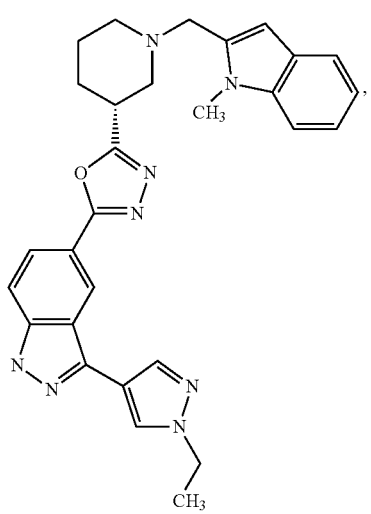
272
-continued
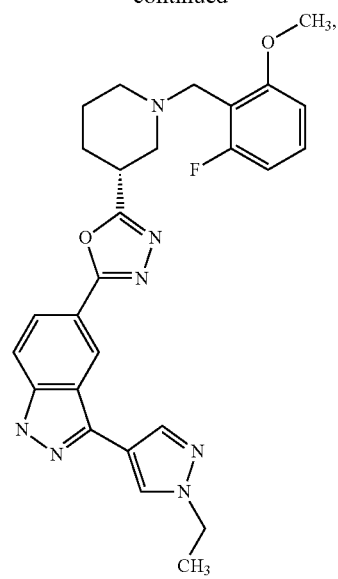
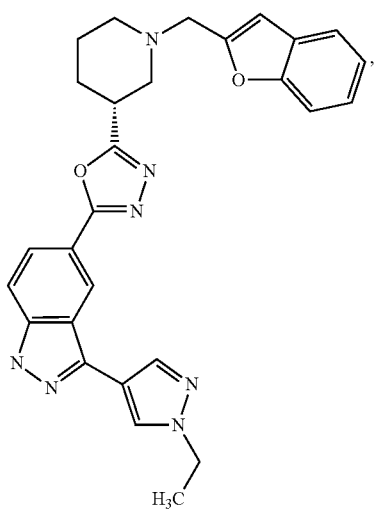
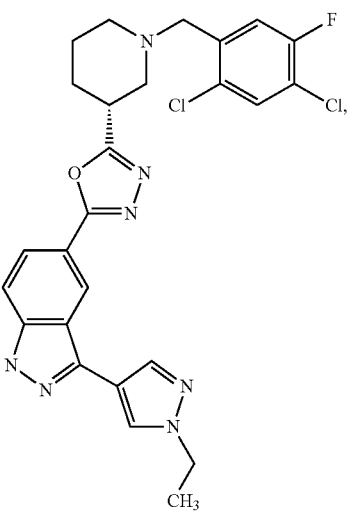

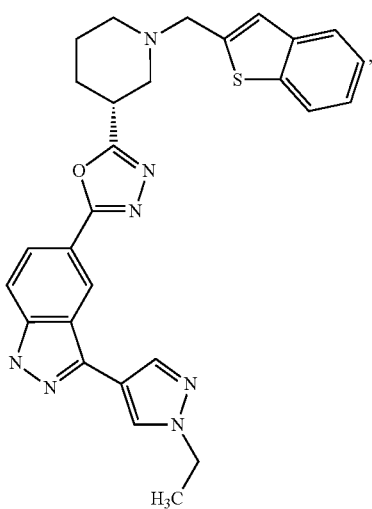
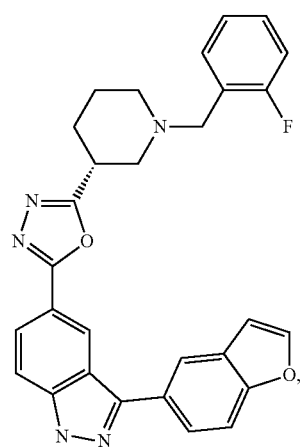
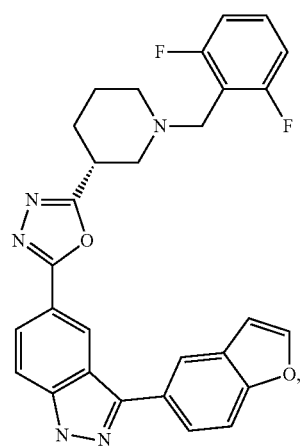
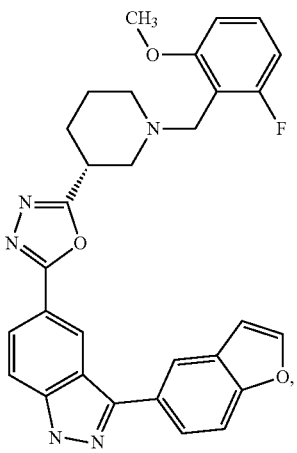
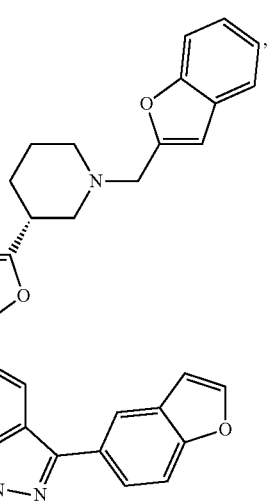
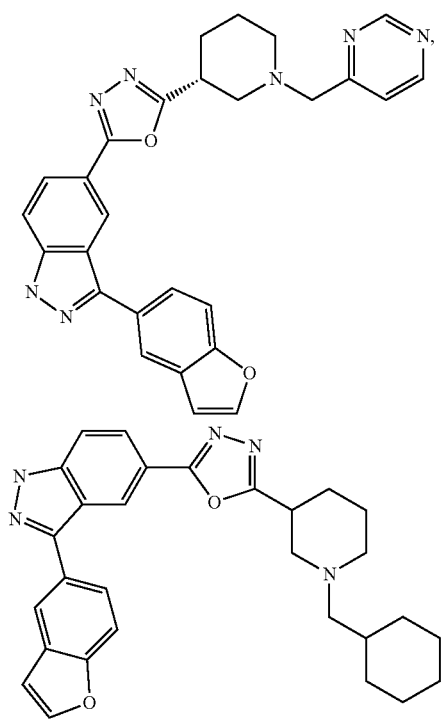

275
-continued
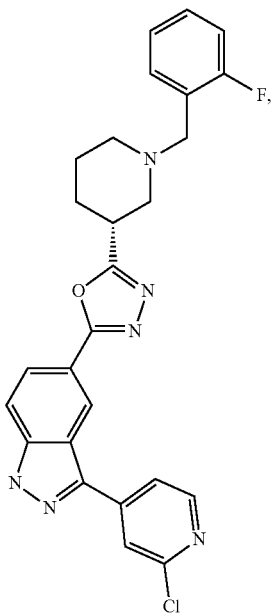
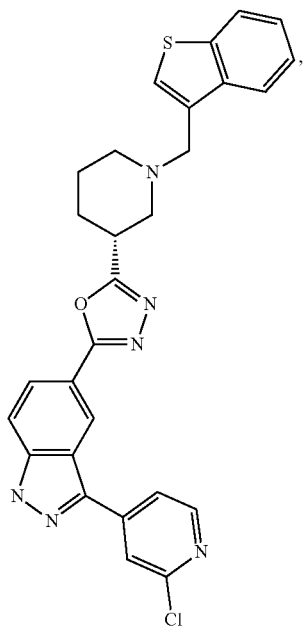
276
-continued
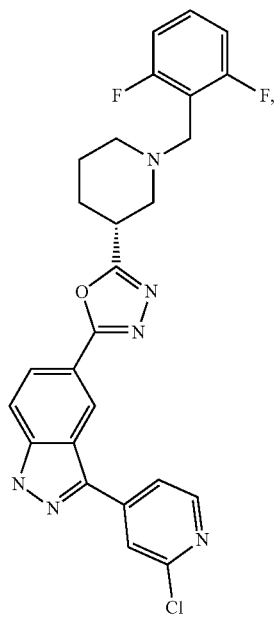
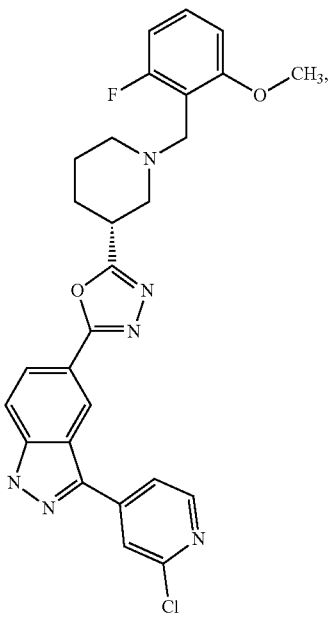

277
-continued
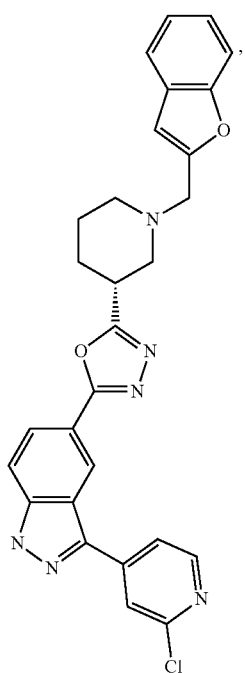
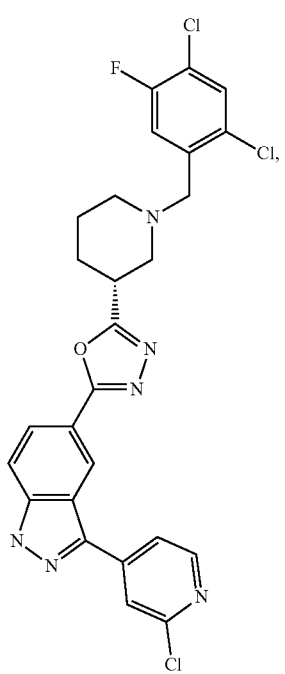
278
-continued
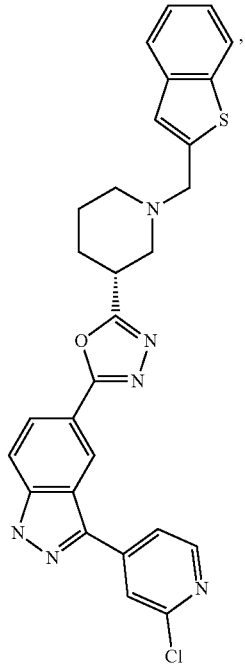
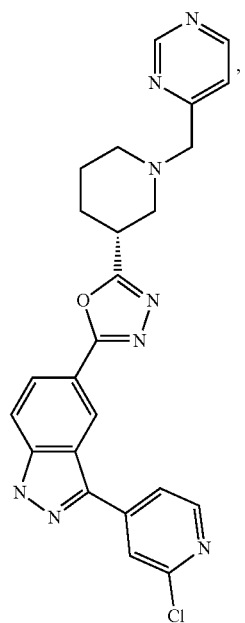

279
-continued
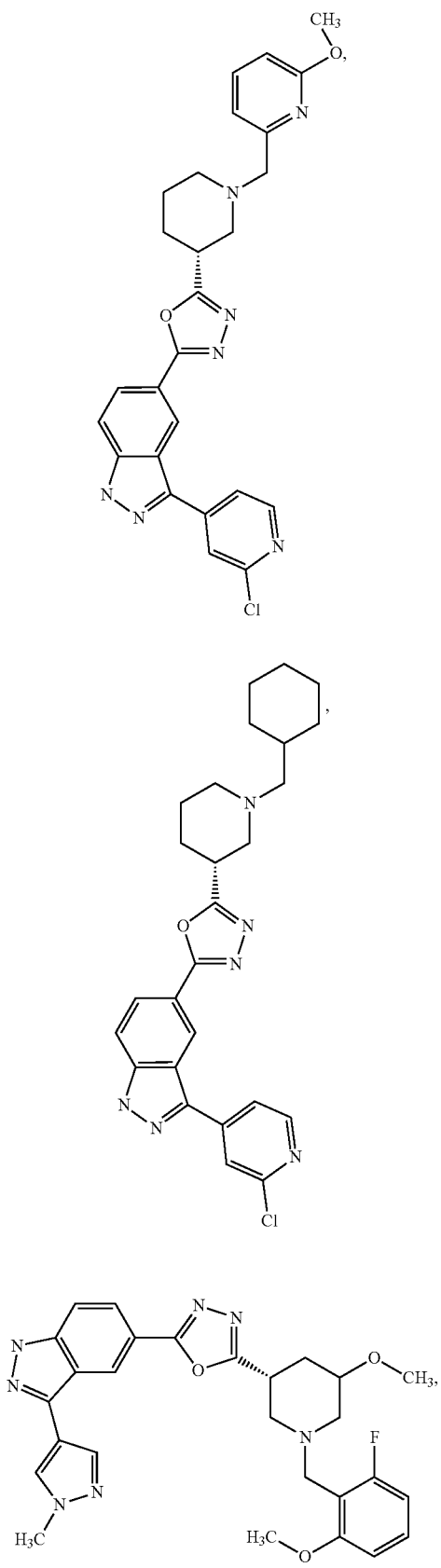
280
-continued
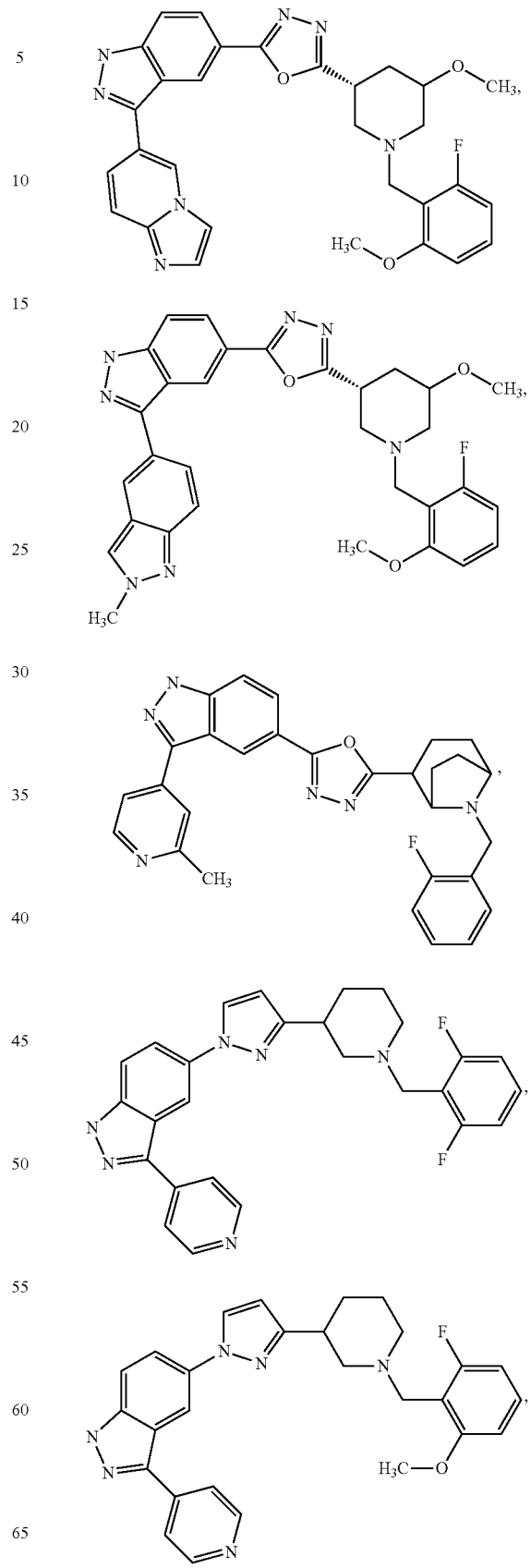

281
-continued
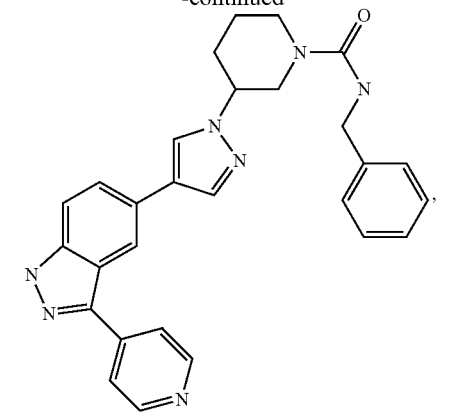
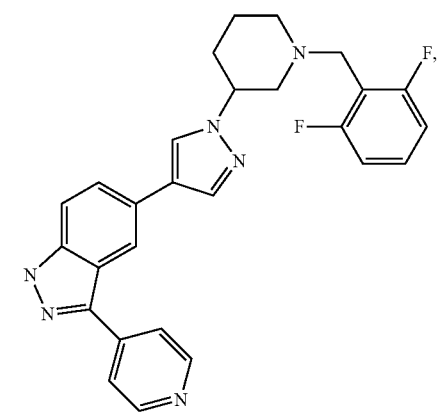
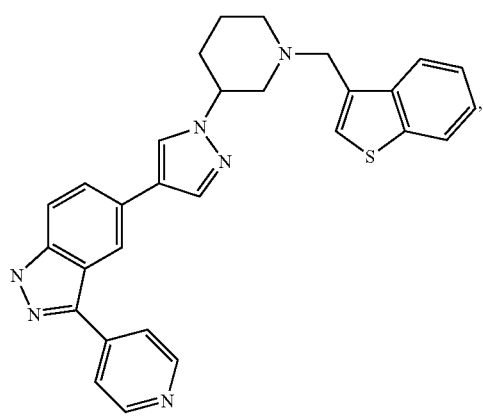
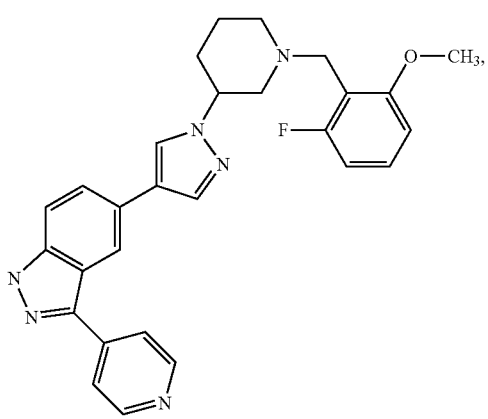
282
-continued
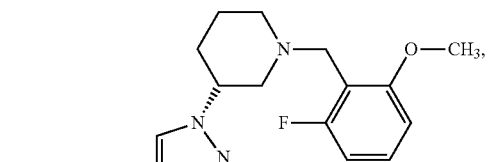
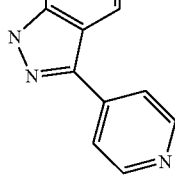
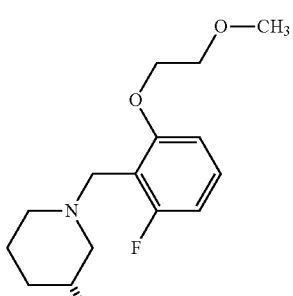
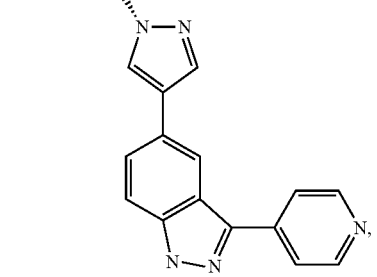
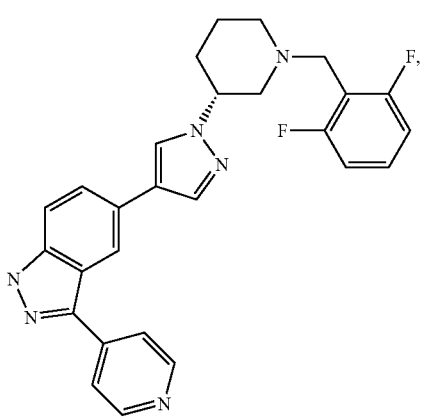

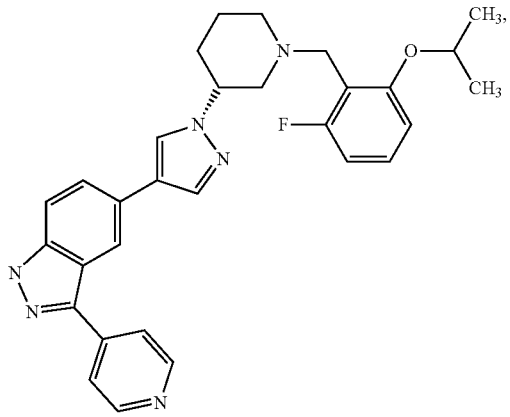
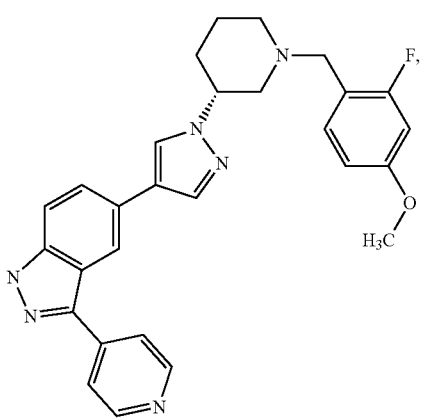
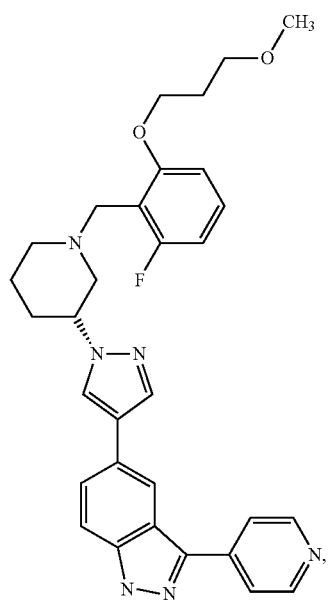
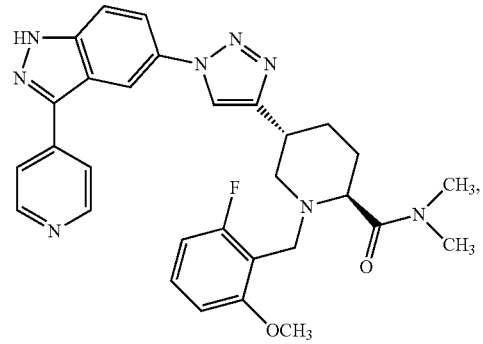
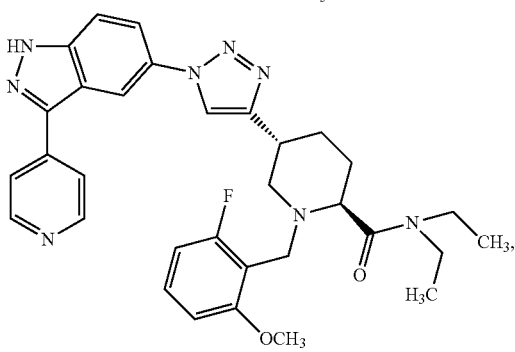
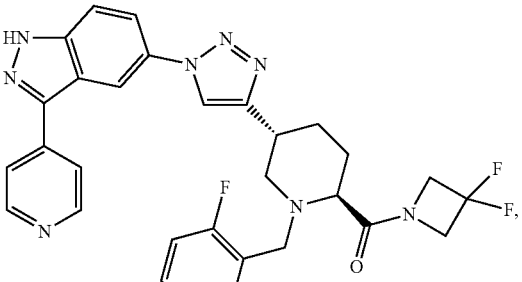
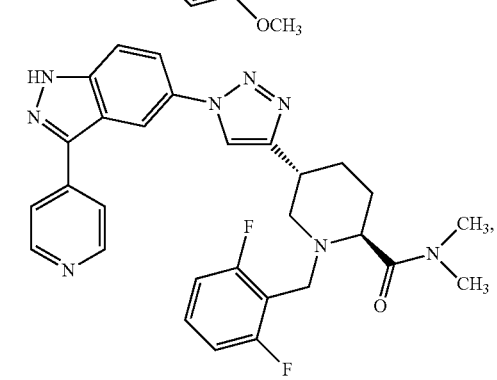
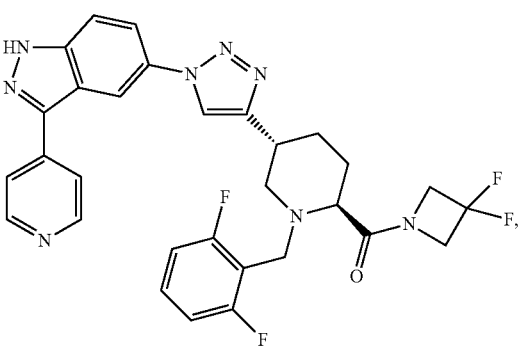

-continued
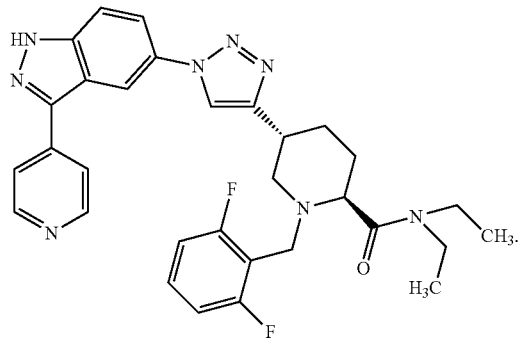
and
5. A compound selected from the group consisting of
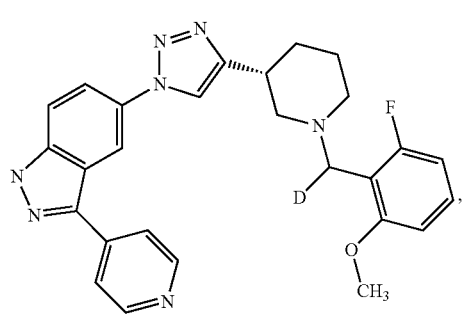
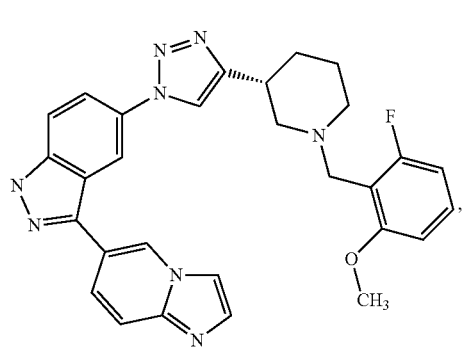
-continued
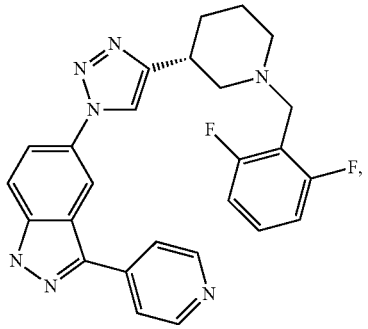
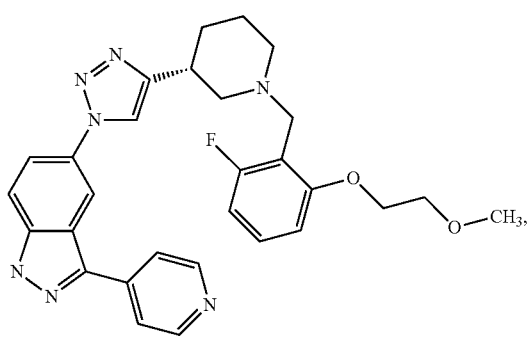
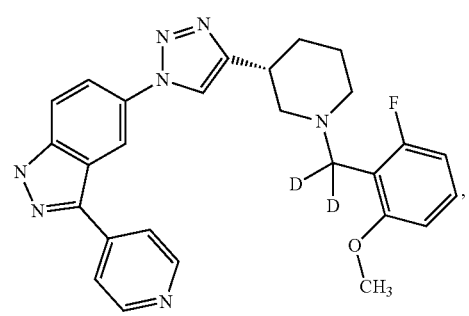
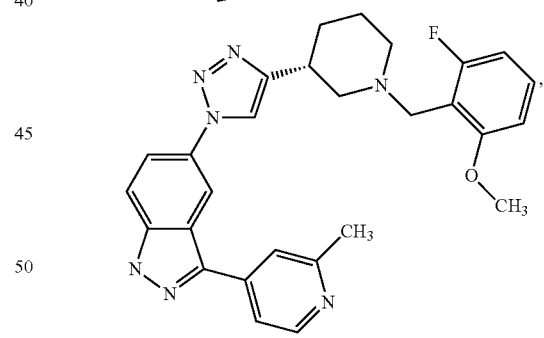

287
-continued
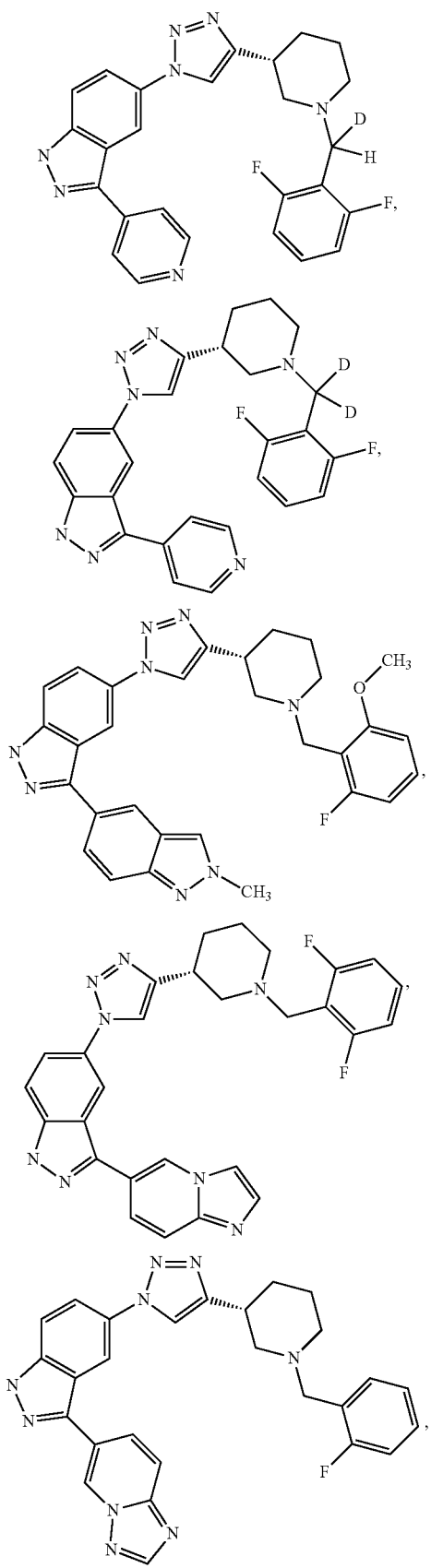
288
-continued
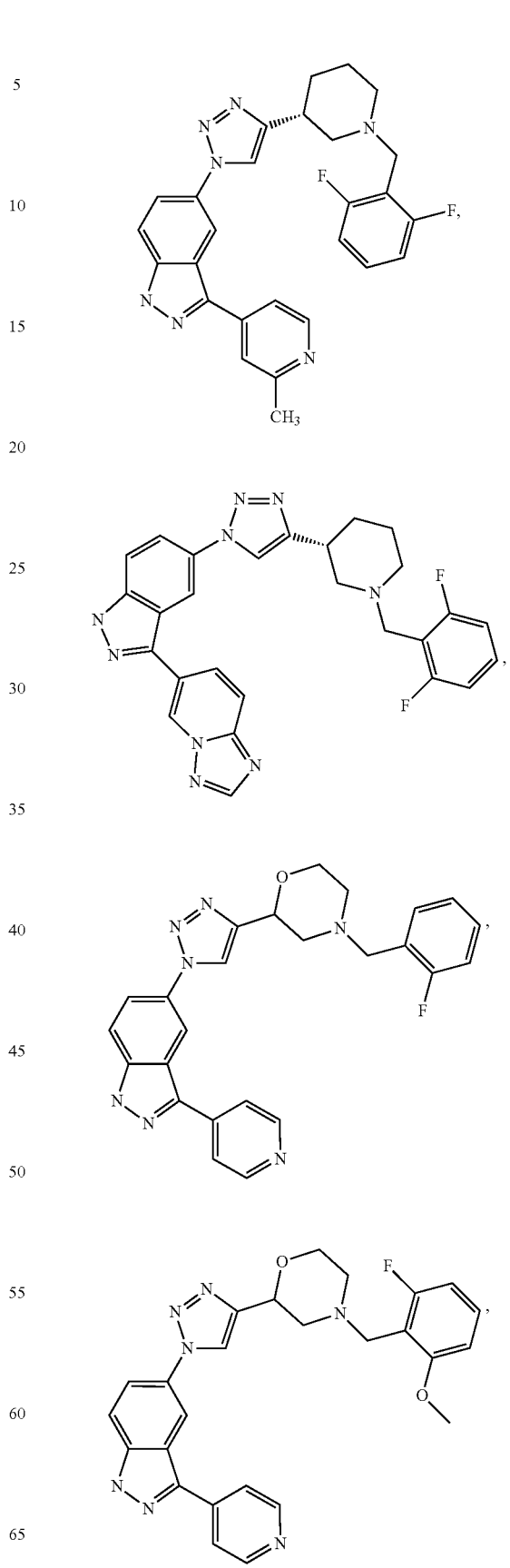

-continued
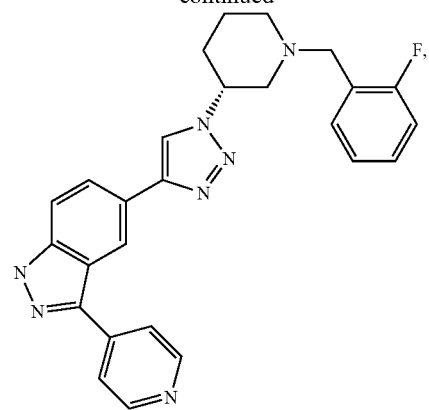
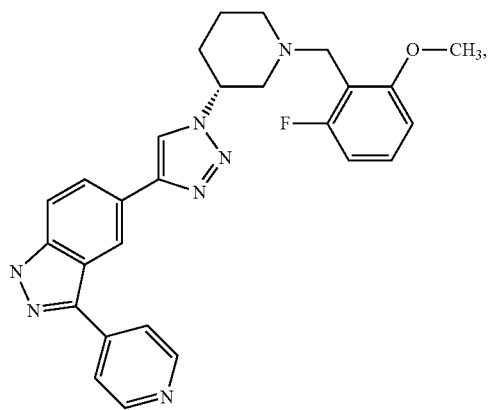
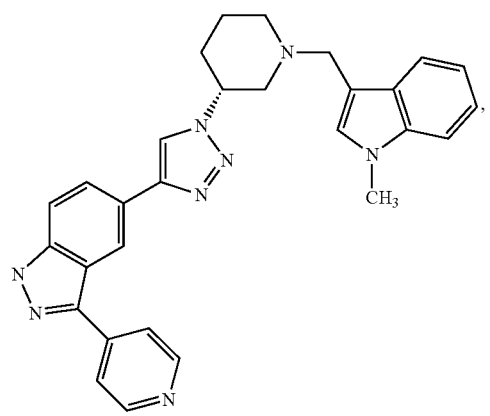
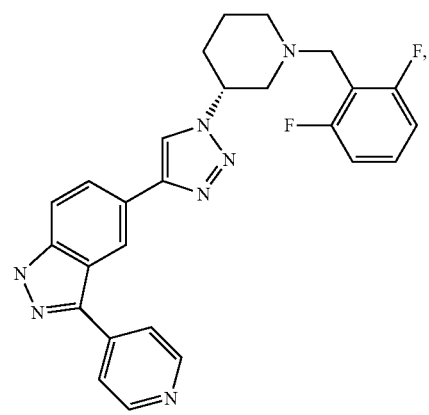
-continued
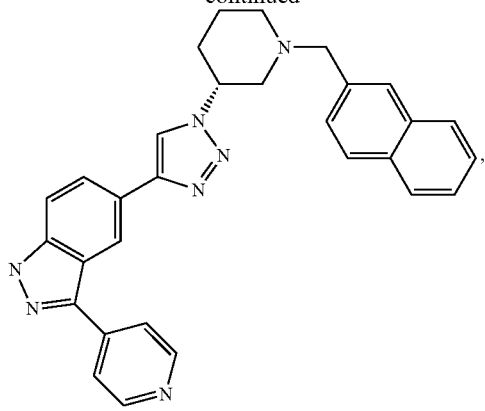
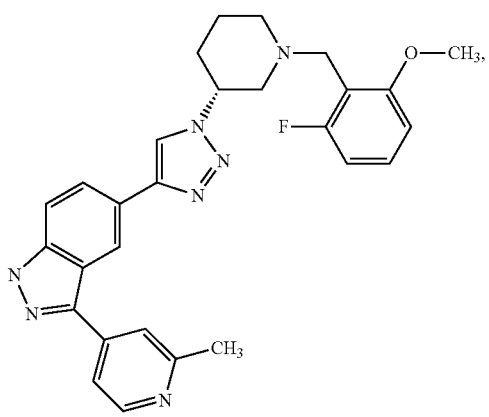
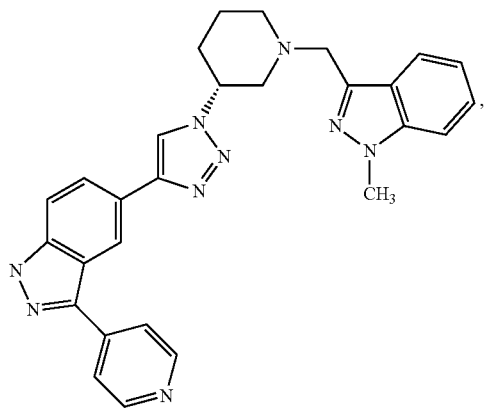
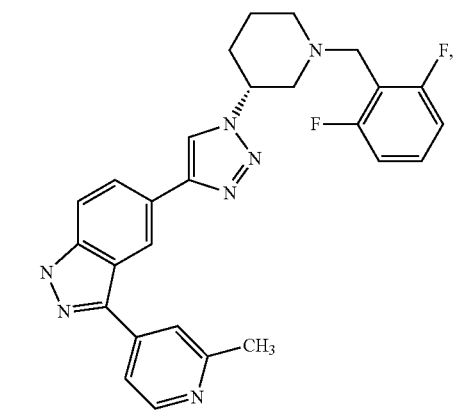

291
-continued
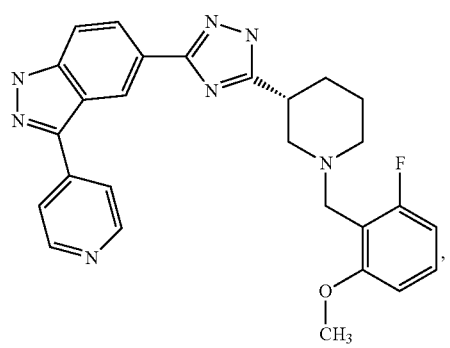
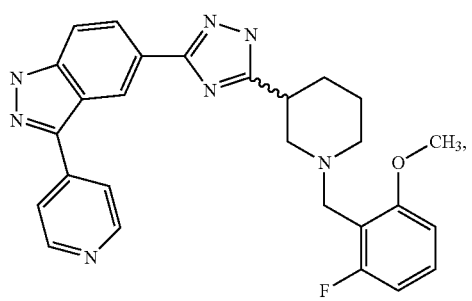
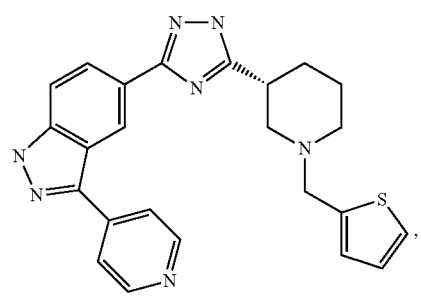
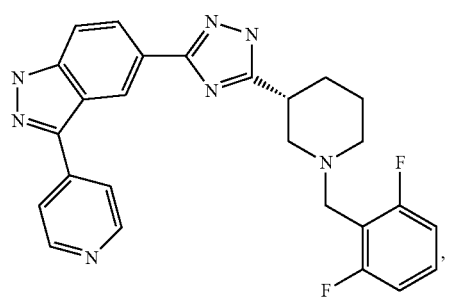
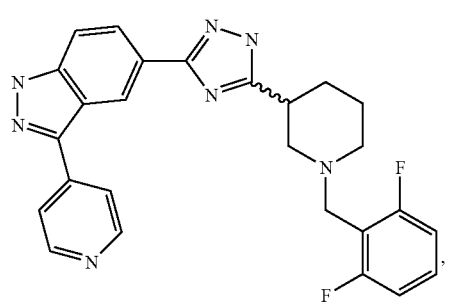
292
-continued
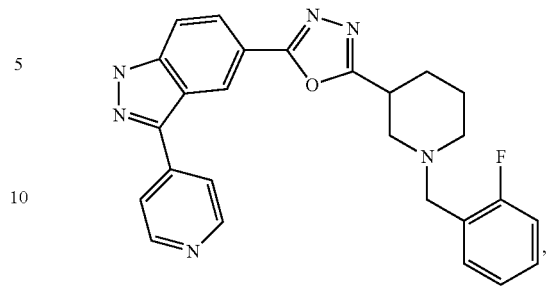
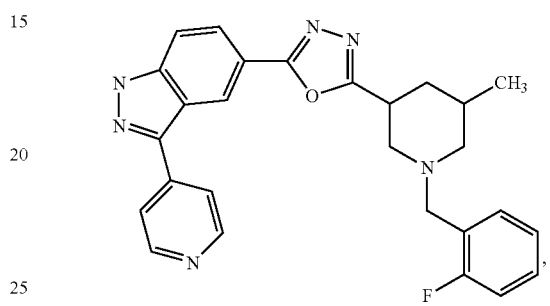
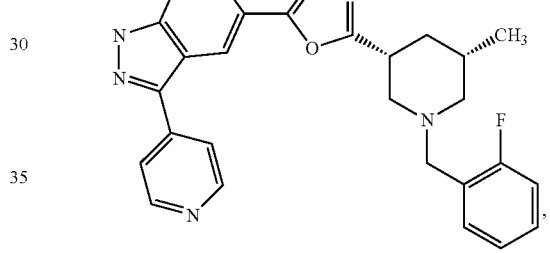
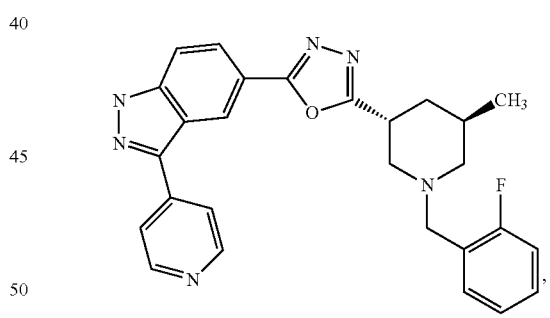
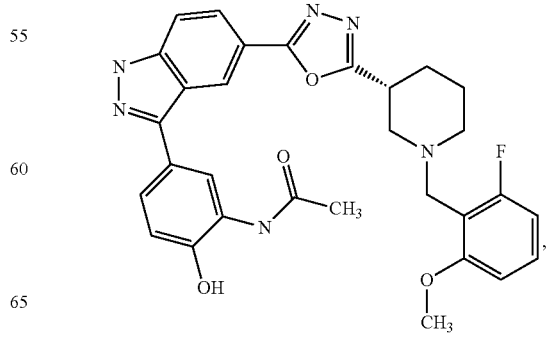

293
-continued
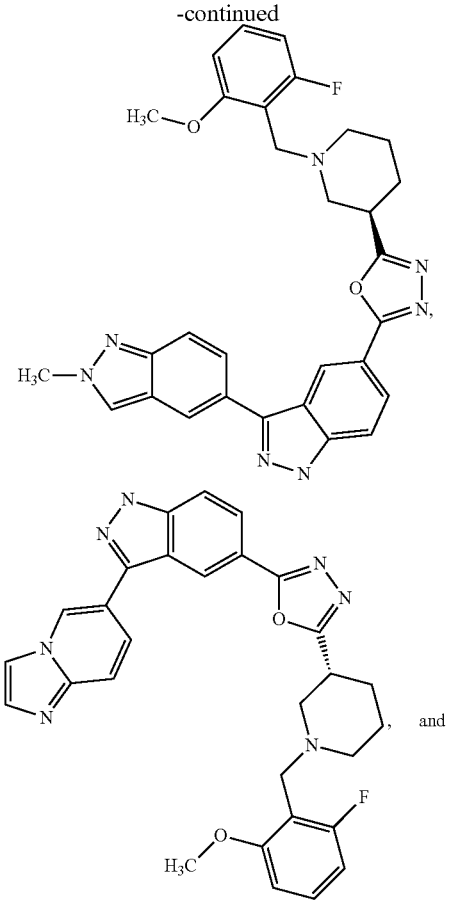
and
294
-continued
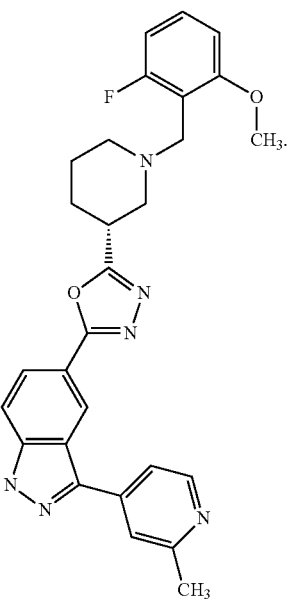
6. A pharmaceutical composition comprising a compound of claim 1 and a pharmaceutically acceptable carrier.
* * * * *